United States Patent
Thorarensen et al.

(10) Patent No.: US 10,703,756 B2
(45) Date of Patent: Jul. 7, 2020

(54) PYRROLO[2,3-D]PYRIMIDINYL, PYRROLO[2,3-B]PYRAZINYL, PYRROLO[2,3-B]PYRIDINYL ACRYLAMIDES AND EPOXIDES THEREOF

(71) Applicant: Pfizer Inc., New York, NY (US)

(72) Inventors: Atli Thorarensen, Stow, MA (US); Matthew Frank Brown, Stonington, CT (US); Agustin Casimiro-Garcia, Concord, MA (US); Ye Che, Groton, CT (US); Mark Edward Flanagan, Gales Ferry, CT (US); Adam Matthew Gilbert, Guilford, CT (US); Matthew Merrill Hayward, Old Lyme, CT (US); Jean-Baptiste Telliez, Lexington, MA (US); Rayomand Jal Unwalla, Bedford, MA (US); John I. Trujillo, Ledyard, CT (US); Sidney Xi Liang, Bethany, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/569,874

(22) PCT Filed: Apr. 19, 2016

(86) PCT No.: PCT/IB2016/052220
§ 371 (c)(1),
(2) Date: Oct. 27, 2017

(87) PCT Pub. No.: WO2016/178110
PCT Pub. Date: Nov. 10, 2016

(65) Prior Publication Data
US 2019/0002466 A1      Jan. 3, 2019

Related U.S. Application Data

(60) Provisional application No. 62/155,824, filed on May 1, 2015.

(51) Int. Cl.
C07D 487/04      (2006.01)

(52) U.S. Cl.
CPC ................... C07D 487/04 (2013.01)

(58) Field of Classification Search
CPC .................................................. C07D 487/04
See application file for complete search history.

(56) References Cited

U.S. PATENT DOCUMENTS

| | | |
|---|---|---|
| 8,222,038 B2 | 7/2012 | Kinoshiro et al. |
| 2005/0085518 A1 | 4/2005 | Dai et al. |
| 2015/0158864 A1 | 6/2015 | Thorarensen et al. |

FOREIGN PATENT DOCUMENTS

| | | |
|---|---|---|
| JP | 2011-513262 | 4/2011 |
| JP | 2013-529204 | 7/2013 |
| WO | 99/65908 A1 | 12/1999 |
| WO | 99/65909 A1 | 12/1999 |
| WO | 01/42246 A2 | 6/2001 |
| WO | 02/00661 A1 | 1/2002 |
| WO | 02/096909 A1 | 12/2002 |
| WO | 2004/046112 A2 | 6/2004 |
| WO | 2005/021568 A2 | 3/2005 |
| WO | 2007/012953 A2 | 2/2007 |
| WO | 2009/005112 A1 | 1/2009 |
| WO | 2009/106442 A1 | 9/2009 |
| WO | 2010/016005 A1 | 2/2010 |
| WO | 2011/029046 A1 | 3/2011 |
| WO | 2011/144585 A1 | 11/2011 |
| WO | 2014/172513 A2 | 10/2014 |
| WO | 2015/083028 A1 | 6/2015 |
| WO | WO 2015083028 * | 6/2015 ............ C07D 471/04 |

OTHER PUBLICATIONS

Flitsch et al, "Biohydroxylation Reactions Catalyzed by Enzymes and Whole-Cell Systems", Bioorganic Chemistry 27(2):81-90 (1999).
Kisseleva et al, "Signaling through the JAK/STAT pathway, recent advances and future challenges", Gene 285:1-24 (2002).
Murray, "The JAK-STAT Signaling Pathway: Input and Output Integration", The Journal of Immunology 178:2623-2629 (2007).
Neubauer et al, "Jak2 Deficiency Defines an Essential Developmental Checkpoint in Definitive Hematopoiesis", Cell 93:397-409 (1998).
O'Shea et al, "Cytokine Signaling in 2002: New Surprises in the Jak/Stat Pathway", Cell 109:S121-S131 (2002).
Parganas et al, "Jak2 Is Essential for Signaling through a Variety of Cytokine Receptors", Cell 93:385-395 (1998).
PCT International Search Report and Writen Opinion for International Patent Application No. PCT/IB2016/052220 dated Jun. 27, 2016.
Thoma et al, "Selective inhibitors of the Janus kinase Jak3—Are they effective?", Bioorganic & Medicinal Chemistry Letters 24:4617-4621 (2014).
Yamaoka et al, "The Janus kinases (Jaks)", Genome Biology 5:253 (2004).

* cited by examiner

Primary Examiner — Noble E Jarrell
(74) Attorney, Agent, or Firm — A. David Joran

(57) ABSTRACT

The present invention provides pharmaceutically active pyrrolo[2,3-d]pyrimidinyl, pyrrolo[2,3-b]pyrazinyl, and pyrrolo[2,3-b]pyridinyl acrylamides, epoxides, and analogues thereof. Such compounds are useful for inhibiting Janus Kinase (JAK). This invention also is directed to compositions comprising methods for making such compounds, and methods for treating and preventing conditions mediated by JAK.

5 Claims, No Drawings

PYRROLO[2,3-D]PYRIMIDINYL, PYRROLO[2,3-B]PYRAZINYL, PYRROLO[2,3-B]PYRIDINYL ACRYLAMIDES AND EPOXIDES THEREOF

FIELD OF THE INVENTION

The present invention provides pharmaceutically active pyrrolo[2,3-d]pyrimidinyl, pyrrolo[2,3-b]pyrazinyl, and pyrrolo[2,3-b]pyridinyl acrylamides, epoxides and analogues thereof. Such compounds are useful for inhibiting one or more Janus Kinase (JAK). This invention also is directed to compositions comprising methods for making such compounds, and methods for treating and preventing conditions mediated by JAK.

BACKGROUND OF THE INVENTION

Protein kinases are families of enzymes that catalyze the phosphorylation of specific residues in proteins, broadly classified into tyrosine and serine/threonine kinases. Inappropriate kinase activity, arising from mutation, over-expression, or inappropriate regulation, dys-regulation or de-regulation, as well as over- or under-production of growth factors or cytokines has been implicated in many diseases, including but not limited to cancer, cardiovascular diseases, allergies, asthma and other respiratory diseases, autoimmune diseases, inflammatory diseases, bone diseases, metabolic disorders, and neurological and neurodegenerative disorders such as Alzheimer's disease. Inappropriate kinase activity triggers a variety of biological cellular responses relating to cell growth, cell differentiation, survival, apoptosis, mitogenesis, cell cycle control, and cell mobility implicated in the aforementioned and related diseases.

Thus, protein kinases have emerged as an important class of enzymes as targets for therapeutic intervention. In particular, the JAK family of cellular protein tyrosine kinases (JAK1, JAK2, JAK3, and Tyk2) play a central role in cytokine signaling (Kisseleva et al., *Gene*, 2002, 285, 1; Yamaoka et al. Genome Biology, 2004, 5, 253)). Upon binding to their receptors, cytokines activate JAK enzymes which then phosphorylate the cytokine receptor, thereby creating docking sites for signaling molecules, notably, members of the signal transducer and activator of transcription (STAT) family that ultimately lead to gene expression. Numerous cytokines are known to activate the JAK family. These cytokines include, the IFN family (IFN-alpha, IFN-beta, IFN-omega, Limitin, IFN-gamma, IL-10, IL-19, IL-20, IL-22), the gp130 family (IL-6, IL-11, OSM, LIF, CNTF, NNT-1/BSF-3, G-CSF, CT-1, Leptin, IL-12, IL-23, IL-27 and IL-35), gamma-common chain family (IL-2, IL-4, IL-7, IL-9, IL-15, IL-21), and IL-13, TLSP, IL-3 family (IL-3, IL-5, GM-CSF), single chain family (EPO, GH, PRL, TPO), receptor tyrosine kinases (EGF, PDGF, CSF-1, HGF), and G-protein coupled receptors (AT1).

There remains a need for new compounds that effectively and selectively inhibit specific JAK enzymes, and JAK3 in particular. JAK3 is a member of the Janus family of protein kinases composed of JAK1, JAK2, JAK3 and TYK2, and is expressed to various levels in all tissues. Many cytokine receptors signal through pairs of JAK kinases in the following combinations: JAK1/JAK2, JAK1/JAK3, JAK1/TYK2, JAK2/TYK2 or JAK2/JAK2. Animal studies have shown that JAK3 is implicated in the development, function and homeostasis of the immune system. Modulation of immune activity through inhibition of JAK3 kinase activity can prove useful in the treatment of various immune disorders (Murray, P. J. *J. Immunol.*, 178, 2623-2629 (2007); Kisseleva, T., et al., *Gene*, 285, 1-24 (2002); O'Shea, J. J., et al., *Cell*, 109, (suppl.) S121-S131 (2002)) while avoiding JAK2 dependent erythropoietin (EPO) and thrombopoietin (TPO) signaling (Neubauer, H., et al., *Cell*, 93(3), 397-409 (1998); Parganas, E., et al., *Cell*, 93(3), 385-95 (1998)).

SUMMARY OF THE INVENTION

The present invention provides a compound having the structure:

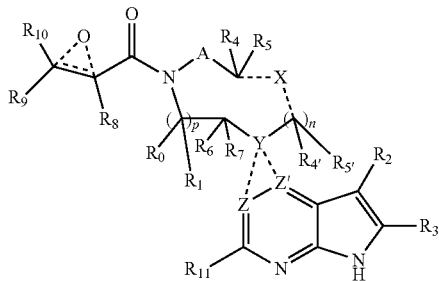

or a pharmaceutically acceptable salt or solvate thereof, or an enantiomer or diastereomer thereof, and wherein $R_2$ is selected from the group consisting of hydrogen, deuterium, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, ($C_1$-$C_6$ linear or branched chain alkyl)heterocyclic, $C_1$-$C_6$ linear or branched chain perfluoroalkyl, $C_1$-$C_6$ linear or branched chain alkoxy, $C_1$-$C_6$ linear or branched chain perfluoroalkoxy, halogen, cyano, hydroxyl, amino, carboxy, aminocarbonyl, ($C_1$-$C_6$ linear or branched chain alkyl)aminocarbonylamino, ($C_1$-$C_6$ linear or branched chain alkyl)aminocarbonyl, —$SOR_{12}$, —$SO_2R_{12}$, —$NR_{13}SO_2R_{12}$, —$SO_2NR_{13}R_{14}$, and —$NR_{13}SO_2NR_{14}R_{15}$; where said alkyl, aryl and heteroaryl is independently optionally substituted with one or more substituents selected from the group consisting of halo, hydroxy, methoxy, amino, cyano, alkylamino, dialkylamino, $CF_3$, aminocarbonyl, ($C_1$-$C_6$ linear or branched chain alkyl) aminocarbonyl, and $C_3$-$C_6$ cycloalkyl;

the dotted lines to the O atom may be present or absent, and if present, the resulting ring forms an epoxide, or if absent, an ethylene results;

$R_3$ is selected from the group consisting of hydrogen, deuterium, $C_1$-$C_6$ linear or branched chain alkyl, $C_1$-$C_6$ linear or branched chain perfluoroalkyl, halogen, and cyano;

A is —$(CR_aR_b)_q$—$(CR_cR_d)_r$—, wherein $R_a$, $R_b$, $R_c$ and $R_d$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, alkylaryl, (aryl)$C_1$-$C_6$ linear or branched chain alkyl, (heteroaryl)$C_1$-$C_6$ linear or branched chain alkyl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl;

$R_0$, $R_1$, $R_4$, $R_5$, $R_{4'}$, $R_{5'}$, $R_6$, $R_7$, $R_8$, $R_9$ and $R_{10}$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl; where, alternatively, $R_0$ or $R_1$, and/or $R_6$ or $R_7$, respectively together with either of $R_4$, $R_5$, $R_{4'}$, $R_{5'}$, $R_a$, $R_b$, $R_c$ or $R_d$, may independently form a bond or a $C_1$-$C_6$ linear alkyl chain; and/or, alternatively, $R_4$ or $R_5$, respectively together with either of $R_a$, $R_b$, $R_c$ or $R_d$, may independently form a bond or a $C_1$-$C_6$ linear alkyl chain; and/or, alternatively, $R_8$ and $R_9$ may together form a 3-6-membered ring optionally containing one or two O or N atoms; $R_{11}$ is hydrogen or deuterium; $R_{12}$, $R_{13}$, $R_{14}$ and $R_{15}$ are independently selected from hydrogen, $C_1$-$C_6$ linear or branched chain alkyl, $C_1$-$C_6$ linear or branched chain perfluoroalkyl, $C_6$-$C_{10}$ aryl, alkylaryl, and (aryl)$C_1$-$C_6$ linear or branched chain alkyl; Y is O or N, where when Y is O, n is 0;

one and only one of the dotted bonds to Z and Z' constitutes a single bond, the other being absent, and either Z is C when the dotted bond to Z is a single bond, and Z' is N or $CR_{16}$; or, Z is $CR_{16}$ or N when the dotted bond to Z' is a single bond, and Z' is C; where $R_{16}$ is H, $C_1$-$C_4$ alkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, or ($C_1$-$C_6$ linear or branched chain alkyl)heterocyclic, where said alkyl is further optionally substituted with one or more substituents selected from the group consisting of halo, hydroxy, methoxy, amino, $CF_3$, and $C_3$-$C_6$ cycloalkyl;

X and the dotted bonds thereto may be present or absent, whereby, (a) if X is present, Y N, and X is —$(CR_eR_f)_s$—, where $R_e$ and $R_f$ are independently hydrogen, deuterium, halo, hydroxy, $C_1$-$C_4$ alkoxy, amino, $CF_3$, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, ($C_1$-$C_6$ linear or branched chain alkyl)heteroaryl, (heteroaryl)$C_1$-$C_6$ linear or branched chain alkyl, or (heterocyclic)$C_1$-$C_6$ linear or branched chain alkyl, and said dotted bonds are present and are single bonds, where when n is 0, X and Y are bonded directly; and (b) if X is absent, said dotted bonds are absent and n is 0, and when Y is N, either (i) said N atom is substituted by H, or (ii) Z is C or N, Z' is C, the dotted bond to Z' is a single bond, the dotted bond to Z being absent, and said Y being an N atom together with $R_2$ and the atoms intervening therebetween form a 6-membered ring optionally substituted by $C_1$-$C_6$ linear or branched chain alkyl or $C_3$-$C_6$ cycloalkyl; and, n, p, q, r and s are independently 0, 1 or 2.

In other aspects, the present invention also provides:

pharmaceutical compositions which comprise a pharmaceutically acceptable carrier and a compound of the invention;

methods for treating or preventing a disorder or condition selected from rheumatoid arthritis, myositis, vasculitis, pemphigus, bullous pemphigoid, inflammatory bowel disease including Crohn's disease and ulcerative colitis, celiac diseases, proctitis, eosinophilic gastroenteritis, or mastocytosis, Alzheimer's disease, lupus, nephritis, systemic lupus erythematosus, psoriasis, eczema dermatitis, pruritus or other pruritic conditions, vitiligo, alopecia, autoimmune thyroid disorders, multiple sclerosis, major depression disorder, allergy, asthma, Sjogren's disease, Reiter's syndrome, polymyositis-dermatomyositis, systemic sclerosis, polyarteritis nodosa, dry eye syndrome, Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, membranous glomerulopathy, organ transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, or xeno transplantation, including Cogan's syndrome, ankylosing spondylitis, Wegener's granulomatosis, autoimmune alopecia, Type I or juvenile onset diabetes, and complications from diabetes, or thyroiditis, chronic pulmonary obstructive disorder, acute respiratory disease, cachexia, cancer, including alimentary/gastrointestinal tract cancer, colon cancer, liver cancer, skin cancer including mast cell tumor and squamous cell carcinoma, breast and mammary cancer, ovarian cancer, prostate cancer, leukemia, adult T cell leukemia activated B-cell like, diffuse large B cell lymphoma, kidney cancer, lung cancer, muscle cancer, bone cancer, bladder cancer, brain cancer, melanoma including oral and metastatic melanoma, Kaposi's sarcoma septic shock, cardiopulmonary dysfunction, acute myeloid leukemia, T cell acute lymphoblastic leukemia, multiple myeloma, myeloproliferative disorders, proliferative diabetic retinopathy, or angiogenic-associated disorders including solid tumors, pancreatic cancer, brain tumors, gliomas including astrocytoma, oligodendroglioma, and glioblastoma, acute CNS trauma including traumatic brain injury, encephalitis, stroke, and spinal cord injury, epilepsy, seizures, chronic neuroinflammation associated with neurodegeneration including Alzheimer's disease, Parkinson's disease, Amyotropic Lateral Sclerosis, Huntington's disease, cerebral ischemia, fronto-temporal lobe dementia, and with neuropsychiatric disorders including schizophrenia, bipolar disorder, treatment resistant depression, Post Traumatic Stress Disorder, anxiety, and auto-antibodies mediated encephalopathies, Eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization, comprising the step of administering to a subject an effective amount of a composition comprising a compound or a pharmaceutically acceptable salt thereof set forth herein;

methods for treating conditions or disorders including atopic dermatitis, eczema, psoriasis, scleroderma, lupus, pruritus, other pruritic conditions, allergic reactions including allergic dermatitis in mammal, horse allergic diseases including bite hypersensitivity, summer eczema, sweet itch in horses, heaves, inflammatory airway disease, recurrent airway obstruction, airway hyper-responsiveness, and chronic obstruction pulmonary disease by administering to a mammal in need a therapeutically effective amount of a compound of the invention, or a pharmaceutically acceptable salt thereof; and, methods for the preparation of compounds of the present invention. The present invention will be further understood from the following description given by way of example only. The present invention is directed to a class of pyrrolo[2,3-d]pyrimidinyl, pyrrolo[2,3-b]pyrazinyl, and pyrrolo[2,3-b]pyridinyl acrylamides and analogues thereof. In particular, the present invention is directed to pyrrolo[2,3-b]pyrimidinyl, pyrrolo[2,3-b]pyrazinyl, and pyrrolo[2,3-b]pyridinyl acrylamides and epoxides which are useful as inhibitors of JAK, and particularly JAK3. While the present invention is not so limited, an appreciation of various aspects of the invention will be gained through the following discussion and the examples.

The term "alkyl", alone or in combination, means an acyclic, saturated hydrocarbon group of the formula $C_nH_{2n+1}$ which may be linear or branched. Examples of such groups include methyl, ethyl, n-propyl, isopropyl, n-butyl, isobutyl, sec-butyl, tert-butyl, pentyl, iso-amyl and hexyl. Unless otherwise specified, an alkyl group comprises from 1 to 6 carbon atoms. The carbon atom content of alkyl and various other hydrocarbon-containing moieties is indicated by a prefix designating a lower and upper number of carbon atoms in the moiety, that is, the prefix $C_i$-$C_j$ indicates a moiety of the integer "i" to the integer "j" carbon atoms, inclusive. Thus, for example, $C_1$-$C_6$ alkyl refers to alkyl of one to six carbon atoms, inclusive.

The term "hydroxy," as used herein, means an OH radical. The term "heterocyclic" refers to a saturated or partially saturated (i.e. non aromatic) heterocycle which may be attached via a ring nitrogen atom (when the heterocycle is attached to a carbon atom) or a ring carbon atom (in all cases). Equally, when substituted, the substituent may be located on a ring nitrogen atom (if the substituent is joined through a carbon atom) or a ring carbon atom (in all cases). Specific examples include oxiranyl, aziridinyl, oxetanyl, azetidinyl, tetrahydrofuranyl, pyrrolidinyl, tetrahydropyranyl, piperidinyl, 1,4-dioxanyl, morpholinyl, piperazinyl, azepanyl, oxepanyl, oxazepanyl and diazepinyl.

The term "aryl" refers to an aromatic monocyclic or bicyclic hydrocarbon which may be attached via a ring carbon atom. Equally, when substituted, the substituent may be located on a ring carbon atom. Specific examples include phenyl, toluyl, xylyl, trimethylphenyl, and naphthyl. Examples of aryl substituents include alkyl, hydroxyl, halo, nitrile, alkoxy, trifluoromethyl, carboxamido, SO$_2$Me, benzyl, and substituted benzyl.

The term "heteroaryl" refers to an aromatic heterocycle which may be attached via a ring carbon atom (in all cases) or a ring nitrogen atom with an appropriate valency (when the heterocycle is attached to a carbon atom). Equally, when substituted, the substituent may be located on a ring carbon atom (in all cases) or a ring nitrogen atom with an appropriate valency (if the substituent is joined through a carbon atom). Specific examples include thienyl, furanyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridyl, pyridazinyl, pyrimidinyl and pyrazinyl. The term "cycloalkyl" means a monocyclic, saturated hydrocarbon group of the formula $C_nH_{2n-1}$. Examples include cyclopropyl, cyclobutyl, cyclopentyl, cyclohexyl, and cycloheptyl. Unless otherwise specified, a cycloalkyl group comprises from 3 to 8 carbon atoms.

The terms "halo" and "halogen" refer to fluoride (F), chloride (Cl), bromide (Br) or iodide (I).

The term "mammal" refers to human, livestock or companion animals.

The term "companion animal" or "companion animals" refers to animals kept as pets or household animal. Examples of companion animals include dogs, cats, and rodents including hamsters, guinea pigs, gerbils and the like, rabbits, ferrets and birds.

The term "livestock" refers to animals reared or raised in an agricultural setting to make products such as food or fiber, or for its labor. In some embodiments, livestock are suitable for consumption by mammals, for example humans. Examples of livestock animals include cattle, goats, horses, pigs, sheep, including lambs, and rabbits, as well as birds, such as chickens, ducks and turkeys.

The term "treating" or "treatment" means an alleviation of symptoms associated with a disease, disorder or condition, or halt of further progression or worsening of those symptoms. Depending on the disease and condition of the patient, the term "treatment" as used herein may include one or more of curative, palliative and prophylactic treatment. Treatment can also include administering a pharmaceutical formulation of the present invention in combination with other therapies.

The term "therapeutically-effective" indicates the capability of an agent to prevent, or improve the severity of, the disorder, while avoiding adverse side effects typically associated with alternative therapies. The phrase "therapeutically-effective" is to be understood to be equivalent to the phrase "effective for the treatment, prevention, or amelioration", and both are intended to qualify the amount of each agent for use in the combination therapy which will achieve the goal of improvement in the severity of cancer, cardiovascular disease, or pain and inflammation and the frequency of incidence over treatment of each agent by itself, while avoiding adverse side effects typically associated with alternative therapies.

"Pharmaceutically acceptable" means suitable for use in mammals, companion animals or livestock animals.

If substituents are described as being "independently selected" from a group, each substituent is selected independent of the other. Each substituent therefore may be identical to or different from the other substituent(s).

DETAILED DESCRIPTION OF THE INVENTION

The present invention is related to novel compounds which are selective JAK3 modulators useful for the treatment of diseases and conditions associated with dysregulation of the JAK3. The present invention further provides pharmaceutical compositions comprising such JAK3 modulators as well as methods of treating and/or preventing such diseases and conditions. Accordingly, the present invention provides a compound having the structure:

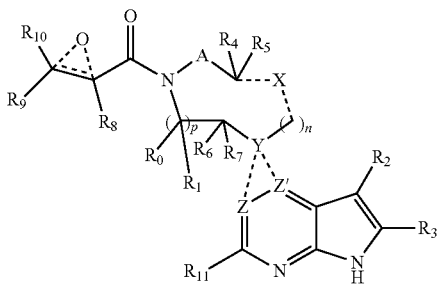

or a pharmaceutically acceptable salt or solvate thereof, or an enantiomer or diastereomer thereof, and wherein variables are defined above.

In one embodiment, the invention provides a compound having the structure:

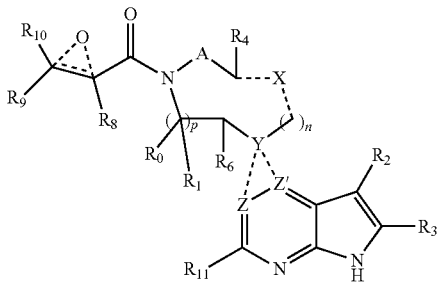

or a pharmaceutically acceptable salt or solvate thereof, or an enantiomer or diastereomer thereof, and wherein $R_2$ is selected from the group consisting of hydrogen, deuterium, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, ($C_1$-$C_6$ linear or branched chain alkyl)heterocyclic, $C_1$-$C_6$ linear or branched chain perfluoroalkyl, $C_1$-$C_6$ linear or branched chain alkoxy, $C_1$-$C_6$ linear or branched chain perfluoroalkoxy, halogen, cyano, hydroxyl, amino, carboxy, aminocarbonyl, ($C_1$-$C_6$ linear or branched chain alkyl)aminocarbonylamino, ($C_1$-$C_6$ linear or branched chain alkyl)aminocarbonyl, —$SOR_{12}$, —$SO_2R_{12}$, —$NR_{13}SO_2R_{12}$, —$SO_2NR_{13}R_{14}$, and —$NR_{13}SO_2NR_{14}R_{15}$; where said alkyl, aryl and heteroaryl is independently optionally substituted with one or more substituents selected from the group consisting of halo, hydroxy, methoxy, amino, cyano, alkylamino, dialkylamino, $CF_3$, aminocarbonyl, ($C_1$-$C_6$ linear or branched chain alkyl)aminocarbonyl, and $C_3$-$C_6$ cycloalkyl;

$R_3$ is selected from the group consisting of hydrogen, deuterium, $C_1$-$C_6$ linear or branched chain alkyl, $C_1$-$C_6$ linear or branched chain perfluoroalkyl, halogen, and cyano;

A is —$(CR_aR_b)_q$—$(CR_cR_d)_r$—, wherein $R_a$, $R_b$, $R_c$ and $R_d$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, alkylaryl, (aryl)$C_1$-$C_6$ linear or branched chain alkyl, (heteroaryl)$C_1$-$C_6$ linear or branched chain alkyl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl;

$R_0$, $R_1$, $R_4$, $R_6$, $R_8$, $R_9$ and $R_{10}$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl; where, alternatively, $R_0$ or $R_1$, and/or $R_6$, respectively together with either of $R_4$, $R_a$, $R_b$, $R_c$ or $R_d$, may independently form a bond or a $C_1$-$C_6$ linear alkyl chain; and/or, alternatively, $R_4$, respectively together with either of $R_a$, $R_b$, $R_c$ or $R_d$, may independently form a bond or a $C_1$-$C_6$ linear alkyl chain; and/or, alternatively, $R_8$ and $R_9$ may together form a 3-6-membered ring optionally containing one or two O or N atoms; $R_{11}$ is hydrogen or deuterium;

$R_{12}$, $R_{13}$, $R_{14}$ and $R_{15}$ are independently selected from hydrogen, $C_1$-$C_6$ linear or branched chain alkyl, $C_1$-$C_6$ linear or branched chain perfluoroalkyl, $C_6$-$C_{10}$ aryl, alkylaryl, and (aryl)$C_1$-$C_6$ linear or branched chain alkyl;

Y is O or N, where when Y is O, n is 0;

the dotted lines to the O atom may be present or absent, and if present, the resulting ring forms an epoxide, or if absent, an ethylene results;

one and only one of the dotted bonds to Z and Z' constitutes a single bond, the other being absent, and either Z is C when the dotted bond to Z is a single bond, and Z' is N or $CR_{16}$; or, Z is $CR_{16}$ or N when the dotted bond to Z' is a single bond, and Z' is C; where $R_{16}$ is H, $C_1$-$C_4$ alkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, or ($C_1$-$C_6$ linear or branched chain alkyl)heterocyclic, where said alkyl is further optionally substituted with one or more substituents selected from the group consisting of halo, hydroxy, methoxy, amino, $CF_3$, and $C_3$-$C_6$ cycloalkyl;

X and the dotted bonds thereto may be present or absent, whereby, (a) if X is present, Y is N, and X is —$(CR_eR_f)_s$—, where $R_e$ and $R_f$ are independently hydrogen, deuterium, halo, hydroxy, $C_1$-$C_4$ alkoxy, amino, $CF_3$, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, ($C_1$-$C_6$ linear or branched chain alkyl)heteroaryl, (heteroaryl)$C_1$-$C_6$ linear or branched chain alkyl, or (heterocyclic)$C_1$-$C_6$ linear or branched chain alkyl, and said dotted bonds are present and are single bonds, where when n is 0, X and Y are bonded directly; and (b) if X is absent, said dotted bonds are absent and n is 0, and when Y is N, either (i) said N atom is substituted by H, or (ii) Z is C or N, Z' is C, the dotted bond to Z' is a single bond, the dotted bond to Z being absent, and said Y being an N atom together with $R_2$ and the atoms intervening therebetween form a 6-membered ring optionally substituted by $C_1$-$C_6$ linear or branched chain alkyl or $C_3$-$C_6$ cycloalkyl; and, n, p, q, r and s are independently 0, 1 or 2.

In another embodiment, the invention provides a compound having the structure:

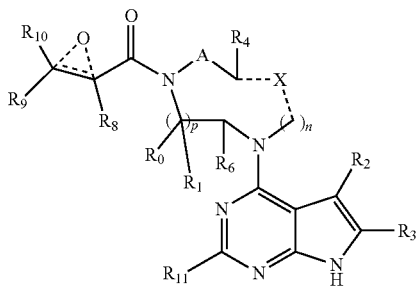

or a pharmaceutically acceptable salt or solvate thereof, or an enantiomer or diastereomer thereof, and wherein $R_2$ is selected from the group consisting of hydrogen, deuterium, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, ($C_1$-$C_6$ linear or branched chain alkyl)heterocyclic, $C_1$-$C_6$ linear or branched chain perfluoroalkyl, $C_1$-$C_6$ linear or branched chain alkoxy, $C_1$-$C_6$ linear or branched chain perfluoroalkoxy, halogen, cyano, hydroxyl, amino, carboxy, aminocarbonyl, ($C_1$-$C_6$ linear or branched chain alkyl)aminocarbonylamino, ($C_1$-$C_6$ linear or branched chain alkyl)aminocarbonyl, —$SOR_{12}$, —$SO_2R_{12}$, —$NR_{13}SO_2R_{12}$, —$SO_2NR_{13}R_{14}$, and —$NR_{13}SO_2NR_{14}R_{15}$; where said alkyl, aryl and heteroaryl is independently optionally substituted with one or more substituents selected from the group consisting of halo, hydroxy, methoxy, amino, cyano, alkylamino, dialkylamino, $CF_3$, aminocarbonyl, ($C_1$-$C_6$ linear or branched chain alkyl)aminocarbonyl, and $C_3$-$C_6$ cycloalkyl;

$R_3$ is selected from the group consisting of hydrogen, deuterium, $C_1$-$C_6$ linear or branched chain alkyl, $C_1$-$C_6$ linear or branched chain perfluoroalkyl, halogen, and cyano;

A is —$(CR_aR_b)_q$—$(CR_cR_d)_r$—, wherein $R_a$, $R_b$, $R_c$ and $R_d$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, alkylaryl, (aryl)$C_1$-$C_6$ linear or branched chain alkyl, (heteroaryl)$C_1$-$C_6$ linear or branched chain alkyl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl;

$R_0$, $R_1$, $R_4$, $R_6$, $R_8$, $R_9$ and $R_{10}$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl; where, alternatively, $R_0$ or $R_1$, and/or $R_6$, respectively together with either of $R_4$, $R_a$, $R_b$, $R_c$ or $R_d$, may independently form a bond or a $C_1$-$C_6$ linear alkyl chain; and/or, alternatively, $R_4$, respectively together with either of $R_a$, $R_b$, $R_c$ or $R_d$, may independently form a bond or a $C_1$-$C_6$ linear alkyl chain; and/or, alternatively, $R_8$ and $R_9$ may together form a 3-6-membered ring optionally containing one or two O or N atoms;

Y is O or N, where when Y is O, n is 0;

$R_{11}$ is hydrogen or deuterium;

$R_{12}$, $R_{13}$, $R_{14}$ and $R_{15}$ are independently selected from hydrogen, $C_1$-$C_6$ linear or branched chain alkyl, $C_1$-$C_6$ linear or branched chain perfluoroalkyl, $C_6$-$C_{10}$ aryl, alkylaryl, and (aryl)$C_1$-$C_6$ linear or branched chain alkyl;

X and the dotted bonds thereto may be present or absent, whereby, (a) if X is present, Y is N, and X is —$(CReRf)s$—, where Re and Rf are independently hydrogen, deuterium, halo, hydroxy, C1-C4 alkoxy, amino, CF3, C1-C6 linear or branched chain alkyl, C3-C6 cycloalkyl, C6-C10 aryl, monocyclic or bi-cyclic heteroaryl, comprising 5- and/or 6-membered rings, (aryl)C1-C6 linear or branched chain alkyl, (C1-C6 linear or branched chain alkyl)heteroaryl, (heteroaryl)C1-C6 linear or branched chain alkyl, or (heterocyclic)C1-C6 linear or branched chain alkyl, and said dotted bonds are present and are single bonds, where when n is 0, X and Y are bonded directly; and (b) if X is absent, said dotted bonds are absent and n is 0, and when Y is N, either (i) said N atom is substituted by H, or (ii) Z is C or N, Z' is C, the dotted bond to Z' is a single bond, the dotted bond to Z being absent, and said Y being an N atom together with R2 and the atoms intervening therebetween form a 6-membered ring optionally substituted by C1-C6 linear or branched chain alkyl or C3-C6 cycloalkyl; and, n, p, q, r and s are independently 0, 1 or 2.

In another embodiment, the invention provides the compound having the structure:

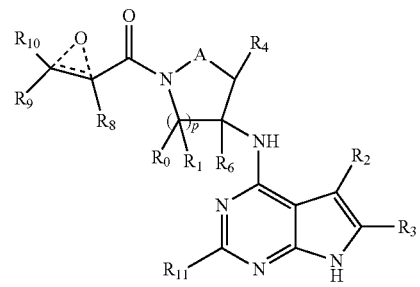

or a pharmaceutically acceptable salt or solvate thereof, or an enantiomer or diastereomer thereof, and wherein $R_2$ is selected from the group consisting of hydrogen, deuterium, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, ($C_1$-$C_6$ linear or branched chain alkyl)heterocyclic, $C_1$-$C_6$ linear or branched chain perfluoroalkyl, $C_1$-$C_6$ linear or branched chain alkoxy, $C_1$-$C_6$ linear or branched chain perfluoroalkoxy, halogen, cyano, hydroxyl, amino, carboxy, aminocarbonyl, ($C_1$-$C_6$ linear or branched chain alkyl)aminocarbonylamino, ($C_1$-$C_6$ linear or branched chain alkyl)aminocarbonyl, —$SOR_{12}$, —$SO_2R_{12}$, —$NR_{13}SO_2R_{12}$, —$SO_2NR_{13}R_{14}$, and —$NR_{13}SO_2NR_{14}R_{15}$; where said alkyl, aryl and heteroaryl is independently optionally substituted with one or more substituents selected from the group consisting of halo, hydroxy, methoxy, amino, cyano, alkylamino, dialkylamino, $CF_3$, aminocarbonyl, ($C_1$-$C_6$ linear or branched chain alkyl)aminocarbonyl, and $C_3$-$C_6$ cycloalkyl;

$R_3$ is selected from the group consisting of hydrogen, deuterium, $C_1$-$C_6$ linear or branched chain alkyl, $C_1$-$C_6$ linear or branched chain perfluoroalkyl, halogen, and cyano; A is —$(CR_aR_b)_q$—$(CR_cR_d)_r$—, wherein $R_a$, $R_b$, $R_c$ and $R_d$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, alkylaryl, (aryl)$C_1$-$C_6$ linear or branched chain alkyl, (heteroaryl)$C_1$-$C_6$ linear or branched chain alkyl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl;

the dotted lines to the O atom may be present or absent, and if present, the resulting ring forms an epoxide, or if absent, an ethylene results;

$R_0$, $R_1$, $R_4$, $R_6$, $R_8$, $R_9$ and $R_{10}$ are independently selected from hydrogen, deuterium, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl; where, alternatively, $R_0$ or $R_1$, and/or $R_6$, respectively together with either of $R_4$, $R_a$, $R_b$, $R_c$ or $R_d$, may independently form a bond or a $C_1$-$C_6$ linear alkyl chain; and/or, alternatively, $R_4$, respectively together with either of $R_a$, $R_b$, $R_c$ or $R_d$, may independently form a bond or a $C_1$-$C_6$ linear alkyl chain; and/or, alternatively, $R_8$ and $R_9$ may together form a 3-6-membered ring optionally containing one or two 0 or N atoms; $R_{11}$ is hydrogen or deuterium;

$R_{12}$, $R_{13}$, $R_{14}$ and $R_{15}$ are independently selected from hydrogen, $C_1$-$C_6$ linear or branched chain alkyl, $C_1$-$C_6$ linear or branched chain perfluoroalkyl, $C_6$-$C_{10}$ aryl, alkylaryl, and (aryl)$C_1$-$C_6$ linear or branched chain alkyl; and, p, q, and rare independently 0, 1 or 2.

In another embodiment, the invention provides the compound having the structure:

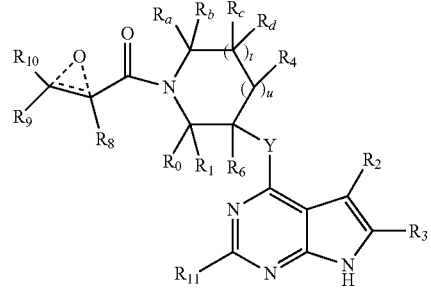

or a pharmaceutically acceptable salt or solvate thereof, or an enantiomer or diastereomer thereof, and wherein $R_2$ is selected from the group consisting of hydrogen, deuterium, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, ($C_1$-$C_6$ linear or branched chain alkyl)heterocyclic, $C_1$-$C_6$ linear or branched chain perfluoroalkyl, $C_1$-$C_6$ linear or branched chain alkoxy, $C_1$-$C_6$ linear or branched chain perfluoroalkoxy, halogen, cyano, hydroxyl, amino, carboxy, aminocarbonyl, ($C_1$-$C_6$ linear or branched chain alkyl)aminocarbonylamino, ($C_1$-$C_6$ linear or branched chain alkyl)aminocarbonyl, —$SOR_{12}$, —$SO_2R_{12}$, —$NR_{13}SO_2R_{12}$, —$SO_2NR_{13}R_{14}$, and —$NR_{13}SO_2NR_{14}R_{15}$; where said alkyl, aryl and heteroaryl is independently optionally substituted with one or more substituents selected from the group consisting of halo, hydroxy, methoxy, amino, cyano, alkylamino, dialkylamino, $CF_3$, aminocarbonyl, ($C_1$-$C_6$ linear or branched chain alkyl) aminocarbonyl, and $C_3$-$C_6$ cycloalkyl;

$R_3$ is selected from the group consisting of hydrogen, deuterium, $C_1$-$C_6$ linear or branched chain alkyl, $C_1$-$C_6$ linear or branched chain perfluoroalkyl, halogen, and cyano; $R_a$, $R_b$, $R_c$ and $R_d$ are independently selected from hydrogen, $C_1$-$C_6$ linear or branched chain alkyl, $C_1$-$C_6$ linear or branched chain perfluoroalkyl, aryl, alkylaryl, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl;

the dotted lines to the O atom may be present or absent, and if present, the resulting ring forms an epoxide, or if absent, an ethylene results;

Y is O or N where N may be substituted by H or alkyl;
$R_0$, $R_1$, $R_4$, $R_6$, $R_8$, $R_9$ and $R_{10}$ are independently selected from hydrogen, deuterium $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/ or 6-membered rings, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl; where, alternatively, $R_0$ or $R_1$, and/or $R_6$, respectively together with either of $R_4$, $R_a$, $R_b$, $R_c$ or $R_d$, may independently form a bond or a $C_1$-$C_6$ linear alkyl chain; and/or, alternatively, $R_4$, respectively together with either of $R_a$, $R_b$, $R_c$ or $R_d$, may independently form a bond or a $C_1$-$C_6$ linear alkyl chain; and/or, alternatively, $R_8$ and $R_9$ may together form a 3-6-membered ring optionally containing one or two 0 or N atoms; $R_{11}$ is hydrogen or deuterium;

$R_{12}$, $R_{13}$, $R_{14}$ and $R_{15}$ are independently selected from hydrogen, deuterium $C_1$-$C_6$ linear or branched chain alkyl, $C_1$-$C_6$ linear or branched chain perfluoroalkyl, $C_6$-$C_{10}$ aryl, alkylaryl, and (aryl)$C_1$-$C_6$ linear or branched chain alkyl; and, t and u are independently 0, 1 or 2.

In another embodiment, the invention provides the compound having the structure:

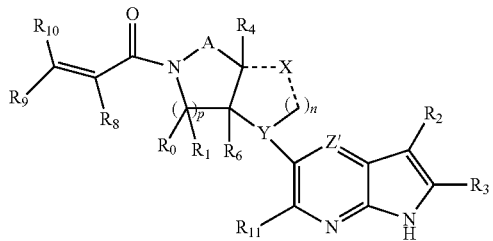

or a pharmaceutically acceptable salt or solvate thereof, or an enantiomer or diastereomer thereof, and wherein $R_2$ is selected from the group consisting of hydrogen, deuterium, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, ($C_1$-$C_6$ linear or branched chain alkyl)heterocyclic, $C_1$-$C_6$ linear or branched chain perfluoroalkyl, $C_1$-$C_6$ linear or branched chain alkoxy, $C_1$-$C_6$ linear or branched chain perfluoroalkoxy, halogen, cyano, hydroxyl, amino, carboxy, aminocarbonyl, ($C_1$-$C_6$ linear or branched chain alkyl)aminocarbonylamino, ($C_1$-$C_6$ linear or branched chain alkyl)aminocarbonyl, —$SOR_{12}$, —$SO_2R_{12}$, —$NR_{13}SO_2R_{12}$, —$SO_2NR_{13}R_{14}$, and —$NR_{13}SO_2NR_{14}R_{15}$; where said alkyl, aryl and heteroaryl is independently optionally substituted with one or more substituents selected from the group consisting of halo, hydroxy, methoxy, amino, cyano, alkylamino, dialkylamino, $CF_3$, aminocarbonyl, ($C_1$-$C_6$ linear or branched chain alkyl)aminocarbonyl, and $C_3$-$C_6$ cycloalkyl;

$R_3$ is selected from the group consisting of hydrogen, deuterium, $C_1$-$C_6$ linear or branched chain alkyl, $C_1$-$C_6$ linear or branched chain perfluoroalkyl, halogen, and cyano;

A is —$(CR_aR_b)_q$—$(CR_cR_d)_r$—, wherein $R_a$, $R_b$, $R_c$ and $R_d$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, alkylaryl, (aryl)$C_1$-$C_6$ linear or branched chain alkyl, (heteroaryl)$C_1$-$C_6$ linear or branched chain alkyl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl;

Y is O or N, where when Y is O, n is 0;

Z' is $CR_{18}$ or N; where $R_{16}$ is H, $C_1$-$C_4$ alkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, or ($C_1$-$C_6$ linear or branched chain akyl)heterocyclic, where said alkyl is further optionally substituted with one or more substituents selected from the group consisting of halo, hydroxy, methoxy, amino, $CF_3$, and $C_3$-$C_6$ cycloalkyl;

$R_a$, $R_b$, $R_c$ and $R_d$ are independently selected from hydrogen, deuterium $C_1$-$C_6$ linear or branched chain alkyl, $C_1$-$C_6$ linear or branched chain perfluoroalkyl, aryl, alkylaryl, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, wherein said alkyl is further optionally substituted with one or more substituents selected from the group consisting of halo, hydroxy, methoxy, amino, alkylamino, dialkylamino, $CF_3$, and $C_3$-$C_6$ cycloalkyl, where said alkyl is further optionally substituted with one or more substituents selected from the group consisting of halo, hydroxy, methoxy, amino, alkylamino, dialkylamino, $CF_3$, and $C_3$-$C_6$ cycloalkyl;

$R_0$, $R_1$, $R_4$, $R_6$, $R_8$, $R_9$ and $R_{10}$ are independently selected from hydrogen, deuterium $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl; where, alternatively, $R_0$ or $R_1$, and/or R %, respectively together with either of $R_4$, $R_a$, $R_b$, $R_c$ or $R_d$, may independently form a bond or a $C_1$-$C_6$ linear alkyl chain; and/or, alternatively, $R_4$, respectively together with either of $R_a$, $R_b$, $R_c$ or $R_d$, may independently form a bond or a $C_1$-$C_6$ linear alkyl chain; and/or, alternatively, R % and $R_9$ may together form a 3-6-membered ring optionally containing one or two 0 or N atoms; $R_{11}$ is hydrogen or deuterium; CR'$R_{12}$, $R_{13}$, $R_{14}$ and $R_{15}$ are independently selected from hydrogen, $C_1$-$C_6$ linear or branched chain alkyl, $C_1$-$C_6$ linear or branched chain perfluoroalkyl, $C_6$-$C_{10}$ aryl, alkylaryl, and (aryl)$C_1$-$C_6$ linear or branched chain alkyl;

X and the dotted bonds thereto may be present or absent, whereby, (a) if X is present, Y is N, and X is —(CR$_e$R$_f$)$_s$—, where R$_e$ and R$_f$ are independently hydrogen, deuterium, halo, hydroxy, $C_1$-$C_4$ alkoxy, amino, $CF_3$, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, ($C_1$-$C_6$ linear or branched chain alkyl)heteroaryl, (heteroaryl)$C_1$-$C_6$ linear or branched chain alkyl, or (heterocyclic)$C_1$-$C_6$ linear or branched chain alkyl, and said dotted bonds are present and are single bonds, where when n is 0, X and Y are bonded directly; and (b) if X is absent, said dotted bonds are absent and n is 0, and when Y is N, said N atom is substituted by H; and, n, p, q, r and s are independently 0, 1 or 2.

In another embodiment, the invention provides the compound having the structure:

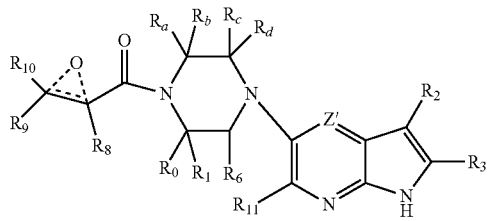

or a pharmaceutically acceptable salt thereof, and wherein $R_2$ is selected from the group consisting of hydrogen, deuterium, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, ($C_1$-$C_6$ linear or branched chain alkyl)heterocyclic, $C_1$-$C_6$ linear or branched chain perfluoroalkyl, $C_1$-$C_6$ linear or branched chain alkoxy, $C_1$-$C_6$ linear or branched chain perfluoroalkoxy, halogen, cyano, hydroxyl, amino, carboxy, aminocarbonyl, ($C_1$-$C_6$ linear or branched chain alkyl)aminocarbonylamino, ($C_1$-$C_6$ linear or branched chain alkyl)aminocarbonyl, —$SOR_{12}$, —$SO_2R_{12}$, —$NR_{13}SO_2R_{12}$, —$SO_2NR_{1b}R_{14}$, and —$NR_{13}SO_2NR_{14}R_{15}$; where said alkyl, aryl and heteroaryl is independently optionally substituted with one or more substituents selected from the group consisting of halo, hydroxy, methoxy, amino, cyano, alkylamino, dialkylamino, $CF_3$, aminocarbonyl, ($C_1$-$C_6$ linear or branched chain alkyl)aminocarbonyl, and $C_3$-$C_6$ cycloalkyl;

$R_3$ is selected from the group consisting of hydrogen, deuterium, $C_1$-$C_6$ linear or branched chain alkyl, $C_1$-$C_6$ linear or branched chain perfluoroalkyl, halogen, and cyano;

Z' is $CR_{16}$ or N; where $R_{16}$ is H, $C_1$-$C_4$ alkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, or ($C_1$-$C_6$ linear or branched chain akyl)heterocyclic, where said alkyl is further optionally substituted with one or more substituents selected from the group consisting of halo, hydroxy, methoxy, amino, $CF_3$, and $C_3$-$C_6$ cycloalkyl;

the dotted lines to the O atom may be present or absent, and if present, the resulting ring forms an epoxide, or if absent, an ethylene results;

$R_0$, $R_1$, $R_6$, $R_8$, $R_9$ and $R_{10}$ are independently selected from hydrogen, deuterium $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/ or 6-membered rings, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl; where, alternatively, $R_0$ or $R_1$, and/or $R_6$, respectively together with either of $R_a$, $R_b$, $R_c$ or $R_d$, may independently form a bond or a $C_1$-$C_6$ linear alkyl chain; and/or, alternatively, $R_4$, respectively together with either of $R_a$, $R_b$, $R_c$ or $R_d$, may independently form a bond or a $C_1$-$C_6$ linear alkyl chain; and/or, alternatively, $R_8$ and $R_9$ may together form a 3-6-membered ring optionally containing one or two O or N atoms; $R_{11}$ is hydrogen or deuterium; and, $R_{12}$, $R_{13}$, $R_{14}$ and $R_{15}$ are independently selected from hydrogen, deuterium $C_1$-$C_6$ linear or branched chain alkyl, $C_1$-$C_6$ linear or branched chain perfluoroalkyl, $C_6$-$C_{10}$ aryl, alkylaryl, and (aryl)$C_1$-$C_6$ linear or branched chain alkyl.

In another embodiment, the invention provides the compound having the structure:

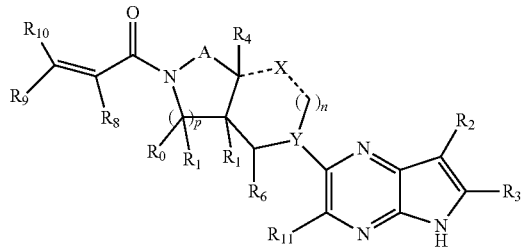

or a pharmaceutically acceptable salt or solvate thereof, or an enantiomer or diastereomer thereof, and wherein $R_2$ is selected from the group consisting of hydrogen, deuterium, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, ($C_1$-$C_6$ linear or branched chain alkyl)heterocyclic, $C_1$-$C_6$ linear or branched chain perfluoroalkyl, $C_1$-$C_6$ linear or branched chain alkoxy, $C_1$-$C_6$ linear or branched chain perfluoroalkoxy, halogen, cyano, hydroxyl, amino, carboxy, aminocarbonyl, ($C_1$-$C_6$ linear or branched chain alkyl)aminocarbonylamino, ($C_1$-$C_6$ linear or branched chain alkyl)aminocarbonyl, —$SOR_{12}$, —$SO_2R_{12}$, —$NR_{13}SO_2R_{12}$, —$SO_2NR_{13}R_{14}$, and —$NR_{13}SO_2NR_{14}R_{15}$; where said alkyl, aryl and heteroaryl is independently optionally substituted with one or more substituents selected from the group consisting of halo, hydroxy, methoxy, amino, cyano, alkylamino, dialkylamino, $CF_3$, aminocarbonyl, ($C_1$-$C_6$ linear or branched chain alkyl) aminocarbonyl, and $C_3$-$C_6$ cycloalkyl;

$R_3$ is selected from the group consisting of hydrogen, deuterium, $C_1$-$C_6$ linear or branched chain alkyl, $C_1$-$C_6$ linear or branched chain perfluoroalkyl, halogen, and cyano;

A is —$(CR_aR_b)_q$—$(CR_cR_d)_r$—, wherein $R_a$, $R_b$, $R_c$ and $R_d$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, alkylaryl, (aryl)$C_1$-$C_6$ linear or branched chain alkyl, (heteroaryl)$C_1$-$C_6$ linear or branched chain alkyl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl;

$R_a$, $R_b$, $R_c$ and $R_d$ are independently selected from hydrogen, $C_1$-$C_6$ linear or branched chain alkyl, $C_1$-$C_6$ linear or branched chain perfluoroalkyl, aryl, alkylaryl, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, wherein said alkyl is further optionally substituted with one or more substituents selected from the group consisting of halo, hydroxy, methoxy, amino, alkylamino, dialkylamino, $CF_3$, and $C_3$-$C_6$ cycloalkyl, where said alkyl is further optionally substituted with one or more substituents selected from the group consisting of halo, hydroxy, methoxy, amino, alkylamino, dialkylamino, $CF_3$, and $C_3$-$C_6$ cycloalkyl;

$R_0$, $R_1$, $R_4$, $R_6$, $R_8$, $R_9$ and $R_{10}$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl; where, alternatively, $R_0$ or $R_1$, and/or $R_6$, respectively together with either of $R_4$, $R_a$, $R_b$, $R_c$ or $R_d$, may independently form a bond or a $C_1$-$C_6$ linear alkyl chain; and/or, alternatively, $R_4$, respectively together with either of $R_a$, $R_b$, $R_c$ or $R_d$, may independently form a bond or a $C_1$-$C_6$ linear alkyl chain; and/or, alternatively, $R_8$ and $R_9$ may together form a 3-6-membered ring optionally containing one or two 0 or N atoms; and, $R_{11}$ is hydrogen or deuterium;

Y is O or N, where when Y is O, n is 0;

$R_{12}$, $R_{13}$, $R_{14}$ and $R_{15}$ are independently selected from hydrogen, $C_1$-$C_6$ linear or branched chain alkyl, $C_1$-$C_6$ linear or branched chain perfluoroalkyl, $C_6$-$C_{10}$ aryl, alkylaryl, and (aryl)$C_1$-$C_6$ linear or branched chain alkyl;

X and the dotted bonds thereto may be present or absent, whereby, (a) if X is present, Y is N, and X is —$(CR_eR_f)_s$—, where $R_e$ and $R_f$ are independently hydrogen, deuterium, halo, hydroxy, $C_1$-$C_4$ alkoxy, amino, $CF_3$, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, ($C_1$-$C_6$ linear or branched chain alkyl)heteroaryl, (heteroaryl)$C_1$-$C_6$ linear or branched chain alkyl, or (heterocyclic)$C_1$-$C_6$ linear or branched chain alkyl, and said dotted bonds are present and are single bonds, where when n is 0, X and Y are bonded directly; and (b) if X is absent, said dotted bonds are absent and n is 0, and when Y is N, said N atom is substituted by H; and, n, p, q, r and s are independently 0, 1 or 2.

The present invention also provides compound having the structure:

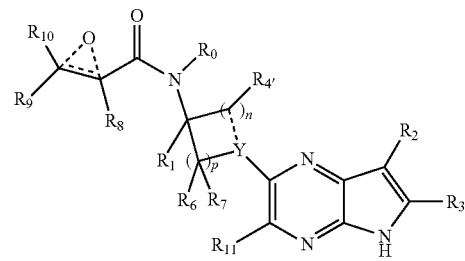

or a pharmaceutically acceptable salt or solvate thereof, or an enantiomer or diastereomer thereof, and wherein $R_2$ is selected from the group consisting of hydrogen, deuterium, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, ($C_1$-$C_6$ linear or branched chain alkyl)heterocyclic, $C_1$-$C_6$ linear or branched chain perfluoroalkyl, $C_1$-$C_6$ linear or branched chain alkoxy, $C_1$-$C_6$ linear or branched chain perfluoroalkoxy, halogen, cyano, hydroxyl, amino, carboxy, aminocarbonyl, ($C_1$-$C_6$ linear or branched chain alkyl)aminocarbonylamino, ($C_1$-$C_6$ linear or branched chain alkyl)aminocarbonyl, —$SOR_{12}$, —$SO_2R_{12}$, —$NR_{13}SO_2R_{12}$, —$SO_2NR_{13}R_{14}$, and —$NR_{13}SO_2NR_{14}R_{15}$; where said alkyl, aryl and heteroaryl is independently optionally substituted with one or more substituents selected from the group consisting of halo, hydroxy, methoxy, amino, cyano, alkylamino, dialkylamino, $CF_3$, aminocarbonyl, ($C_1$-$C_6$ linear or branched chain alkyl) aminocarbonyl, and $C_3$-$C_6$ cycloalkyl;

the dotted lines to the O atom may be present or absent, and if present, the resulting ring forms an epoxide, or if absent, an ethylene results;

$R_3$ is selected from the group consisting of hydrogen, deuterium, $C_1$-$C_6$ linear or branched chain alkyl, $C_1$-$C_6$ linear or branched chain perfluoroalkyl, halogen, and cyano;

$R_0$ is selected from hydrogen, $C_1$-$C_6$ linear or branched chain alkyl, and $C_1$-$C_6$ linear or branched chain perfluoroalkyl;

$R_1$, $R_4$, $R_5$, $R_{4'}$, $R_6$, $R_7$, $R_8$, $R_9$ and $R_{10}$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl; where $R_8$ and $R_9$ may together form a 3-6-membered ring optionally containing one or two O or N atoms; $R_{11}$ is hydrogen or deuterium; $R_{12}$, $R_{13}$, $R_{14}$ and $R_{15}$ are independently selected from hydrogen, $C_1$-$C_6$ linear or branched chain alkyl, $C_1$-$C_6$ linear or branched chain perfluoroalkyl, $C_6$-$C_{10}$ aryl, alkylaryl, and (aryl)$C_1$-$C_6$ linear or branched chain alkyl;

Y is O or N, where when Y is N, the dash bond is a single bond or N is substituted by H or alkyl, and the dash bond thereto is absent, and when Y is O, the dash bond thereto is absent;

and, n and p are independently 0, 1 or 2.

In another embodiment, the invention provides the compound having the structure:

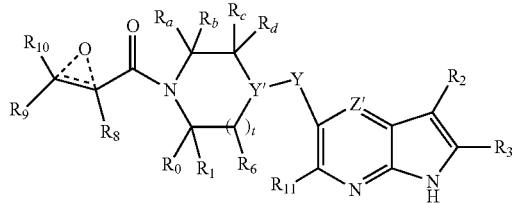

or a pharmaceutically acceptable salt thereof, and wherein $R_2$ is selected from the group consisting of hydrogen, deuterium, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, ($C_1$-$C_6$ linear or branched chain alkyl)heterocyclic, $C_1$-$C_6$ linear or branched chain perfluoroalkyl, $C_1$-$C_6$ linear or branched chain alkoxy, $C_1$-$C_6$ linear or branched chain perfluoroalkoxy, halogen, cyano, hydroxyl, amino, carboxy, aminocarbonyl, ($C_1$-$C_6$ linear or branched chain alkyl)aminocarbonylamino, ($C_1$-$C_6$ linear or branched chain alkyl) aminocarbonyl, —$SOR_{12}$, —$SO_2R_{12}$, —$NR_{13}SO_2R_{12}$, —$SO_2NR_{13}R_{14}$, and —$NR_{13}SO_2NR_{14}R_{15}$; where said alkyl, aryl and heteroaryl is independently optionally substituted with one or more substituents selected from the group consisting of halo, hydroxy, methoxy, amino, cyano, alkylamino, dialkylamino, $CF_3$, aminocarbonyl, ($C_1$-$C_6$ linear or branched chain alkyl)aminocarbonyl, and $C_3$-$C_6$ cycloalkyl;

$R_3$ is selected from the group consisting of hydrogen, deuterium, $C_1$-$C_6$ linear or branched chain alkyl, $C_1$-$C_6$ linear or branched chain perfluoroalkyl, halogen, and cyano;

Z' is $CR_{16}$ or N; where $R_{16}$ is H, $C_1$-$C_4$ alkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, or ($C_1$-$C_6$ linear or branched chain akyl)heterocyclic, where said alkyl is further optionally substituted with one or more substituents selected from the group consisting of halo, hydroxy, methoxy, amino, $CF_3$, and $C_3$-$C_6$ cycloalkyl;

the dotted lines to the O atom may be present or absent, and if present, the resulting ring forms an epoxide, or if absent, an ethylene results;

$R_0$, $R_1$, $R_6$, $R_8$, $R_9$ and $R_{10}$ are independently selected from hydrogen, deuterium $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl; where, alternatively, $R_0$ or $R_1$, and/or $R_6$, respectively together with either of $R_a$, $R_b$, $R_c$ or $R_d$, may independently form a bond or a $C_1$-$C_6$ linear alkyl chain; and/or, alternatively, $R_4$, respectively together with either of $R_a$, $R_b$, $R_c$ or $R_d$, may independently form a bond or a $C_1$-$C_6$ linear alkyl chain; and/or, alternatively, $R_8$ and $R_9$ may together form a 3-6-membered ring optionally containing one or two O or N atoms; $R_{11}$ is hydrogen or deuterium;

Y is either a bond, O or N, where N may be substituted by hydrogen or linear or branched chain $C_1$-$C_6$ alkyl;

Y' is $CR_{17}$ or N, where Y' is $CR_{17}$ when Y is N or O; where $R_{17}$ is hydrogen, linear or branched chain $C_1$-$C_4$ alkyl, or $C_6$-$C_{10}$ aryl; $R_{12}$, $R_{13}$, $R_{14}$ and $R_{15}$ are independently selected from hydrogen, deuterium $C_1$-$C_6$ linear or branched chain alkyl, $C_1$-$C_6$ linear or branched chain perfluoroalkyl, $C_6$-$C_{10}$ aryl, alkylaryl, and (aryl)$C_1$-$C_6$ linear or branched chain alkyl;

and, t is 0, 1 or 2.

The present invention also provides a pharmaceutical or a veterinary composition comprising a compound described above, or a pharmaceutically acceptable salt thereof, and a pharmaceutically acceptable carrier.

Specifically, the invention provides compounds selected from the group consisting of:

2-{[(2S)-1-acryloylpyrrolidin-2-yl]methoxy}-N-[(2S)-1-methoxypropan-2-yl]-5H-pyrrolo[2,3-b]pyrazine-7-carboxamide;

2-[(1-acryloylpiperidin-4-yl)amino]-N-(3-fluorobenzyl)-5H-pyrrolo[2,3-b]pyrazine-7-carboxamide;

2-[(1-acryloylpiperidin-4-yl)amino]-N-(2-cyclopropylethyl)-5H-pyrrolo[2,3-b]pyrazine-7-carboxamide;

2-[(1-acryloylpiperidin-4-yl)amino]-N-benzyl-5H-pyrrolo[2,3-b]pyrazine-7-carboxamide;

2-[(1-acryloylpiperidin-4-yl)oxy]-N-[(2R)-1-methoxypropan-2-yl]-5H-pyrrolo[2,3-b]pyrazine-7-carboxamide;

2-[(1-acryloylpiperidin-4-yl)oxy]-N-[(2S)-1-methoxypropan-2-yl]-5H-pyrrolo[2,3-b]pyrazine-7-carboxamide;

2-(4-acryloylpiperazin-1-yl)-N-[(2S)-1-methoxypropan-2-yl]-5H-pyrrolo[2,3-b]pyrazine-7-carboxamide;

2-(4-acryloylpiperazin-1-yl)-N-[(2R)-1-cyanobutan-2-yl]-5H-pyrrolo[2,3-b]pyrazine-7-carboxamide;

2-{[(3S,4R)-1-acryloyl-3-methoxypiperidin-4-yl]amino}-N-[(2R)-1-methoxypropan-2-yl]-5H-pyrrolo[2,3-b]pyrazine-7-carboxamide; and, 2-(4-acryloylpiperazin-1-yl)-N-[(2R)-4,4,4-trifluoro-2-methylbutyl]-5H-pyrrolo[2,3-b]pyrazine-7-carboxamide.

The present invention also provides a pharmaceutical or a veterinary composition comprising a compound described above, or a pharmaceutically acceptable salt thereof, and a pharmaceutically acceptable carrier.

The present invention also provides a method for treating or preventing a disorder or condition selected from rheumatoid arthritis, myositis, vasculitis, pemphigus, bullous pemphigoid, inflammatory bowel disease including Crohn's disease and ulcerative colitis, celiac diseases, proctitis, eosinophilic gastroenteritis, or mastocytosis, Alzheimer's disease, lupus, nephritis, systemic lupus erythematosus, psoriasis, eczema dermatitis, pruritus or other pruritic conditions, vitiligo, alopecia, autoimmune thyroid disorders, multiple sclerosis, major depression disorder, allergy, asthma, Sjogren's disease, Reiter's syndrome, polymyositis-dermatomyositis, systemic sclerosis, polyarteritis nodosa, dry eye syndrome, Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, membranous glomerulopathy, organ transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, or xeno transplantation, including Cogan's syndrome, ankylosing spondylitis, Wegener's granulomatosis, autoimmune alopecia, Type I or juvenile onset diabetes, and complications from diabetes, or thyroiditis, chronic pulmonary obstructive disorder, acute respiratory disease, cachexia, cancer, including alimentary/gastrointestinal tract cancer, colon cancer, liver cancer, skin cancer including mast cell tumor and squamous cell carcinoma, breast and mammary cancer, ovarian cancer, prostate cancer, leukemia, adult T cell leukemia activated B-cell like, diffuse large B cell lymphoma, kidney cancer, lung cancer, muscle cancer, bone cancer, bladder cancer, brain cancer, melanoma including oral and metastatic melanoma, Kaposi's sarcoma septic shock, cardiopulmonary dysfunction, acute myeloid leukemia, T cell acute lymphoblastic leukemia, multiple myeloma, myeloproliferative disorders, proliferative diabetic retinopathy, or angiogenic-associated disorders including solid tumors, pancreatic cancer, brain tumors, gliomas including astrocytoma, oligodendroglioma, and glioblastoma, acute CNS trauma including traumatic brain injury, encephalitis, stroke, and spinal cord injury, epilepsy, seizures, chronic neuroinflammation associated with neurodegeneration including Alzheimer's disease, Parkinson's disease, Amyotropic Lateral Sclerosis, Huntington's disease, cerebral ischemia, fronto-temporal lobe dementia, and with neuropsychiatric disorders including schizophrenia, bipolar disorder, treatment resistant depression, Post Traumatic Stress Disorder, anxiety, and auto-antibodies mediated encephalopathies, Eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization, comprising the step of administering to a subject an effective amount of a composition comprising a compound set forth hereinabove.

The present invention also provides a method for treating or preventing inflammatory bowel disease by administering to a mammal in need a therapeutically effective amount of a compound described above, or a pharmaceutically acceptable salt thereof.

More generally, the present invention provides a method of treating a disorder or condition related to dysregulation of JAK, and particularly of JAK3, in a subject, comprising administering to the subject a therapeutically effective amount of the compound described above, or a pharmaceutically acceptable salt thereof.

In certain embodiments, the therapeutically effective amount used in accord with the method is from 0.01 mg/kg of body weight/day to 100 mg/kg of body weight/day. In certain other embodiments, the therapeutically effective amount used in accord with the method is the therapeutically effective amount is from 0.1 mg/kg of body weight/day to 10 mg/kg of body weight/day. In the practice of the method, the compound is preferably selected from those specified above.

In certain embodiments, the therapeutically effective amount used in accord with the method is from 0.01 mg/kg of body weight/day to 100 mg/kg of body weight/day. In certain other embodiments, the therapeutically effective amount used in accord with the method is wherein the therapeutically effective amount is from 0.1 mg/kg of body weight/day to 10 mg/kg of body weight/day. In accord with the method, the mammal treated with the compound of the invention is selected from companion animals, dogs, and livestock. In certain embodiments, the compound of the invention, or a pharmaceutically acceptable salt thereof, may be administered in accord with the method orally, parenterally, or topically.

Compounds that have the same molecular formula but differ in the nature or sequence of bonding of their atoms or the arrangement of their atoms in space are termed "isomers". Isomers that differ in the arrangement of their atoms in space are termed "stereoisomers". It will be appreciated by those skilled in the art that the compound of the invention can exist as cis- and trans-achiral diastereomers.

Included within the scope of the described compounds are all isomers (e.g. cis-, trans-, or diastereomers) of the compounds described herein alone as well as any mixtures. All of these forms, including enantiomers, diastereomers, cis, trans, syn, anti, solvates (including hydrates), tautomers, and mixtures thereof, are included in the described compounds. Stereoisomeric mixtures, e.g. mixtures of diastereomers, can be separated into their corresponding isomers in a known manner by means of suitable separation methods. Diastereomeric mixtures for example may be separated into their individual diastereomers by means of fractionated crystallization, chromatography, solvent distribution, and similar procedures. This separation may take place either at the level of one of the starting compounds or in a compound of the invention itself. Enantiomers may be separated through the formation of diastereomeric salts, for example by salt formation with an enantiomer-pure chiral acid, or by means of chromatography, for example by HPLC, using chromatographic substrates with chiral ligands.

In therapeutic use for treating disorders in a mammal, a compound of the present invention or its pharmaceutical compositions can be administered orally, parenterally, topically, rectally, transmucosally, or intestinally. Parenteral administrations include indirect injections to generate a systemic effect or direct injections to the afflicted area. Topical administrations include the treatment of skin or organs readily accessible by local application, for example, eyes or ears. It also includes transdermal delivery to generate a systemic effect. The rectal administration includes the form of suppositories. The preferred routes of administration are oral and parenteral.

Pharmaceutically acceptable salts of the compounds of the invention include the acid addition and base salts thereof. Suitable acid addition salts are formed from acids which form non-toxic salts. Examples include the acetate, adipate, aspartate, benzoate, besylate, bicarbonate/carbonate, bisulphate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts. For a review on suitable salts, see *Handbook of Pharmaceutical Salts: Properties, Selection, and Use* by Stahl and Wermuth (Wiley-VCH, 2002).

Pharmaceutically acceptable salts of compounds of the invention, may be prepared, respectively, by one or more of three methods: (i) by reacting the compound with the desired acid or base; (ii) by removing an acid- or base-labile protecting group from a suitable precursor of the compound of the invention, or by ring-opening a suitable cyclic precursor, for example, a lactone or lactam, using the desired acid or base; or (iii) by converting one salt of the compound of the invention, to another by reaction with an appropriate acid or base or by means of a suitable ion exchange column. All three reactions are typically carried out in solution. The resulting salt may precipitate out and be collected by filtration or may be recovered by evaporation of the solvent. The degree of ionization in the resulting salt may vary from completely ionized to almost non-ionized.

Pharmaceutical compositions of the present invention may be manufactured by methods well known in the art, e.g., by means of conventional mixing, dissolving, granulation, dragee-making, levigating, emulsifying, encapsulating, entrapping, lyophilizing processes or spray drying.

Pharmaceutical compositions for use in accordance with the present invention may be formulated in conventional manner using one or more pharmaceutically acceptable carriers comprising excipients and auxiliaries, which facilitate processing of the active compound into preparations, which can be used pharmaceutically. Proper formulation is dependent upon the route of administration chosen. Pharmaceutically acceptable excipients and carriers are generally known to those skilled in the art and are thus included in the instant invention. Such excipients and carriers are described, for example, in "Remington's Pharmaceutical Sciences" Mack Pub. Co., New Jersey (1991). The formulations of the invention can be designed to be short-acting, fast-releasing, long-acting, and sustained-releasing. Thus, the pharmaceutical formulations can also be formulated for controlled release or for slow release.

Pharmaceutical compositions suitable for use in the present invention include compositions wherein the active ingredients are contained in an amount sufficient to achieve the intended purpose, i.e., control or the treatment of disorders or diseases. More specifically, a therapeutically effective amount means an amount of compound effective to prevent, alleviate or ameliorate symptoms/signs of disease or prolong the survival of the subject being treated.

The quantity of active component, which is the compound of this invention, in the pharmaceutical composition and unit dosage form thereof, may be varied or adjusted widely depending upon the manner of administration, the potency of the particular compound and the desired concentration. Determination of a therapeutically effective amount is well within the capability of those skilled in the art. Generally, the quantity of active component will range between 0.01% to 99% by weight of the composition.

Generally, a therapeutically effective amount of dosage of active component will be in the range of about 0.01 to about 100 mg/kg of body weight/day, preferably about 0.1 to about 10 mg/kg of body weight/day, more preferably about 0.3 to 3 mg/kg of body weight/day, even more preferably about 0.3 to 1.5 mg/kg of body weight/day It is to be understood that the dosages may vary depending upon the requirements of each subject and the severity of the disorders or diseases being treated.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Also, it is to be understood that the initial dosage administered may be increased beyond the above upper level in order to rapidly achieve the desired plasma concentration. On the other hand, the initial dosage may be smaller than the optimum and the daily dosage may be progressively increased during the course of treatment depending on the particular situation. If desired, the daily dose may also be divided into multiple doses for administration, e.g., two to four times per day.

Compounds of the present invention are directed to pyrrolo[2,3-d]pyrimidinyl, pyrrolo[2,3,D]pyrazinyl, and pyrrolo[2,3-d]pyridinyl acrylamides and epoxides useful as Janus Kinase inhibitors (JAK-1). They are useful as therapeutic agents in connection with the treating or preventing a disorder or condition selected from rheumatoid arthritis, myositis, vasculitis, pemphigus, bullous pemphigoid, inflammatory bowel disease including Crohn's disease and ulcerative colitis, celiac diseases, proctitis, eosinophilic gastroenteritis, or mastocytosis, Alzheimer's disease, lupus, nephritis, systemic lupus erythematosus, psoriasis, eczema dermatitis, pruritus or other pruritic conditions, vitiligo, alopecia, autoimmune thyroid disorders, multiple sclerosis, major depression disorder, allergy, asthma, Sjogren's disease, Reiter's syndrome, polymyositis-dermatomyositis, systemic sclerosis, polyarteritis nodosa, dry eye syndrome, Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, membranous glomerulopathy, organ transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, or xeno transplantation, including Cogan's syndrome, ankylosing spondylitis, Wegener's granulomatosis, autoimmune alopecia, Type I or juvenile onset diabetes, and complications from diabetes, or thyroiditis, chronic pulmonary obstructive disorder, acute respiratory disease, cachexia, cancer, including alimentary/gastrointestinal tract cancer, colon cancer, liver cancer, skin cancer including mast cell tumor and squamous cell carcinoma, breast and mammary cancer, ovarian cancer, prostate cancer, leukemia, adult T cell leukemia activated B-cell like, diffuse large B cell lymphoma, kidney cancer, lung cancer, muscle cancer, bone cancer, bladder cancer, brain cancer, melanoma including oral and metastatic melanoma, Kaposi's sarcoma septic shock, cardiopulmonary dysfunction, acute myeloid leukemia, T cell acute lymphoblastic leukemia, multiple myeloma, myeloproliferative disorders, proliferative diabetic retinopathy, or angiogenic-associated disorders including solid tumors, pancreatic cancer, brain tumors, gliomas including astrocytoma, oligodendroglioma, and glioblastoma, acute CNS trauma including traumatic brain injury, encephalitis, stroke, and spinal cord injury, epilepsy, seizures, chronic neuroinflammation associated with neurodegeneration including Alzheimer's disease, Parkinson's disease, Amyotropic Lateral Sclerosis, Huntington's disease, cerebral ischemia, fronto-temporal lobe dementia, and with neuropsychiatric disorders including schizophrenia, bipolar disorder, treatment resistant depression, Post Traumatic Stress Disorder, anxiety, and autoantibodies mediated encephalopathies, Eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization, and other indications where immunosuppression/immunomodulation would be desirable, comprising the step of administering to a subject an effective amount of a compound of the invention.

There are substantial needs for safe and efficacious agents to control disorders related to JAK, such as atopic dermatitis, both in human and animals. The market for treating atopic dermatitis in animals is currently dominated by corticosteroids, which cause distressing and undesirable side effects in animals, specifically in companion animals such as dogs. APOQUEL™ is a pan-JAK inhibitor recently approved for atopic dermatitis in canines. Antihistamines are also used, but are poorly effective. A canine formulation of cyclosporine (ATOPICA™) is currently being marketed for atopic dermatitis, but is expensive and has a slow onset of efficacy. In addition, there are GI toleration issues with ATOPICA™. Compounds of the present invention are JAK inhibitors with selective efficacy against JAK3. These compounds are expected to provide an alternative to steroid usage and provide resolution of chronic pruritus and inflammation that would either persist in atopic dermatitis or slowly regress following removal of allergen or causative agent, such as fleas in flea-allergic dermatitis.

Compounds of the present invention may be administered in a pharmaceutically acceptable form either alone or in combination with one or more additional agents which modulate a mammalian immune system or with anti-inflammatory agents. These agents may include but are not limited to cyclosporin A (e.g., Sandimmune® or Neoral®, rapamycin, FK-506 (tacrolimus), leflunomide, deoxyspergualin, mycophenolate (e.g., Celicept™, azathioprine (e.g., Imurann™), daclizumab (e.g., Zenapax™), OKT3 (e.g., Orthocolone™), AtGam™, aspirin, acetaminophen, ibuprofen, naproxen, piroxicam, and anti-inflammatory steroids (e.g., prednisolone or dexamethasone), IFN-beta, teriflunomide, Laquinimod, glatiramer acetate, dimethyl fumerate, rituximab, fingolimod, natalizumab, alemtuzumab, mitoxantrone. Sulfasalazine (Azulfidine), Mesalamine (Apriso, Asacol, Lialda, others), balsalazide (Colazal) and olsalazine (Dipentum), and mercaptopurine (Purinethol), antibiotics (antimycobacterial drugs, eg. Metronidazole, ciprofloxacin), Ustekinumab and vedolizumab These agents may be administered as part of the same or separate dosage forms, via the same or different routes of administration, and on the same or different administration schedules according to standard pharmaceutical practice known to one skilled in the art.

Accordingly, the invention provides methods of treating or preventing a disease, condition or disorder associated with JAK in a subject, such as a human or non-human mammal, comprising administering an effective amount of one or more compounds described herein to the subject. Suitable subjects that can be treated include domestic or wild animals, companion animals, such as dogs, cats, horses and the like; livestock including, cows and other ruminants, pigs, poultry, rabbits and the like; primates, for example monkeys, such as rhesus monkeys and cynomolgus (also known as crab-eating or long-tailed) monkeys, marmosets, tamarins, chimpanzees, macaques and the like; and rodents, such as rats, mice, gerbils, guinea pigs and the like. In one embodiment, the compound is administered in a pharmaceutically acceptable form, optionally in a pharmaceutically acceptable carrier.

Another embodiment provides a method of selectively inhibiting a JAK3 enzyme, which includes contacting the JAK enzyme with either a non-therapeutic amount or a therapeutically effective amount of one or more of the presently taught compounds. Such methods can occur in vive or in vitro. In vitro contact can involve a screening assay to determine the efficacy of the one or more compounds against a selected enzyme at various amounts or concentrations. In vivo contact with a therapeutically effective amount of the one or more compounds can involve treatment of a described disease, disorder or condition or prophylaxis of organ transplant rejection in the animal in which the contact occurs. The effect of the one or more compounds on the JAK enzyme and/or host animal can also be determined or measured. Methods for determining JAK activity include those described in the Examples as well as those disclosed in WO99/65908, WO 99/65909, WO01/42246, WO02/00661, WO02/096909, WO2004/046112 and WO2007/012953.

Chemical Synthesis

The following schemes and written descriptions provide general details regarding the preparation of the compounds of the invention. It will be apparent to those skilled in the art that sensitive functional groups may need to be protected (PG) and deprotected during the synthesis of a compound of the invention. Protection and deprotection may be achieved by conventional methods, as described, for example, in

*Protective Groups in Organic Synthesis* by T. W. Greene and P. G. M. Wuts, John Wiley & Sons Inc. (1999), and references therein.

Several methods exist for the preparation of such compounds, which are well known to those skilled in the art and have been described in texts such as Advanced Organic Chemistry by J. March, John Wiley & Sons (1985). It is noted that certain compounds of the invention can be obtained by functional group transformations at a late stage of the synthesis. Such functional group transformations may include one step or multiple steps, for example, reduction of an ester to an alcohol, reoxidation to an aldehyde, addition of an organomagesium reagent to form a secondary alcohol, reoxidation to a ketone and, finally, addition of an organomagesium reagent to yield a tertiary alcohol. The intermediates and compounds were named using ChemDraw11 (CambridgeSoft) structure to name converter or ACD Labs Name Software v12. The inclusion of rac- (or racemic) modifier indicates material is racemic. When rac- (or racemic) is included with R,S indications this is intended to convey relative stereochemistry, however in the absence of the rac- (or racemic) notation the compounds absolute stereochemistry is known. In some instances the rac- (or racemic) notation conveys the stereochemistry of a fragment of the compound, while the R,S designation conveys absolute stereochemistry of another portion. For cases where racemates are separated into their constituent enantiomers the absolute stereochemistry is arbitrarily assigned, unless otherwise noted. Accordingly, the actual absolute enantiomeric form of the biologically active compound may differ from the arbitrarily assigned stereochemcial designation.

In executing the synthesis of the compounds of the invention, one skilled in the art will recognize the need to sample and assay reaction mixtures prior to work up in order to monitor the progress of reactions and decide whether the reaction should be continued or whether it is ready to be worked up to obtain the desired product. Common methods for assaying reaction mixtures include thin-layer chromatography (TLC), liquid chromatography/mass spectroscopy (LCMS), and nuclear magnetic resonance (NMR).

One skilled in the art will also recognize that the compounds of the invention may be prepared as mixtures of diastereomers or geometric isomers (e.g., cis and trans substitution on a cycloalkane ring). These isomers can be separated by standard chromatographic techniques, such as normal phase chromatography on silica gel, reverse phase preparative high pressure liquid chromatography or supercritical fluid chromatography. One skilled in the art will also recognize that some compounds of the invention are chiral and thus may be prepared as racemic or scalemic mixtures of enantiomers. Several methods are available and are well known to those skilled in the art for the separation of enantiomers. A preferred method for the routine separation enantiomers is supercritical fluid chromatography employing a chiral stationary phase.

EXPERIMENTAL SECTION

Except where otherwise noted, reactions were run under an atmosphere of nitrogen. Chromatography on silica gel was carried out using 250-400 mesh silica gel using pressurized nitrogen (~10-15 psi) to drive solvent through the column ("flash chromatography"). Where indicated, solutions and reaction mixtures were concentrated by rotary evaporation under vacuum.

Examples 1-81 were prepared as described in the Scheme below:

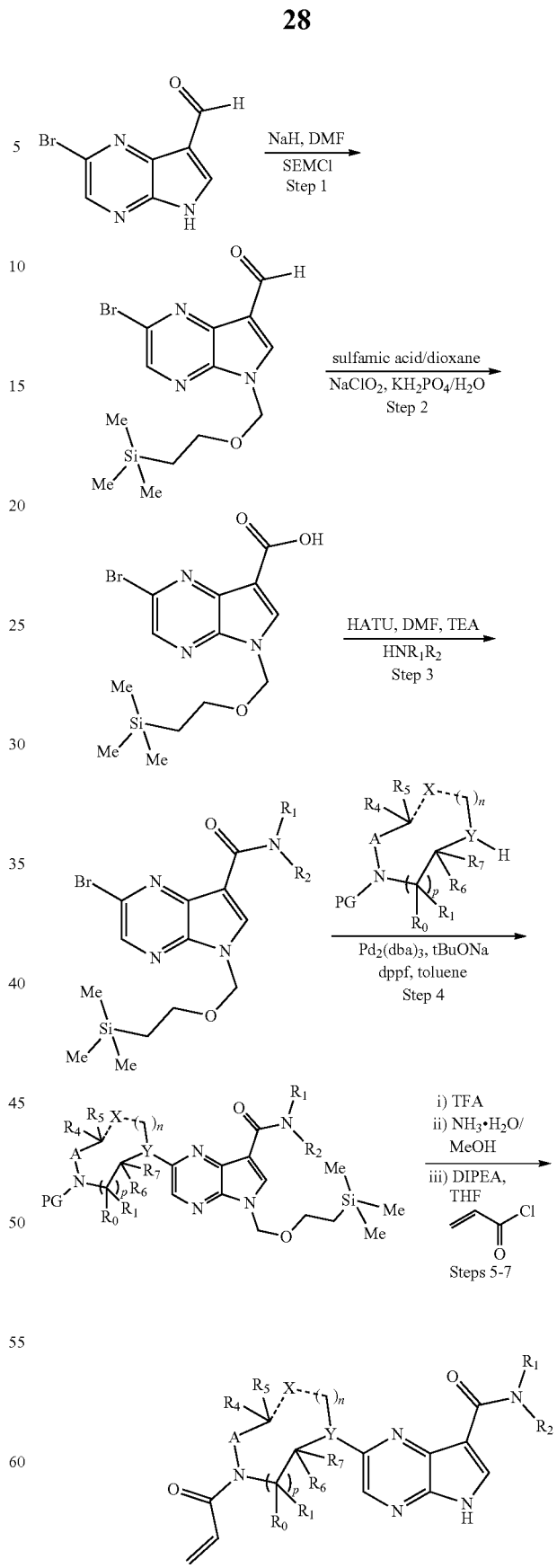

Example 1 Step 0

2-Bromo-5H-pyrrolo[2,3-b]pyrazine-7-carbaldehyde. To a suspension of (2-bromo-5H-pyrrolo[2,3-b]pyrazin-7-yl)methanol (127 g, 556 mmol, described in U.S. Ser. No. 14/559,294) in acetone (2.5 L) was added dropwise Jones reagent (253 mL, 675 mmol, 2.67 M) below 10° C. After the addition, the resulting mixture was stirred at room temperature for 50 min, during which time the suspension became clear and a brown solid precipitated. The three batches were combined for workup together. The reaction mixture was quenched with i-PrOH (60 mL) and filtered, the filter cake was washed with acetone (1 L x 2), the combined filtrate was evaporated to give 2-bromo-5H-pyrrolo[2,3-b]pyrazine-7-carbaldehyde (320 g, 84.4%) as a yellow solid. (A stock of Jones reagent (2.67 M) was prepared by carefully adding concentrated $H_2SO_4$ (184 mL) to $CrO_3$ (213.6 g) then diluting to 800 mL with $H_2O$.)

Step 1 2-Bromo-5-{[2-(trimethylsilyl)ethoxy]methyl}-5H-pyrrolo[2,3-b]pyrazine-7-carbaldehyde To a suspension of NaH (60% dispersion in oil, 5.1 g, 127 mmol) in DMF (200 mL) was added 2-bromo-5H-pyrrolo[2,3-b]pyrazine-7-carbaldehyde (Step 0, 19 g, 84.1 mmol) and the reaction was stirred at 0° C. for 10 minutes. SEM-Cl (17 g, 102 mmol) was added dropwise at 0° C. and the reaction stirred at room temperature for 3 hours. The reaction was quenched by the addition of ice-water (600 mL) and extracted into EtOAc (2×500 mL). The combined organic layers were washed with water (600 mL), brine (3×600 mL), dried over sodium sulphate and concentrated in vacuo. The residue was purified using silica gel column chromatography eluting with 0.25-25% EtOAc in petroleum ether to afford the title compound as a yellow solid (15 g, 25%). MS m/z 358 $[M^{81}Br+H]^+$

Example 1 Step 2

2-Bromo-5-{[2-(trimethylsilyl)ethoxy]methyl})-5H-pyrrolo[2,3-b]pyrazine-7-carboxylic acid To a solution of 2-bromo-5-{[2-(trimethylsilyl)ethoxy]methyl}-5H-pyrrolo[2,3-b]pyrazine-7-carbaldehyde (Example 1 Step 1, 19 g, 53.4 mmol) and sulfamic acid (26 g, 268 mmol) in dioxane and water (200 mL, 1:1) was added a solution of $NaClO_2$ (7.23 g, 80 mmol) and $KH_2PO_4$ (36.4 g, 268 mmol) in water (50 mL) at 0° C. over 20 minutes. The reaction was stirred at room temperature for 16 hours and then partitioned between EtOAc (500 mL) and water (200 mL). The aqueous layer was further extracted with EtOAc (200 mL), the organic layers combined, washed with water (300 mL), brine (300 mL), dried over sodium sulphate and concentrated in vacuo. The residue was triturated with TBME to afford the title compound as a white solid (14.5 g, 73%). $^1$H NMR (400 MHz, DMSO-$d_6$): δ ppm 12.66 (br s, 1H), 8.80-8.72 (m, 1H), 8.58 (s, 1H), 5.72-5.64 (m, 2H), 3.56 (t, J=7.8 Hz, 2H), 0.83 (t, J=8.0 Hz, 2H), −0.01 (s, 9H).

Example 1 Step 3

(R)-2-bromo-N-(1-methoxypropan-2-yl)-5-{[2-(trimethylsilyl)ethoxy]methyl}-5H-pyrrolo[2,3-b]pyrazine-7-carboxamide To a solution of 2-bromo-5-{[2-(trimethylsilyl)ethoxy]methyl}-5H-pyrrolo[2,3-b]pyrazine-7-carboxylic acid (Example 1 Step 2, 6 g, 16.12 mmol) and HATU (7.35 g, 19.3 mmol) in DMF (160 mL) was added TEA (4.89 g, 48.3 mmol) followed by (R)-1-methoxypropan-2-amine (2.15 g, 24.2 mmol) and the reaction was stirred at room temperature for 18 hours. The reaction was concentrated in vacuo and partitioned between EtOAc and water. The aqueous layer was further extracted with EtOAc (2×10 mL) and the organic layers were combined, washed with brine, dried over sodium sulphate and concentrated in vacuo. The residue was purified using silica gel column chromatography eluting with 10-50% EtOAc in petroleum ether to afford the title compound as a white solid (6.2 g, 87%). MS m/z 445 $[M^{81}Br+H]^+$ The following Preparations were prepared according to the method described for Example 1 Step 3 using 2-bromo-5-{[2-(trimethylsilyl)ethoxy]methyl}-5H-pyrrolo[2,3-b]pyrazine-7-carboxylic acid (Example 1 Step 2) and the appropriate amine.

| Prep No. | Name | Structure | Data/SM |
|---|---|---|---|
| Ex 4 Step 3 | (S)-2-bromo-N-(1-methoxypropan-2-yl)-5-{[2-(trimethylsilyl)ethoxy]methyl}-5H-pyrrolo[2,3-b]pyrazine-7-carboxamide | (structure) | MS m/z 445 $[M^{81}Br+H]^+$ (S)-1-methoxypropan-2-amine. |

-continued

| Prep No. | Name | Structure | Data/SM |
|---|---|---|---|
| Ex 22 Step 3 | 2-bromo-N-(3,3,3-trifluoropropyl)-5-{[2-(trimethylsilyl)ethoxy]methyl}-5H-pyrrolo[2,3-b]pyrazine-7-carboxamide | 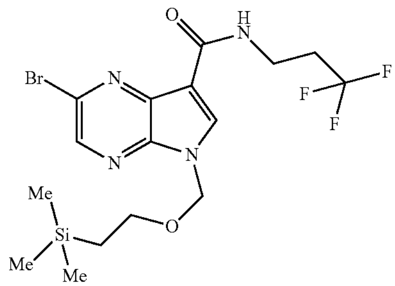 [SMILES: C[Si](C)(C)CCOCn1cc(C(=O)NCCC(F)(F)F)c2nc(Br)cnc21] | Taken on directly to the next step. 3,3,3-trifluoropropylamine. |
| Ex 25 Step 3 | 2-bromo-5-[(3,3-dimethylbutoxy)methyl]-N-ethyl-5H-pyrrolo[2,3-b]pyrazine-7-carboxamide | 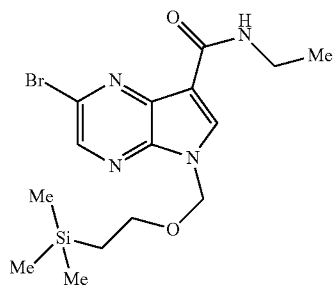 [SMILES: CCNC(=O)c1cn(COCC[Si](C)(C)C)c2ncc(Br)nc12] | Taken on directly to the next step. Ethylamine. |
| Ex 62 Step 3 | azetidin-1-yl(2-bromo-5-{[2-(trimethylsilyl)ethoxy]methyl}-5H-pyrrolo[2,3-b]pyrazin-7-yl)methanone | 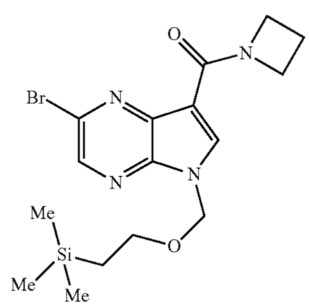 [SMILES: C[Si](C)(C)CCOCn1cc(C(=O)N2CCC2)c2nc(Br)cnc21] | MS m/z 413 [M$^{81}$Br + H]$^+$ Using TBTU with DIPEA and azetidine. |
| Ex 64 Step 3 | 2-bromo-N-isopropyl-5-((2-(trimethylsilyl)ethoxy)methyl)-5H-pyrrolo[2,3-b]pyrazine-7-carboxamide | 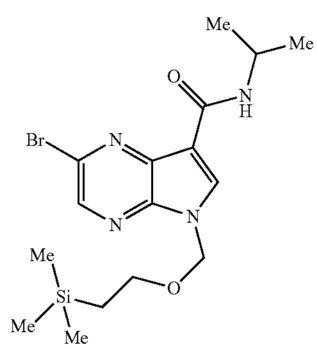 [SMILES: CC(C)NC(=O)c1cn(COCC[Si](C)(C)C)c2ncc(Br)nc12] | $^1$H NMR (400 MHz, CDCl$_3$): δ ppm 8.40 (s, 1H), 8.31 (s, 1H), 7.71-7.69 (m, 1H), 5.64 (s, 2H), 4.39-4.27 (m, 1H), 3.56-3.50 (m, 1H), 1.33 (s, 3H), 1.32 (s, 3H), 0.92-0.88 (m, 2H), −0.04 (s, 9H). Isopropylamine. |

Example 54 Step 4 tert-Butyl (S)-3-[(7-[((R)-1-methoxypropan-2-yl)carbamoyl]-5-{[2-(trimethylsilyl)ethoxy]methyl}-5H-pyrrolo[2,3-b]pyrazin-2-yl)oxy]pyrrolidine-1-carboxylate Method A wherein Y═O To a solution of (R)-2-bromo-N-(1-methoxypropan-2-yl)-5-{[2-(trimethylsilyl)ethoxy]methyl}-5H-pyrrolo[2,3-b]pyrazine-7-carboxamide (Example 1 Step 3, 700 mg, 1.58 mmol), tert-butyl (S)-3-hydroxypyrrolidine-1-carboxylate (443 mg, 2.37 mmol) and sodium tert-butoxide (455 mg, 4.74 mmol) in toluene (20 mL) was added Pd$_2$dba$_3$ (145 mg, 0.158 mmol) followed by dppf (114 mg, 0.21 mmol) and the reaction was heated to 110° C. for 18 hours. The reaction was concentrated in vacuo and purified using silica gel column chromatography eluting with 20-66% EtOAc in petroleum ether to afford the title compound as a yellow oil (550 mg, 63%).

MS m/z 572 [M+Na]$^+$

The following Preparations were prepared according to Method A wherein Y═O as described for Example 54 Step 4 using the appropriate heteroaryl bromide and alcohol:

| Prep No. | Name | Structure | Data/SM |
|---|---|---|---|
| Ex 49 Step 4 | tert-butyl (R)-3-[(7-[((S)-1-methoxypropan-2-yl)carbamoyl]-5-{[2-(trimethylsilyl)ethoxy]methyl}-5H-pyrrolo[2,3-b]pyrazin-2-yl)oxy]piperidine-1-carboxylate | 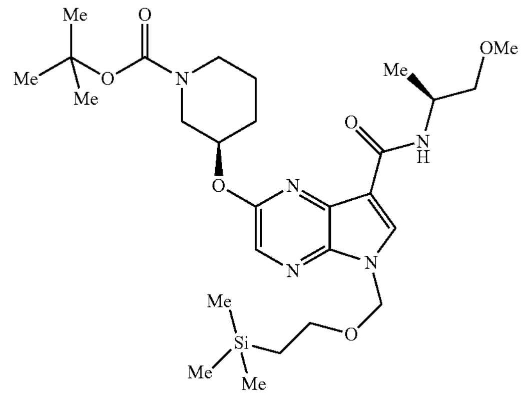 [SMILES: COC[C@H](C)NC(=O)c1cn(COCC[Si](C)(C)C)c2ncc(O[C@@H]3CCCN(C(=O)OC(C)(C)C)C3)nc12] | MS m/z 586 [M + Na]+ (S)-2-bromo-N-(1-methoxypropan-2-yl)-5-{[2-(trimethylsilyl)ethoxy]methyl}-5H-pyrrolo[2,3-b]pyrazine-7-carboxamide (Example 4 Step 3) and tert-butyl (S)-3-hydroxypiperidine-1-carboxylate. |
| Ex 50 Step 4 | tert-butyl (S)-3-[(7-[((S)-1-methoxypropan-2-yl)carbamoyl]-5-{[2-(trimethylsilyl)ethoxy]methyl}-5H-pyrrolo[2,3-b]pyrazin-2-yl)oxy]piperidine-1-carboxylate | 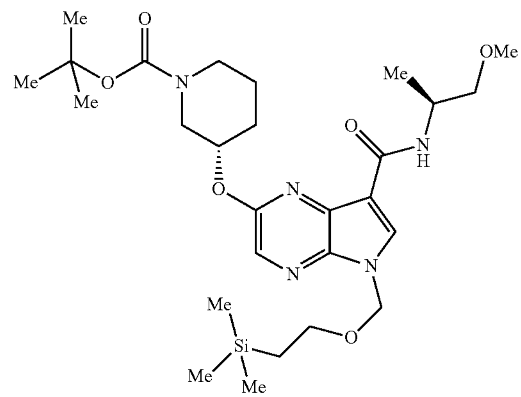 [SMILES: COC[C@H](C)NC(=O)c1cn(COCC[Si](C)(C)C)c2ncc(OC3CCCN(C(=O)OC(C)(C)C)C3)nc12] | MS m/z 586 [M + Na]+ (S)-2-bromo-N-(1-methoxypropan-2-yl)-5-{[2-(trimethylsilyl)ethoxy]methyl}-5H-pyrrolo[2,3-b]pyrazine-7-carboxamide (Example 4 Step 3) and tert-butyl (R)-3-hydroxypiperidine-1-carboxylate. |
| Ex 51 Step 4 | Racemic-tert-butyl-3-[(7-[((S)-1-methoxypropan-2-yl)carbamoyl]-5-{[2-(trimethylsilyl)ethoxy]methyl}-5H-pyrrolo[2,3-b]pyrazin-2-yl)oxy]piperidine-1-carboxylate | 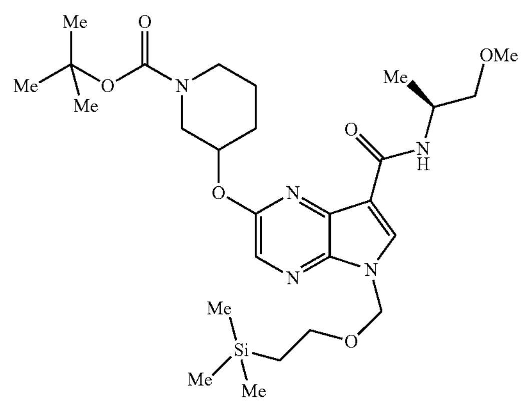 | (S)-2-bromo-N-(1-methoxypropan-2-yl)-5-{[2-(trimethylsilyl)ethoxy]methyl}-5H-pyrrolo[2,3-b]pyrazine-7-carboxamide (Example 4 Step 3) and racemic-tert-butyl-3-hydroxypiperidine-1-carboxylate. Taken on directly to the next step. |
| Ex 7 Step 4 | Racemic-tert-butyl 2-{[(7-[((S)-1-methoxypropan-2-yl)carbamoyl]-5-{[2-(trimethylsilyl)ethoxy]methyl}-5H-pyrrolo[2,3-b]pyrazin-2-yl)oxy]methyl}pyrrolidine-1-carboxylate | 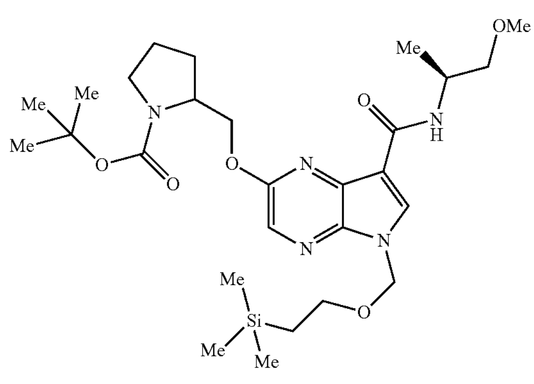 [SMILES: COC[C@H](C)NC(=O)c1cn(COCC[Si](C)(C)C)c2ncc(OCC3CCCN3C(=O)OC(C)(C)C)nc12] | MS m/z 586 [M + Na]+ (S)-2-bromo-N-(1-methoxypropan-2-yl)-5-{[2-(trimethylsilyl)ethoxy]methyl}-5H-pyrrolo[2,3-b]pyrazine-7-carboxamide (Example 4 Step 3) and racemic-tert-butyl 2-(hydroxymethyl)pyrrolidine-1-carboxylate at 100° C. and using cesium carbonate as base. |

-continued

| Prep No. | Name | Structure | Data/SM |
|---|---|---|---|
| Ex 10 Step 4 | Racemic-tert-butyl 3-{[(7-[((S)-1-methoxypropan-2-yl)carbamoyl]-5-{[2-(trimethylsilyl)ethoxy]methyl}-5H-pyrrolo[2,3-b]pyrazin-2-yl)oxy]methyl}pyrrolidine-1-carboxylate | 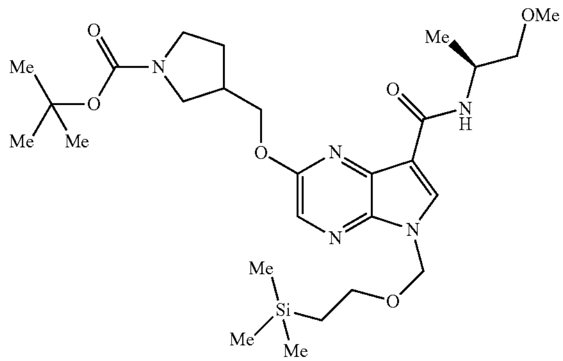 [SMILES: COC[C@H](C)NC(=O)c1cn(COCC[Si](C)(C)C)c2ncc(OCC3CCN(C(=O)OC(C)(C)C)C3)nc12] | MS m/z 586 [M + Na]+ (S)-2-bromo-N-(1-methoxypropan-2-yl)-5-{[2-(trimethylsilyl)ethoxy]methyl}-5H-pyrrolo[2,3-b]pyrazine-7-carboxamide (Example 4 Step 3) and racemic tert-butyl 3-(hydroxymethyl)pyrrolidine-1-carboxylate at 100° C. |
| Ex 13 Step 4 | Racemic-tert-butyl 3-{[(7-[((R)-1-methoxypropan-2-yl)carbamoyl]-5-{[2-(trimethylsilyl)ethoxy]methyl}-5H-pyrrolo[2,3-b]pyrazin-2-yl)oxy]methyl}pyrrolidine-1-carboxylate | 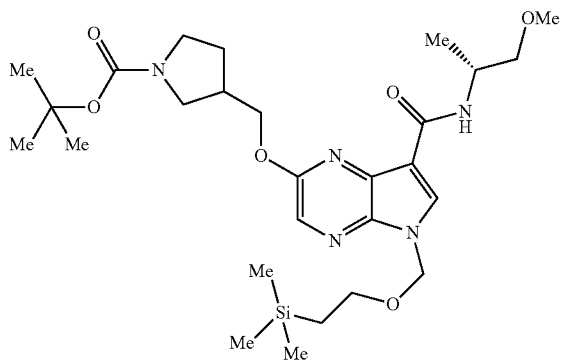 [SMILES: COC[C@@H](C)NC(=O)c1cn(COCC[Si](C)(C)C)c2ncc(OCC3CCN(C(=O)OC(C)(C)C)C3)nc12] | MS m/z 586 [M + Na]+ (R)-2-bromo-N-(1-methoxypropan-2-yl)-5-{[2-(trimethylsilyl)ethoxy]methyl}-5H-pyrrolo[2,3-b]pyrazine-7-carboxamide (Example 1 Step 3) and racemic tert-butyl 3-(hydroxymethyl)pyrrolidine-1-carboxylate at 100° C. |
| Ex 52 Step 4 | tert-butyl (S)-3-[(7-[((S)-1-methoxypropan-2-yl)carbamoyl]-5-{[2-(trimethylsilyl)ethoxy]methyl}-5H-pyrrolo[2,3-b]pyrazin-2-yl)oxy]pyrrolidine-1-carboxylate | 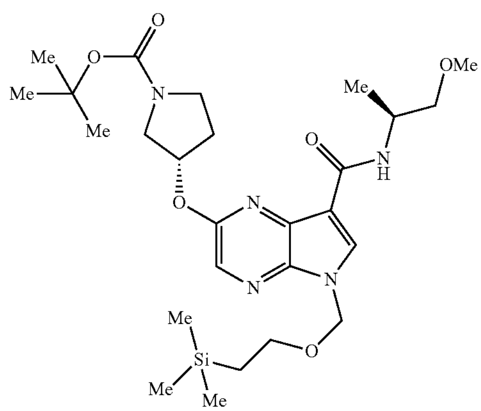 [SMILES: COC[C@H](C)NC(=O)c1cn(COCC[Si](C)(C)C)c2ncc(O[C@H]3CCN(C(=O)OC(C)(C)C)C3)nc12] | MS m/z 572 [M + Na]+ (S)-2-bromo-N-(1-methoxypropan-2-yl)-5-{[2-(trimethylsilyl)ethoxy]methyl}-5H-pyrrolo[2,3-b]pyrazine-7-carboxamide (Example 4 Step 3) and tert-butyl (S)-3-hydroxypyrrolidine-1-carboxylate. |
| Ex 53 Step 4 | tert-butyl (R)-3-[(7-[((S)-1-methoxypropan-2-yl)carbamoyl]-5-{[2-(trimethylsilyl)ethoxy]methyl}-5H-pyrrolo[2,3-b]pyrazin-2-yl)oxy]pyrrolidine-1-carboxylate. | 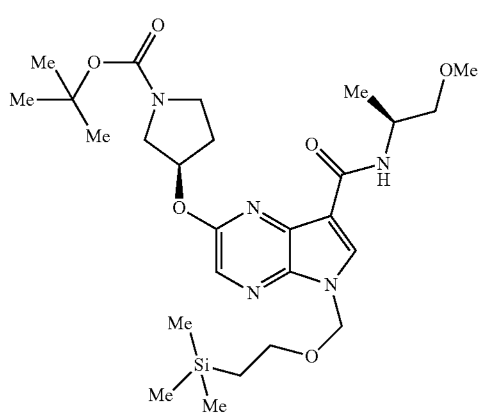 [SMILES: COC[C@H](C)NC(=O)c1cn(COCC[Si](C)(C)C)c2ncc(O[C@@H]3CCN(C(=O)OC(C)(C)C)C3)nc12] | MS m/z 572 [M + Na]+ (S)-2-bromo-N-(1-methoxypropan-2-yl)-5-{[2-(trimethylsilyl)ethoxy]methyl}-5H-pyrrolo[2,3-b]pyrazine-7-carboxamide (Example 4 Step 3) and tert-butyl (R)-3-hydroxypyrrolidine-1-carboxylate. |

-continued

| Prep No. | Name | Structure | Data/SM |
|---|---|---|---|
| Ex 71 Step 4 | Trans-racemic-benzyl-4-[(7-[((S)-1-methoxypropan-2-yl)carbamoyl]-5-{[2-(trimethylsilyl)ethoxy]methyl}-5H-pyrrolo[2,3-b]pyrazin-2-yl)oxy]-2-methylpiperidine-1-carboxylate | 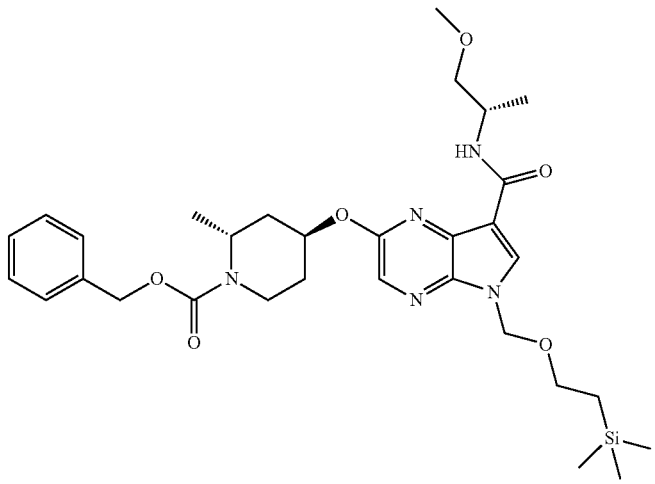 [SMILES: COC[C@H](C)NC(=O)c1cn(COCC[Si](C)(C)C)c2ncc(O[C@H]3CCN(C(=O)OCc4ccccc4)[C@H](C)C3)nc12] | MS m/z 612 [M + H]+ Trans-racemic-benzyl (2R,4S)-4-hydroxy-2-methylpiperidine-1-carboxylate (Bioorg. Chem. (1999), 27 (2), 81-90) and (S)-2-bromo-N-(1-methoxypropan-2-yl)-5-{[2-(trimethylsilyl)ethoxy]methyl}-5H-pyrrolo[2,3-b]pyrazine-7-carboxamide (Example 4 Step 3). |
| Ex 61 Step 4 | tert-butyl 4-{[7-(ethylcarbamoyl)-5-{[2-(trimethylsilyl)ethoxy]methyl}-5H-pyrrolo[2,3-b]pyrazin-2-yl]oxy}-4-methylpiperidine-1-carboxylate | 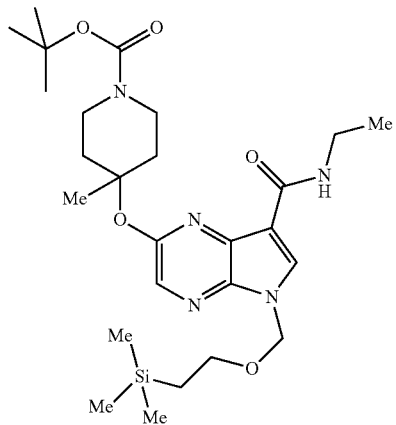 [SMILES: CCNC(=O)c1cn(COCC[Si](C)(C)C)c2ncc(OC3(C)CCN(C(=O)OC(C)(C)C)CC3)nc12] | 6 h's missing 43 reqd, 37 obsvd $^1$H NMR (400 MHz, DMSO-d$_6$) □ ppm 8.43 (s, 1 H) 8.08 (s, 1 H) 7.69 (t, J = 5.02 Hz, 1 H) 5.63 (s, 2 H) 3.71 (d, J = 13.05 Hz, 2 H) 3.49-3.60 (m, 3 H) 3.38-3.46 (m, 2 H) 3.03-3.23 (m, 3 H) 2.19-2.37 (m, 2 H) 1.59-1.79 (m, 2 H) 1.32-1.47 (m, 9 H) 1.21 (m, 3 H) 0.82 (m, 2 H) 0.09 (s, 9 H))2-bromo-5-[(3,3-dimethylbutoxy)methyl]-N-ethyl-5H-pyrrolo[2,3-b]pyrazine-7-carboxamide and tert-butyl 4-hydroxy-4-methylpiperidine-1-carboxylate (Example 25 Step 3). |
| Ex 46 Step 4 | Trans-racemic-tert-butyl 4-{[7-(ethylcarbamoyl)-5-{[2-(trimethylsilyl)ethoxy]methyl}-5H-pyrrolo[2,3-b]pyrazin-2-yl]oxy}-3-methylpiperidine-1-carboxylate | 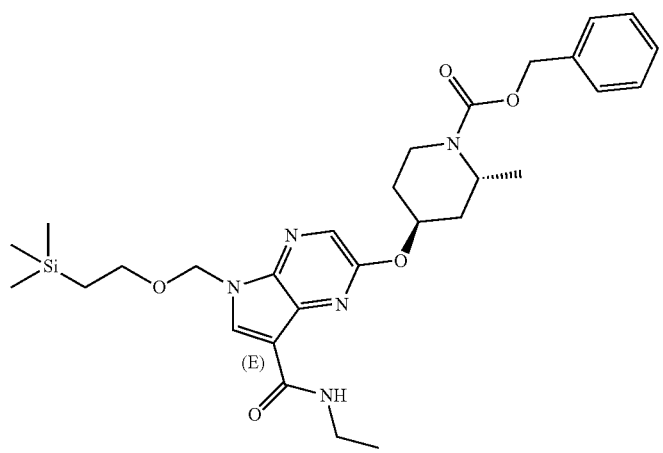 [SMILES: CCNC(=O)c1cn(COCC[Si](C)(C)C)c2ncc(O[C@H]3CCN(C(=O)OCc4ccccc4)[C@H](C)C3)nc12] | 2-bromo-5-[(3,3-dimethylbutoxy)methyl]-N-ethyl-5H-pyrrolo[2,3-b]pyrazine-7-carboxamide and trans-racemic-tert-butyl 4-hydroxy-3-methylpiperidine-1-carboxylate (Example 25 Step 3). Taken on directly to the next step. |

| Prep No. | Name | Structure | Data/SM |
|---|---|---|---|
| Ex 77 Step 4 | Trans-racemic-benzyl 4-{[7-(ethylcarbamoyl)-5-{[2-(trimethylsilyl)ethoxy]methyl}-5H-pyrrolo[2,3-b]pyrazin-2-yl]oxy}-2-methylpiperidine-1-carboxylate | 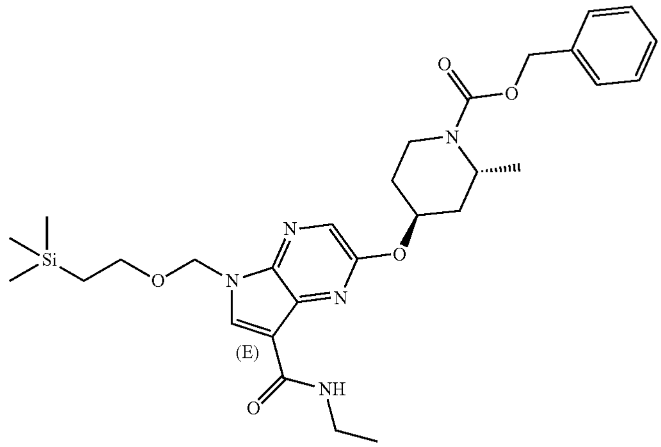 [SMILES: CCNC(=O)c1cn(COCC[Si](C)(C)C)c2ncc(O[C@H]3CCN(C(=O)OCc4ccccc4)[C@H](C)C3)nc12] | 2-bromo-5-[(3,3-dimethylbutoxy)methyl]-N-ethyl-5H-pyrrolo[2,3-b]pyrazine-7-carboxamide (Bioorg. Med. Chem. (1999), 27 (2), 81-90) and trans-racemic-benzyl 4-hydroxy-2-methylpiperidine-1-carboxylate (Example 25 Step 3). Taken on directly to the next step. |
| Ex 80 Step 4 | Cis-racemic-benzyl 5-[(7-[((1-methoxypropan-2-yl)carbamoyl]-5-{[2-(trimethylsilyl)ethoxy]methyl}-5H-pyrrolo[2,3-b]pyrazin-2-yl)oxy]-2-methylpiperidine-1-carboxylate | 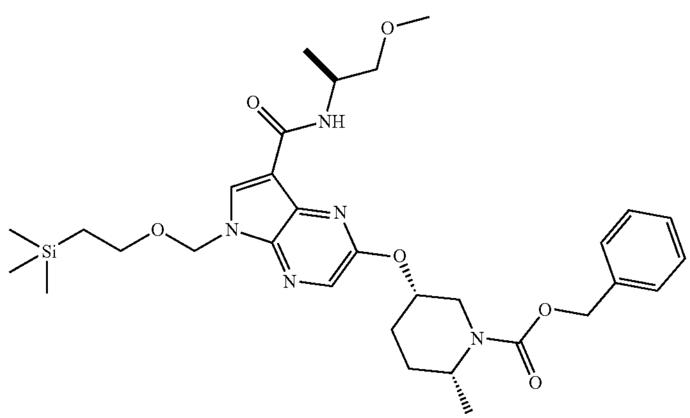 [SMILES: COC[C@H](C)NC(=O)c1cn(COCC[Si](C)(C)C)c2ncc(O[C@H]3CC[C@@H](C)N(C(=O)OCc4ccccc4)C3)nc12] | MS m/z 612 [M + H]$^+$ (S)-2-bromo-N-(1-methoxypropan-2-yl)-5-{[2-(trimethylsilyl)ethoxy]methyl}-5H-pyrrolo[2,3-b]pyrazine-7-carboxamide (Example 4 Step 3) and cis-racemic-benzyl 5-hydroxy-2-methylpiperidine-1-carboxylate. |

Example 1 Step 4 tert-Butyl-(cis-racemic)-4-methoxy-3-[(7-[((S)-1-methoxypropan-2-yl)carbamoyl]-5-{[2-(trimethylsilyl)ethoxy]methyl}-5H-pyrrolo[2,3-b]pyrazin-2-yl)amino]piperidine-1-carboxylate Method B wherein Y═N To a mixture of (S)-2-bromo-N-(1-methoxypropan-2-yl)-5-{[2-(trimethylsilyl)ethoxy]methyl}-5H-pyrrolo[2,3-b]pyrazine-7-carboxamide (Example 4 Step 3, 1 g, 2.26 mmol), tert-butyl (cis-racemic)-3-amino-4-methoxypiperidine-1-carboxylate (675 mg, 2.93 mmol) and sodium tert-butoxide (650 mg, 6.77 mmol) in toluene (40 mL) was added Pd$_2$(dba)$_3$ (207 mg, 0.23 mmol) and the reaction was heated to 110° C. under nitrogen for 18 hours. The reaction was concentrated in vacuo and purified using silica gel column chromatography eluting with 20-66% EtOAc in petroleum ether to afford the title compound as a yellow solid (1.2 g, 78%).

MS m/z 615 [M+Na]$^+$

The following Preparations were prepared according to Method B wherein Y═N as described for Example 1 Step 4 using the appropriate heteroaryl bromide and amine with either sodium tert-butoxide or cesium carbonate as base.

| Prep No. | Name | Structure | Data/SM |
|---|---|---|---|
| Ex 4 Step 4 | tert-butyl (cis-racemic)-4-methoxy-3-[(7-[((R)-1-methoxypropan-2-yl)carbamoyl]-5-{[2-(trimethylsilyl)ethoxy]methyl}-5H-pyrrolo[2,3-b]pyrazin-2-yl)amino]piperidine-1-carboxylate | 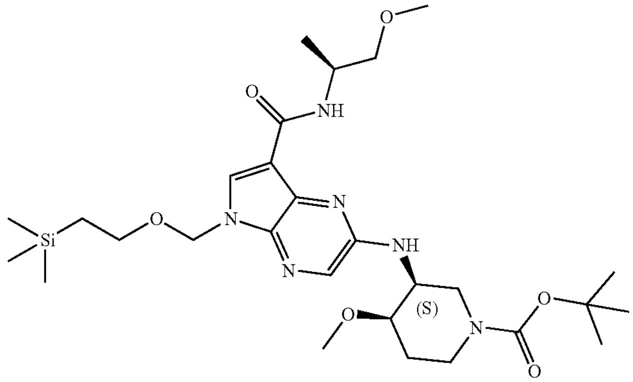 | MS m/z 593 [M + H]+ tert-butyl (cis-racemic)-3-amino-4-methoxypiperidine-1-carboxylate and (S)-2-bromo-N-(1-methoxypropan-2-yl)-5-{[2-(trimethylsilyl)ethoxy]methyl}-5H-pyrrolo[2,3-b]pyrazine-7-carboxamide (Example 4 Step 3). |
| Ex 16 Step 4 | Racemic-tert-butyl 3-{[(7-[((S)-1-methoxypropan-2-yl)carbamoyl]-5-{[2-(trimethylsilyl)ethoxy]methyl}-5H-pyrrolo[2,3-b]pyrazin-2-yl)amino]methyl}pyrrolidine-1-carboxylate | 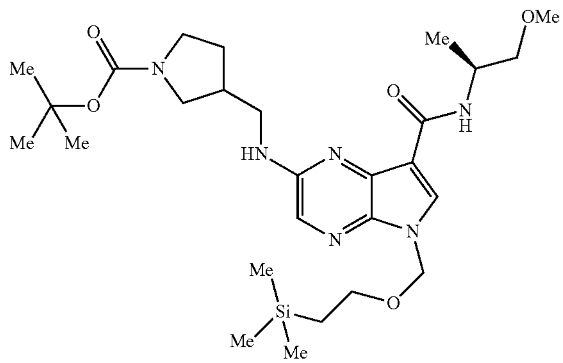 [SMILES: COC[C@H](C)NC(=O)c1cn(COCC[Si](C)(C)C)c2ncc(NCC3CCN(C(=O)OC(C)(C)C)C3)nc12] | MS m/z 593 [M + Na]+ (S)-2-bromo-N-(1-methoxypropan-2-yl)-5-{[2-(trimethylsilyl)ethoxy]methyl}-5H-pyrrolo[2,3-b]pyrazine-7-carboxamide (Example 4 Step 3) and racemic tert-butyl 3-(aminomethyl)pyrrolidine-1-carboxylate. |
| Ex 19 Step 4 | Racemic-tert-butyl 3-{[(7-[((R)-1-methoxypropan-2-yl)carbamoyl]-5-{[2-(trimethylsilyl)ethoxy]methyl}-5H-pyrrolo[2,3-b]pyrazin-2-yl)amino]methyl}pyrrolidine-1-carboxylate | 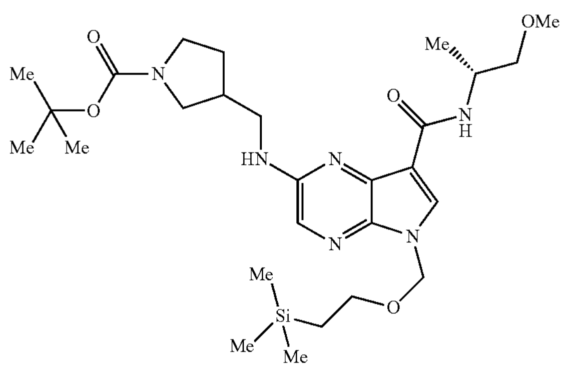 | MS m/z 593 [M + Na]+ (R)-2-bromo-N-(1-methoxypropan-2-yl)-5-{[2-(trimethylsilyl)ethoxy]methyl}-5H-pyrrolo[2,3-b]pyrazine-7-carboxamide (Example 1 Step 3) and racemic tert-butyl 3-(aminomethyl)pyrrolidine-1-carboxylate. |
| Ex 22 Step 4 | Cis-racemic-tert-butyl 2-methyl-4-[(7-[(3,3,3-trifluoropropyl)carbamoyl]-5-{[2-(trimethylsilyl)ethoxy]methyl}-5H-pyrrolo[2,3-b]pyrazin-2-yl)amino]piperidine-1-carboxylate | 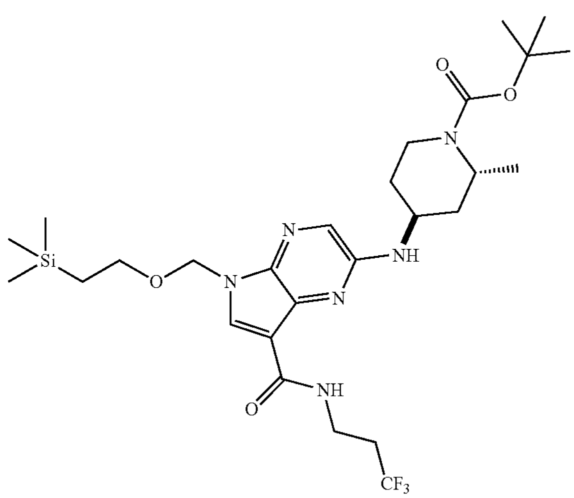 | 2-bromo-N-(3,3,3-trifluoropropyl)-5-{[2-(trimethylsilyl)ethoxy]methyl}-5H-pyrrolo[2,3-b]pyrazine-7-carboxamide (Example 22 Step 3) and cis-racemic tert-butyl 4-amino-2-methylpiperidine-1-carboxylate. Taken on directly to the next step |

-continued

| Prep No. | Name | Structure | Data/SM |
|---|---|---|---|
| Ex 25 Step 4 | Trans-racemic-tert-butyl 4-{[7-(ethylcarbamoyl)-5-{[2-(trimethylsilyl)ethoxy]methyl}-5H-pyrrolo[2,3-b]pyrazin-2-yl]amino}-3-methoxypiperidine-1-carboxylate | 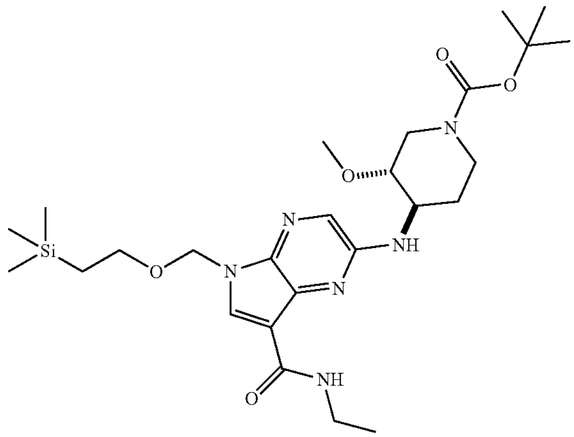 | MS m/z 571 [M + Na]+ 2-bromo-5-[(3,3-dimethylbutoxy)methyl]-N-ethyl-5H-pyrrolo[2,3-b]pyrazine-7-carboxamide and trans-racemic-tert-butyl 4-amino-3-methoxypiperidine-1-carboxylate (Example 25 Step 3). |
| Ex 65 Step 4 | Cis-racemic-benzyl-5-[(7-[((S)-1-methoxypropan-2-yl)carbamoyl]-5-{[2-(trimethylsilyl)ethoxy]methyl}-5H-pyrrolo[2,3-b]pyrazin-2-yl)amino]-2-methylpiperidine-1-carboxylate | 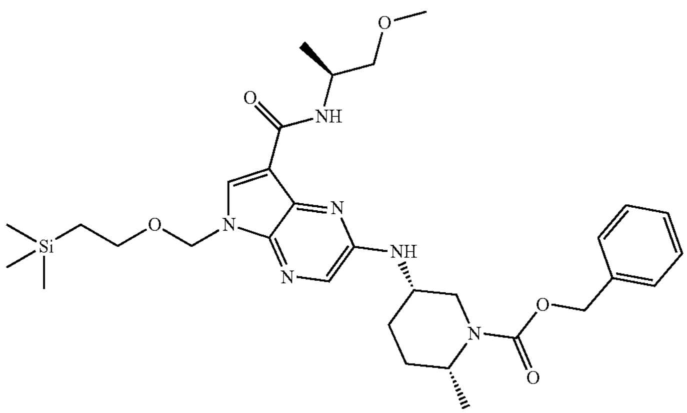 [SMILES: COC[C@H](C)NC(=O)c1cn(COCC[Si](C)(C)C)c2ncc(N[C@H]3CC[C@@H](C)N(C(=O)OCc4ccccc4)C3)nc12] | MS m/z 611 [M + H]+ Cis-racemic-benzyl 5-amino-2-methylpiperidine-1-carboxylate (WO2010016005) and (S)-2-bromo-N-(1-methoxypropan-2-yl)-5-{[2-(trimethylsilyl)ethoxy]methyl}-5H-pyrrolo[2,3-b]pyrazine-7-carboxamide (Example 4 Step 3). |
| Ex 68 Step 4 | Cis-racemic-benzyl-5-[(7-[((R)-1-methoxypropan-2-yl)carbamoyl]-5-{[2-(trimethylsilyl)ethoxy]methyl}-5H-pyrrolo[2,3-b]pyrazin-2-yl)amino]-2-methylpiperidine-1-carboxylate | 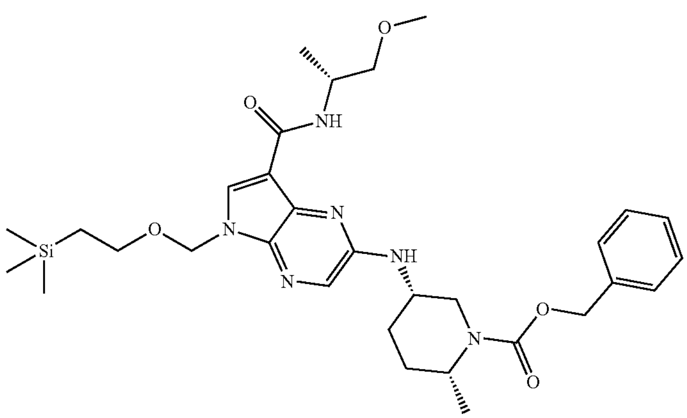 [SMILES: COC[C@@H](C)NC(=O)c1cn(COCC[Si](C)(C)C)c2ncc(N[C@H]3CC[C@@H](C)N(C(=O)OCc4ccccc4)C3)nc12] | MS m/z 611 [M + H]+ Cis-racemic-benzyl 5-amino-2-methylpiperidine-1-carboxylate (WO2010016005) and (R)-2-bromo-N-(1-methoxypropan-2-yl)-5-{[2-(trimethylsilyl)ethoxy]methyl}-5H-pyrrolo[2,3-b]pyrazine-7-carboxamide (Example 1 Step 3). |

| Prep No. | Name | Structure | Data/SM |
|---|---|---|---|
| Ex 28 Step 4 | Racemic tert-butyl 3-{[7-(ethylcarbamoyl)-5-{[2-(trimethylsilyl)ethoxy]methyl}-5H-pyrrolo[2,3-b]pyrazin-2-yl](methyl)amino}pyrrolidine-1-carboxylate | 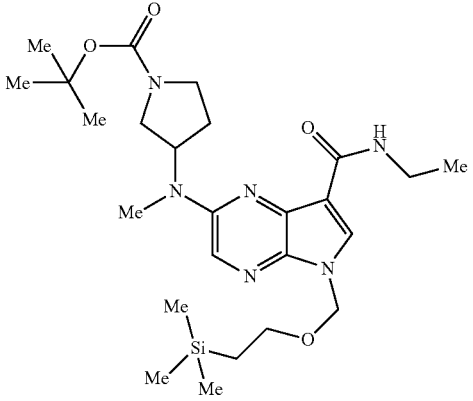 [SMILES: CCNC(=O)c1cn(COCC[Si](C)(C)C)c2ncc(N(C)C3CCN(C(=O)OC(C)(C)C)C3)nc12] | Taken on directly to the next step. 2-bromo-5-[(3,3-dimethylbutoxy)methyl]-N-ethyl-5H-pyrrolo[2,3-b]pyrazine-7-carboxamide (Example 25 Step 3) and racemic tert-butyl 3-(methylamino)pyrrolidine-1-carboxylate. |
| Ex 59 Step 4 | tert-butyl {1-[7-(ethylcarbamoyl)-5-{[2-(trimethylsilyl)ethoxy]methyl}-5H-pyrrolo[2,3-b]pyrazin-2-yl]azetidin-3-yl}methylcarbamate | 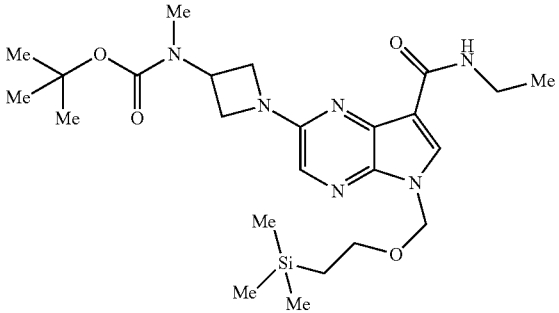 [SMILES: CCNC(=O)c1cn(COCC[Si](C)(C)C)c2ncc(N3CC(N(C)C(=O)OC(C)(C)C)C3)nc12] | MS m/z 527 [M + Na]+ 2-bromo-5-[(3,3-dimethylbutoxy)methyl]-N-ethyl-5H-pyrrolo[2,3-b]pyrazine-7-carboxamide (Example 25 Step 3) and tert-butyl azetidin-3-yl(methyl)carbamate. |
| Ex 74 Step 4 | Cis-racemic-benzyl 5-{[7-(ethylcarbamoyl)-5-{[2-(trimethylsilyl)ethoxy]methyl}-5H-pyrrolo[2,3-b]pyrazin-2-yl]amino}-2-methylpiperidine-1-carboxylate | 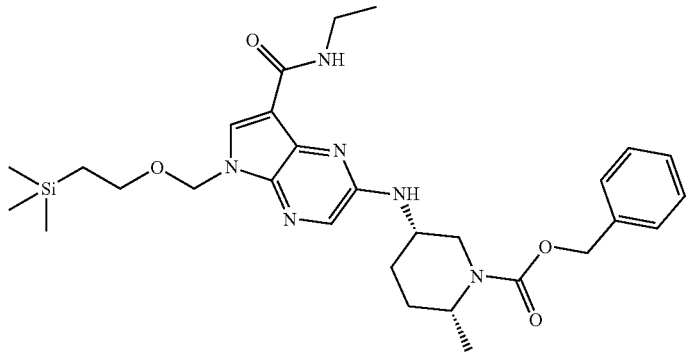 [SMILES: CCNC(=O)c1cn(COCC[Si](C)(C)C)c2ncc(N[C@H]3CC[C@@H](C)N(C(=O)OCc4ccccc4)C3)nc12] | MS m/z 567 [M + H]+ 2-bromo-5-[(3,3-dimethylbutoxy)methyl]-N-ethyl-5H-pyrrolo[2,3-b]pyrazine-7-carboxamide (Example 25 Step 3) and cis-racemic-benzyl 5-amino-2-methylpiperidine-1-carboxylate. |

-continued

| Prep No. | Name | Structure | Data/SM |
|---|---|---|---|
| Ex 31 Step 4 | Trans-racemic-tert-butyl 4-{[7-(ethylcarbamoyl)-5-{[2-(trimethylsilyl)ethoxy]methyl}-5H-pyrrolo[2,3-b]pyrazin-2-yl]amino}-3-hydroxypiperidine-1-carboxylate | 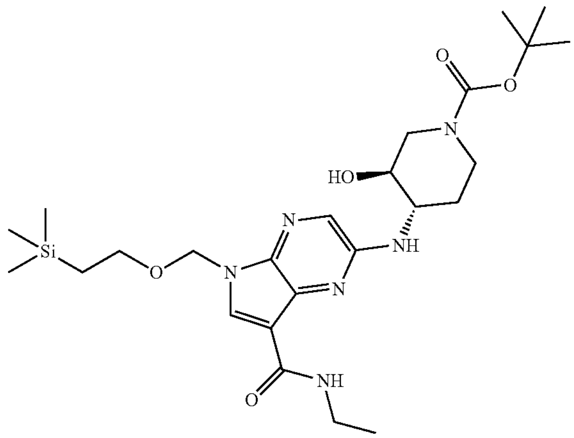 [SMILES: CCNC(=O)c1cn(COCC[Si](C)(C)C)c2ncc(N[C@H]3CCN(C(=O)OC(C)(C)C)C[C@@H]3O)nc12] | MS m/z 535 [M + H]+ 1H NMR (400 MHz, DMSO-d6) δ ppm 8.17-8.25 (m, 1 H) 8.07-8.14 (m, 1 H) 7.86 (s, 1 H) 7.32-7.34 (m, 1 H) 5.46-5.59 (m, 2 H) 5.27-5.29 (m, 1 H) 3.98 (br. s., 1 H) 3.83 (d, 1 H) 3.72 (br. s, 1 H) 3.45-3.55 (m, 3 H) 2.61-3.33 (m, 2 H) 2.15 (d, 1 H) 1.42 (s, 9 H) 1.12-1.31 (m, 5 H) 0.81 (t, 3 H) 0.09 (s, 9 H) 2-bromo-5-[(3,3-dimethylbutoxy)methyl]-N-ethyl-5H-pyrrolo[2,3-b]pyrazine-7-carboxamide (Example 25 Step 3) and trans-racemic-tert-butyl 4-amino-3-hydroxypiperidine-1-carboxylate. |
| Ex 34 Step 4 | Racemic-tert-butyl 3-{[7-(ethylcarbamoyl)-5-{[2-(trimethylsilyl)ethoxy]methyl}-5H-pyrrolo[2,3-b]pyrazin-2-yl]amino}piperidine-1-carboxylate | 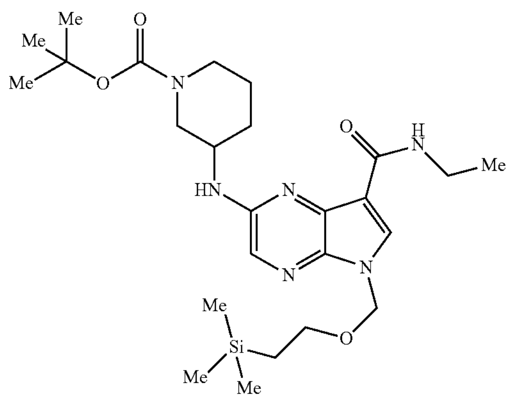 [SMILES: CCNC(=O)c1cn(COCC[Si](C)(C)C)c2ncc(NC3CCCN(C(=O)OC(C)(C)C)C3)nc12] | 2-bromo-5-[(3,3-dimethylbutoxy)methyl]-N-ethyl-5H-pyrrolo[2,3-b]pyrazine-7-carboxamide (Example 25 Step 3) and racemic-tert-butyl 3-aminopiperidine-1-carboxylate. Taken on directly to the next step. |
| Ex 37 Step 4 | Cis-racemic-tert-butyl 4-{[7-(ethylcarbamoyl)-5-{[2-(trimethylsilyl)ethoxy]methyl}-5H-pyrrolo[2,3-b]pyrazin-2-yl]amino}-3-methylpiperidine-1-carboxylate | 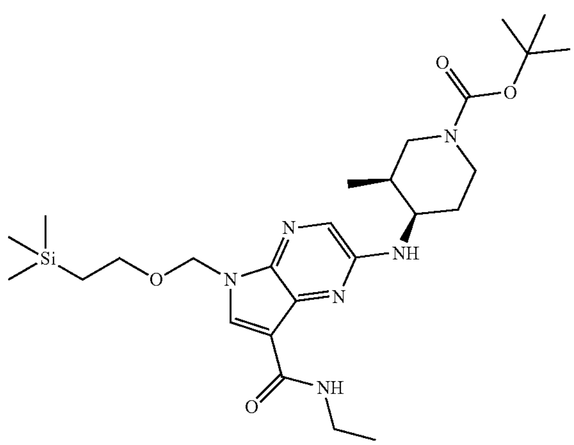 [SMILES: CCNC(=O)c1cn(COCC[Si](C)(C)C)c2ncc(N[C@@H]3CCN(C(=O)OC(C)(C)C)C[C@@H]3C)nc12] | 1H NMR (400 MHz, CDCl3): δ ppm 8.24-8.07 (m, 1H), 8.03 (s, 1H), 7.69-7.59 (m, 1H), 5.55 (s, 2H), 4.41 (br s, 1H), 4.26-3.98 (m, 2H), 3.77-3.60 (m, 1H), 3.57-3.35 (m, 4H), 2.88 (t, 1H), 2.58 (br s, 1H), 2.21-2.20 (m, 1H), 1.50-1.45 (m, 9H), 1.36-1.25 (m, 4H), 1.03 (d, 4H), 0.93-0.84 (m, 2H), −0.33-−0.11 (m, 9H). 2-bromo-5-[(3,3-dimethylbutoxy)methyl]-N-ethyl-5H-pyrrolo[2,3-b]pyrazine-7-carboxamide (Example 25 Step 3) and cis-racemic-tert-butyl 4-amino-3-methylpiperidine-1-carboxylate (US 20050085518). |

| Prep No. | Name | Structure | Data/SM |
|---|---|---|---|
| Ex 40 Step 4 | Trans-racemic-tert-butyl 4-{[7-(ethylcarbamoyl)-5-{[2-(trimethylsilyl)ethoxy]methyl}-5H-pyrrolo[2,3-b]pyrazin-2-yl]amino}-2-methylpiperidine-1-carboxylate | 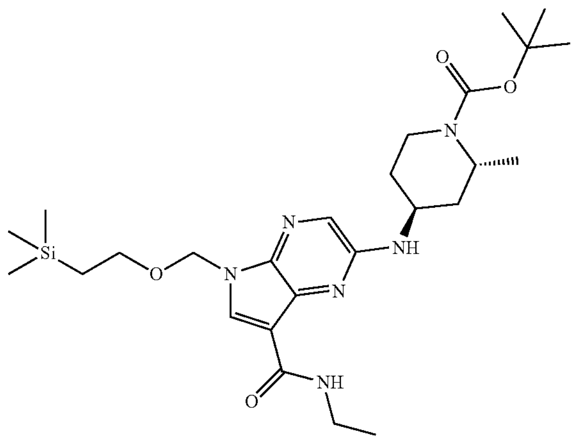 [SMILES: CCNC(=O)c1cn(COCC[Si](C)(C)C)c2ncc(N[C@H]3CCN(C(=O)OC(C)(C)C)[C@H](C)C3)nc12] | ¹H NMR (400 MHz, DMSO-d₆): δ ppm 8.18-8.07 (m, 2H), 7.73 (s, 1H), 7.04 (d, J = 7.3 Hz, 1H), 5.57-5.47 (m, 2H), 4.40 (br s, 1H), 4.24-4.06 (m, 1H), 3.93 (d, J = 13.1 Hz, 1H), 3.55-3.34 (m, 4H), 3.08-2.86 (m, 1H), 2.07-1.98 (m, 1H), 1.91 (d, J = 12.5 Hz, 1H), 1.52-1.33 (m, 10H), 1.29-1.11 (m, 7H), 0.80 (t, J = 7.9 Hz, 2H), 0.06--0.19 (m, 9H). 2-bromo-5-[(3,3-dimethylbutoxy)methyl]-N-ethyl-5H-pyrrolo[2,3-b]pyrazine-7-carboxamide (Example 25 Step 3) and trans-racemic-tert-butyl 4-amino-2-methylpiperidine-1-carboxylate. |
| Ex 60 Step 4 | tert-butyl 4-{[7-(ethylcarbamoyl)-5-{[2-(trimethylsilyl)ethoxy]methyl}-5H-pyrrolo[2,3-b]pyrazin-2-yl](methyl)amino}piperidine-1-carboxylate | 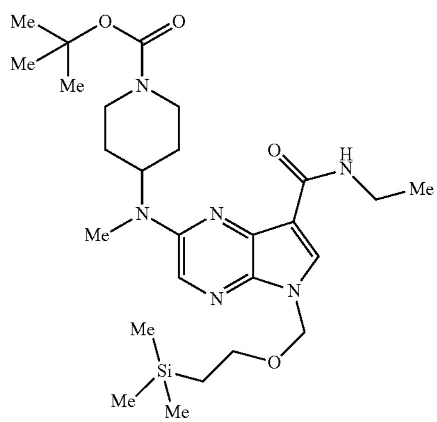 [SMILES: CCNC(=O)c1cn(COCC[Si](C)(C)C)c2ncc(N(C)C3CCN(C(=O)OC(C)(C)C)CC3)nc12] | MS m/z 533 [M + H]⁺ 2-bromo-5-[(3,3-dimethylbutoxy)methyl]-N-ethyl-5H-pyrrolo[2,3-b]pyrazine-7-carboxamide (Example 25 Step 3) and tert-butyl 4-(methylamino)piperidine-1-carboxylate. |
| Ex 43 Step 4 | Trans-racemic-tert-butyl 4-{[7-(ethylcarbamoyl)-5-{[2-(trimethylsilyl)ethoxy]methyl}-5H-pyrrolo[2,3-b]pyrazin-2-yl]amino}-3-methylpiperidine-1-carboxylate | 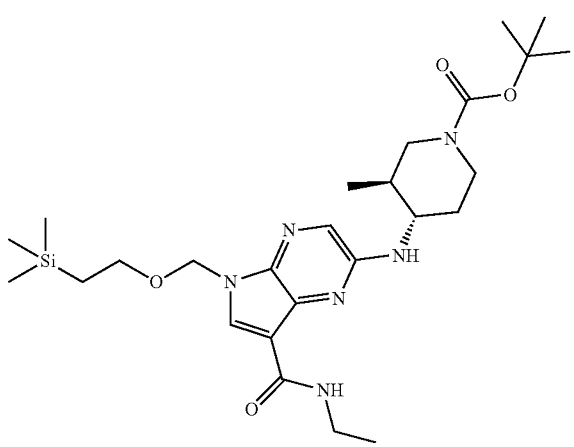 [SMILES: CCNC(=O)c1cn(COCC[Si](C)(C)C)c2ncc(N[C@H]3CCN(C(=O)OC(C)(C)C)C[C@@H]3C)nc12] | ¹H NMR (400 MHz, DMSO-d₆): δ ppm 8.14-8.07 (m, 2H), 7.86 (s, 1H), 7.23-7.22 (m, 1H), 5.52 (s, 2H), 4.15-4.05 (m, 1H), 3.80-3.50 (m, 4H), 3.40-3.30 (m, 1H), 3.25-3.05 (m, 2H), 2.25-2.15 (m, 1H), 1.75-1.60 (m, 2H), 1.40 (s, 9H), 1.25-1.10 (m, 5H), 0.90-0.75 (m, 5H), -0.08 (s, 9H). 2-bromo-5-[(3,3-dimethylbutoxy)methyl]-N-ethyl-5H-pyrrolo[2,3-b]pyrazine-7-carboxamide (Example 25 Step 3) and trans-racemic-tert-butyl 4-amino-3-methylpiperidine-1-carboxylate (US 20050085518). |

| Prep No. | Name | Structure | Data/SM |
|---|---|---|---|
| Ex 62 Step 4 | tert-butyl 4-{[7-(azetidin-1-ylcarbonyl)-5-{[2-(trimethylsilyl)ethoxy]methyl}-5H-pyrrolo[2,3-b]pyrazin-2-yl](methyl)amino}piperidine-1-carboxylate | 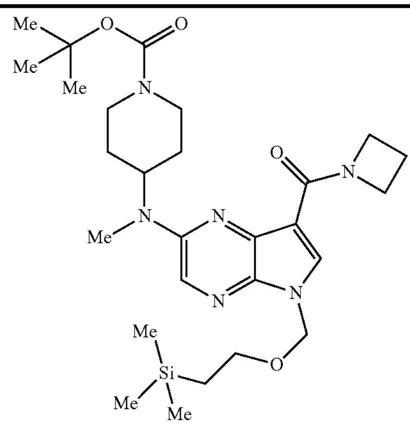 | MS m/z 567 [M + Na]⁺ Azetidin-1-yl(2-bromo-5-{[2-(trimethylsilyl)ethoxy]methyl}-5H-pyrrolo[2,3-b]pyrazin-7-yl)methanone (Example 62 Step 3) and tert-butyl 4-(methylamino)piperidine-1-carboxylate. |
| Ex 63 Step 4 | tert-butyl 2-(methoxymethyl)-4-(7-(((R)-1-methoxypropan-2-yl)carbamoyl)-5-((2-(trimethylsilyl)ethoxy)methyl)-5H-pyrrolo[2,3-b]pyrazin-2-yl)-2-methylpiperazine-1-carboxylate | 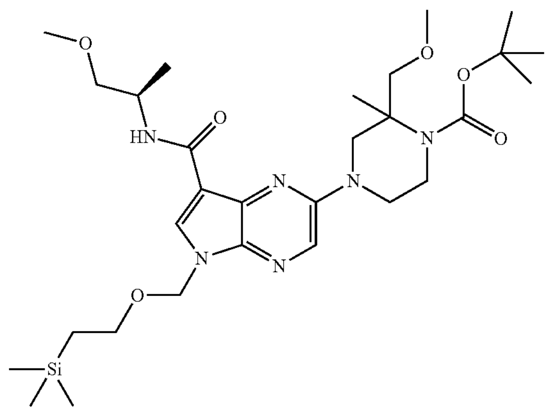 [SMILES: COC[C@@H](C)NC(=O)c1cn(COCC[Si](C)(C)C)c2ncc(N3CCN(C(=O)OC(C)(C)C)C(C)(COC)C3)nc12] | (S)-2-bromo-N-(1-methoxypropan-2-yl)-5-{[2-(trimethylsilyl)ethoxy]methyl}-5H-pyrrolo[2,3-b]pyrazine-7-carboxamide (Example 4 Step 3) and racemic-benzyl-5-amino-2-methoxymethyl-2-methylpiperidine-1-carboxylate. Taken on directly to the next step. |
| Ex 64 Step 4 | tert-butyl 4-((7-(isopropylcarbamoyl)-5-((2-(trimethylsilyl)ethoxy)methyl)-5H-pyrrolo[2,3-b]pyrazin-2-yl)(methyl)amino)piperidine-1-carboxylate | 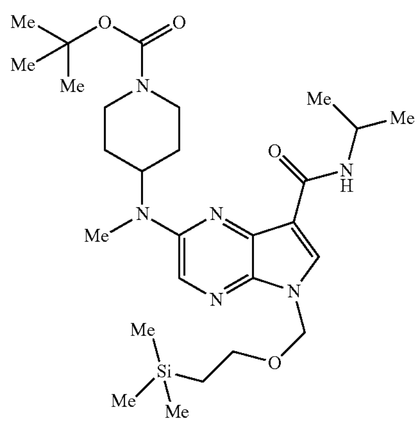 [SMILES: CC(C)NC(=O)c1cn(COCC[Si](C)(C)C)c2ncc(N(C)C3CCN(C(=O)OC(C)(C)C)CC3)nc12] | 2-bromo-N-isopropyl-5-((2-(trimethylsilyl)ethoxy)methyl)-5H-pyrrolo[2,3-b]pyrazine-7-carboxamide (Example 64 Step 3) and tert-butyl 4-(methylamino)piperidine-1-carboxylate. MS m/z 569 [M + H]⁺ |

Examples 56 and 56 Step 4

Cis-racemic-tert-butyl 4-[(7-[((S)-1-methoxypropan-2-yl)carbamoyl]-5-{[2-(trimethylsilyl)ethoxy]methyl}-5H-pyrrolo[2,3-b]pyrazin-2-yl)amino]-2-methylpiperidine-1-carboxylate The title compound was prepared according to the method described for Example 1 Step 4 using (S)-2-bromo-N-(1-methoxypropan-2-yl)-5-{[2-(trimethylsilyl)ethoxy]methyl}-5H-pyrrolo[2,3-b]pyrazine-7-carboxamide (Example 4 Step 3) and cis-racemic-tert-butyl 4-amino-2-methylpiperidine-1-carboxylate.

¹H NMR (400 MHz, DMSO-d₆): δ ppm 8.39-8.37 (m, 0.5H), 8.30-8.28 (m, 0.5H), 8.09-8.07 (m, 1H), 7.82 (s, 1H), 7.17-7.13 (m, 1H), 5.53-5.50 (m, 2H), 4.25-4.15 (m, 1H), 4.10-3.90 (m, 3H), 3.75-3.70 (m, 1H), 3.51-3.47 (m, 2H), 3.40-3.27 (m, 4H), 2.05-1.95 (m, 1H), 1.95-1.60 (m, 3H), 1.40 (s, 9H), 1.17-1.10 (m, 7H), 0.80 (t, 2H), −0.07 (s, 9H).

The residue was separated into the two cis-isomers using preparative chiral column chromatography according to the conditions described below:

Column: OD (250×30 mm, 10 micron); Mobile phase: 40% IPA in NH₃/H₂O

Flow rate: 70 mL/min.

The two cis-isomers were arbitrarily assigned absolute stereochemistry:

Example 55 Step 4

Pk1: tert-butyl-(2S,4S)-4-[(7-[((S)-1-methoxypropan-2-yl)carbamoyl]-5-{[2-(trimethylsilyl)ethoxy]methyl}-5H-pyrrolo[2,3-b]pyrazin-2-yl)amino]-2-methylpiperidine-1-carboxylate

Example 56 Step 4

Pk2: tert-butyl-(2R,4R)-4-[(7-[((S)-1-methoxypropan-2-yl)carbamoyl]-5-{[2-(trimethylsilyl)ethoxy]methyl}-5H-pyrrolo[2,3-b]pyrazin-2-yl)amino]-2-methylpiperidine-1-carboxylate

Examples 57 and 58 Step 4

Cis-racemic-tert-butyl-4-[(7-[((R)-1-methoxypropan-2-yl)carbamoyl]-5-{[2-(trimethylsilyl)ethoxy]methyl}-5H-pyrrolo[2,3-b]pyrazin-2-yl)amino]-2-methylpiperidine-1-carboxylate The title compound was prepared according to the method described for Example 1 Step 4 using (R)-2-bromo-N-(1-methoxypropan-2-yl)-5-{[2-(trimethylsilyl)ethoxy]methyl}-5H-pyrrolo[2,3-b]pyrazine-7-carboxamide (Example 1 Step 3) and cis-racemic-tert-butyl 4-amino-2-methylpiperidine-1-carboxylate. $^1$H NMR (400 MHz, DMSO-$d_6$): δ ppm 8.39-8.37 (m, 0.5H), 8.30-8.28 (m, 0.5H), 8.09-8.07 (m, 1H), 7.82 (s, 1H), 7.17-7.13 (m, 1H), 5.53-5.50 (m, 2H), 4.25-4.15 (m, 1H), 4.10-3.90 (m, 3H), 3.75-3.70 (m, 1H), 3.51-3.47 (m, 2H), 3.40-3.27 (m, 4H), 2.05-1.95 (m, 1H), 1.95-1.60 (m, 3H), 1.40 (s, 9H), 1.17-1.10 (m, 7H), 0.80 (t, 2H), −0.07 (s, 9H).

The residue was separated into its cis-isomers using preparative chiral column chromatography according to the conditions described below:
Column: OD (250×30 mm, 10 micron); Mobile phase: 45% IPA in NH$_3$/H$_2$O
Flow rate: 80 mL/min.
The two cis-isomers were arbitrarily assigned absolute stereochemistry:

Example 57 Step 4 tert-butyl-(2S,4S)-4-[(7-[((R)-1-methoxypropan-2-yl)carbamoyl]-5-{[2-(trimethylsilyl)ethoxy]methyl}-5H-pyrrolo[2,3-b]pyrazin-2-yl)amino]-2-methylpiperidine-1-carboxylate

Example 58 Step 4 tert-butyl-(2R,4R)-4-[(7-[((R)-1-methoxypropan-2-yl)carbamoyl]-5-{[2-(trimethylsilyl)ethoxy]methyl}-5H-pyrrolo[2,3-b]pyrazin-2-yl)amino]-2-methylpiperidine-1-carboxylate

Example 1 Steps 5-7

2-{[(cis-racemic)-1-acryloyl-4-methoxypiperidin-3-yl]amino}-N-[(2S)-1-methoxypropan-2-yl]-5H-pyrrolo[2,3-b]pyrazine-7-carboxamide To a solution of tert-butyl (cis-racemic)-4-methoxy-3-[(7-[((S)-1-methoxypropan-2-yl)carbamoyl]-5-{[2-(trimethylsilyl)ethoxy]methyl}-5H-pyrrolo[2,3-b]pyrazin-2-yl)amino]piperidine-1-carboxylate (Example 1 Step 4, 1.2 g, 2.02 mmol) in DCM (40 mL) was added TFA (12 mL) and the reaction was stirred at room temperature for 3 hours. The reaction was concentrated in vacuo. The residue was dissolved in MeOH (30 mL) and treated with 28% aqueous ammonia (10 mL). The reaction was stirred at room temperature for 18 hours. The reaction was concentrated in vacuo and the residue dissolved in THF (30 mL) and water (30 mL). To the solution was added DIPEA (792 mg, 6.13 mmol) followed by acryloyl chloride (370 mg, 4.08 mmol) dropwise at 0° C. The reaction was stirred at 0° C. for 2 hours before concentrating in vacuo. The residue was purified using silica gel column chromatography eluting with 10% MeOH in DCM followed by Preparative HPLC to afford the title compound as a grey solid (350 mg, 41%).
Preparative HPLC Method:
Column: Phenomenex Gemini C18 250×21.2 mm, 8 micron.
Mobile phase: From 22-42% MeCN in water, both mobile phases modified with ammonia (pH=10).
QC Analytical LCMS Method:
Column: Ultimate XB-C18, 3×50 mm, 3 micron
Mobile phase: From 1-100% MeCN in water, both mobile phases modified with 0.1% TFA
$^1$H NMR (400 MHz, DMSO-$d_6$): δ ppm 12.11 (br s, 1H), 8.29-8.26 (m, 1H), 7.89-7.85 (m, 2H), 6.94-6.84 (m, 2H), 6.14-6.10 (m, 1H), 5.71-5.67 (m, 1H), 4.69-4.66 (m, 0.5H), 4.33-4.11 (m, 3.5H), 3.70-3.60 (m, 2H), 3.45-3.34 (m, 5H), 3.00-2.80 (m, 4H), 1.78-1.63 (m, 2H), 1.22 (d, 3H).
Rt=3.31 minutes MS m/z 439 [M+Na]$^+$ The cis-racemic material was separated into its enantiomers using preparative chiral column chromatography according to the conditions described below:
Preparative Chiral Method:
Column: OD (250×30 mm, 10 micron); Mobile phase: 35% MeOH in NH$_3$/H$_2$O
Flow rate: 80 mL/min
QC Analytical LCMS Method:
Column: Chiralcel OD-3 150×4.6 mm, 3 micron; Mobile phase: MeOH (0.05% DEA) in CO$_2$ from 5-40%; Flow rate: 2.5 mL/min
The two enantiomers were arbitrarily assigned absolute stereochemistry:

First Eluting Isomer: Example 2

2-{[(3S,4R)-1-acryloyl-4-methoxypiperidin-3-yl]amino}-N-[(2S)-1-methoxypropan-2-yl]-5H-pyrrolo[2,3-b]pyrazine-7-carboxamide; Rt=7.55 minutes MS m/z 439 [M+Na]$^+$

Second Eluting Isomer: Example 3

2-{[(3R,4S)-1-acryloyl-4-methoxypiperidin-3-yl]amino}-N-[(2S)-1-methoxypropan-2-yl]-5H-pyrrolo[2,3-b]pyrazine-7-carboxamide; Rt=8.62 minutes MS m/z 439 [M+Na]$^+$

Example 4

2-{[(cis-racemic)-1-acryloyl-4-methoxypiperidin-3-yl]amino}-N-[(2R)-1-methoxypropan-2-yl]-5H-pyrrolo[2,3-b]pyrazine-7-carboxamide The title compound was prepared and purified according to the method described for Example 1 Steps 6-7 using tert-butyl (cis-racemic)-4-methoxy-3-[(7-[((R)-1-methoxypropan-2-yl)carbamoyl]-5-{[2-(trimethylsilyl)ethoxy]methyl}-5H-pyrrolo[2,3-b]pyrazin-2-yl)amino]piperidine-1-carboxylate (Example 4 Step 4) and an HPLC gradient of from 19-39% MeCN in water, both mobile phases modified with ammonia (pH=10).

$^1$H NMR (400 MHz, DMSO-$d_6$): δ ppm 12.11 (br s, 1H), 8.29-8.26 (m, 1H), 7.89-7.85 (m, 2H), 6.94-6.84 (m, 2H), 6.14-6.10 (m, 1H), 5.71-5.67 (m, 1H), 4.69-4.66 (m, 0.5H), 4.33-4.11 (m, 3.5H), 3.70-3.60 (m, 2H), 3.45-3.34 (m, 5H), 3.00-2.80 (m, 4H), 1.78-1.63 (m, 2H), 1.22 (d, 3H).

Rt=3.31 minutes MS m/z 439 [M+Na]$^+$

The cis-racemic material was separated into its enantiomers using preparative chiral column chromatography according to the conditions described below;

Column: OD (250×30 mm, 10 micron); Mobile phase: 25% MeOH in NH$_3$/H$_2$O

Flow rate: 70 mL/min

QC Analytical LCMS Method:

Column: Chiralpak AD-H 250×4.6 mm, 5 micron; Mobile phase: IPA (0.05% DEA) in CO$_2$ from 5-40%;

Flow rate: 2.5 mL/min

The two enantiomers were arbitrarily assigned absolute stereochemistry:

First Eluting Isomer: Example 5

2-{[(3S,4R)-1-acryloyl-4-methoxypiperidin-3-yl]amino}-N-[(2R)-1-methoxypropan-2-yl]-5H-pyrrolo[2,3-b]pyrazine-7-carboxamide; Rt=8.57 minutes MS m/z 439 [M+Na]$^+$ Second Eluting Isomer: Example 6

2-{[(3R,4S)-1-acryloyl-4-methoxypiperidin-3-yl]amino}-N-[(2R)-1-methoxypropan-2-yl]-5H-pyrrolo[2,3-b]pyrazine-7-carboxamide; Rt=8.99 minutes MS m/z 439 [M+Na]$^+$ Example 7

Racemic-2-[(1-acryloylpyrrolidin-2-yl)methoxyl]-N-[(2S)-1-methoxypropan-2-yl]-5H-pyrrolo[2,3-b]pyrazine-7-carboxamide The title compound was prepared and purified according to the method described for Example 1 Steps 5-7 using racemic-tert-butyl 2-{[(7-[((S)-1-methoxypropan-2-yl)carbamoyl]-5-{[2-(trimethylsilyl)ethoxy]methyl}-5H-pyrrolo[2,3-b]pyrazin-2-yl)oxy]methyl}pyrrolidine-1-carboxylate (Example 7 Step 4) and an HPLC gradient of from 29-49% MeCN in water, both mobile phases modified with ammonia (pH=10). $^1$H NMR (400 MHz, DMSO-$d_6$): δ ppm 12.48 (br s, 1H), 8.20-8.18 (m, 1H), 8.11-7.99 (m, 2H), 6.75-6.60 (m, 0.5H), 6.58-6.56 (m, 0.5H), 6.16-6.12 (m, 1H), 5.69-5.66 (m, 1H), 4.59-4.18 (m, 4H), 3.70-3.27 (m, 7H), 2.09-1.91 (m, 4H), 1.23 (d, 3H).

The racemic material was separated into its enantiomers using preparative chiral column chromatography according to the conditions described below;

Column: WEEK-1 (300×25 mm, 5 micron); Mobile phase: 20% MeOH in NH$_3$/H$_2$O

Flow rate: 60 mL/min

QC Analytical LCMS Method:

Column: Whelk-O1 (250×4.6 mm, 5 micron); Mobile phase: 50% EtOH with 5% DEA in CO$_2$.

Flow rate: 2 mL/min

The two enantiomers were arbitrarily assigned absolute stereochemistry:

First Eluting Isomer: Example 8

2-{[(2S)-1-acryloylpyrrolidin-2-yl]methoxy}-N-[(2S)-1-methoxypropan-2-yl]-5H-pyrrolo[2,3-b]pyrazine-7-carboxamide; Rt=5.53 minutes MS m/z 410 [M+Na]$^+$ Second Eluting Isomer: Example 9

2-{[(2R)-1-acryloylpyrrolidin-2-yl]methoxy}-N-[(2S)-1-methoxypropan-2-yl]-5H-pyrrolo[2,3-b]pyrazine-7-carboxamide; Rt=6.51 minutes MS m/z 410 [M+Na]$^+$ Example 10

Racemic-2-[(1-acryloylpyrrolidin-3-yl)methoxyl]-N-[(2S)-1-methoxypropan-2-yl]-5H-pyrrolo[2,3-b]pyrazine-7-carboxamide The title compound was prepared and purified according to the method described for Example 1 using racemic-tert-butyl 3-{[(7-[((S)-1-methoxypropan-2-yl)carbamoyl]-5-{[2-(trimethylsilyl)ethoxy]methyl}-5H-pyrrolo[2,3-b]pyrazin-2-yl)oxy]methyl}pyrrolidine-1-carboxylate (Example 10 Step 4). The residue was purified by silica gel column chromatography eluting with 5% MeOH in DCM followed by preparative HPLC using a gradient of from 20-40% MeCN in water, both mobile phases modified with ammonia (pH=10). $^1$H NMR (400 MHz, DMSO-$d_6$): δ ppm 12.58 (brs, 1H), 8.19 (s, 1H), 8.11-8.09 (m, 1H), 8.04 (s, 1H), 6.62-8.56 (m, 1H), 6.16-6.11 (m, 1H), 5.68-5.63 (m, 1H), 4.42-4.39 (m, 2H), 4.25-4.15 (m, 1H), 3.85-3.32 (m, 10H), 2.16-2.06 (m, 1H), 1.88-1.74 (m, 1H), 1.21 (d, 3H). Rt=3.34 minutes MS m/z 410 [M+Na]$^+$ The racemic material was separated into its enantiomers using preparative chiral column chromatography according to the conditions described below;

Column: AD (250×30 mm), 5 micron

Mobile phase: 30% EtOH in NH/H$_2$O; Flow rate: 60 mL/min

QC Analytical LCMS Method:

Column: Chiralcel OD-H (250×4.6 mm, 5 micron); Mobile phase: A/B=75/25 A: Hexane with 0.1% DEA, B: Ethanol; Flow rate: 0.5 mL/min The two enantiomers were arbitrarily assigned absolute stereochemistry:

First Eluting Isomer: Example 11

2-{[(3S)-1-acryloylpyrrolidin-3-yl]methoxy}-N-[(2S)-1-methoxypropan-2-yl]-5H-pyrrolo[2,3-b]pyrazine-7-carboxamide This isomer was purified for a second time using chiral preparative HPLC using column OD (250×30 mm, 5 micron) and eluting with 35% EtOH in NH$_3$/H2O with a flow rate of 50 mL/min to obtain the chirally pure title compound.

Rt=21.64 minutes, 95% de; MS m/z 410 [M+Na]$^+$

Second Eluting Isomer: Example 12

2-{[(3R)-1-acryloylpyrrolidin-3-yl]methoxy}-N-[(2S)-1-methoxypropan-2-yl]-5H-pyrrolo[2,3-b]pyrazine-7-carboxamide Rt=23.87 minutes, 99% de; MS m/z 410 [M+Na]$^+$

Example 13—Intermediate

Racemic-2-[(1-acryloylpyrrolidin-3-yl)methoxyl]-N-[(2R)-1-methoxypropan-2-yl]-5H-pyrrolo[2,3-b]pyrazine-7-carboxamide The title compound was prepared and purified according to the method described for Example 1 Steps 5-7 using racemic-tert-butyl 3-{[(7-[((R)-1-methoxypropan-2-yl)carbamoyl]-5-{[2-(trimethylsilyl)ethoxy]methyl}-5H-pyrrolo[2,3-b]pyrazin-2-yl)oxy]methyl}pyrrolidine-1-carboxylate (Preparation 13 Step 4). The residue was purified by silica gel column chromatography eluting with 5% MeOH in DCM followed by preparative HPLC using a gradient of from 20-40% MeCN in water, both mobile phases modified with ammonia (pH=10).

MS m/z 410 [M+Na]$^+$

The racemic material was separated into its enantiomers using preparative chiral column chromatography according to the conditions described below; Column: AD (250×30 mm), 5 micron; Mobile phase: 30% EtOH in NH$_3$/H$_2$O; Flow rate: 60 mL/min QC Analytical LCMS Method:
Column: Chiralpak AD-3 (150×4.6 mm, 3 micron); Mobile phase: 5-40% EtOH with 0.05% DEA in CO$_2$;
Flow rate: 2.5 mL/min
The two enantiomers were arbitrarily assigned absolute stereochemistry:

First Eluting Isomer: Example 14

2-{[(3R)-1-acryloylpyrrolidin-3-yl]methoxy}-N-[(2R)-1-methoxypropan-2-yl]-5H-pyrrolo[2,3-b]pyrazine-7-carboxamide. $^1$H NMR (400 MHz, DMSO-d$_6$): δ ppm 12.57 (br s, 1H), 8.19 (s, 1H), 8.12-8.09 (m, 1H), 8.04 (s, 1H), 6.62-6.58 (m, 1H), 6.16-6.11 (m, 1H), 5.68-5.65 (m, 1H), 4.43-4.39 (m, 2H), 4.25-4.15 (m, 1H), 3.90-3.55 (m, 5H), 3.44-3.28 (m, 4H), 2.90-2.70 (m, 1H), 2.20-2.05 (m, 1H), 1.90-1.75 (m, 1H), 1.22 (d, 3H).
Rt=5.04 minutes; 99% de; MS m/z 410 [M+Na]$^+$ Second Eluting Isomer: Example 15

2-{[(3S)-1-acryloylpyrrolidin-3-yl]methoxy}-N-[(2R)-1-methoxypropan-2-yl]-5H-pyrrolo[2,3-b]pyrazine-7-carboxamide $^1$H NMR (400 MHz, DMSO-d$_6$): δ ppm 12.57 (br s, 1H), 8.19 (s, 1H), 8.12-8.09 (m, 1H), 8.04 (s, 1H), 6.62-6.55 (m, 1H), 6.15-6.10 (m, 1H), 5.6-5.65 (m, 1H), 4.48-4.45 (m, 1H), 4.35-4.32 (m, 1H), 4.19-4.17 (m, 1H), 3.90-3.55 (m, 3H), 3.50-3.30 (m, 6H), 2.84-2.74 (m, 1H), 2.14-2.00 (m, 1H), 1.87-1.75 (m, 1H), 1.20 (d, 3H). Rt=5.44 minutes, 91% de; MS m/z 410 [M+Na]$^+$

Example 16

Racemic-2-{[(1-acryloylpyrrolidin-3-yl)methyl]amino}-N-(2S)-(1-methoxypropan-2-yl)-5H-pyrrolo[2,3-b]pyrazine-7-carboxamide The title compound was prepared and purified according to the method described for Example 1 using racemic-tert-butyl 3-{[(7-[((S)-1-methoxypropan-2-yl)carbamoyl]-5-{[2-(trimethylsilyl)ethoxy]methyl}-5H-pyrrolo[2,3-b]pyrazin-2-yl)amino]methyl}pyrrolidine-1-carboxylate (Example 16 Step 4). The residue was purified by silica gel column chromatography eluting with 5% MeOH in DCM followed by preparative HPLC using a gradient of from 19-39% MeCN in water, both mobile phases modified with ammonia (pH=10).

MS m/z 409 [M+Na]$^+$

The racemic material was separated into its enantiomers using preparative chiral column chromatography according to the conditions described below;
Column: OJ (250×30 mm), 5 micron; Mobile phase: 20% EtOH in NH$_3$/H$_2$O
Flow rate: 60 mL/min
QC Analytical LCMS Method:
Column: Chiralcel OJ-3 (150×4.6 mm, 3 micron); Mobile phase: 5-40% EtOH with 0.05% DEA in CO$_2$;
Flow rate: 2.5 mL/min
The two enantiomers were arbitrarily assigned absolute stereochemistry:

First Eluting Isomer: Example 17

2-({[(3S)-1-acryloylpyrrolidin-3-yl]methyl}amino)-N-[(2S)-1-methoxypropan-2-yl]-5H-pyrrolo[2,3-b]pyrazine-7-carboxamide. $^1$H NMR (400 MHz, DMSO-d$_6$): δ ppm 12.08 (brs, 1H), 8.41-8.36 (m, 1H), 7.87 (s, 1H), 7.72 (m, 1H), 7.30-7.20 (m, 1H), 6.60-6.50 (m, 1H), 6.20-6.10 (m, 1H), 5.66-5.62 (m, 1H), 4.25-4.15 (m, 1H), 3.75-3.50 (m, 7H), 3.40-3.10 (m, 4H), 2.66-2.40 (m, 1H), 2.08-1.95 (m, 1H), 1.78-1.60 (m, 1H), 1.18 (d, 3H). Rt=4.22 minutes; 99% de; MS m/z 409 [M+Na]$^+$ Second Eluting Isomer: Example 18

2-({[(3R)-1-acryloylpyrrolidin-3-yl]methyl}amino)-N-[(2S)-1-methoxypropan-2-yl]-5H-pyrrolo[2,3-b]pyrazine-7-carboxamide. $^1$H NMR (400 MHz, DMSO-d$_6$): δ ppm 12.06 (brs, 1H), 8.42-8.38 (m, 1H), 7.86 (s, 1H), 7.72 (m, 1H), 7.25-7.23 (m, 1H), 6.57-6.52 (m, 1H), 6.14-6.09 (m, 1H), 5.66-5.62 (m, 1H), 4.21-4.18 (m, 1H), 3.67-3.17 (m, 10.5H), 2.67-2.50 (m, 1.5H), 2.08-1.98 (m, 1H), 1.78-1.60 (m, 1H), 1.18 (d, 3H). Rt=4.63 minutes, 98% de; MS m/z 409 [M+Na]$^+$

Example 19

Racemic-2-{[(1-acryloylpyrrolidin-3-yl)methyl]amino}-N-(2R)-(1-methoxypropan-2-yl)-5H-pyrrolo[2,3-b]pyrazine-7-carboxamide The title compound was prepared and purified according to the method described for Example 1 Steps 5-7 using racemic-tert-butyl 3-{[(7-[((R)-1-methoxypropan-2-yl)carbamoyl]-5-{[2-(trimethylsilyl)ethoxy]methyl}-5H-pyrrolo[2,3-b]pyrazin-2-yl)amino]methyl}pyrrolidine-1-carboxylate (Example 19 Step 4). The residue was purified by silica gel column chromatography eluting with 5% MeOH in DCM followed by preparative HPLC using a gradient of from 15-35% MeCN in water, both mobile phases modified with ammonia (pH=10).

MS m/z 409 [M+Na]$^+$

The racemic material was separated into its enantiomers using preparative chiral column chromatography according to the conditions described below;
Column: AD (250×30 mm), 5 micron; Mobile phase: 30% IPA in NH$_3$/H$_2$O
Flow rate: 60 mL/min
QC Analytical LCMS Method:
Column: Chiralcel OD-H (250×4.6 mm, 5 micron)

Mobile phase: A/B=75/25 A: Hexane with 0.1% DEA, B: Ethanol; Flow rate: 0.5 mL/min The two enantiomers were arbitrarily assigned absolute stereochemistry:

First Eluting Isomer: Example 20

2-({[(3S)-1-acryloylpyrrolidin-3-yl]methyl}amino)-N-[(2R)-1-methoxypropan-2-yl]-5H-pyrrolo[2,3-b]pyrazine-7-carboxamide. $^1$H NMR (400 MHz, DMSO-$d_6$): δ ppm 12.08 (brs, 1H), 8.41-8.36 (m, 1H), 7.86 (s, 1H), 7.72 (s, 1H), 7.22-7.21 (m, 1H), 6.57-6.49 (m, 1H), 6.13-6.08 (m, 1H), 5.66-5.62 (m, 1H), 4.25-4.15 (m, 1H), 3.80-3.20 (m, 11H), 2.70-2.40 (m, 1H), 2.08-1.98 (m, 1H), 1.98-1.75 (m, 1H), 1.18 (d, 3H). Rt=26.79 minutes, 98% de; MS m/z 409 [M+Na]$^+$ Second Eluting Isomer: Example 21

2-({[(3R)-1-acryloylpyrrolidin-3-yl]methyl}amino)-N-[(2R)-1-methoxypropan-2-yl]-5H-pyrrolo[2,3-b]pyrazine-7-carboxamide. $^1$H NMR (400 MHz, DMSO-$d_6$): δ ppm 12.08 (br s, 1H), 8.42-8.38 (m, 1H), 7.87 (s, 1H), 7.72 (s, 1H), 7.25-7.24 (m, 1H), 6.60-6.50 (m, 1H), 6.13-6.09 (m, 1H), 5.66-5.63 (m, 1H), 4.25-4.15 (m, 1H), 3.75-3.15 (m, 11H), 2.67-2.50 (m, 1H), 2.08-1.98 (m, 1H), 1.98-1.75 (m, 1H), 1.18 (d, 3H). Rt=30.55 minutes, 89% de; MS m/z 409 [M+Na]$^+$ Example 22

Cis-racemic 2-{[1-acryloyl-2-methylpiperidin-4-yl]amino}-N-(3,3,3-trifluoropropyl)-5H-pyrrolo[2,3-b]pyrazine-7-carboxamide The title compound was prepared and purified according to the method described for Example 1 Steps 5-7 using cis-racemic-tert-butyl 2-methyl-4-[(7-[(3,3,3-trifluoropropyl)carbamoyl]-5-{[2-(trimethylsilyl)ethoxy]methyl}-5H-pyrrolo[2,3-b]pyrazin-2-yl)amino]piperidine-1-carboxylate (Example 22 Step 4). The residue was purified by silica gel column chromatography eluting with 0-10% MeOH in DCM followed by preparative HPLC using a gradient of from 27-47% MeCN in water, both mobile phases modified with ammonia (pH=10).

$^1$H NMR (400 MHz, DMSO-$d_6$): δ ppm 12.17 (br s, 1H), 8.40-8.37 (m, 1H), 7.92 (s, 1H), 7.97 (s, 1H), 7.09-7.07 (m, 1H), 6.82-6.75 (m, 1H), 6.14-6.09 (m, 1H), 5.68-5.65 (m, 1H), 4.40-4.38 (m, 1H), 4.10-4.00 (m, 2H), 3.64-3.58 (m, 2H), 3.35-3.33 (m, 1H), 2.60-2.56 (m, 2H), 1.99-1.90 (m, 3H), 1.77-1.76 (m, 1H), 1.22 (d, 3H).

The cis-racemic material was separated into its enantiomers using preparative chiral column chromatography according to the conditions described below;

Column: IC (250×50 mm), 10 micron; Mobile phase: 45% EtOH in NH$_3$/H$_2$O

Flow rate: 80 mL/min

QC Analytical SFC Method:

Column: IC-3 (150×4.6 mm, 3 micron); Mobile phase: 40% EtOH with 0.05% DEA in CO$_2$ Flow rate: 2.35 mL/min QC Analytical LC/MS Method:

Column: Ultimate XB-C18, 3 um, 3×50 mm; Rt=3.59 min. Mobile phase: 1% AcCN/H2O (0.1% TFA) to 100% AcCN/H2O (0.1% TFA); λ=220 nM The two enantiomers were arbitrarily assigned absolute stereochemistry Example 23

2-{[(2R,4R)-1-acryloyl-2-methylpiperidin-4-yl]amino}-N-(3,3,3-trifluoropropyl)-5H-pyrrolo[2,3-b]pyrazine-7-carboxamide. $^1$H NMR (400 MHz, DMSO-$d_6$): δ ppm 12.17 (brs, 1H), 8.40-8.37 (m, 1H), 7.92 (s, 1H), 7.97 (s, 1H), 7.09-7.07 (m, 1H), 6.82-8.75 (m, 1H), 6.14-6.09 (m, 1H), 5.68-5.65 (m, 1H), 4.40-4.38 (m, 1H), 4.10-4.00 (m, 2H), 3.64-3.58 (m, 2H), 3.35-3.33 (m, 1H), 2.60-2.56 (m, 2H), 1.99-1.90 (m, 3H), 1.77-1.76 (m, 1H), 1.22 (d, 3H).

Chiral SFC analysis: Rt=3.63, >98% ee, SFC; MS m/z 447 (M+Na)$^+$

Example 24

2-{[(2R,4R)-1-acryloyl-2-methylpiperidin-4-yl]amino}-N-(3,3,3-trifluoropropyl)-5H-pyrrolo[2,3-b]pyrazine-7-carboxamide. $^1$H NMR (400 MHz, DMSO-$d_6$): δ ppm 12.17 (brs, 1H), 8.40-8.37 (m, 1H), 7.92 (s, 1H), 7.97 (s, 1H), 7.09-7.07 (m, 1H), 6.82-8.75 (m, 1H), 6.14-6.09 (m, 1H), 5.68-5.65 (m, 1H), 4.40-4.38 (m, 1H), 4.10-4.00 (m, 2H), 3.64-3.58 (m, 2H), 3.35-3.33 (m, 1H), 2.60-2.56 (m, 2H), 1.99-1.90 (m, 3H), 1.77-1.76 (m, 1H), 1.22 (d, 3H).

Chiral SFC analysis: Rt=6.02, >98% ee, SFC; MS m/z 447 (M+Na)$^+$

Example 25

Trans-racemic-2-{[1-acryloyl-3-methoxypiperidin-4-yl]amino}-N-ethyl-5H-pyrrolo[2,3-b]pyrazine-7-carboxamide The title compound was prepared and purified according to the method described for Example 1 Steps 5-7 using trans-racemic-tert-butyl 4-{[7-(ethylcarbamoyl)-5-{[2-(trimethylsilyl)ethoxy]methyl}-5H-pyrrolo[2,3-b]pyrazin-2-yl]amino}-3-methoxypiperidine-1-carboxylate (Example 25 Step 4). The residue was purified by silica gel column chromatography eluting with 2-10% MeOH in DCM followed by preparative HPLC using a gradient of from 14-34% MeCN in water, both mobile phases modified with ammonia (pH=10).

$^1$H NMR (400 MHz, MeOH-$d_4$): δ ppm 8.63 (br s, 1H), 7.93 (s, 1H), 7.80 (s, 1H), 6.88-6.80 (m, 1H), 6.27-6.22 (m, 1H), 5.80-5.77 (m, 1H), 4.20-4.05 (m, 1.5H), 3.90-3.45 (m, 9.5H), 2.28-2.17 (m, 1H), 1.66-1.64 (m, 1H), 1.38-1.30 (m, 3H).

MS m/z 373 [M+H]$^+$

The trans-racemic material was separated into its enantiomers using preparative chiral column chromatography according to the conditions described below; Column: OD (250×30 mm), 10 micron; Mobile phase: 50% EtOH in NH$_3$/H$_2$O Flow rate: 80 mL/min QC Analytical LCMS Method:

Column: Chiralcel OD-H (150×4.6 mm, 5 micron); Mobile phase: 40% MeOH with 0.05% DEA in CO$_2$;

Flow rate: 2.35 mL/min

The two isomers were arbitrarily assigned absolute stereochemistry

First Eluting Isomer: Example 26

2-{[(3R,4R)-1-acryloyl-3-methoxypiperidin-4-yl]amino}-N-ethyl-5H-pyrrolo[2,3-b]pyrazine-7-carboxamide. Rt=2.57 minutes, 100% de; MS m/z 373 [M+H]$^+$ Second Eluting Isomer: Example 27

2-{[(3S,4S)-1-acryloyl-3-methoxypiperidin-4-yl]amino}-N-ethyl-5H-pyrrolo[2,3-b]pyrazine-7-carboxamide. Rt=5.28 minutes, 99% de, MS m/z 395 [M+Na]$^+$ Example 28

Racemic-2-[(1-acryloylpyrrolidin-3-yl)(methyl)amino]-N-ethyl-5H-pyrrolo[2,3-b]pyrazine-7-carboxamide The title compound was prepared and purified according to the method described for Example 1 Steps 5-7 using racemic-tert-butyl 3-{[7-(ethylcarbamoyl)-5-{[2-(tri-methylsilyl)ethoxy]methyl}-5H-pyrrolo[2,3-b]pyrazin-2-yl](methyl)amino}pyrrolidine-1-carboxylate (Example 28 Step 4). The residue was purified by silica gel column chromatography eluting with 5% MeOH in DCM followed by preparative HPLC using a gradient of from 19-39% MeCN in water, both mobile phases modified with ammonia (pH=10).
$^1$H NMR (400 MHz, DMSO-d$_6$): δ ppm 12.20 (br s, 1H), 8.11-8.02 (m, 3H), 6.67-6.59 (m, 1H), 6.18-6.12 (m, 1H), 5.71-5.65 (m, 1H), 5.13-5.02 (m, 1H), 3.91-3.40 (m, 4H), 3.40-3.30 (m, 2H), 3.02 (s, 3H), 2.20-2.10 (m, 2H), 1.14 (t, 3H). MS m/z 343 [M+H]$^+$ The racemic material was separated into its enantiomers using preparative chiral column chromatography according to the conditions described below;
Column: AS (250×30 mm), 5 micron; Mobile phase: 35% EtOH in NH$_3$/H$_2$O
Flow rate: 50 mL/min
QC Analytical LCMS Method:
Column: Chiralpak AS-H (250×4.6 mm, 5 micron); Mobile phase: 5-40% EtOH with 0.05% DEA in CO$_2$;
Flow rate: 2.35 mL/min
The two isomers were arbitrarily assigned absolute stereochemistry First Eluting Isomer: Example 29

2-{[(3R)-1-acryloylpyrrolidin-3-yl](methyl)amino}-N-ethyl-5H-pyrrolo[2,3-b]pyrazine-7-carboxamide. Rt=8.02 minutes MS m/z 343 [M+H]$^+$ Second Eluting Isomer: Example 30

2-{[(3S)-1-acryloylpyrrolidin-3-yl](methyl)amino}-N-ethyl-5H-pyrrolo[2,3-b]pyrazine-7-carboxamide. Rt=8.32 minutes MS m/z 343 [M+H]$^+$ Example 31

Trans-racemic-2-{[(3S,4S)-1-acryloyl-3-hydroxypiperidin-4-yl]amino}-N-ethyl-5H-pyrrolo[2,3-b]pyrazine-7-carboxamide The title compound was prepared and purified according to the method described for Example 1 Steps 5-7 using trans-racemic-tert-butyl 4-{[7-(ethylcarbamoyl)-5-{[2-(trimethylsilyl)ethoxy]methyl}-5H-pyrrolo[2,3-b]pyrazin-2-yl]amino}-3-hydroxypiperidine-1-carboxylate (Example 31 Step 4). The residue was purified using silica gel column chromatography eluting with 0-10% MeOH in DCM followed by preparative HPLC using a gradient of from 6-26% MeCN in water, both mobile phases modified with ammonia (pH=10) using Kromasil Eternity XT18 (250×21.2 mm), 10 micron).
$^1$H NMR (400 MHz, DMSO-d$_6$): δ ppm 12.06 (br s, 1H), 8.20-8.17 (m, 1H), 7.87 (s, 1H), 7.76-7.75 (m, 1H), 7.01-6.96 (m, 1H), 6.84-6.80 (m, 1H), 6.13-6.08 (m, 1H), 5.69-5.66 (m, 1H), 5.17-5.15 4.37-4.35 (m, 0.5H), 4.00-3.75 (m, 3H), 3.60-3.20 (m, 5H), 2.80-2.75 (m, 0.5H), 2.30-2.10 (m, 1H), 1.40-1.30 (m, 1H), 1.19 (t, 3H). MS m/z 359 [M+H]$^+$
The racemic material was separated into its enantiomers using preparative chiral column chromatography according to the conditions described below;
Column: OJ (200×30 mm), 5 micron. Mobile phase: 20% EtOH in NH$_3$/H$_2$O
Flow rate: 60 mL/min
QC Analytical LCMS Method:
Column: Chiralcel OJ-H (250×4.6 mm, 5 micron); Mobile phase: 5-40% MeOH with 0.05% DEA in CO$_2$; Flow rate: 2.5 mL/min
The two isomers were arbitrarily assigned absolute stereochemistry First Eluting Isomer: Example 32

2-{[(3S,4S)-1-acryloyl-3-hydroxypiperidin-4-yl]amino}-N-ethyl-5H-pyrrolo[2,3-b]pyrazine-7-carboxamide. Rt=6.93 minutes MS m/z 359 [M+H]$^+$ Second Eluting Isomer: Example 33

2-{[(3R,4R)-1-acryloyl-3-hydroxypiperidin-4-yl]amino}-N-ethyl-5H-pyrrolo[2,3-b]pyrazine-7-carboxamide. Rt=7.43 minutes MS m/z 359 [M+H]$^+$ Example 34

Racemic-2-[(1-acryloylpiperidin-3-yl)amino]-N-ethyl-5H-pyrrolo[2,3-b]pyrazine-7-carboxamide The title compound was prepared and purified according to the method described for Example 1 Steps 5-7 using racemic-tert-butyl 3-{[7-(ethylcarbamoyl)-5-{[2-(trimethylsilyl)ethoxy]methyl-5H}-pyrrolo[2,3-b]pyrazin-2-yl]amino}piperidine-1-carboxylate (Example 34 Step 4). The residue was purified using silica gel column chromatography eluting with 0-11% MeOH in DCM. $^1$H NMR (400 MHz, DMSO-d$_6$): δ ppm 12.09 (br s, 1H), 8.19-8.05 (m, 1H), 7.91 (s, 1H), 7.77-7.74 (m, 1H), 7.10-7.00 (m, 1H), 6.91-6.85 (m, 1H), 6.59-6.54 (m, 0.5H), 6.17-6.07 (m, 1H), 5.72-5.52 (m, 1.5H), 4.77-4.75 (m, 1H), 3.98-3.80 (m, 3H), 3.19-3.16 (m, 1H), 2.09-2.06 (m, 1H), 1.84-1.83 (m, 1H), 1.63-1.51 (m, 2H), 1.15-1.12 (m, 3H).
The racemic material was separated into its enantiomers using preparative chiral column chromatography.
SFC separation condition:
Column: OJ (250×30 mm, 5 um); Mobil Phase 25% EtOH/NH3/H2O; Flow rate=60 mL/min.
Prep HPLC:
Column: Kromasil Eternity XT C18 25*21.2*10 μm
Mobile Phase: 10% MeCN to 30% MeCN/H2O (0.225% FA)

LC/MS Analysis:
Column: UltimateXB-C18, 3 μm, 3*50 mm, Rt=3.38 min
Mobile Phase 1% MeCN/H2O to 100% MeCN/H$_2$O (0.1% TFA); A=220 nm
Chiral SFC Analysis:
Column: Chiralpak AS-H 250*4.mm, ID 5 μM; Rt=6.92
Mobile Phase: EtOH (0.05% DEA) in CO2 from 5% to 40%; Flow rate: 2.35 mL/min; λ=220 nm
The two isomers were arbitrarily assigned absolute stereochemistry.

Example 35

2-{[(3R)-1-acryloylpiperidin-3-yl]amino}-N-ethyl-5H-pyrrolo[2,3-b]pyrazine-7-carboxamide 1H NMR as above. Rt (chiral SFC)=6.92; Rt (LC)=3.38; MS m/z 365 (M+Na)$^+$ Example 36

2-{[(3S)-1-acryloylpiperidin-3-yl]amino}-N-ethyl-5H-pyrrolo[2,3-b]pyrazine-7-carboxamide 1H NMR as above. Rt (chiral SFC)=7.81 Rt (LC)=3.38; MS m/z 365 (M+Na)$^+$ Example 37

Cis-racemic-2-{[(3S,4R)-1-acryloyl-3-methylpiperidin-4-yl]amino}-N-ethyl-5H-pyrrolo[2,3-b]pyrazine-7-carboxamide The title compound was prepared and purified according to the method described for Example 1 Steps 5-7 using cis-racemic-tert-butyl 4-{[7-(ethylcarbamoyl)-5-{[2-(trimethylsilyl)ethoxy]methyl}-5H-pyrrolo[2,3-b]pyrazin-2-yl]amino}-3-methylpiperidine-1-carboxylate (Example 37 Step 4). The residue was purified using silica gel column chromatography eluting with 2-10% MeOH in DCM followed by preparative HPLC eluting with 19-39% MeCN in water modified with 0.05% ammonia. $^1$H NMR (400 MHz, DMSO-d$_6$): δ ppm 12.07 (br s, 1H), 8.20-8.17 (m, 1H), 7.87 (s, 1H), 7.72 (s, 1H), 6.99-6.82 (m, 2H), 6.14-6.10 (m, 1H), 5.70-5.67 (m, 1H), 4.39-4.37 (m, 1H), 4.12-4.09 (m, 1H), 3.71-3.68 (m, 1H), 3.41-3.16 (m, 3H), 2.97-2.83 (m, 1H), 2.14-2.10 (m, 1H), 1.64-1.62 (m, 1H), 1.31-1.18 (m, 4H), 0.98 (d, 3H).
MS m/z 357 [M+H]$^+$
The cis-racemic material was separated into its enantiomers using preparative chiral column chromatography according to the conditions described below;
Column: OD (250×30 mm), 5 micron; Mobile phase: 40% EtOH in NH$_3$/H$_2$O in supercritical CO$_2$
Flow rate: 50 mL/min
QC Analytical LCMS Method:
Column: Chiralpak AS-H (250×4.6 mm, 5 micron); Mobile phase: 5-40% MeOH with 0.05% DEA in CO$_2$; Flow rate: 2.35 mL/min
The two isomers were arbitrarily assigned absolute stereochemistry First Eluting Isomer: Example 38

2-{[(3S,4R)-1-acryloyl-3-methylpiperidin-4-yl]amino}-N-ethyl-5H-pyrrolo[2,3-b]pyrazine-7-carboxamide.
Rt=5.99 minutes MS m/z 357 [M+H]$^+$ Second Eluting Isomer: Example 39

2-{[(3R,4S)-1-acryloyl-3-methylpiperidin-4-yl]amino}-N-ethyl-5H-pyrrolo[2,3-b]pyrazine-7-carboxamide.
Rt=6.47 minutes. MS m/z 357 [M+H]$^+$ Example 40

Trans-racemic-2-{[(2R,4S)-1-acryloyl-2-methylpiperidin-4-yl]amino}-N-ethyl-5H-pyrrolo[2,3-b]pyrazine-7-carboxamide The title compound was prepared and purified according to the method described for Example 1 Steps 5-7 using trans-racemic-tert-butyl 4-{[7-(ethylcarbamoyl)-5-{[2-(trimethylsilyl)ethoxy]methyl}-5H-pyrrolo[2,3-b]pyrazin-2-yl]amino}-2-methylpiperidine-1-carboxylate (Example 40 Step 4). The residue was purified using silica gel column chromatography eluting with 0-12% MeOH in DCM.
$^1$H NMR (400 MHz, DMSO-d$_6$): δ ppm 12.08 (br s, 1H), 8.18-8.15 (m, 1H), 7.88 (s, 1H), 7.68 (m, 1H), 6.93-6.79 (m, 2H), 6.11-6.07 (m, 1H), 5.67-5.64 (m, 1H), 4.91 (br s, 0.5H), 4.49-4.44 (br m, 1H), 4.25-4.17 (m, 1H), 4.05-3.95 (m, 0.5H), 3.42-3.39 (m, 2.5H), 2.95-2.85 (m, 0.5H), 2.11-1.97 (m, 2H), 1.50-1.16 (m, 8H).
The trans-racemic material was separated into its enantiomers using preparative chiral column chromatography according to the conditions described below;
Column: OJ (250×30 mm), 20 micron
Mobile phase: 35% MeOH in NH$_3$/H$_2$O; Flow rate: 80 mL/min
QC Analytical LCMS Method:
Column: Chiralcel OJ-H (250×4.6 mm, 5 micron); Mobile phase: 5-40% MeOH with 0.05% DEA in CO$_2$; Flow rate: 2.5 mL/min
The two isomers were arbitrarily assigned absolute stereochemistry First Eluting Isomer: Example 41

2-{[(2R,4S)-1-acryloyl-2-methylpiperidin-4-yl]amino}-N-ethyl-5H-pyrrolo[2,3-b]pyrazine-7-carboxamide.
Rt=6.83 minutes MS m/z 357 [M+H]$^+$ Second Eluting Isomer: Example 42

2-{[(2S,4R)-1-acryloyl-2-methylpiperidin-4-yl]amino}-N-ethyl-5H-pyrrolo[2,3-b]pyrazine-7-carboxamide.
Rt=7.83 minutes MS m/z 357 [M+H]$^+$ Example 43

Trans-racemic-2-{[(3R,4R)-1-acryloyl-3-methylpiperidin-4-yl]amino}-N-ethyl-5H-pyrrolo[2,3-b]pyrazine-7-carboxamide The title compound was prepared and purified according to the method described for Example 1 Steps 5-7 using trans-racemic-tert-butyl 4-{[7-(ethylcarbamoyl)-5-{[2-(trimethylsilyl)ethoxy]methyl}-5H-pyrrolo[2,3-b]pyrazin-2-yl]amino}-3-methylpiperidine-1-carboxylate (Example 43 Step 4). The residue was purified using silica gel column chromatography eluting with 7% MeOH in EtOAc followed by preparative HPLC eluting with 25-45% MeCN in water modified with ammonia to pH=10. $^1$H NMR (400 MHz, DMSO-d$_e$): δ ppm 12.06 (br s, 1H), 8.17-8.15 (m, 1H), 7.87 (s, 1H), 7.81-7.79 (m, 1H), 6.98-6.96 (m, 1H), 6.87-6.81 (m, 1H), 6.13-6.08 (m, 1H), 5.68-5.65 (m, 1H), 4.20-4.10 (m, 1.5H), 3.82-3.78 (m, 1.5H), 3.45-3.16 (m, 4H), 2.33-2.30 (m, 1H), 1.77-1.67 (m, 2H), 1.20-1.17 (m, 3H), 0.85-0.81 (m, 3H).
MS m/z 357 [M+H]$^+$ The trans-racemic material was separated into its enantiomers using preparative chiral column chromatography according to the conditions described below;

Column: OD (250×30 mm), 10 micron; Mobile phase: 50% MeOH in NH$_3$/H$_2$O

Flow rate: 70 mL/min

QC Analytical LCMS Method:

Column: Chiralcel OD-H (250×4.6 mm, 5 micron); Mobile phase: 40% MeOH with 0.05% DEA in CO$_2$;

Flow rate: 2.35 mL/min

The two isomers were arbitrarily assigned absolute stereochemistry

First Eluting Isomer: Example 44

2-{[(3R,4R)-1-acryloyl-3-methylpiperidin-4-yl]amino}-N-ethyl-5H-pyrrolo[2,3-b]pyrazine-7-carboxamide. Rt=4.24 minutes MS m/z 357 [M+H]$^+$ Second Eluting Isomer: Example 45

2-{[(3S,4S)-1-acryloyl-3-methylpiperidin-4-yl]amino}-N-ethyl-5H-pyrrolo[2,3-b]pyrazine-7-carboxamide. Rt=6.76 minutes MS m/z 357 [M+H]$^+$ Example 46

Trans-racemic-2-{[1-acryloyl-3-methylpiperidin-4-yl]oxy}-N-ethyl-5H-pyrrolo[2,3-b]pyrazine-7-carboxamide The title compound was prepared and purified according to the method described for Example 1 Steps 5-7 using trans-racemic-tert-butyl 4-{[7-(ethylcarbamoyl)-5-{[2-(trimethylsilyl)ethoxy]methyl}-5H-pyrrolo[2,3-b]pyrazin-2-yl]oxy}-3-methylpiperidine-1-carboxylate (Example 46 Step 4). The residue was purified using silica gel column chromatography eluting with 0-30% MeOH in DCM followed by preparative HPLC eluting with 26-46% MeCN in water with ammonia to pH=10. $^1$H NMR (400 MHz, DMSO-d$_6$): δ ppm 12.53 (br s, 1H), 8.25 (s, 1H), 8.13 (s, 1H), 7.82-7.79 (m, 1H), 6.93-6.82 (m, 1H), 6.15-6.11 (m, 1H), 5.71-5.68 (m, 1H), 5.00-4.94 (m, 1H), 4.24-4.19 (m, 1H), 4.03-3.99 (m, 1H), 3.47-3.42 (m, 3.5H), 3.17-3.14 (m, 1H), 2.86-2.84 (m, 0.5H), 2.29-2.26 (m, 1H), 2.00-1.80 (m, 1H), 1.60-1.40 (m, 1H), 1.23 (t, 3H), 1.00 (t, 3H). MS m/z 380 [M+Na]$^+$ The trans-racemic material was separated into its enantiomers using preparative chiral column chromatography according to the conditions described below;

Column: Chiralcel-OD (250×30 mm), 10 micron; Mobile phase: 35% EtOH in NH/H$_2$O Flow rate: 70 mL/min QC Analytical LCMS Method:

Column: Chiralcel OD-3 (150×4.6 mm, 5 micron); Mobile phase: 5-40% MeOH with 0.05% DEA in CO$_2$; Flow rate: 2.5 mL/min The two enantiomers were arbitrarily assigned absolute stereochemistry First Eluting Isomer: Example 47

2-{[(3R,4R)-1-acryloyl-3-methylpiperidin-4-yl]oxy}-N-ethyl-5H-pyrrolo[2,3-b]pyrazine-7-carboxamide. Rt=6.75 minutes MS m/z 380 [M+Na]$^+$ Second Eluting Isomer: Example 48

2-{[(3S,4S)-1-acryloyl-3-methylpiperidin-4-yl]oxy}-N-ethyl-5H-pyrrolo[2,3-b]pyrazine-7-carboxamide. Rt=7.57 minutes MS m/z 380 [M+Na]$^+$ The following Examples were prepared according to the methods described for Example 1 Steps 5-7 using the appropriate pyrrolopyrazine. The steps may be carried out in any order to maximize yield.

Prep HPLC Method A:

Column: Kromasil Eternity XT C18 250×21.2 mm, 10 micron.

Mobile phase: From 9-29% MeCN in water, both mobile phases modified with 0.05% ammonia QC Analytical LCMS Method:

Column: Xterra, 4.6×150 mm, 3.5 micron

Mobile phase: From 0-60% MeCN in 20 mM ammonium carbonate in water, over 10 minutes, hold at 60% for 5 minutes, flow rate 1 mL/min.

Purification Method B:

Silica gel column chromatography eluting with 7% MeOH in EtOAc followed by preparative HPLC eluting with 20-40% MeCN in water modified with ammonia to pH=10.

| Example | Name/Structure | SM | Data |
|---|---|---|---|
| 49 | 2-{[(3R)-1-acryloylpiperidin-3-yl]oxy}-N-[(2S)-1-methoxypropan-2-yl]-5H-pyrrolo[2,3-b]pyrazine-7-carboxamide | tert-butyl (R)-3-[(7-[((S)-1-methoxypropan-2-yl)carbamoyl]-5-{[2-(trimethylsilyl)ethoxy]methyl}-5H-pyrrolo[2,3-b]pyrazin-2-yl)oxy]piperidine-1-carboxylate (Example 49 Step 4). | $^1$H NMR (400 MHz, DMSO-d$_6$): δ ppm 12.58 (br s, 1H), 8.20 (s, 1H), 8.03-7.92 (m, 2H), 6.87-6.83 (m, 0.5H), 6.55-6.53 (m, 0.5H), 6.09-5.99 (m, 1H), 5.70-5.67 (m, 0.5H), 5.48-5.46 (m, 0.5H), 5.18-5.10 (m, 1H), 4.22-4.19 (m, 2H), 3.99-3.96 (m, 0.5H), 3.80-3.75 (m, 1.5H), 3.75-3.70 (m, 0.5H), 3.42-3.29 (m, 5.5H), 2.12-1.75 (m, 3H), 1.60-1.50 (br m, 1H), 1.20 (d, 3H). 25-45% MeCN in water (with ammonia pH = 10). Rt = 3.49 minutes MS m/z 410 [M + Na]$^+$ |

| Example | Name/Structure | SM | Data |
|---|---|---|---|
| 50 | 2-{[(3S)-1-acryloylpiperidin-3-yl]oxy}-N-[(2S)-1-methoxypropan-2-yl]-5H-pyrrolo[2,3-b]pyrazine-7-carboxamide | tert-butyl (S)-3-[(7-[((S)-1-methoxypropan-2-yl)carbamoyl]-5-{[2-(trimethylsilyl)ethoxy]methyl}-5H-pyrrolo[2,3-b]pyrazin-2-yl)oxy]piperidine-1-carboxylate (Example 50 Step 4). | $^1$H NMR (400 MHz, DMSO-$d_6$): δ ppm 12.58 (br s, 1H), 8.20 (s, 1H), 8.05-7.93 (m, 2H), 6.90-6.86 (m, 0.5H), 6.58-6.57 (m, 0.5H), 6.09-6.00 (m, 1H), 5.70-5.67 (m, 0.5H), 5.50-5.48 (m, 0.5H), 5.14-5.08 (m, 1H), 4.24-4.22 (m, 1H), 4.01-3.96 (m, 1H), 3.80-3.70 (m, 2H), 3.43-3.28 (m, 6H), 2.18-2.12 (m, 1H), 1.95-1.75 (m, 2H), 1.58-1.50 (m, 1H), 1.58-1.50 (br m, 1H), 1.20 (m, 3H). 23-43% MeCN in water (with ammonia pH = 10). Rt = 3.53 minutes MS m/z 410 [M + Na]$^+$ |
| 51 | Racemic-2-[(1-acryloylpiperidin-3-yl)oxy]-N-[(2S)-1-methoxypropan-2-yl]-5H-pyrrolo[2,3-b]pyrazine-7-carboxamide | Racemic-tert-butyl-3-[(7-[((S)-1-methoxypropan-2-yl)carbamoyl]-5-{[2-(trimethylsilyl)ethoxy]methyl}-5H-pyrrolo[2,3-b]pyrazin-2-yl)oxy]piperidine-1-carboxylate (Example 51 Step 4). | $^1$H NMR (400 MHz, DMSO-$d_6$): δ ppm 12.59 (br s, 1H), 8.20 (s, 1H), 8.05-7.93 (m, 2H), 6.88-6.87 (m, 0.5H), 6.57-6.55 (m, 0.5H), 6.11-6.00 (m, 1H), 5.70-5.68 (m, 0.5H), 5.48-5.45 (m, 0.5H), 5.15-5.09 (m, 1H), 4.22-4.19 (m, 1H), 3.99-3.70 (m, 4H), 3.42-3.29 (m, 5H), 2.14-1.70 (m, 3H), 1.57-1.50 (m, 1H), 1.20 (d, 3H). Rt = 3.95 minutes MS m/z 410 [M + Na]$^+$ |
| 52 | 2-{[(3S)-1-acryloylpyrrolidin-3-yl]oxy}-N-[(2S)-1-methoxypropan-2-yl]-5H-pyrrolo[2,3-b]pyrazine-7-carboxamide | tert-butyl (S)-3-[(7-[((S)-1-methoxypropan-2-yl)carbamoyl]-5-{[2-(trimethylsilyl)ethoxy]methyl}-5H-pyrrolo[2,3-b]pyrazin-2-yl)oxy]pyrrolidine-1-carboxylate (Example 52 Step 4). | $^1$H NMR (400 MHz, MeOH-$d_4$): δ ppm 8.53-8.48 (m, 1H), 8.14 (s, 1H), 7.99 (s, 1H), 6.71-6.57 (m, 1H), 6.32-6.28 (m, 1H), 5.79-5.72 (m, 2H), 4.40-4.30 (m, 1H), 4.10-3.75 (m, 4H), 3.80-3.53 (m, 3H), 3.31 (s, 3H), 2.45-2.37 (m, 2H), 1.34 (d, 3H). 18-38% MeCN in water (with ammonia pH = 10). MS m/z 396 [M + Na]$^+$ |

| Example | Name/Structure | SM | Data |
|---|---|---|---|
| 53 | 2-{[(3R)-1-acryloylpyrrolidin-3-yl]oxy}-N-[(2S)-1-methoxypropan-2-yl]-5H-pyrrolo[2,3-b]pyrazine-7-carboxamide<br>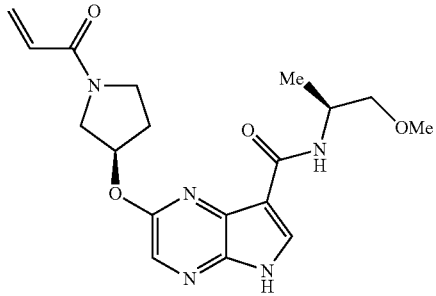 [SMILES: C=CC(=O)N1CC[C@@H](Oc2cnc3[nH]cc(C(=O)N[C@@H](C)COC)c3n2)C1] | tert-butyl (R)-3-[(7-[((S)-1-methoxypropan-2-yl)carbamoyl]-5-{[2-(trimethylsilyl)ethoxy]methyl}-5H-pyrrolo[2,3-b]pyrazin-2-yl)oxy]pyrrolidine-1-carboxylate (Example 53 Step 4). | $^1$H NMR (400 MHz, MeOH-$d_4$): δ ppm 8.53-8.48 (m, 1H), 8.16 (s, 1H), 8.01 (s, 1H), 6.73-6.56 (m, 1H), 6.33-6.29 (m, 1H), 5.81-5.72 (m, 2H), 4.40-4.35 (m, 1H), 4.20-4.15 (m, 0.5H), 4.00-3.80 (m, 3.5H), 3.75-3.65 (m, 0.5H), 3.60-3.50 (m, 2.5H), 3.43 (s, 3H), 2.48-2.40 (m, 2H), 1.38 (d, 3H). 18-38% MeCN in water (with ammonia pH = 10). MS m/z 396 [M + Na]$^+$ |
| 54 | 2-{[(3S)-1-acryloylpyrrolidin-3-yl]oxy}-N-[(2R)-1-methoxypropan-2-yl]-5H-pyrrolo[2,3-b]pyrazine-7-carboxamide<br>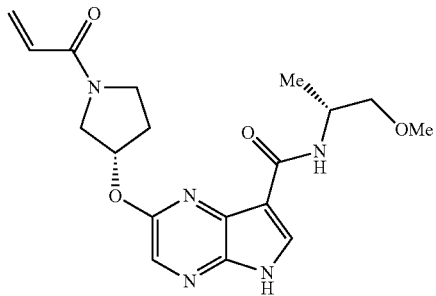 [SMILES: C=CC(=O)N1CC[C@H](Oc2cnc3[nH]cc(C(=O)N[C@H](C)COC)c3n2)C1] | tert-butyl (S)-3-[(7-[((R)-1-methoxypropan-2-yl)carbamoyl]-5-{[2-(trimethylsilyl)ethoxy]methyl}-5H-pyrrolo[2,3-b]pyrazin-2-yl)oxy]pyrrolidine-1-carboxylate (Example 54 Step 4). | $^1$H NMR (400 MHz, MeOH-$d_4$): δ ppm 8.53-8.48 (m, 1H), 8.16 (s, 1H), 8.01 (s, 1H), 6.70-6.58 (m, 1H), 6.34-6.29 (m, 1H), 5.81-5.72 (m, 2H), 4.40-4.30 (m, 1H), 4.20-4.15 (m, 0.5H), 4.00-3.80 (m, 3.5H), 3.75-3.65 (m, 0.5H), 3.60-3.50 (m, 2.5H), 3.43 (s, 3H), 2.50-2.39 (m, 2H), 1.38 (d, 3H). 18-38% MeCN in water (with ammonia pH = 10). MS m/z 396 [M + Na]$^+$ |
| 55 | 2-{[(2S,4S)-1-acryloyl-2-methylpiperidin-4-yl]amino}-N-[(2S)-1-methoxypropan-2-yl]-5H-pyrrolo[2,3-b]pyrazine-7-carboxamide<br>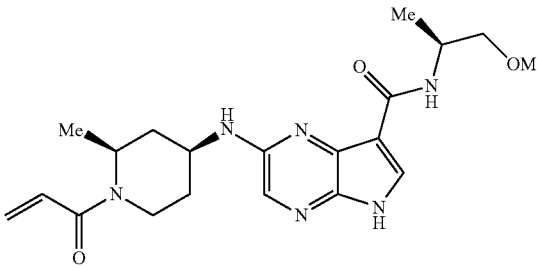 | tert-butyl (2S,4S)-4-[(7-[((S)-1-methoxypropan-2-yl)carbamoyl]-5-{[2-(trimethylsilyl)ethoxy]methyl}-5H-pyrrolo[2,3-b]pyrazin-2-yl)amino]-2-methylpiperidine-1-carboxylate (Example 55 Step 4). | $^1$H NMR (400 MHz, DMSO-$d_6$): δ ppm 12.09 (br s, 1H), 8.30-8.28 (m, 1H), 7.87 (s, 1H), 7.78 (s, 1H), 7.06-7.04 (m, 1H), 6.81-6.75 (m, 1H), 6.13-6.03 (m, 1H), 5.67-5.64 (m, 1H), 4.41-4.40 (m, 1H), 4.20-3.94 (m, 3H), 3.20-3.15 (m, 6H), 2.10-1.90 (m, 3H), 1.80-1.70 (m, 1H), 1.22-1.14 (m, 6H). 24-44% MeCN in water (with ammonia pH = 10). MS m/z 400 [M + Na]$^+$ |

-continued

| Example | Name/Structure | SM | Data |
|---|---|---|---|
| 56 | 2-{[(2R,4R)-1-acryloyl-2-methylpiperidin-4-yl]amino}-N-[(2S)-1-methoxypropan-2-yl]-5H-pyrrolo[2,3-b]pyrazine-7-carboxamide | tert-butyl (2R,4R)-4-[(7-[((S)-1-methoxypropan-2-yl)carbamoyl]-5-{[2-(trimethylsilyl)ethoxy]methyl}-5H-pyrrolo[2,3-b]pyrazin-2-yl)amino]-2-methylpiperidine-1-carboxylate (Example 56 Step 4). | $^1$H NMR (400 MHz, DMSO-$d_6$): δ ppm 12.08 (br s, 1H), 8.39-8.37 (m, 1H), 7.86 (s, 1H), 7.77 (s, 1H), 7.10-7.08 (m, 1H), 6.81-6.75 (m, 1H), 6.13-6.09 (m, 1H), 5.67-5.64 (m, 1H), 4.45-4.40 (m, 1H), 4.20-4.00 (m, 3H), 3.40-3.20 (m, 6H), 2.10-1.70 (m, 4H), 1.21-1.15 (m, 6H). 21-41% MeCN in water (with ammonia pH = 10). MS m/z 423 [M + Na]$^+$ |
| 57 | 2-{[(2S,4S)-1-acryloyl-2-methylpiperidin-4-yl]amino}-N-[(2R)-1-methoxypropan-2-yl]-5H-pyrrolo[2,3-b]pyrazine-7-carboxamide | tert-butyl (2S,4S)-4-[(7-[((R)-1-methoxypropan-2-yl)carbamoyl]-5-{[2-(trimethylsilyl)ethoxy]methyl}-5H-pyrrolo[2,3-b]pyrazin-2-yl)amino]-2-methylpiperidine-1-carboxylate (Example 57 Step 4). | $^1$H NMR (400 MHz, DMSO-$d_6$): δ ppm 11.94 (br s, 1H), 8.39-8.37 (m, 1H), 7.88 (s, 1H), 7.77 (s, 1H), 7.09-7.07 (m, 1H), 6.81-6.75 (m, 1H), 6.13-6.08 (m, 1H), 5.67-5.64 (m, 1H), 4.45-4.40 (m, 1H), 4.20-3.99 (m, 3H), 3.40-3.20 (m, 6H), 2.04-1.75 (m, 4H), 1.21-1.15 (m, 6H). MS m/z 401 [M + H]$^+$ 100% ee. 25-45% MeCN in water (with ammonia pH = 10). |
| 58 | 2-{[(2R,4R)-1-acryloyl-2-methylpiperidin-4-yl]amino}-N-[(2R)-1-methoxypropan-2-yl]-5H-pyrrolo[2,3-b]pyrazine-7-carboxamide | tert-butyl (2R,4R)-4-[(7-[((R)-1-methoxypropan-2-yl)carbamoyl]-5-{[2-(trimethylsilyl)ethoxy]methyl}-5H-pyrrolo[2,3-b]pyrazin-2-yl)amino]-2-methylpiperidine-1-carboxylate (Example 58 Step 4). | $^1$H NMR (400 MHz, DMSO-$d_6$): δ ppm 12.02 (br s, 1H), 8.39-8.37 (m, 1H), 7.88 (s, 1H), 7.77 (s, 1H), 7.08-7.07 (m, 1H), 6.81-6.75 (m, 1H), 6.13-6.08 (m, 1H), 5.67-5.64 (m, 1H), 4.45-4.35 (m, 1H), 4.25-4.00 (m, 3H), 3.40-3.25 (m, 6H), 2.10-1.70 (m, 4H), 1.21-1.15 (m, 6H). MS m/z 401 [M + H]$^+$ 98% ee. 22-42% MeCN in water (with ammonia pH = 10). |
| 59 | 2-{3-[acryloyl(methyl)amino]azetidin-1-yl}-N-ethyl-5H-pyrrolo[2,3-b]pyrazine-7-carboxamide | tert-butyl {1-[7-(ethylcarbamoyl)-5-{[2-(trimethylsilyl)ethoxy]methyl}-5H-pyrrolo[2,3-b]pyrazin-2-yl]azetidin-3-yl}methylcarbamate (Example 59 Step 4). | Rt = 7.50 minutes MS m/z 329 [M + H]$^+$ Using Prep HPLC Method A. $^1$H NMR (400 MHz, DMSO-$d_6$): δ ppm 12.28 (br s, 1H), 8.15-8.13 (m, 1H), 8.05 (s, 1H), 7.73 (s, 1H), 6.82-6.75 (m, 1H), 6.18-6.09 (m, 1H), 5.75-5.72 (m, 1H), 5.34-5.16 (m, 1H), 4.35-4.34 (m, 2H), 4.21-4.13 (m, 2H), 3.40-3.06 (m, 5H), 1.34 (t, 3H). |

| Example | Name/Structure | SM | Data |
|---|---|---|---|
| 60 | 2-[(1-acryloylpiperidin-4-yl)(methyl)amino]-N-ethyl-5H-pyrrolo[2,3-b]pyrazine-7-carboxamide | tert-butyl 4-{[7-(ethylcarbamoyl)-5-{[2-(trimethylsilyl)ethoxy]methyl}-5H-pyrrolo[2,3-b]pyrazin-2-yl](methyl)amino}piperidine-1-carboxylate (Example 60 Step 4). | PM B.<br>¹H NMR (400 MHz, DMSO-d₆): δ ppm 12.15 (br s, 1H), 8.13-8.11 (m, 1H), 8.03 (s, 1H), 7.99 (s, 1H), 6.89-6.82 (m, 1H), 6.14-6.09 (m, 1H), 5.70-5.67 (m, 1H), 4.63-4.55 (m, 1H), 4.23-4.20 (m, 1H), 3.41-3.33 (m, 2H), 3.21-3.15 (m, 1H), 2.94 (s, 3H), 2.77-2.71 (m, 1H), 1.74-1.64 (m, 4H), 1.21-1.18 (m, 3H).<br>MS m/z 357 [M + H]⁺ |
| 61 | 2-[(1-acryloyl-4-methylpiperidin-4-yl)oxy]-N-ethyl-5H-pyrrolo[2,3-b]pyrazine-7-carboxamide | tert-butyl 4-{[7-(ethylcarbamoyl)-5-{[2-(trimethylsilyl)ethoxy]methyl}-5H-pyrrolo[2,3-b]pyrazin-2-yl]oxy}-4-methylpiperidine-1-carboxylate (Example 61 Step 4). | ¹H NMR (400 MHz, DMSO-d₆): δ ppm 12.71 (br s, 1H), 8.20 (s, 1H), 8.01 (s, 1H), 7.73-7.70 (m, 1H), 6.86-6.79 (m, 1H), 6.13-6.08 (m, 1H), 5.69-5.66 (m, 1H), 4.16-4.13 (m, 1H), 3.88-3.85 (m, 1H), 3.31-3.11 (m, 4H), 2.39-2.33 (m, 2H), 1.83-1.68 (m, 5H), 1.22-1.15 (m, 3H).<br>MS m/z 380 [M + Na]⁺<br>31-51% MeCN in water with ammonia to pH = 10. |
| 62 | 1-(4-{[7-(azetidin-1-ylcarbonyl)-5H-pyrrolo[2,3-b]pyrazin-2-yl](methyl)amino}piperidin-1-yl)prop-2-en-1-one | tert-butyl 4-{[7-(azetidin-1-ylcarbonyl)-5-{[2-(trimethylsilyl)ethoxy]methyl}-5H-pyrrolo[2,3-b]pyrazin-2-yl](methyl)amino}piperidine-1-carboxylate (Example 62 Step 4). | ¹H NMR (400 MHz, DMSO-d₆): δ ppm 12.15 (br s, 1H), 7.95-7.94 (m, 2H), 6.90-6.83 (m, 1H), 6.15-6.10 (m, 1H), 5.71-5.68 (m, 1H), 4.70-4.60 (m, 2H), 4.60-4.40 (br m, 2H), 4.22-4.19 (m, 1H), 4.10-3.95 (m, 2H), 3.22-3.18 (m, 1H), 2.91 (s, 3H), 2.80-2.70 (m, 1H), 2.30-2.22 (m, 2H), 1.70-1.63 (m, 4H).<br>MS m/z 369 [M + H]⁺<br>10-30% MeCN in water with ammonia to pH = 10, PM A. |

-continued

| Example | Name/Structure | SM | Data |
|---|---|---|---|
| 63 | 2-(4-acryloyl-3-(methoxymethyl)-3-methylpiperazin-1-yl)-N-((R)-1-methoxypropan-2-yl)-5H-pyrrolo[2,3-b]pyrazine-7-carboxamide | tert-butyl 2-(methoxymethyl)-4-(7-(((R)-1-methoxypropan-2-yl)carbamoyl)-5-((2-(trimethylsilyl)ethoxy)methyl)-5H-pyrrolo[2,3-b]pyrazin-2-yl)-2-methylpiperazine-1-carboxylate (Example 63 Step 4). | $^1$H NMR (400 MHz, DMSO-d$_6$): δ ppm 12.18 (br s, 1H), 8.40-8.37 (m, 1H), 8.00 (s, 1H), 7.91 (s, 1H), 6.81-6.75 (m, 1H), 6.06-6.01 (m, 1H), 5.66-5.63 (m, 1H), 4.18-3.62 (m, 9H), 3.44-3.40 (m, 2H), 3.31 (s, 3H), 3.19 (s, 1H), 1.42 (s, 3H), 1.22 (s, 3H). MS m/z 431 [M + H]$^+$ 20-40% MeCN in water with ammonia to pH = 10. |
| 64 | 2-[(1-acryloylpiperidin-4-yl)(methyl)amino]-N-(propan-2-yl)-5H-pyrrolo[2,3-b]pyrazine-7-carboxamide | tert-butyl 4-((7-(isopropylcarbamoyl)-5-((2-(trimethylsilyl)ethoxy)methyl)-5H-pyrrolo[2,3-b]pyrazin-2-yl)(methyl)amino)piperidine-1-carboxylate (Example 64 Step 4). | $^1$H NMR (400 MHz, DMSO-d$_6$): δ ppm 8.09-8.07 (m, 1H), 8.02 (s, 1H), 7.97 (s, 1H), 6.89-6.82 (m, 1H), 6.14-6.09 (m, 1H), 5.70-5.67 (m, 1H), 4.64-4.56 (m, 2H), 4.24-4.21 (m, 1H), 4.12-4.05 (m, 1H), 3.19-3.16 (m, 1H), 2.92 (s, 3H), 2.74-2.68 (m, 1H), 1.74-1.61 (m, 4H), 1.23 (s, 3H), 1.22 (s, 3H). MS m/z 393 [M + Na]$^+$ 22-42% MeCN in water with ammonia to pH = 10. |

Example 65

Cis-racemic-2-{[1-acryloyl-6-methylpiperidin-3-yl]amino}-N-[(2S)-1-methoxypropan-2-yl]-5H-pyrrolo[2,3-b]pyrazine-7-carboxamide To a solution of cis-racemic-benzyl-5-[(7-[((S)-1-methoxypropan-2-yl)carbamoyl]-5-{[2-(trimethylsilyl)ethoxy]methyl}-5H-pyrrolo[2,3-b]pyrazin-2-yl)amino]-2-methylpiperidine-1-carboxylate (Example 65 Step 4, 620 mg, 1.02 mmol) in MeOH (20 mL) was added palladium on carbon (100 mg) and the reaction was stirred at room temperature under a balloon of hydrogen for 18 hours. Further palladium on carbon (200 mg) was added and the reaction continued at 30° C. for 4 hours. The reaction was filtered through Celite and the filtrate concentrated in vacuo. The residue was dissolved in THF/water (20 mL/5 mL) and treated with DIPEA (262 mg, 2.03 mmol) followed by acryloyl chloride (138 mg, 1.52 mmol) at 0° C. The reaction was stirred at this temperature for 4 hours. Additional acryloyl chloride (46 mg) was added and the reaction stirred at room temperature for 3 hours. The reaction was diluted with EtOAc and concentrated in vacuo. The residue was purified using silica gel column chromatography eluting with 5% MeOH in DCM before dissolving in DCM (15 mL) and treating with TFA (4 mL). The reaction was stirred at room temperature for 5 hours, concentrated in vacuo and dissolved in MeOH. Ammonia (4 mL) was added and the mixture stirred at room temperature for 4 hours. The solution was concentrated in vacuo and purified using silica gel column chromatography eluting with 5% MeOH in DCM to afford the title compound as a yellow solid (230 mg, 73%). $^1$H NMR (400 MHz, DMSO-d$_6$): δ ppm 12.11 (br s, 1H), 8.30-8.10 (br m, 1H), 7.89 (s, 1H), 7.70 (s, 1H), 7.05-7.04 (m, 1H), 6.90-6.60 (m, 1H), 6.11-6.05 (m, 1H), 5.70-5.60 (m, 1H), 4.80-4.60 (m, 1H), 4.50-4.30 (m, 1H), 4.20-3.70 (m, 2H), 3.36-3.22 (m, 3H), 3.00-2.85 (m, 1H), 1.99-1.94 (m, 2H), 1.80-1.55 (m, 4H), 1.30-1.10 (m, 6H). MS m/z 401 [M+H]$^+$ The cis-racemic material was separated into its enantiomers using preparative chiral column chromatography according to the conditions described below;

Column: AD (250×30 mm), 5 micron; Mobile phase: 25% MeOH in NH$_3$/H$_2$O; Flow rate: 60 mL/min QC Analytical LCMS Method:

Column: Chiralpak AD-3 (150×4.6 mm, 3 micron); Mobile phase: 5-40% MeOH with 0.05% DEA in CO$_2$; Flow rate: 2.5 mL/min The two enantiomers were arbitrarily assigned absolute stereochemistry First Eluting Isomer: Example 66

2-{[(3R,6S)-1-acryloyl-6-methylpiperidin-3-yl]amino}-N-[(2S)-1-methoxypropan-2-yl]-5H-pyrrolo[2,3-b]pyrazine-7-carboxamide. Rt=4.64 minutes MS m/z 401 [M+H]$^+$ Second Eluting Isomer: Example 67

2-{[(3S,6R)-1-acryloyl-6-methylpiperidin-3-yl]amino}-N-[(2S)-1-methoxypropan-2-yl]-5H-pyrrolo[2,3-b]pyrazine-7-carboxamide. Rt=4.97 minutes MS m/z 401 [M+H]$^+$ Example 68

Cis-racemic-2-{[1-acryloyl-6-methylpiperidin-3-yl]amino}-N-[(2R)-1-methoxypropan-2-yl]-5H-pyrrolo[2,3-b]pyrazine-7-carboxamide The title compound was prepared according to the method described for Example 65 using cis-racemic-benzyl-5-[(7-[((R)-1-methoxypropan-2-yl)carbamoyl]-5-{[2-(trimethylsilyl)ethoxy]methyl}-5H-pyrrolo[2,3-b]pyrazin-2-yl)amino]-2-methylpiperidine-1-carboxylate (Example 68 Step 4). The residue was purified using silica gel column chromatography eluting with 5% MeOH in DCM followed by preparative HPLC (Phenomenex Gemini C18 (250×21.2, 10 micron), gradient time 10 minutes, flow rate 30 mL/min) using a gradient of 27-57% MeCN in water modified with 0.225% formic acid. $^1$H NMR (400 MHz, DMSO-d$_6$): δ ppm 8.31-8.24 (br m, 1H), 7.93 (s, 1H), 7.72 (s, 1H), 7.06-7.04 (m, 1H), 6.90-6.65 (br m, 1H), 6.15-6.05 (m, 1H), 5.70-5.60 (m, 1H), 4.85-4.60 (m, 1H), 4.50-4.40 (m, 1H), 4.20-3.60 (m, 3H), 3.22 (s, 3H), 3.05-2.60 (m, 2H), 2.05-1.90 (m, 1H), 1.75-1.55 (m, 3H), 1.25-1.05 (m, 6H). MS m/z 423 [M+Na]$^+$ During the purification of the cis-racemic material, the corresponding cis enantiomers were also isolated: SFC analysis: Chiralcel OD-3, 150×4.6 mm, 3 micron Mobile phase: 5-40% MeOH with 0.05% DEA in CO$_2$, flow rate 2.5 mL/min.

The two enantiomers were arbitrarily assigned absolute stereochemistry.

First Eluting Isomer: Example 69

2-{[(3R,6S)-1-acryloyl-6-methylpiperidin-3-yl]amino}-N-[(2R)-1-methoxypropan-2-yl]-5H-pyrrolo[2,3-b]pyrazine-7-carboxamide Rt=7.83 minutes MS m/z 423 [M+H]$^+$ Second Eluting Isomer: Example 70

2-{[(3S,6R)-1-acryloyl-6-methylpiperidin-3-yl]amino}-N-[(2R)-1-methoxypropan-2-yl]-5H-pyrrolo[2,3-b]pyrazine-7-carboxamide Rt=8.69 minutes. MS m/z 423 [M+H]$^+$ Example 71

Trans-racemic-2-{[1-acryloyl-2-methylpiperidin-4-yl]oxy}-N-[(2S)-1-methoxypropan-2-yl]-5H-pyrrolo[2,3-b]pyrazine-7-carboxamide The title compound was prepared according to the method described for Example 65 using trans-racemic-benzyl-4-[(7-[((S)-1-methoxypropan-2-yl)carbamoyl]-5-{[2-(trimethylsilyl)ethoxy]methyl}-5H-pyrrolo[2,3-b]pyrazin-2-yl)oxy]-2-methylpiperidine-1-carboxylate (Example 71 Step 4). The residue was purified using silica gel column chromatography eluting with 0-5% MeOH in DCM followed by preparative HPLC eluting with 25-45% MeCN in water modified with 0.1% TFA. LCMS analysis: Ultimate XB-C-18 (50×3 mm, 3 micron); 1-100% MeCN in water with 0.1% TFA. Rt=3.46 minutes MS m/z 402 [M+H]$^+$ $^1$H NMR (400 MHz, MeOH-d$_4$): δ ppm 8.13 (s, 1H), 7.91 (s, 1H), 6.85-6.78 (m, 1H), 6.23-6.19 (m, 1H), 5.77-5.74 (m, 1H), 5.57-5.50 (m, 1H), 5.15-5.00 (m, 1H), 4.70-4.55 (m, 1H), 4.45-4.40 (m, 1H), 4.20-4.10 (br m, 0.5H), 3.60-3.50 (m, 2H), 3.40 (s, 3H), 3.15-3.05 (br m, 0.5H), 2.50-2.40 (m, 1H), 2.20-2.10 (m, 1H), 2.00-1.80 (br m, 1H), 1.70-1.55 (br m, 1H), 1.45-1.30 (m, 6H).

The trans-racemic material was separated into its enantiomers using preparative chiral column chromatography according to the conditions described below;

Column: AS (250×30 mm), 5 micron; Mobile phase: 25% MeOH in NH$_3$/H$_2$O

Flow rate: 50 mL/min

QC Analytical LCMS Method:

Column: Chiralpak AS-H (250×4.6 mm, 5 micron); Mobile phase: 5-40% MeOH with 0.05% DEA in CO$_2$; Flow rate: 2.35 mL/min The two enantiomers were arbitrarily assigned absolute stereochemistry First Eluting Isomer: Example 72

2-{[(2R,4S)-1-acryloyl-2-methylpiperidin-4-yl]oxy}-N-[(2S)-1-methoxypropan-2-yl]-5H-pyrrolo[2,3-b]pyrazine-7-carboxamide. Rt=5.80 minutes. MS m/z 402 [M+H]$^+$ Second Eluting Isomer: Example 73

2-{[(2S,4R)-1-acryloyl-2-methylpiperidin-4-yl]oxy}-N-[(2S)-1-methoxypropan-2-yl]-5H-pyrrolo[2,3-b]pyrazine-7-carboxamide. Rt=6.10 minutes. MS m/z 402 [M+H]$^+$ Example 74

Cis-racemic-2-{[1-acryloyl-6-methylpiperidin-3-yl]amino}-N-ethyl-5H-pyrrolo[2,3-b]pyrazine-7-carboxamide The title compound was prepared according to the method described for Example 65, using cis-racemic-benzyl 5-{[7-(ethylcarbamoyl)-5-{[2-(trimethylsilyl)ethoxy]methyl}-5H-pyrrolo[2,3-b]pyrazin-2-yl]amino}-2-methylpiperidine-1-carboxylate (Example 74, Step 4). The residue was purified using silica gel column chromatography eluting with 5% MeOH in DCM followed by preparative HPLC eluting with 21-41% MeCN in water modified with ammonia to pH=10. $^1$H NMR (400 MHz, DMSO-d$_6$): δ ppm 11.87 (br s, 1H), 8.06 (br s, 1H), 7.86 (s, 1H), 7.74 (s, 1H), 6.78-6.71 (m, 2H), 6.11-6.06 (m, 1H), 5.66-5.63 (m, 1H), 4.55 (br m, 2H), 3.80-3.70 (br m, 1H), 3.50-3.30 (m, 2H), 2.75-2.60 (m, 1H), 2.00-1.90 (m, 1H), 1.78-1.72 (m, 3H), 1.24-1.12 (m, 6H). MS m/z 357 [M+H]$^+$ The cis-racemic material was separated into its enantiomers using preparative chiral column chromatography according to the conditions described below;

Column: OJ (250×30 mm), 20 micron; Mobile phase: 40% MeOH in NH$_3$/H$_2$O

Flow rate: 80 mL/min

QC Analytical LCMS Method:

Column: Xtimate C18 (5×30 mm, 3 μm); Mobile phase: 1%-100% MeCN/H$_2$O (0.05% TFA)

Rt=3.33 min. The two enantiomers were arbitrarily assigned absolute stereochemistry.

First Eluting Isomer: Example 75

2-{[(3S,6R)-1-acryloyl-6-methylpiperidin-3-yl]amino}-N-ethyl-5H-pyrrolo[2,3-b]pyrazine-7-carboxamide.
Rt=5.97 minutes. MS m/z 357 [M+H]+

Second Eluting Isomer: Example 76

2-{[(3R,6S)-1-acryloyl-8-methylpiperidin-3-yl]amino}-N-ethyl-5H-pyrrolo[2,3-b]pyrazine-7-carboxamide.
Rt=6.32 minutes. MS m/z 357 [M+H]+

Example 77

Trans-racemic-2-{[1-acryloyl-2-methylpiperidin-4-yl]oxy}-N-ethyl-5H-pyrrolo[2,3-b]pyrazine-7-carboxamide The title compound was prepared according to the method described for Example 65 using trans-racemic-benzyl 4-{[7-(ethylcarbamoyl)-5-{[2-(trimethylsilyl)ethoxy]methyl}-5H-pyrrolo[2,3-b]pyrazin-2-yl]oxy}-2-methylpiperidine-1-carboxylate (Example 77 Step 4). The residue was purified using silica gel column chromatography eluting with 10% MeOH in DCM followed by preparative HPLC eluting with 26-46% MeCN in water with ammonia to pH=10.
$^1$H NMR (400 MHz, DMSO-$d_6$): δ ppm 12.60 (br s, 1H), 8.20 (s, 1H), 7.97 (s, 1H), 7.85-7.82 (m, 1H), 6.87-6.81 (m, 1H), 6.13-6.09 (m, 1H), 5.70-5.67 (m, 1H), 5.56-5.52 (m, 1H), 5.00-4.90 (br m, 1H), 4.60-4.40 (br m, 1H), 4.20-4.00 (br m, 1H), 3.10-2.90 (br m, 1H), 2.30-2.17 (m, 3H), 1.85-1.50 (br m, 2H), 1.32-1.22 (m, 3H), 1.20 (t, 3H). MS m/z 380 [M+Na]+
QC Analytical LCMS Method:
Column: XB-C18, 3 um (3×50 mm); Mobile phase: 1%-100% MeCN/H$_2$O (0.1% TFA)
Rt=3.50 min
The trans-racemic material was separated into its enantiomers using preparative chiral column chromatography according to the conditions described below;
Prep SFC Method
ChiralPak AS (250×30 mm), 5 micron; Mobile phase: 20% MeOH with 0.1% NH$_3$.H$_2$O in supercritical CO$_2$; Flow rate: 60 mL/min
Chiral SFC Analysis Method:
Column: Chiralpak AS-H (250×30 mm), 5 micron; Mobile phase: 5-40% MeOH with 0.05% DEA in CO$_2$; Flow rate: 2.5 mL/min
The two enantiomers were arbitrarily assigned absolute stereochemistry.

First Eluting Isomer: Example 78

2-{[(2R,4S)-1-acryloyl-2-methylpiperidin-4-yl]oxy}-N-ethyl-5H-pyrrolo[2,3-b]pyrazine-7-carboxamide.
Rt=6.22 minutes MS m/z 380 [M+Na]+

Second Eluting Isomer: Example 79

2-{[(2S,4R)-1-acryloyl-2-methylpiperidin-4-yl]oxy}-N-ethyl-5H-pyrrolo[2,3-b]pyrazine-7-carboxamide.
Rt=6.55 minutes MS m/z 380 [M+Na]+

Example 80

Cis-racemic-2-{[1-acryloyl-6-methylpiperidin-3-yl]oxy}-N-[(2S)-1-methoxypropan-2-yl]-5H-pyrrolo[2,3-b]pyrazine-7-carboxamide The title compound was prepared according to the method described for Example 65 using cis-racemic-benzyl 5-[(7-[(1-methoxypropan-2-yl)carbamoyl]-5-{[2-(trimethylsilyl)ethoxy]methyl}-5H-pyrrolo[2,3-b]pyrazin-2-yl)oxy]-2-methylpiperidine-1-carboxylate (Example 80 Step 4). The residue was purified using preparative HPLC eluting with 25-45% MeCN in water with 0.05% ammonia. $^1$H NMR (400 MHz, DMSO-$d_6$): δ ppm 12.60 (br s, 1H), 8.21 (s, 1H), 8.01 (s, 1H), 7.97-7.85 (m, 1H), 6.90-6.83 (m, 1H), 6.13-6.09 (m, 1H), 5.75-5.60 (m, 1H), 5.10-4.70 (m, 2H), 4.50-4.40 (m, 0.5H), 4.30-4.10 (m, 1.5H), 3.23 (s, 3H), 2.90-2.50 (m, 2H), 2.20-2.10 (m, 1H), 1.90-1.70 (m, 3H), 1.30-1.10 (m, 6H).
MS m/z 402 [M+H]+
QC Analytical LCMS Method:
Column: Ultimate XB-C18, 3 μm, 3×50 mm; Mobile phase: 1-100% CH$_3$CN/H2O (0.1% TFA)
Flow rate: 2.35 mL/min. Rt=3.60 min.
The cis-racemic material was separated into its enantiomers using preparative chiral column chromatography according to the conditions described below;
Column: OJ (250×30 mm), 5 micron; Mobile phase: 20% EtOH in NH$_3$.H$_2$O
Flow rate: 60 mL/min
Chiral SFC Analysis Method:
Column: Chiralpak AS-H (250×30 mm), 5 micron; Mobile phase: 5-40% EtOH with 0.05% DEA in CO$_2$;
Flow rate: 2.35 mL/min
The two enantiomers were arbitrarily assigned absolute stereochemistry.

First Eluting Isomer: Example 81

2-{[(3R,6S)-1-acryloyl-6-methylpiperidin-3-yl]oxy}-N-[(2S)-1-methoxypropan-2-yl]-5H-pyrrolo[2,3-b]pyrazine-7-carboxamide
Rt=5.74 minutes. MS m/z 402 [M+H]+

Second Eluting Isomer: Example 82

2-{[(3S,6R)-1-acryloyl-6-methylpiperidin-3-yl]oxy}-N-[(2S)-1-methoxypropan-2-yl]-5H-pyrrolo[2,3-b]pyrazine-7-carboxamide. Rt=6.78 minutes. MS m/z 402 [M+H]+

Examples 83-87 were prepared as described in the Scheme Below:

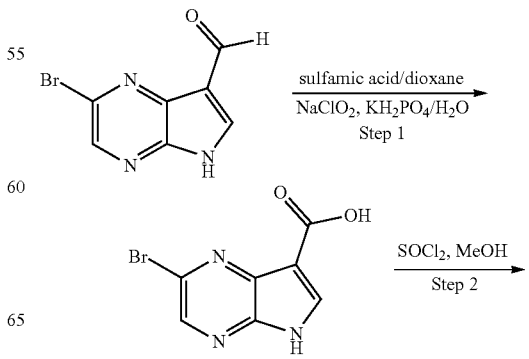

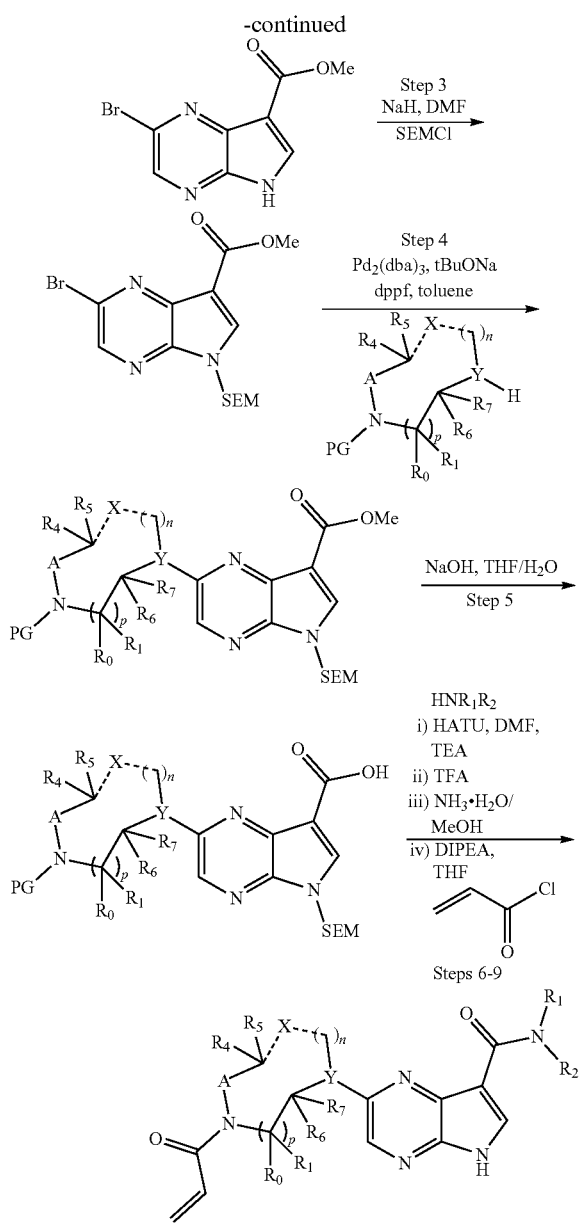

Example 83 Step 1

2-Bromo-5H-pyrrolo[2,3-b]pyrazine-7-carboxylic acid

To a solution of 2-bromo-5H-pyrrolo[2,3-b]pyrazine-7-carbaldehyde (75 g, 333 mmol) and sulfamic acid (163 g, 1667 mmol) in dioxane and water (1.5 L, v:v 4:1) was added a solution of NaClO$_2$ (36.4 g, 400 mmol) and KH$_2$PO$_4$ (227 g, 1667 mol) in water (0.5 L) dropwise over 40 minutes followed by stirring at room temperature for 18 hours. The reaction was partitioned between EtOAc (2 L) and water (1 L). The aqueous layer was further extracted with EtOAc (1.5 L) and the organic layers were combined, washed with water (1 L), dried over sodium sulphate and concentrated in vacuo to afford the title compound as a yellow solid (120 g, 75%). MS m/z 507 [2M+Na]$^+$

Example 83 Step 2

Methyl 2-bromo-5H-pyrrolo[2,3-b]pyrazine-7-carboxylate

To a suspension of 2-bromo-5H-pyrrolo[2,3-b]pyrazine-7-carboxylic acid (Example 83 Step 1, 145 g, 602 mmol) in MeOH (1.5 L) at 0° C. was added thionyl chloride (93 g, 781 mmol) dropwise over 40 minutes. The reaction was heated to reflux for 4 hours before cooling and concentrating in vacuo. The resulting solid was triturated with TBME to afford the title compound as a yellow solid (109 g, 71%) that was taken directly on to the next step.

Example 83 Step 3

Methyl 2-bromo-5-((2-(trimethylsilylethoxy)methyl-5H-pyrrolo[2,3-b]pyrazine-7-carboxylate To a suspension of NaH (60% dispersion in oil, 11.9 g, 297 mmol) in DMF (500 mL) at 0° C. was added methyl 2-bromo-5H-pyrrolo[2,3-b]pyrazine-7-carboxylate (Example 83 Step 2, 55 g, 228 mmol). The reaction was stirred at 0° C. for 10 minutes followed by the addition of SEMCl (49.3 g, 251 mmol) and stirring at room temperature for 3 hours. The reaction was poured into ice-water (1.5 L) and extracted into EtOAc (3×1.5 L). The combined organic layers were washed with water (2 L), brine (3×1.5 L), dried over sodium sulphate and concentrated in vacuo. The residue was triturated with TBME to afford the title compound as a white solid (105 g, 60%). $^1$H NMR (400 MHz, DMSO-d$_6$): δ ppm 8.88 (s, 1H), 8.61 (s, 1H), 5.70 (br s, 2H), 3.86 (br s, 3H), 3.58-3.54 (m, 2H), 0.85-0.81 (m, 2H), −0.09 (s, 9H).

Example 83 Step 4

Methyl 2-(4-(tert-butoxycarbonyl)-3,3-dimethylpiperazin-1-yl)-5-((2-(trimethylsilyl)ethoxy)methyl-5H-pyrrolo[2,3-b]pyrazine-7-carboxylate To a solution of methyl 2-bromo-5-((2-(trimethylsilyl)ethoxy)methyl)-5H-pyrrolo[2,3-b]pyrazine-7-carboxylate (Example 83 Step 3, 4.51 g, 11.7 mmol) and tert-butyl 2,2-dimethylpiperazine-1-carboxylate (5 g, 23.33 mmol) in anhydrous toluene (100 mL) was added dppf (420 mg, 0.758 mmol) followed by cesium carbonate (7.6 g, 23.33 mmol). The reaction was degassed and purged with nitrogen before the addition of Pd$_2$(dba)$_3$ (534 mg, 0.583 mmol) and heating to 100° C. for 12 hours. The reaction was cooled, filtered and the filtrate concentrated in vacuo. The residue was purified using silica gel column chromatography eluting with 10-80% EtOAc in petroleum ether to afford the title compound as a red oil (5.24 g, 86%). MS m/z 520 [M+H]$^+$

Example 83 Step 5

2-(4-(tert-Butoxycarbonyl)-3,3-dimethylpiperazin-1-yl)-5-((2-(trimethylsilylethoxy)methyl-5H-pyrrolo[2,3-b]pyrazine-7-carboxylic acid To a solution of methyl 2-(4-(tert-butoxycarbonyl)-3,3-dimethylpiperazin-1-yl)-5-((2-(trimethylsilyl)ethoxy)methyl)-5H-pyrrolo[2,3-b]pyrazine-7-carboxylate (Example 83 Step 4, 5.24 g, 10.08 mmol) in THF (100 mL) and water (30 mL) was added sodium hydroxide (3.23 g, 80.7 mmol) and the reaction was heated to 70° C. for 12 hours.

Further sodium hydroxide (3.23 g, 80.7 mmol) was added and the reaction continued heating at 70° C. for 16 hours followed by heating at 75° C. for 60 hours. The reaction was cooled and acidified with 0.5M HCl (100 mL) to pH=5-6. The solution was extracted into EtOAc (2×50 mL), the organic layers were combined, washed with brine (100 mL), dried over sodium sulphate and concentrated in vacuo. The residue was purified using silica gel column chromatography eluting with 30-80% EtOAc in petroleum ether to afford the title compound as a yellow solid (3.4 g, 67%). $^1$H NMR (400 MHz, DMSO-d$_6$): δ ppm 12.02 (br s, 1H), 8.34 (s, 1H), 7.96 (s, 1H), 5.58 (s, 2H), 3.83-3.78 (m, 4H), 3.60-3.51 (m, 4H), 1.44 (s, 9H), 1.36 (s, 6H), 0.86-0.80 (m, 2H), −0.09 (s, 9H).

MS m/z 506 [M+H]$^+$

The following Preparations were prepared according to the methods described for Example 83 Steps 4 and 5 using methyl 2-bromo-5-((2-(trimethylsilyl)ethoxy)methyl)-5H-pyrrolo[2,3-b]pyrazine-7-carboxylate (Example 83 Step 3) and the appropriate amine or alcohol.

and treated with TFA (2 mL) at 0° C. The reaction was stirred at room temperature for 12 hours before concentrating in vacuo and azeotroping with MeOH. The residue was dissolved in MeOH (6 mL) and treated with aqueous ammonia (3 mL) at 0° C. The reaction was stirred at room temperature for 2 hours, concentrated in vacuo and dissolved in THF (5 mL) and water (5 mL). DIPEA (186 mg, 1.44 mmol) followed by acryloyl chloride (64.8 mg, 0.72 mmol) were added and the reaction stirred at room temperature for 2 hours. Additional DIPEA (186 mg, 1.44 mmol) and acryloyl chloride (64.8 mg, 0.72 mmol) were added and the reaction continued for 6 hours. The reaction was concentrated in vacuo and purified using silica gel column chromatography eluting with 0-20% MeOH in DCM followed by preparative HPLC to afford the title compound as a yellow solid (72 mg, 41%).

Preparative HPLC conditions:

Column: YMC-Actus Triart C18 1 50×30 mm×5 μm; Mobile phase: 26-46% MeCN in water modified with

| Prep No. | Name | Structure | Data/SM |
|---|---|---|---|
| 84 Steps 4 and 5 | 2-(3-((tert-butoxycarbonyl)(methyl)amino)azetidin-1-yl)-5-((2-(trimethylsilyl)ethoxy)methyl)-5H-pyrrolo[2,3-b]pyrazine-7-carboxylic acid | 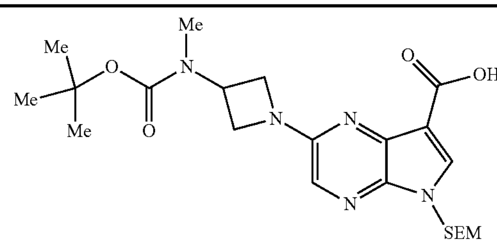 | tert-butyl azetidin-3-yl(methyl)carbamate $^1$H NMR (400 MHz, DMSO-d$_6$): δ ppm 12.08 (br s, 1H), 8.37 (s, 1H), 7.71 (s, 2H), 4.28-4.24 (m, 2H), 4.10-4.01 (m, 2H), 3.54-3.51 (m, 2H), 2.89 (s, 3H), 1.41 (s, 9H), 0.84-0.80 (m, 2H), −0.08 (s, 9H). ok MS m/z 478 [M + H]$^+$ |
| 87 Steps 4 and 5 | (R)-2-((1-(tert-butoxycarbonyl)pyrrolidin-3-yl)oxy)-5-((2-(trimethylsilyl)ethoxy)methyl)-5H-pyrrolo[2,3-b]pyrazine-7-carboxylic acid | 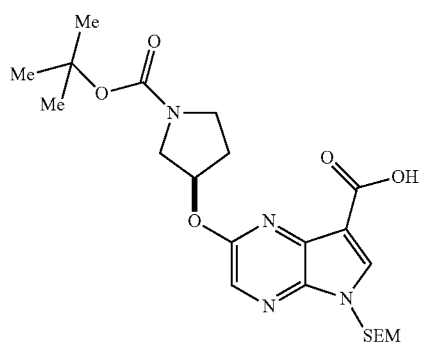 | tert-butyl (R)-3-hydroxypyrrolidine-1-carboxylate Taken on directly to the next step. |

Example 83 Steps 6-9

2-(4-acryloyl-3,3-dimethylpiperazin-1-yl)-N-(prop-2-yn-1-yl)-5H-pyrrolo[2,3-b]pyrazine-7-carboxamide To a solution of 2-(4-(tert-butoxycarbonyl)-3,3-dimethylpiperazin-1-yl)-5-((2-(trimethylsilyl)ethoxy)methyl)-5H-pyrrolo[2,3-b]pyrazine-7-carboxylic acid (Example 83 Steps 4 and 5, 0.6 g, 1.19 mmol) and 2-propynylamine (196 mg, 3.56 mmol) in DMF (10 mL) was added HATU (0.902 mmol, 2.37 mmol) followed by triethylamine (360 mg, 3.56 mmol). The reaction was stirred at room temperature for 12 hours. The reaction was diluted with water (20 mL) and extracted into EtOAc (3×20 mL). The combined organic layers were concentrated in vacuo and purified using silica gel column chromatography eluting with 50-100% EtOAc in petroleum ether. The residue was dissolved in DCM (6 mL)

0.225% formic acid. $^1$H NMR (400 MHz, DMSO-d$_6$): δ ppm 12.31 (br s, 1H), 8.40-8.38 (m, 1H), 8.08 (s, 1H), 7.99 (s, 1H), 6.80-6.73 (m, 1H), 6.06-6.02 (m, 1H), 5.65-5.62 (m, 1H), 4.19-4.18 (m, 2H), 3.96-3.88 (m, 4H), 3.69-3.67 (m, 2H), 3.27 (s, 1H), 1.54 (s, 6H).

MS m/z 389 [M+Na]$^+$

Examples 84-87 were prepared according to the method described for Example 83 Steps 6-9 using the appropriate acid and amine as described below:

Prep Method A (PM A):

Kromasil Etemity XT C18 250×21.2×10 micron, mobile phase: 9-29% MeCN in water modified with ammonia to pH=10.

Prep Method B (PM B):

Phenomenex Gemini C18 250×21.2×10 micron, mobile phase 26-46% MeCN in water modified with ammonia to pH=10.

| Example | Name/Structure | SM | Data |
| --- | --- | --- | --- |
| 84 | 2-{3-[acryloyl(methyl)amino]azetidin-1-yl}-N-(2-methoxyethyl)-5H-pyrrolo[2,3-b]pyrazine-7-carboxamide | 2-{3-[(tert-butoxycarbonyl)(methyl)amino]azetidin-1-yl}-5-{[2-(trimethylsilyl)ethoxy]methyl}-5H-pyrrolo[2,3-b]pyrazine-7-carboxylic acid (Example 84 Steps 4 and 5) and 2-methoxyethylamine. | PM A $^1$H NMR (400 MHz, DMSO-d$_6$): δ ppm 12.25 (br s, 1H), 8.42 (br s, 1H), 8.07 (s, 1H), 7.72 (s, 1H), 6.81-6.74 (m, 1H), 6.17-6.13 (m, 1H), 5.74-5.71 (m, 1H), 5.27 (br s, 1H), 4.35-4.33 (m, 2H), 4.19-4.05 (m, 2H), 3.54-3.37 (m, 7H), 3.35-3.16 (m, 3H). MS m/z 359 [M + H]$^+$ |
| 85 | 2-{3-[acryloyl(methyl)amino]azetidin-1-yl}-N-[(2S)-1-methoxypropan-2-yl]-5H-pyrrolo[2,3-b]pyrazine-7-carboxamide | 2-{3-[(tert-butoxycarbonyl)(methyl)amino]azetidin-1-yl}-5-{[2-(trimethylsilyl)ethoxy]methyl}-5H-pyrrolo[2,3-b]pyrazine-7-carboxylic acid (Example 85 Steps 4 and 5) and (S)-1-methoxypropan-2-amine. | PM A with 11-31% MeCN. $^1$H NMR (400 MHz, DMSO-d$_6$): δ ppm 12.27 (br s, 1H), 8.37-8.35 (m, 1H), 8.04 (s, 1H), 7.71 (s, 1H), 6.80-6.74 (m, 1H), 6.16-6.08 (m, 1H), 5.76-5.71 (m, 1H), 5.30-5.24 (m, 1H), 4.31-4.25 (m, 2H), 4.20-4.05 (m, 3H), 3.44-3.30 (m, 5H), 3.16-3.04 (m, 3H), 1.22-1.18 (m, 3H). MS m/z 373 [M + H]$^+$ |
| 86 | 2-{3-[acryloyl(methyl)amino]azetidin-1-yl}-N-[(2R)-1-methoxypropan-2-yl]-5H-pyrrolo[2,3-b]pyrazine-7-carboxamide | 2-{3-[(tert-butoxycarbonyl)(methyl)amino]azetidin-1-yl}-5-{[2-(trimethylsilyl)ethoxy]methyl}-5H-pyrrolo[2,3-b]pyrazine-7-carboxylic acid (Example 86 Steps 4 and 5) and (R)-1-methoxypropan-2-amine | PM B. $^1$H NMR (400 MHz, DMSO-d$_6$): δ ppm 12.27 (br s, 1H), 8.37-8.35 (m, 1H), 8.04 (s, 1H), 7.71 (s, 1H), 6.80-6.73 (m, 1H), 6.22-6.08 (m, 1H), 5.73-5.71 (m, 1H), 5.30-5.24 (m, 1H), 4.33-4.30 (m, 2H), 4.25-4.05 (m, 3H), 3.41-3.30 (m, 5H), 3.29-3.04 (m, 3H), 1.21-1.18 (m, 3H). MS m/z 373 [M + H]$^+$ |

| Example | Name/Structure | SM | Data |
|---|---|---|---|
| 87 | (R)-2-[(1-acryloylpyrrolidin-3-yl)oxy]-N-ethyl-5H-pyrrolo[2,3-b]pyrazine-7-carboxamide | (R)-2-((1-(tert-butoxycarbonyl)pyrrolidin-3-yl)oxy)-5-[(2-(trimethylsilyl)ethoxy)methyl]-5H-pyrrolo[2,3-b]pyrazine-7-carboxylic acid (Example 87 Steps 4 and 5). | $^1$H NMR (400 MHz, DMSO-$d_6$): δ ppm 12.56 (br s, 1H), 8.19 (s, 1H), 8.00 (s, 1H), 7.86-7.82 (m, 1H), 6.63-6.55 (m, 1H), 6.18-6.13 (m, 1H), 5.71-5.64 (m, 2H), 3.98-3.68 (m, 3.5H), 3.50-3.38 (m, 2.5H), 2.36-2.22 (m, 2H), 1.22-1.18 (m, 3H). |

Examples 88-90 were prepared as described in the Scheme below:

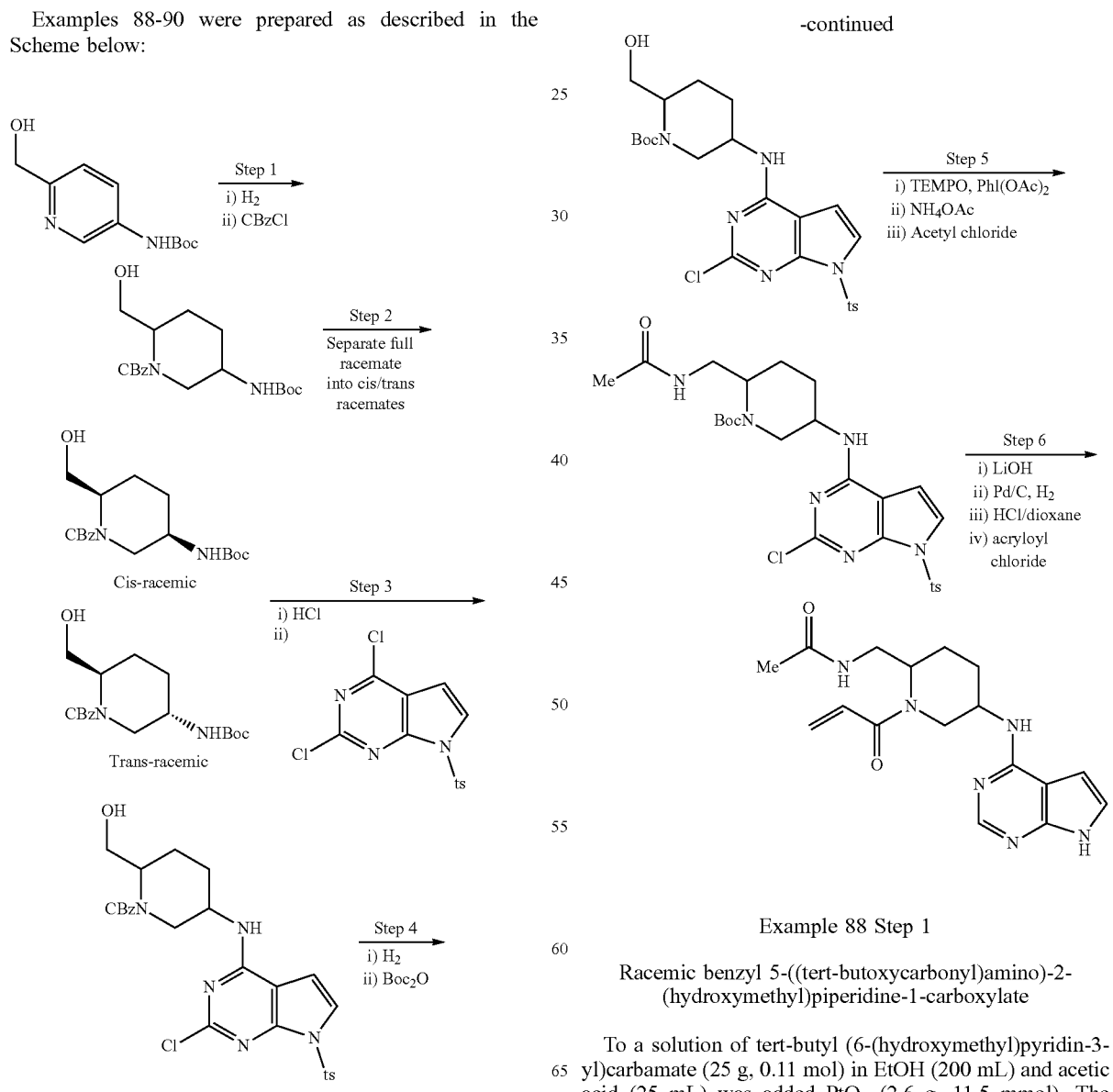

Example 88 Step 1

Racemic benzyl 5-((tert-butoxycarbonyl)amino)-2-(hydroxymethyl)piperidine-1-carboxylate To a solution of tert-butyl (6-(hydroxymethyl)pyridin-3-yl)carbamate (25 g, 0.11 mol) in EtOH (200 mL) and acetic acid (25 mL) was added $PtO_2$ (2.6 g, 11.5 mmol). The reaction was degassed under vacuum and purged with hydrogen three times before stirring under 55 psi of hydrogen at 50° C. for 72 hours. The reaction was cooled, filtered, and the filtrate neutralised with saturated aqueous $NaHCO_3$ solution. The solution was concentrated in vacuo and the residue extracted into EtOAc (5×100 mL). The combined organic layers were washed with brine (200 mL), dried over sodium sulphate and concentrated in vacuo. Part of the residue (5 g, 0.022 mmol) was dissolved in THF (100 mL) and water (50 mL). $NaHCO_3$ (3.7 g, 0.044 mmol) was added followed by CbzCl (4.4 g, 0.026 mmol) and the reaction was stirred at room temperature for 2 hours. The reaction was concentrated in vacuo and extracted into EtOAc (3×200 mL). The organic layers were washed with brine (2×200 mL) and concentrated in vacuo. The residue was purified using silica gel column chromatography eluting with 20-30% EtOAc in petroleum ether to afford the title compound as a colorless oil (3 g, 67% over 2 steps).

$^1$H NMR (400 MHz, $CDCl_3$): δ ppm 7.27-7.19 (m, 5H), 5.06-5.02 (m, 2H), 4.54-4.52 (m, 1H), 4.25-3.95 (m, 2H), 3.69-3.30 (m, 3H), 3.10-3.05 (m, 1H), 2.65-2.50 (m, 1H), 1.70-1.28 (m, 12H).

MS m/z 751 $[2M+Na]^+$

Example 88 Step 2

Cis-racemic-benzyl 5-((tert-butoxycarbonyl)amino)-2-(hydroxymethyl)piperidine-1-carboxylate and trans-racemic benzyl 5-((tert-butoxycarbonyl)amino)-2-(hydroxymethyl)piperidine-1-carboxylate The cis and trans racemic benzyl 5-((tert-butoxycarbonyl)amino)-2-(hydroxymethyl)piperidine-1-carboxylate were separated using preparative HPLC using the conditions below:

Column: Phenomenex Synergi C18 (250×77×10 micron).
Mobile phase: 35-53% MeCN in water modified with 10 mM ammonium carbonate
Gradient time: 25 minutes; Flow rate: 140 mL/min
HPLC QC: WatersXbridge 2.1×50 mm×5 micron, 0-60% MeCN in water modified with 0.05% ammonia.

The two enantiomers were assigned stereochemistry.
First Eluting Isomers:
trans racemic benzyl 5-((tert-butoxycarbonyl)amino)-2-(hydroxymethyl)piperidine-1-carboxylate. Rt=3.55 minutes MS m/z 387 $[M+Na]^+$
Second Eluting Isomers:
cis racemic benzyl 5-((tert-butoxycarbonyl)amino)-2-(hydroxymethyl)piperidine-1-carboxylate. Rt=3.59 minutes MS m/z 387 $[M+Na]^+$ Example 88 Step 3

Cis-racemic-benzyl-5-((2-chloro-7-tosyl-7H-pyrrolo[2,3-d]pyrimidin-4-yl)amino)-2-(hydroxymethyl)piperidine-1-carboxylate To a solution of cis racemic benzyl 5-((tert-butoxycarbonyl)amino)-2-(hydroxymethyl)piperidine-1-carboxylate (Example 88 Step 2, 30 g, 82 mmol) in DCM (200 mL) was added 4M HCl in dioxane (150 mL) at 0° C. and the reaction was stirred at this temperature for 2 hours. The reaction was concentrated in vacuo and part of the residue (14 g, 46 mmol) was dissolved in n-BuOH (200 mL). DIPEA (13.2 g, 102 mmol) followed by 2,4-dichloro-7-tosyl-7H-pyrrolo[2,3-d]pyrimidine (16 g, 47 mmol) were added and the reaction heated to 50° C. for 18 hours. The reaction was cooled, concentrated in vacuo and partitioned between EtOAc (200 mL) and water (200 mL). The aqueous layer was back-washed with EtOAc (2×200 mL) and the organic layers were combined, washed with brine, dried over sodium sulphate and concentrated in vacuo. The residue was purified using preparative HPLC as described below to afford the title compound as a white solid (19 g, 73%).

Column: Gemini 250×50 mm×10 micron; Mobile Phase: 53-100% MeCN in water modified with ammonia pH=10. Flow rate: 80 mL/min. MS m/z 570 $[M^{35}Cl+H]^+$ Example 88 Step 4

Cis-racemic-tert-butyl 5-((2-chloro-7-tosyl-7H-pyrrolo[2,3-d]pyrimidin-4-yl)amino)-2-(hydroxymethyl)piperidine-1-carboxylate To a solution of cis-racemic-benzyl 5-((2-chloro-7-tosyl-7H-pyrrolo[2,3-d]pyrimidin-4-yl)amino)-2-(hydroxymethyl)piperidine-1-carboxylate (Example 88 Step 3, 7.91 g, 13.9 mmol) and di-tert-butyl dicarbonate (3.94 g, 18 mmol) in EtOH (100 mL) and THF (100 mL) was added wet palladium on carbon (800 mg). The reaction was stirred under an atmosphere of hydrogen (hydrogen balloon) for 3 hours. The reaction was filtered through Celite™ and the filtrate concentrated in vacuo. The residue was purified using silica gel column chromatography eluting with 1:1 petroleum ether and EtOAc to afford the title compound as a white solid (5.6 g, 75%).

$^1$H NMR (400 MHz, DMSO-$d_6$): δ ppm 8.10-8.08 (m, 2H), 7.44-7.43 (m, 1H), 7.34-7.27 (m, 2H), 6.44 (br s, 1H), 5.19 (br s, 1H), 4.32-4.28 (m, 2H), 4.10 (br m, 1H), 3.80-3.79 (m, 1H), 3.67-3.64 (m, 1H), 2.75-2.69 (m, 1H), 2.41 (s, 3H), 2.50-2.30 (m, 1H), 2.05-1.97 (m, 1H), 1.83-1.80 (m, 2H), 1.49-1.44 (m, 1H), 1.44 (s, 9H).

Example 88 Step 5

Cis-racemic-tert-butyl 2-(acetamidomethyl-5-((2-chloro-7-tosyl-7H-pyrrolo[2,3-d]pyrimidin-4-yl)amino)piperidine-1-carboxylate To a solution of cis-racemic-tert-butyl 5-((2-chloro-7-tosyl-7H-pyrrolo[2,3-d]pyrimidin-4-yl)amino)-2-(hydroxymethyl)piperidine-1-carboxylate (Example 88 Step 4, 4.3 g, 8 mmol) in DCM (85 mL) was added TEMPO (250 mg, 1.6 mmol) and $PhI(OAc)_2$ (2.97 g, 9.2 mmol) and the reaction was stirred at room temperature for 18 hours. The reaction was washed with ether (100 mL), brine (100 mL), dried over sodium sulphate and concentrated in vacuo. The residue was purified using silica gel column chromatography eluting with 2-50% EtOAc in petroleum ether to afford the aldehyde intermediate as a white solid (1.81 g, 42%).

The solid was dissolved in MeOH (340 mL) and treated with ammonium acetate (26.13 g, 339 mmol) followed by sodium cyanoborohydride (3.41 g, 54 mmol). The reaction was stirred at room temperature for 18 hours. The reaction was diluted with EtOAc (400 mL) and washed with water (200 mL), saturated aqueous $NaHCO_3$ (200 mL), brine (300 mL) dried over sodium sulphate and concentrated in vacuo. The residue was purified using silica gel column chromatography eluting with 0-15% MeOH in DCM to afford the amino intermediate as a white solid (615 mg, 34%).

The solid was dissolved in THF (15 mL) and DCM (15 mL) and treated with triethylamine (363 mg, 3.6 mmol). Acetic anhydride (123 mg, 1.2 mmol) was added and the reaction stirred at room temperature for 2 hours. The reaction was concentrated in vacuo to afford the title compound as a yellow solid (700 mg, 100%). MS m/z 577 [M+H]$^+$ Example 88 Step 6 rac-N-(((2R,5R)-5-((7H-pyrrolo[2,3-d]pyrimidin-4-yl)amino)-1-acryloylpiperidin-2-yl)methyl)acetamide To a solution of cis-racemic-tert-butyl 2-(acetamidomethyl)-5-((2-chloro-7-tosyl-7H-pyrrolo[2,3-d]pyrimidin-4-yl)amino)piperidine-1-carboxylate (Example 88 Step 5, 700 mg, 1.2 mmol) in MeOH (15 mL) and water (3 mL) was added lithium hydroxide (151 mg, 3.6 mmol) and the reaction was stirred at room temperature for 12 hours. The reaction was concentrated in vacuo and the residue purified using 0-15% MeOH in DCM. The residue was dissolved in MeOH (20 mL) and treated with 10% Pd/C (100 mg). The reaction was hydrogenated at 45 psi at 35° C. for 16 hours. The reaction was filtered through Celite and the filtrate concentrated in vacuo. The residue was dissolved in DCM (5 mL) and treated with 4M HCl in dioxane (5 mL) at 0° C. The reaction was stirred at room temperature for 8 hours. The reaction was concentrated in vacuo and dissolved in THF (5 mL) and water (5 mL). DIPEA (464 mg, 3.6 mmol) was added followed by acryloyl chloride at 0° C. and the reaction was stirred at 0° C. for 2 hours. The reaction was concentrated in vacuo and purified using silica gel column chromatography eluting with 10-30% MeOH in DCM to afford the title compound as a white solid (100 mg, 25% over 4 steps).

$^1$H NMR (400 MHz, DMSO-d$_6$): δ ppm 11.52 (br s, 1H), 8.12-8.04 (m, 2H), 7.34-7.32 (m, 1H), 7.09 (s, 1H), 6.76-6.69 (m, 1H), 6.56 (s, 1H), 6.13-6.08 (m, 1H), 5.67-5.64 (m, 1H), 4.61-4.57 (m, 1H), 4.61-4.57 (m, 1H), 4.16-4.06 (m, 2H), 3.29-3.02 (m, 1H), 2.66-2.55 (m, 2H), 1.82-1.59 (m, 7H). LCMS (Ultimate XB-C18 3×50 mm×3 micron); 1-100% MeCN in water modified with 0.1% TFA. Rt=2.46 minutes MS m/z 343 [M+H]+

The cis-racemic material was separated into its enantiomers using preparative chiral column chromatography according to the conditions described below;

Column: Chiralcel OD-H 21×250 mm, 5 uM

Mobile phase: 90:10 CO2/MeOH for 10 min, flow rate 75 mL/min.

The two enantiomers were arbitrarily assigned absolute stereochemistry.

First Eluting Isomer: Example 89

N-{[(2R,5R)-1-acryloyl-5-(7H-pyrrolo[2,3-d]pyrimidin-4-ylamino)piperidin-2-yl]methyl}acetamide Rt=5.84 minutes MS m/z 343 [M+H]$^+$ Second Eluting Isomer: Example 90

N-{[(2S,5S)-1-acryloyl-5-(7H-pyrrolo[2,3-d]pyrimidin-4-ylamino)piperidin-2-yl]methyl}acetamide Rt=7.05 minutes MS m/z 343 [M+H]$^{+ok}$ Examples 91-93 were prepared as described in the Scheme below:

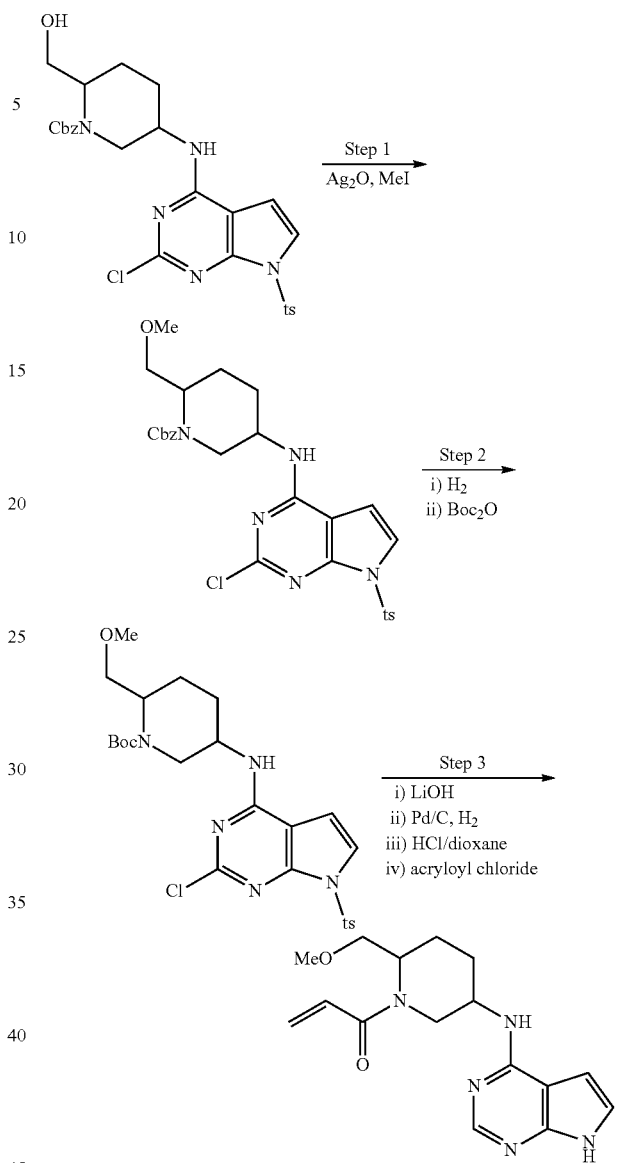

Example 91 Step 1

Cis-racemic-benzyl-5-((2-chloro-7-tosyl-7H-pyrrolo[2,3-d]pyrimidin-4-yl)amino)-2-(methoxymethyl)piperidine-1-carboxylate To a solution of cis-racemic-benzyl 5-((2-chloro-7-tosyl-7H-pyrrolo[2,3-d]pyrimidin-4-yl)amino)-2-(hydroxymethyl)piperidine-1-carboxylate (Example 88 Step 3, 1 g, 1.76 mmol) in anhydrous DMF (15 mL) was added Ag$_2$O (815 mg, 3.51 mmol) followed by methyl iodide (500 mg, 3.51 mmol) and the reaction was stirred at room temperature for 18 hours. Additional methyl iodide (500 mg, 3.51 mmol) was added and the reaction continued for 6 hours. The reaction was concentrated in vacuo and purified using silica gel column chromatography eluting with 0-80% EtOAc in petroleum ether to afford the title compound as a white solid (469 mg, 46%).

Taken on directly to the next step.

Example 91 Step 2

Cis-racemic-tert-butyl-5-((2-chloro-7-tosyl-7H-pyrrolo[2,3-d]pyrimidin-4-yl)amino)-2-(methoxymethyl)piperidine-1-carboxylate The title compound was prepared according to the method described for Example 88 Step 4 using cis-racemic-benzyl-5-((2-chloro-7-tosyl-7H-pyrrolo[2,3-d]pyrimidin-4-yl)amino)-2-(methoxymethyl)piperidine-1-carboxylate (Example 91 Step 1) under 20 psi of hydrogen and taken on directly to the next step.

Example 91 Step 3

Cis-racemic-1-[2-(methoxymethyl-5-(7H-pyrrolo[2,3-d]pyrimidin-4-ylamino)piperidin-1-yl]prop-2-en-1-one The title compound was prepared according to Example 88 Step 6 above using cis-racemic-tert-butyl-5-((2-chloro-7-tosyl-7H-pyrrolo[2,3-d]pyrimidin-4-yl)amino)-2-(methoxymethyl)piperidine-1-carboxylate (Example 91 Step 2). MS m/z 316 [M+H]+

The cis-racemic material was separated into its enantiomers using preparative chiral column chromatography according to the conditions described below;

Column: AD 250×30 mm, 10 micron; Mobile phase: 45% MeOH in water modified with ammonia.

Flow rate: 80 mL/min. LCMS QC: Chiralpak AD-3 150×4.6 mm, 3 micron

Mobile phase: 40% MeOH with 0.05% DEA in $CO_2$; Flow rate: 2.5 mL/min.

The two enantiomers were arbitrarily assigned absolute stereochemistry.

First Eluting Isomer: Example 92

1-[(2R,5R)-2-(Methoxymethyl)-5-(7H-pyrrolo[2,3-d]pyrimidin-4-ylamino)piperidin-1-yl]prop-2-en-1-one.

Rt=2.48 minutes MS m/z 316 [M+H]+

$^1$H NMR (400 MHz, DMSO-$d_6$): δ ppm 11.65 (br s, 1H), 8.10 (s, 1H), 7.14 (s, 1H), 6.85-6.78 (m, 1H), 6.56 (s, 1H), 6.10-6.05 (m, 1H), 5.65-5.62 (m, 1H), 4.90-4.75 (m, 1H), 4.67-4.60 (m, 1.3H), 4.38-4.37 (m, 1H), 4.11-4.09 (m, 0.7H), 3.80-3.50 (m, 1H), 3.45-3.23 (m, 4.3H), 2.93-2.87 (m, 0.7H), 1.98-1.89 (m, 2H), 1.71-1.60 (m, 2H).

Second Eluting Isomer: Example 93

1-[(2S,5S)-2-(Methoxymethyl)-5-(7H-pyrrolo[2,3-d]pyrimidin-4-ylamino)piperidin-1-yl]prop-2-en-1-one.

Rt=3.92 minutes MS m/z 316 [M+H]+

$^1$H NMR (400 MHz, DMSO-$d_6$): δ ppm 11.65 (br s, 1H), 8.10 (s, 1H), 7.14 (s, 1H), 6.85-6.78 (m, 1H), 6.56 (s, 1H), 6.10-6.05 (m, 1H), 5.65-5.62 (m, 1H), 4.90-4.75 (m, 1H), 4.67-4.60 (m, 1.3H), 4.38-4.37 (m, 1H), 4.11-4.09 (m, 0.7H), 3.80-3.50 (m, 1H), 3.45-3.23 (m, 4.3H), 2.93-2.87 (m, 0.7H), 1.98-1.89 (m, 2H), 1.71-1.60 (m, 2H).

Examples 94-96 were prepared according to the following Scheme:

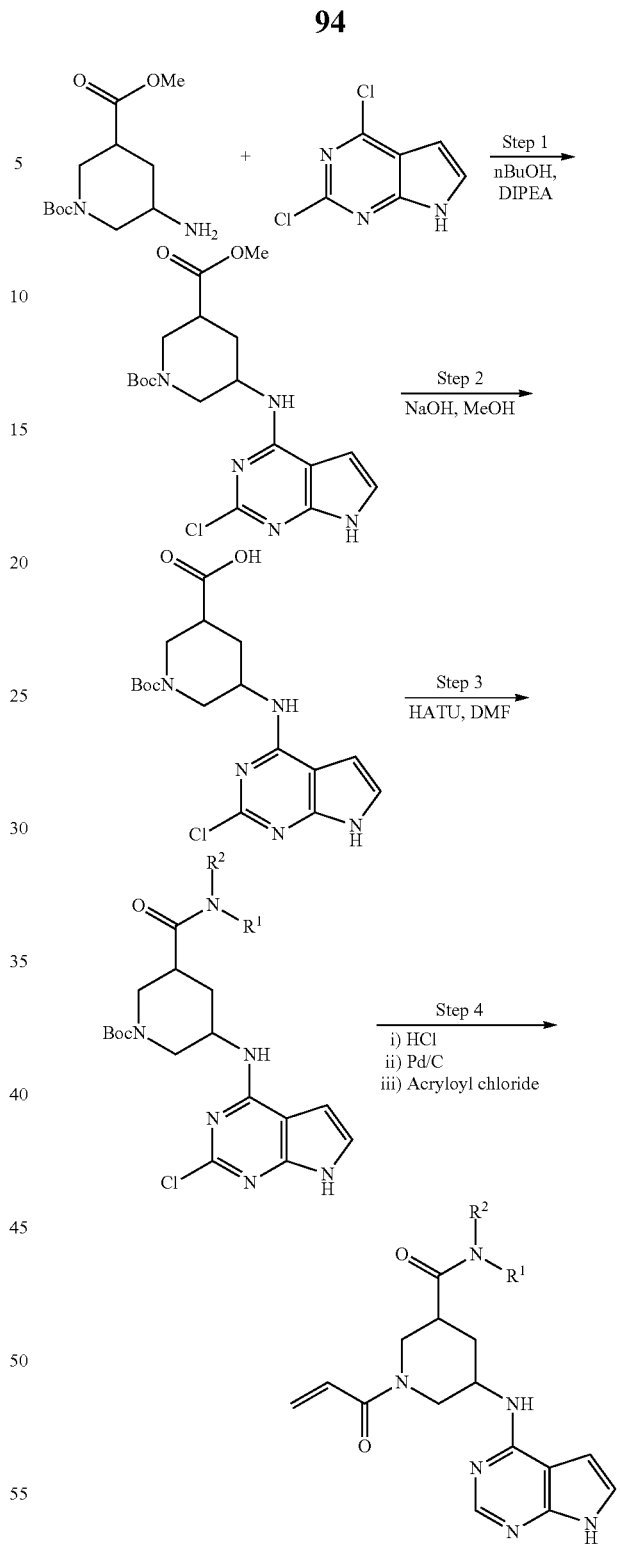

Example 94 Step 1

Cis-racemic-1-(tert-butyl)-3-methyl 5-((2-chloro-7H-pyrrolo[2,3-d]pyrimidin-4-yl)amino)piperidine-1,3-dicarboxylate To a solution of cis-racemic-1-tert-butyl 3-methyl-5-aminopiperidine-1,3-dicarboxylate (WO 200905112, 5 g, 19.3 mmol) in n-BuOH (100 mL) was added 2,4-dichloro-7H-pyrrolo[2,3-d]pyrimidine (4 g, 21.2 mmol) followed by DIPEA (7.47 g, 58 mmol). The reaction was heated to 130° C. for 48 hours. The reaction was cooled, concentrated in vacuo and partitioned between EtOAc (100 mL) and water (100 mL). The organic layer was collected, washed with water (100 mL), brine (100 mL), dried over sodium sulphate and concentrated in vacuo. The residue was purified using silica gel column chromatography eluting with 10-50% EtOAc in petroleum ether to afford the title compound as a white solid (4.4 g, 56%) that was taken directly on to the next step.

Example 94 Step 2

Cis-racemic-1-(tert-butoxycarbonyl)-5-((2-chloro-7H-pyrrolo[2,3-d]pyrimidin-4-yl)amino)piperidine-3-carboxylic acid To a solution of cis-racemic-1-(tert-butyl) 3-methyl 5-((2-chloro-7H-pyrrolo[2,3-d]pyrimidin-4-yl)amino)piperidine-1,3-dicarboxylate (Example 94 Step 1, 4.4 g, 10.73 mmol) in MeOH (50 mL) was added 1M aqueous NaOH solution (43 mL, 43 mmol) dropwise. The reaction was stirred at room temperature for 18 hours before diluting with water (20 mL) and extracting into EtOAc (100 mL). The aqueous phase was acidified with 1 M HCl (aq) until pH=5-6. The aqueous layer was extracted into EtOAc (2×100 mL), the organic layers combined washed with brine, dried over sodium sulphate and concentrated in vacuo to afford the title compound as a white solid (3.7 g, 87%). $^1$H NMR (400 MHz, DMSO-$d_6$): δ ppm 11.72 (br s, 1H), 7.79-7.78 (m, 1H), 7.11 (s, 1H), 6.58 (s, 1H), 4.24-4.01 (m, 3H), 2.72-2.22 (m, 4H), 1.65-1.59 (m, 1H), 1.43 (s, 9H).

Example 94 Step 3

Cis-racemic-tert-butyl-3-((2-chloro-7H-pyrrolo[2,3-d]pyrimidin-4-yl)amino)-5-(dimethylcarbamoyl)piperidine-1-carboxylate To a solution of cis-racemic-1-(tert-butoxycarbonyl)-5-((2-chloro-7H-pyrrolo[2,3-d]pyrimidin-4-yl)amino)piperidine-3-carboxylic acid (Example 94 Step 2, 1 g, 2.53 mmol) in DMF (15 mL) was added HATU (1.15 g, 3.04 mmol) and the mixture was stirred under nitrogen for 30 minutes. Dimethylamine hydrochloride (415 mg, 5.06 mmol) and triethylamine (766 mg, 7.59 mmol) were added and the reaction stirred at room temperature for 18 hours. The reaction was partitioned between EtOAc (20 mL) and water (20 mL). The organic layer was collected, washed with brine, dried over sodium sulphate and concentrated in vacuo. The residue was purified using silica gel column chromatography eluting with 5-10% MeOH in DCM to afford the title compound as a white solid (650 mg, 61%). $^1$H NMR (400 MHz, DMSO-$d_6$): δ ppm 11.71 (br s, 1H), 7.96-7.84 (m, 1H), 7.11 (s, 1H), 6.58 (s, 1H), 4.23-3.96 (m, 3H), 3.17 (s, 3H), 2.95-2.93 (m, 1H), 2.84 (s, 3H), 2.60-2.50 (m, 2H), 2.04-2.00 (m, 1H), 1.80-1.70 (m, 1H), 1.43 (s, 9H).

Example 94 Step 4

Cis-racemic-1-acryloyl-N,N-dimethyl-5-(7H-pyrrolo[2,3-d]pyrimidin-4-yl)amino)piperidine-3-carboxamide To a solution of cis-racemic-tert-butyl 3-((2-chloro-7H-pyrrolo[2,3-d]pyrimidin-4-yl)amino)-5-(dimethylcarbam-oyl)piperidine-1-carboxylate (Example 94 Step 3, 65 mg, 1.53 mmol) in MeOH (20 mL) was added 10% Pd/C (200 mg). The reaction was purged with argon before hydrogenating at 35 psi at 35° C. for 18 hours. The reaction was filtered though Celite® and concentrated in vacuo to give a residue that was dissolved in DCM (15 mL) and treated with 4M HCl in dioxane (4 mL). The reaction was stirred at room temperature for 3 hours before concentrating in vacuo and azeotroping with DCM. The residue was dissolved in THF (15 mL) and water (15 mL). DIPEA was added (1.12 g, 8.64 mmol) and the mixture cooled to 0° C. Acryloyl chloride (235 mg, 2.59 mmol) was added and the reaction stirred at 0° C. for 1 hour. The reaction was partitioned between water (10 mL) and EtOAc (10 mL).

The aqueous layer was collected, concentrated in vacuo and purified using preparative HPLC as described below to afford the title compound as a white solid (140 mg, 19% over three steps).

Column: Agela Durashell C18 250×21.2 mm×5 micron

Mobile phase: 2-20% MeCN in water modified with 0.225% formic acid; Flow rate: 30 mL/min.

LCMS QC: HPLC-AE Ultimate XB-C18 3×50 mm×3 micron

Mobile phase: 1-100% MeCN in water modified with 0.1% TFA.

Rt=2.58 minutes MS m/z 343 [M+H]$^+$ $^1$H NMR (400 MHz, DMSO-$d_6$): δ ppm 11.53 (s, 1H), 8.17-8.10 (m, 1H), 7.43-7.31 (m, 1H), 7.09 (s, 1H), 6.88-6.82 (m, 1H), 6.56 (s, 1H), 6.20-6.14 (m, 1H), 5.76-5.67 (m, 1H), 4.73-4.70 (m, 0.5H), 4.49-4.35 (m, 2.5H), 3.50-3.40 (br m, 1H), 3.08-2.84 (m, 7H), 2.83-2.80 (m, 1H), 2.07-2.04 (m, 1H), 1.89-1.76 (m, 1H).

The cis-racemic material was separated into its enantiomers using preparative chiral column chromatography according to the conditions described below;

Column: AD 250×30 mm, 10 micron; Mobile phase: 40% MeOH in water with NH$_3$:H$_2$O in supercritical CO$_2$; Flow rate: 70 mL/min. LCMS QC: Chiralpak AD-3 150×4.6 mm, 3 micron Mobile phase: 40% MeOH with 0.05% DEA in CO$_2$; Flow rate: 2.5 mL/min.

The two enantiomers were arbitrarily assigned absolute stereochemistry.

First Eluting Isomer: Example 95

1-[(2R,5R)-2-(Methoxymethyl)-5-(7H-pyrrolo[2,3-d]pyrimidin-4-ylamino)piperidin-1-yl]prop-2-en-1-one; Rt=1.43 minutes MS m/z 343 [M+H]$^+$ Second Eluting Isomer: Example 96

1-[(2S,5S)-2-(Methoxymethyl)-5-(7H-pyrrolo[2,3-d]pyrimidin-4-ylamino)piperidin-1-yl]prop-2-en-1-one;

Rt=2.58 minutes MS m/z 343 [M+H]$^+$

Examples 97-99 were prepared according to the following Scheme:

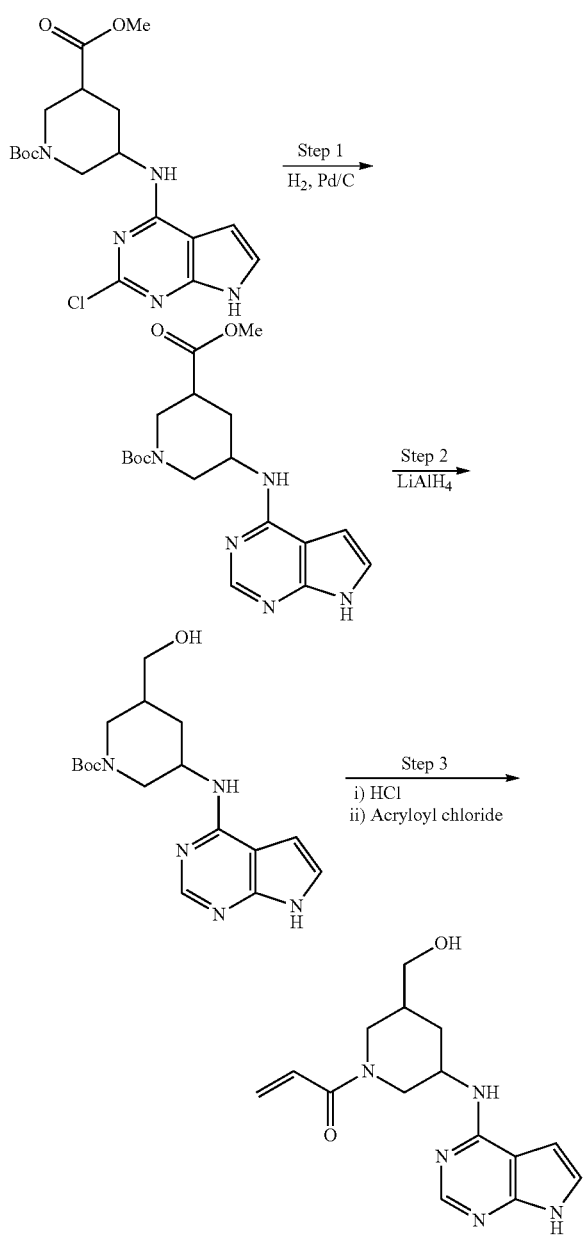

Example 97 Step 1

Cis-racemic-1-(tert-butyl 3-methyl 5-((7H-pyrrolo [2,3-d]pyrimidin-4-yl)amino)piperidine-1,3-dicarboxylate The title compound was prepared according to the hydrogenation method described above in Example 88 Step 4 using cis-racemic-1-(tert-butyl) 3-methyl 5-((2-chloro-7H-pyrrolo[2,3-d]pyrimidin-4-yl)amino)piperidine-1,3-dicarboxylate (Example 94 Step 1).

$^1$H NMR (400 MHz, DMSO-$d_6$): δ ppm 12.50 (br s, 1H), 9.10 (m, 1H), 8.33 (s, 1H), 7.36 (s, 1H), 6.93 (s, 1H), 4.25-4.15 (m, 3H), 3.68 (s, 3H), 2.80-2.60 (m, 3H), 2.38-2.35 (m, 1H), 1.71-1.62 (m, 1H), 1.42 (s, 9H).

Example 97 Step 2

Cis-racemic-tert-butyl 3-((7H-pyrrolo[2,3-d]pyrimidin-4-yl)amino)-5-(hydroxymethyl)piperidine-1-carboxylate To a solution of LiAlH$_4$ (388 mg, 10.2 mmol) in anhydrous THF (20 mL), was added a solution of 1-(tert-butyl) 3-methyl 5-((7H-pyrrolo[2,3-d]pyrimidin-4-yl)amino)piperidine-1,3-dicarboxylate (Example 97 Step 1, 480 mg, 1.28 mmol) in THF (30 mL) dropwise at 0° C. under nitrogen. The reaction was stirred at room temperature for 18 hours. The reaction was cooled to 0° C. and quenched by the addition of water (0.4 mL) followed by 15% aqueous NaOH solution (0.4 mL). Water was then added (1.2 mL) and the mixture stirred at room temperature for 15 minutes. Anhydrous MgSO$_4$ was added and the reaction stirred for 15 minutes followed by filtration through Celite™. The filtrate was concentrated in vacuo to afford the title compound as a colourless solid (120 mg, 27%). MS m/z 348 [M+H]$^+$ Example 97 Step 3 racemic-1-((3R,5S)-3-((7H-pyrrolo[2,3-d]pyrimidin-4-yl)amino)-5-(hydroxymethyl)piperidin-1-yl)prop-2-en-1-one The title compound was prepared according to the acid deprotection method and acylation method as described in Example 94 Step 4 above using cis-racemic-tert-butyl 3-((7H-pyrrolo[2,3-d]pyrimidin-4-yl)amino)-5-(hydroxymethyl)piperidine-1-carboxylate (Example 97 Step 2). $^1$H NMR (400 MHz, DMSO-$d_6$): δ ppm 11.51 (br s, 1H), 8.13-8.09 (m, 1H), 7.34-7.26 (m, 1H), 7.08 (s, 1H), 6.87-6.81 (m, 1H), 6.57 (s, 1H), 6.15-6.09 (m, 1H), 5.72-5.69 (m, 1H), 4.68-4.59 (m, 1H), 4.37-4.33 (m, 1H), 4.15-4.00 (m, 1H), 3.41-3.39 (m, 2H), 2.79-2.68 (m, 1H), 2.33-2.26 (m, 1H), 2.08-2.02 (m, 1H), 1.75-1.65 (m, 1H), 1.38-1.32 (m, 1H). MS m/z 302 [M+H]$^+$ The cis-racemic material was separated into its enantiomers using preparative chiral column chromatography according to the conditions described below; Column: AD 250×30 mm, 5 micron Mobile phase: 30% MeOH in water with NH$_3$:H$_2$O in supercritical CO$_2$; Flow rate: 60 mL/min.

LCMS QC: Chiralpak AD-3 150×4.6 mm, 3 micron; Mobile phase: 5-40% MeOH with 0.05% DEA in CO$_2$; Flow rate: 2.5 mL/min.

The two enantiomers were arbitrarily assigned absolute stereochemistry.

First Eluting Isomer: Example 98

1-[(3S,5R)-3-(hydroxymethyl)-5-(7H-pyrrolo[2,3-d]pyrimidin-4-ylamino)piperidin-1-yl]prop-2-en-1-one.

Rt=5.05 minutes. MS m/z 302 [M+H]$^+$

Second Eluting Isomer: Example 99

1-[(3R,5S)-3-(hydroxymethyl)-5-(7H-pyrrolo[2,3-d]pyrimidin-4-yl)amino)piperidin-1-yl]prop-2-en-1-one.

Rt=5.48 minutes. MS m/z 302 [M+H]$^+$

Examples 100-101 were prepared according to the following Scheme:

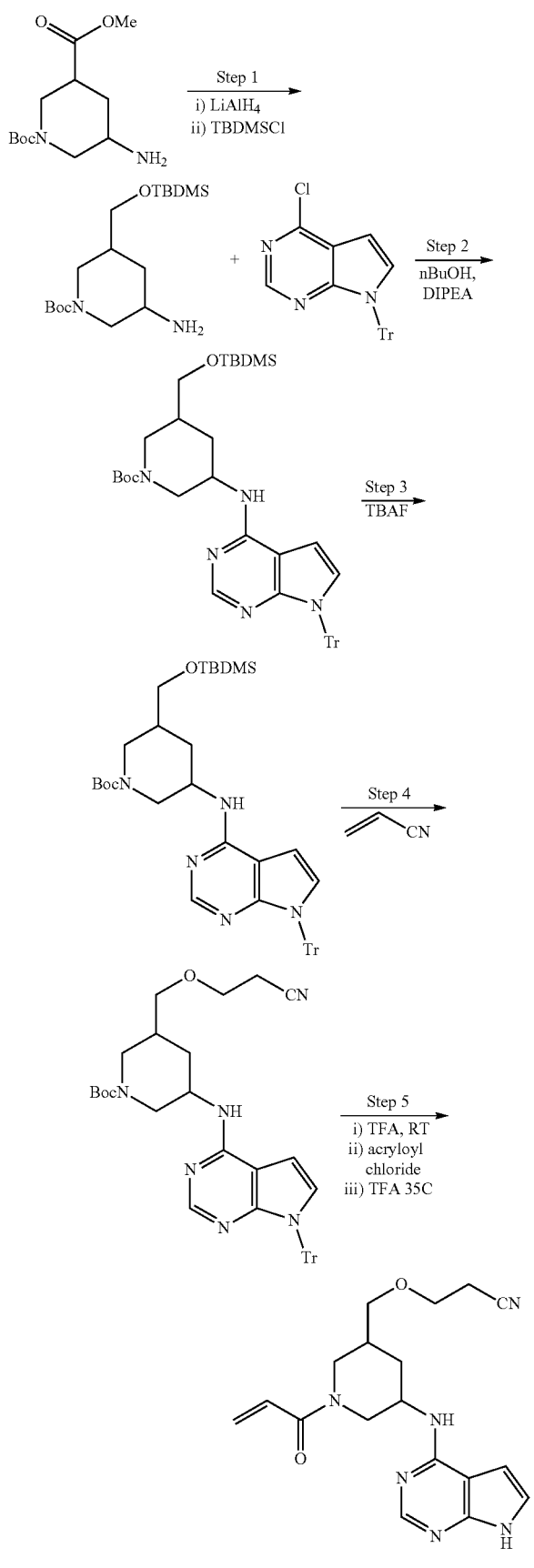

Example 100 Step 1

Cis-racemic-tert-butyl 3-amino-5-(((tert-butyldimethylsilyl)oxy)methyl)piperidine-1-carboxylate

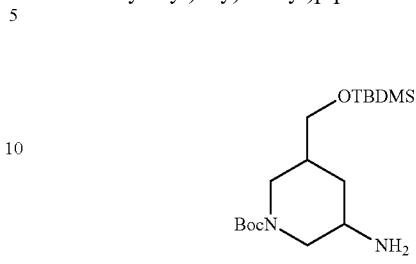

To a solution of LiAlH$_4$ (664 mg, 17.5 mmol) in anhydrous THF (60 mL) was added a solution of cis-racemic-1-tert-butyl 3-methyl-5-aminopiperidine-1,3-dicarboxylate (WO200905112, 4.1 g, 16 mmol) in anhydrous THF (10 mL) dropwise at −10° C. The reaction was stirred at this temperature for 30 minutes before the addition of water (0.7 mL), followed by 15% NaOH (aq) solution (0.7 mL) followed by water (2.1 ml). MgSO$_4$ (3 g) was added and the mixture stirred at room temperature for 30 minutes before filtering and concentrating in vacuo. The residue was dissolved in THF (100 mL) and treated with imidazole (2.3 g, 34 mmol) followed by TBDMSCl (5 g, 34 mmol). The reaction was stirred at 50° C. for 3 hours before concentrating in vacuo. The residue was partitioned between EtOAc (200 mL) and water (100 mL). The organic layer was collected, washed with 0.5M HCl (aq) (200 mL), brine (100 mL) and concentrated in vacuo to afford the title compound as a yellow oil (5.5 g, 94% over 2 steps) that was taken directly on to the next step.

Example 100 Step 2

Cis-racemic-tert-butyl-3-(((tert-butyldimethylsilyl)oxy)methyl-5-((1-trityl-1H-pyrrolo[2,3-d]pyrimidin-4-yl)amino)piperidine-1-carboxylate A solution of cis-racemic-tert-butyl 3-amino-5-(((tert-butyldimethylsilyl)oxy)methyl)piperidine-1-carboxylate (Example 100 Step 1, 5.5 g, 16 mmol), DIPEA (6.2 g, 48 mmol) and 4-chloro-1-trityl-1H-pyrrolo[2,3-d]pyrimidine (see below), 7 g, 17.6 mmol) in nBuOH (100 mL) was heated to 135° C. for 5 days. The reaction was cooled, concentrated in vacuo and purified using silica gel column chromatography eluting with 30-60% EtOAc in petroleum ether to afford the title compound as a yellow solid (5.5 g, 65%).

$^1$H NMR (400 MHz, DMSO-d$_6$): δ ppm 7.71 (s, 1H), 7.37-7.26 (m, 10H), 7.10-7.09 (m, 6H), 6.84 (s, 1H), 6.68 (s, 1H), 4.25-4.11 (m, 2H), 3.58-3.54 (m, 1H), 2.37-2.33 (m, 2H), 2.00-1.90 (m, 1H), 1.75-1.65 (m, 1H), 1.39 (s, 9H), 1.25-1.20 (m, 1H), 0.88-0.75 (m, 11H), −0.05 (s, 6H).

The cis-racemic compound was separated into its enantiomers using the following column conditions: Column: 300×50 mm, 10 micron. Mobile phase: 25% EtOH with 0.1% NH$_3$.H$_2$O in supercritical CO$_2$;
Flow rate: 200 mL/min.
The two enantiomers were arbitrarily assigned absolute stereochemistry:
First Eluting Isomer:
tert-butyl (3S,5R)-3-(((tert-butyldimethylsilyl)oxy)methyl)-5-((1-trityl-1H-pyrrolo[2,3-d]pyrimidin-4-yl)amino)piperidine-1-carboxylate. Rt=3.77 minutes Second Eluting Isomer:

tert-butyl (3R,5S)-3-(((tert-butyldimethylsilyl)oxy)methyl)-5-((1-trityl-1H-pyrrolo[2,3-d]pyrimidin-4-yl)amino)piperidine-1-carboxylate. Rt=4.74 minutes Preparation of 4-chloro-7-trityl-7H-pyrrolo[2,3-d]pyrimidine To a stirred solution of 4-chloro-7H-pyrrolo[2,3-d]pyrimidine (25 g, 130 mmol) in DMF (1 L) was added $Cs_2CO_3$ (128 g, 390 mmol) and trityl chloride (40 g, 143.2 mmol) in portions. After the addition, the mixture was stirred at 40° C. for 4 hours, TLC (petroleum/EtOAc=10:1) indicated the starting material was consumed completely. The reaction was filtered and the filtrate was diluted with water (500 mL) and then extracted with EtOAc (600 mL×3). The combine organic layers were washed with water (1 L× 5) and brine (1 L) successively, dried over Na2SO4 and concentrated to dryness. The crude product was triturated with MTBE to give desired product (50 g, 75%) as a white solid. $^1$H NMR (400 MHz, $CHCl_3$-d) d=8.31 (d, J=1.0 Hz, 1H), 7.37-7.21 (m, 10H), 7.18-7.07 (m, 6H), 6.58 (dd, J=0.8, 3.8 Hz, 1H)

Example 100 Step 3 tert-butyl (3S,5R)-3-(hydroxymethyl)-5-((7-trityl-7H-pyrrolo[2,3-d]pyrimidin-4-yl)amino)piperidine-1-carboxylate To a solution of tert-butyl (3S,5R)-3-(((tert-butyldimethylsilyl)oxy)methyl)-5-((1-trityl-1H-pyrrolo[2,3-d]pyrimidin-4-yl)amino)piperidine-1-carboxylate (Example 100 Step 2, 2.26 g, 3.2 mmol) in THF (50 mL) was added TBAF (1.67 g, 6.4 mmol) dropwise at 45° C. followed by stirring at this temperature for 3 hours. The reaction was cooled, washed with water (200 mL) and concentrated in vacuo. The residue was purified using silica gel column chromatography eluting with 1:1 EtOAc in petroleum ether to afford the title compound as a white solid (1.9 g, 100%). $^1$H NMR (400 MHz, DMSO-$d_6$): δ ppm 7.82-7.72 (m, 1H), 7.40-7.22 (m, 10H), 7.10-7.09 (m, 6H), 6.85-6.83 (m, 1H), 6.68-6.67 (m, 1H), 4.64-4.62 (m, 1H), 4.30-4.07 (m, 4H), 3.32-3.19 (m, 1H), 2.34 (br m, 1H), 1.97 (br m, 2H), 1.63 (br m, 1H), 1.40 (s, 9H). MS m/z 590 [M+H]$^+$ Example 101 Step 3 tert-butyl (3R,5S)-3-(hydroxymethyl)-5-((7-trityl-7H-pyrrolo[2,3-d]pyrimidin-4-yl)amino)piperidine-1-carboxylate The title compound was prepared as described for Example 100 Step 3 using tert-butyl (3R,5S)-3-(((tert-butyldimethylsilyl)oxy)methyl)-5-((7-trityl-7H-pyrrolo[2,3-d]pyrimidin-4-yl)amino)piperidine-1-carboxylate (Example 100 Step 2).

Example 100 Step 4 tert-butyl (3S,5R)-3-((2-cyanoethoxy)methyl)-5-((7-trityl-7H-pyrrolo[2,3-d]pyrimidin-4-yl)amino)piperidine-1-carboxylate To a solution of tert-butyl (3S,5R)-3-(hydroxymethyl)-5-((7-trityl-7H-pyrrolo[2,3-d]pyrimidin-4-yl)amino)piperidine-1-carboxylate (Step 3(i), 300 mg, 0.5 mmol) in anhydrous THF (5 mL) was added NaH (67 mg, 1.75 mmol) at 0° C. under nitrogen and the reaction was stirred at this temperature for 1 hour. Acrylonitrile (93 mg, 1.75 mmol) was added and the reaction stirred at room temperature for 3 hours. The reaction was quenched by the addition of water (2 mL) and concentrated in vacuo. The residue was purified using silica gel column chromatography eluting with 20-80% EtOAc in petroleum ether to afford the title compound as a white solid (190 mg, 60%). 1H NMR (400 MHz, DMSO-d6) δ ppm 1.21-1.29 (m, 1H) 1.40 (s, 11H) 1.57-1.90 (m, 1H) 2.77 (t, J=5.90 Hz, 2H) 3.53-3.63 (m, 2H) 4.10 (br. s., 1H) 4.19-4.29 (m, 1H) 6.68 (d, J=3.76 Hz, 1H) 6.84 (d, J=3.76 Hz, 1H) 7.10 (d, J=7.03 Hz, 7H) 7.23-7.43 (m, 12H) 7.72-7.84 (m, 1H)

Example 101 Step 4 tert-Butyl-(3R,5S)-3-((2-cyanoethoxy)methyl)-5-((7-trityl-7H-pyrrolo[2,3-d]pyrimidin-4-yl)amino)piperidine-1-carboxylate The title compound was prepared according to the method described for Example 100 Step 4 using tert-butyl (3R,5S)-3-(hydroxymethyl)-5-((7-trityl-7H-pyrrolo[2,3-d]pyrimidin-4-yl)amino)piperidine-1-carboxylate (Example 101 Step 3).

Example 100 Step 5

3-{[(3S,5R)-1-Acryloyl-5-(7H-pyrrolo[2,3-d]pyrimidin-4-yl)amino)piperidin-3-yl]methoxy}propanenitrile To a solution of tert-butyl (3S,5R)-3-((2-cyanoethoxy)methyl)-5-((7-trityl-7H-pyrrolo[2,3-d]pyrimidin-4-yl)amino)piperidine-1-carboxylate (Example 100 Step 4, 190 mg, 0.32 mmol) in DCM (5 mL) was added TFA (0.3 mL) at 0° C. and the reaction was stirred at room temperature for 12 hours. The reaction was concentrated in vacuo and dissolved in THF (5 mL) and water (5 mL). The solution was treated with DIPEA (181 mg, 1.4 mmol) followed by acryloyl chloride (63 mg, 0.7 mmol) dropwise at 0° C. The reaction was stirred at 0° C. for 2 hours before concentrating in vacuo and purifying using silica gel column chromatography eluting with 0-20% MeOH in DCM. The residue was dissolved in TFA (5 mL) and stirred at 35° C. for 3 hours. The reaction was concentrated in vacuo and purified using preparative HPLC as described below to afford the title compound as an off-white solid (19 mg, 16% over three steps). Column: Phenomenex Gemini C18 250×21.1 mm, 24 micron. Mobile phase: 21-41% MeCN in water modified with ammonia to pH=10. $^1$H NMR (400 MHz, DMSO-$d_6$): δ ppm 11.53 (br s, 1H), 8.13-8.10 (m, 1H), 7.38-7.30 (m, 1H), 7.09 (s, 1H), 6.88-6.80 (m, 1H), 6.58 (s, 1H), 6.16-6.10 (m, 1H), 5.73-5.71 (m, 1H), 4.73-4.58 (m, 1H), 4.35-4.05 (m, 2H), 3.62-3.59 (m, 2H), 3.43-3.40 (m, 2H), 2.80-2.77 (m, 3H), 2.45-2.33 (m, 1H), 2.08-2.05 (m, 1H), 1.87-1.80 (m, 1H), 1.44-1.35 (m, 1H).

MS m/z 355 [M+H]$^+$

Example 101 Step 5

3-{[(3R,5S)-1-Acryloyl-5-(7H-pyrrolo[2,3-d]pyrimidin-4-ylamino)piperidin-3-yl]methoxy}propanenitrile The title compound was prepared according to the method described for Example 100 Step 5 using tert-butyl (3R,5S)-

3-((2-cyanoethoxy)methyl)-5-((7-trityl-7H-pyrrolo[2,3-d]pyrimidin-4-yl)amino)piperidine-1-carboxylate (Example 101 Step 4) using 27-47% MeCN in water modified with ammonia to pH=10. $^1$H NMR (400 MHz, DMSO-$d_6$): δ ppm 11.52 (br s, 1H), 8.13-8.10 (m, 1H), 7.38-7.30 (m, 1H), 7.09 (s, 1H), 6.85-6.81 (m, 1H), 6.57 (s, 1H), 6.16-6.10 (m, 1H), 5.73-5.71 (m, 1H), 4.71-4.58 (m, 1H), 4.35-4.05 (m, 2H), 3.62-3.59 (m, 2H), 3.43-3.40 (m, 2H), 2.80-2.77 (m, 3H), 2.45-2.33 (m, 1H), 2.08-2.05 (m, 1H), 1.87-1.80 (m, 1H), 1.44-1.35 (m, 1H).

MS m/z 355 [M+H]$^+$

Examples 102-107 were prepared according to the following Scheme:

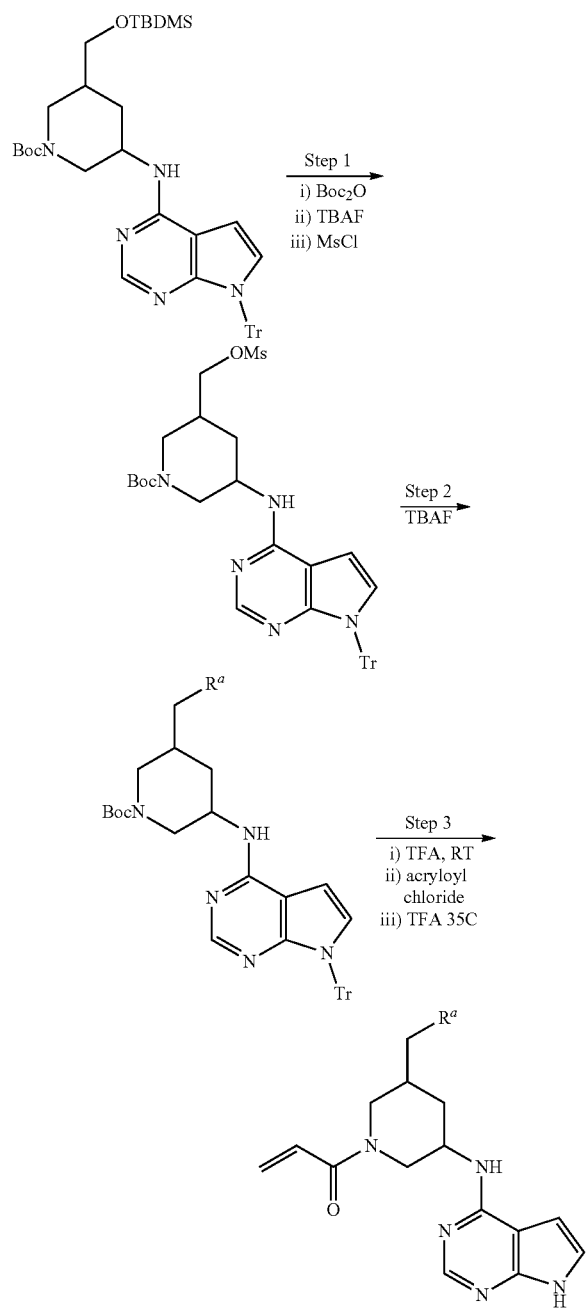

Example 102 Step 1

Cis-racemic-tert-butyl-3-((tert-butoxycarbonyl)(7-trityl-7H-pyrrolo[2,3-d]pyrimidin-4-yl)amino)-5-(((methylsulfonyl)oxy)methyl)piperidine-1-carboxylate A mixture of cis-racemic-tert-butyl-3-(((tert-butyldimethylsilyl)oxy)methyl)-5-((7-trityl-7H-pyrrolo[2,3-d]pyrimidin-4-yl)amino)piperidine-1-carboxylate (cis-racemic Example 100 Step 2, 2 g, 2.84 mmol) in di-tert-butyl dicarbonate (10 mL) was heated to 100° C. for 1 hour. The reaction was cooled, concentrated in vacuo and purified using silica gel column chromatography eluting with 0-40% EtOAc in petroleum ether. The residue was dissolved in THF (30 mL) and treated with TBAF (1.3 g, 5 mmol). The reaction was stirred at 45° C. for 12 hours. The reaction was cooled, washed with brine and concentrated in vacuo. The residue was purified using silica gel column chromatography eluting with 30-70% EtOAc in petroleum ether. Part of the residue (1 g, 1.45 mmol) was dissolved in DCM (10 mL) and treated with TEA (440 mg, 4.35 mmol) followed by mesyl chloride (332 mg, 2.90 mmol) at 0° C., and the reaction was stirred at this temperature for 2 hours. The reaction was quenched by the addition of water (10 mL) and extracted into DCM (20 mL). The organic layer was dried over sodium sulphate, concentrated in vacuo to afford the title compound that was used directly in the next step.

Example 102 Step 2

Cis-racemic-tert-butyl-3-((tert-butoxycarbonyl)(7-trityl-7H-pyrrolo[2,3-d]pyrimidin-4-yl)amino)-5-(fluoromethyl)piperidine-1-carboxylate To a solution of cis-racemic-tert-butyl-3-((tert-butoxycarbonyl)(7-trityl-7H-pyrrolo[2,3-d]pyrimidin-4-yl)amino)-5-(((methylsulfonyl)oxy)methyl)piperidine-1-carboxylate (Example 102 Step 1, 1.08 g, 1.4 mmol) in THF (30 mL) was added TBAF (1.47 g, 5.62 mmol). and the reaction was heated at 80° C. for 12 hours. The reaction was cooled, concentrated in vacuo and purified using silica gel column chromatography eluting with 0-60% EtOAc in petroleum ether to afford the title compound as a white solid (650 mg, 67%). $^1$H NMR (400 MHz, CDCl$_3$): δ ppm 8.38 (s, 1H), 7.28-7.27 (m, 6H), 7.17-7.15 (m, 7H), 6.36-6.35 (m, 1H), 4.34-4.25 (m, 4H), 3.38-3.12 (m, 2H), 2.43-2.40 (m, 1H), 2.17-2.01 (m, 1H), 1.88-1.71 (m, 2H), 1.45 (s, 9H), 1.39 (s, 9H).

Example 102 Step 3

Cis-racemic-1-[3-(fluoromethyl-5-(7H-pyrrolo[2,3-d]pyrimidin-4-ylamino)piperidin-1-yl]prop-2-en-1-one The title compound was prepared according to the method described for Example 100 Step 5 using cis-racemic-tert-butyl-3-((tert-butoxycarbonyl)(7-trityl-7H-pyrrolo[2,3-d]pyrimidin-4-yl)amino)-5-(fluoromethyl)piperidine-1-carboxylate (Example 102 Step 2). The residue was purified using silica gel column chromatography eluting with 0-20% MeOH in DCM followed by preparative HPLC as described below: Column: Phenomenex Gemini C18 250×21.2 mm, 10 micron. Mobile phase: 16-36% MeCN in water modified with ammonia to pH=10.

$^1$H NMR (400 MHz, DMSO-d$_6$): δ ppm 11.55 (br s, 1H), 8.13-8.10 (m, 1H), 7.40-7.32 (m, 1H), 7.11-7.10 (m, 1H), 6.89-6.82 (m, 1H), 6.58-6.57 (m, 1H), 6.18-6.10 (m, 1H), 5.75-5.70 (m, 1H), 4.74-4.30 (m, 4H), 4.17-4.05 (m, 1H), 2.89-2.76 (m, 1H), 2.45-2.42 (m, 1H), 2.05-1.99 (m, 2H), 1.51-1.42 (m, 1H). MS m/z 326 [M+Na]$^+$ The cis-racemic material was separated into its enantiomers using preparative chiral column chromatography according to the conditions described below; Column: Chiralcel AD (250×30 mm, 10 micron).

Mobile phase: 35% MeOH in NH$_3$.H$_2$O. Flow rate: 80 mL/min

The two enantiomers were arbitrarily assigned absolute stereochemistry

First Eluting Isomer: Example 103

1-[(3S,5R)-3-(fluoromethyl)-5-(7H-pyrrolo[2,3-d]pyrimidin-4-ylamino)piperidin-1-yl]prop-2-en-1-one. Rt=7.87 minutes MS m/z 326 [M+Na]$^+$ Second Eluting Isomer: Example 104

1-[(3R,5S)-3-(fluoromethyl)-5-(7H-pyrrolo[2,3-d]pyrimidin-4-ylamino)piperidin-1-yl]prop-2-en-1-one. Rt=9.08 minutes MS m/z 326 [M+Na]$^+$ Example 105 Step 2

Cis-racemic-tert-butyl-3-((tert-butoxycarbonyl)(7-trityl-7H-pyrrolo[2,3-d]pyrimidin-4-yl)amino)-5-(cyanomethyl)piperidine-1-carboxylate To a solution of cis-racemic-tert-butyl-3-((tert-butoxycarbonyl)(7-trityl-7H-pyrrolo[2,3-d]pyrimidin-4-yl)amino)-5-(((methylsulfonyl)oxy)methyl)piperidine-1-carboxylate (Example 102 Step 1, 1.8 g, 2.3 mmol) in DMSO (30 mL) was added potassium cyanide (450 mg, 6.9 mmol) and the reaction was heated to 80° C. for 12 hours. The reaction was cooled, diluted with water (30 mL) and extracted into EtOAc (50 mL). The organic layer was collected, concentrated in vacuo and purified using silica gel column chromatography eluting with 0-50% EtOAc in petroleum ether to afford the title compound as a white solid (1.3 g, 81%).
MS m/z 599 [M−Boc+H]$^+$ Example 105 Step 3

Cis-racemic-[1-acryloyl-5-(7H-pyrrolo[2,3-d]pyrimidin-4-ylamino)piperidin-3-yl]acetonitrile The title compound was prepared according to the method described for Example 100 Step 5 using cis-racemic-tert-butyl 3-((tert-butoxycarbonyl)(7-trityl-7H-pyrrolo[2,3-d]pyrimidin-4-yl)amino)-5-(cyanomethyl)piperidine-1-carboxylate. The residue was purified using silica gel column chromatography eluting with 0-20% MeOH in DCM followed by preparative HPLC as described below: Column: Phenomenex Gemini C18 250×21.2 mm, 10 micron Mobile phase: 12-32% MeCN in water modified with ammonia to pH=10. $^1$H NMR (400 MHz, DMSO-d$_6$): δ ppm 11.55 (brs, 1H), 8.14-8.10 (m, 1H), 7.43-7.36 (m, 1H), 7.10 (s, 1H), 6.89-6.79 (m, 1H), 6.57 (s, 1H), 6.18-6.12 (m, 1H), 5.75-5.73 (m, 1H), 4.74-4.13 (m, 3H), 2.81-2.68 (m, 4H), 2.41-1.93 (m, 2H), 1.53-1.44 (m, 1H). MS m/z 333 [M+Na]$^+$ The cis-racemic material was separated into its enantiomers using preparative chiral column chromatography according to the conditions described below; Column: AD (250×30 mm, 5 micron). Mobile phase: 35% MeOH in NH$_3$.H$_2$O. Flow rate: 50 mL/min The two enantiomers were arbitrarily assigned absolute stereochemistry First Eluting Isomer: Example 106

[(3R,5R)-1-acryloyl-5-(7H-pyrrolo[2,3-d]pyrimidin-4-ylamino)piperidin-3-yl]acetonitrile Rt=7.79 minutes MS m/z 333 [M+Na]$^+$ Second Eluting Isomer: Example 107

[(3S,5S)-1-acryloyl-5-(7H-pyrrolo[2,3-d]pyrimidin-4-ylamino)piperidin-3-yl]acetonitrile Rt=8.35 minutes MS m/z 333 [M+Na]$^+$ Example 108 was prepared according to the following Scheme:

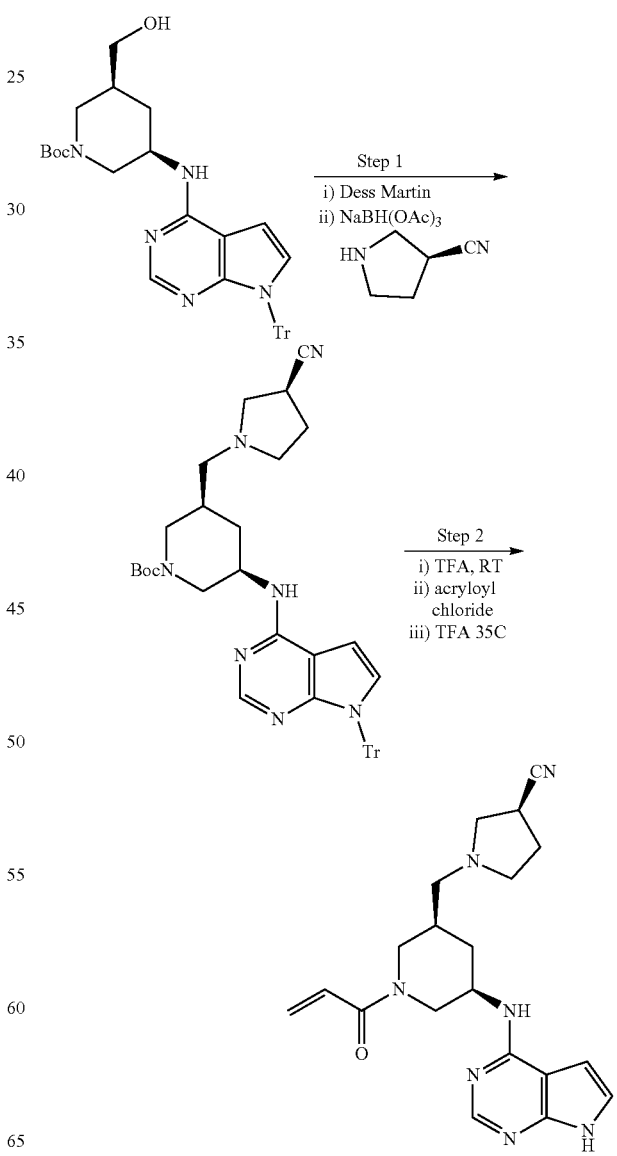

Example 108 Step 1 tert-butyl (3S,5S)-3-(((S)-3-cyanopyrrolidin-1-yl)methyl-5-((7-trityl-7H-pyrrolo[2,3-d]pyrimidin-4-yl)amino)piperidine-1-carboxylate To a solution of tert-butyl (3R,5S)-3-(hydroxymethyl)-5-((7-trityl-7H-pyrrolo[2,3-d]pyrimidin-4-yl)amino)piperidine-1-carboxylate (Example 100 Step 3, 800 mg, 1.36 mmol), in anhydrous DCM (80 mL) was added Dess-Martin reagent (1.03 g, 2.44 mmol) at 0° C. and the reaction was stirred at room temperature for 4 hours. Na$_2$S$_2$O$_3$ (300 mg) and saturated aqueous NaHCO$_3$ solution (50 mL) were added and the mixture stirred for 10 minutes. The solution was partitioned between EtOAc (80 mL) and water (50 mL), the organic layer collected, washed with brine, dried over sodium sulphate and concentrated in vacuo. The residue was purified using silica gel column chromatography eluting with 0-60% EtOAc in petroleum ether. The residue was dissolved in DCM (30 mL) with (S)-pyrrolidine-3-carbonitrile (147 mg, 1.53 mmol) and treated with NaBH(OAc)$_3$ (162 mg, 0.766 mmol) and AcOH (61 mg, 1 mol) at 0° C. The reaction was stirred at room temperature for 48 hours before the addition of further NaBH(OAc)$_3$ (162 mg, 0.766 mmol) and AcOH (61 mg, 1 mol) at 0° C. with further stirring for 5 hours. The reaction was quenched by the addition of saturated aqueous NaHCO$_3$ solution (20 mL) and extracted into EtOAc (2×30 mL). The combined organic layers were washed with brine, dried over sodium sulphate and concentrated in vacuo. The residue was purified using silica gel column chromatography eluting with 0-60% EtOAc in petroleum ether to afford the title compound as an oil (230 mg, 26% over 2 steps). MS m/z 668 [M+H]$^+$

Example 108 Step 2

(S)-1-(((3S,5S)-5-((7H-pyrrolo[2,3-d]pyrimidin-4-yl)amino)-1-acryloylpiperidin-3-yl)methyl)pyrrolidine-3-carbonitrile

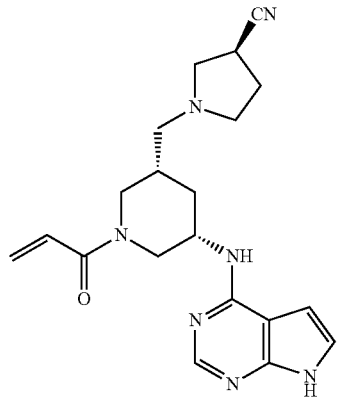 [SMILES: C=CC(=O)N1C[C@H](CN2CC[C@H](C#N)C2)C[C@H](Nc2ncnc3[nH]ccc23)C1]

The title compound was prepared according to the methods described for Example 100 Step 5 using tert-butyl (3S,5S)-3-(((S)-3-cyanopyrrolidin-1-yl)methyl)-5-((7-trityl-7H-pyrrolo[2,3-d]pyrimidin-4-yl)amino)piperidine-1-carboxylate (Example 108 Step 1).

$^1$H NMR (400 MHz, DMSO-d$_6$): δ ppm 11.50 (br s, 1H), 8.12-8.08 (m, 1H), 7.35-7.27 (m, 1H), 7.08 (s, 1H), 6.83-6.80 (m, 1H), 6.56 (s, 1H), 6.16-6.06 (m, 1H), 5.73-5.65 (m, 1H), 4.74-4.57 (m, 1H), 4.37-4.12 (m, 2H), 3.27-3.24 (m, 1H), 2.75-2.70 (m, 5H), 2.62-2.32 (m, 6H), 2.11-1.92 (m, 1H), 1.80-1.70 (m, 1H), 1.31-1.22 (m, 1H). MS m/z 380 [M+H]$^+$ Examples 109-112 were prepared according to the Scheme below:

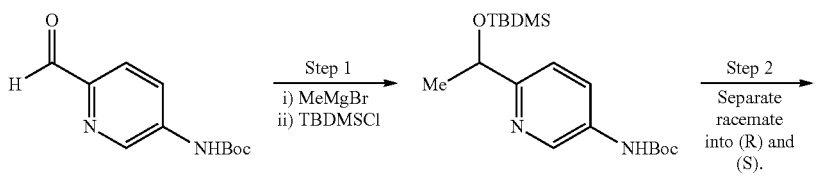

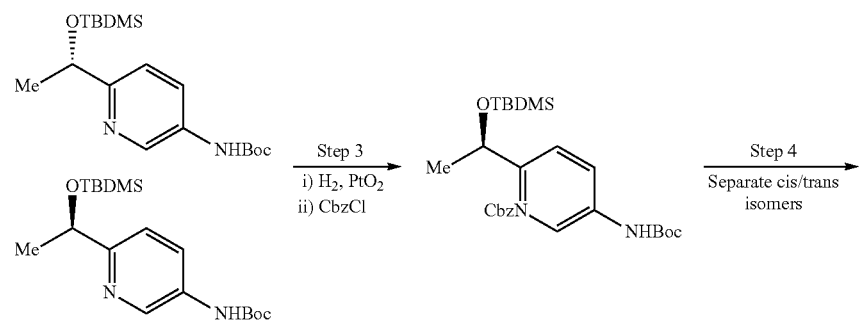

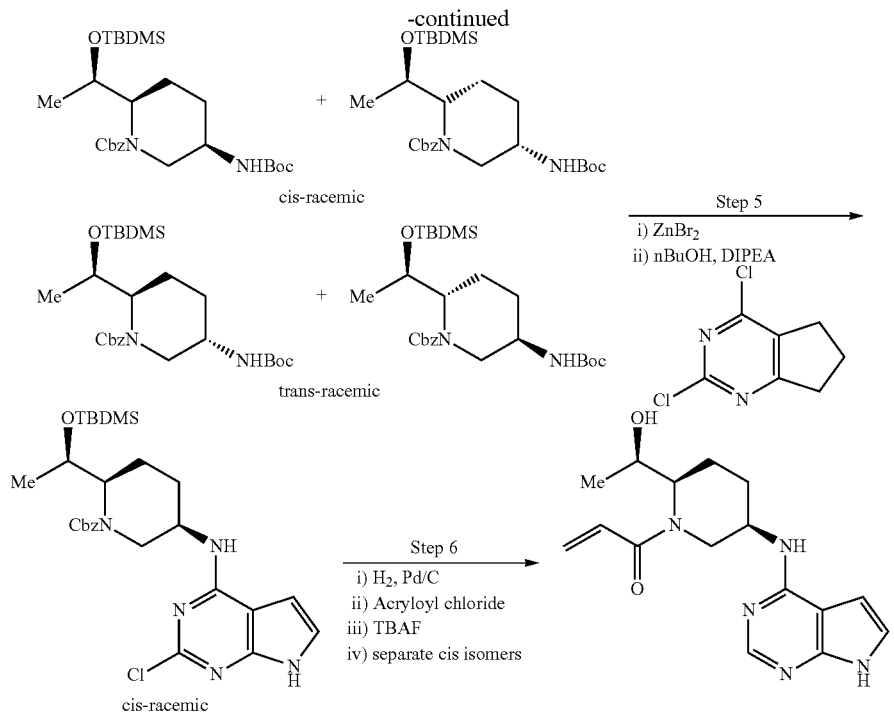

Example 109 Step 1

Racemic-tert-butyl (6-(1-((tert-butyldimethylsilyl)oxy)ethyl)pyridin-3-ylcarbamate

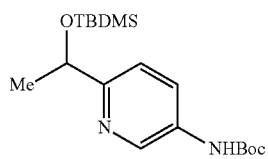 [SMILES: CC(O[Si](C)(C)C(C)(C)C)c1ccc(NC(=O)OC(C)(C)C)cn1]

To a solution of tert-butyl (6-formylpyridin-3-yl)carbamate (8.5 g, 38 mmol) in anhydrous THF (400 mL) was added methyl magnesium bromide (76.5 mL, 229 mmol) at 0° C. The reaction was stirred at room temperature for 18 hours. The reaction was poured into ice-water (1000 mL) and extracted into EtOAc (3×600 mL). The combined organic layers were dried over sodium sulphate and concentrated in vacuo to afford a brown solid as the hydroxyl intermediate. To a solution of this hydroxyl intermediate (26.5 g, 0.11 mol) in THF (400 mL) was added imidazole (15.1 g, 0.223 mmol) followed by TBDMSCl (25 g, 0.17 mmol) at 0° C. The reaction was heated to 70° C. for 5 hours before pouring into ice-water (200 mL) and extracting with EtOAc (2×500 mL). The organic layers were combined, washed with brine (200 mL), dried over sodium sulphate and concentrated in vacuo. The residue was purified using silica gel column chromatography eluting with 0-18% EtOAc in petroleum ether to afford the title compound as a white solid (36 g, 92% over 2 steps). $^1$H NMR (400 MHz, DMSO-$d_6$): δ ppm 9.49 (br s, 1H), 8.49 (s, 1H), 7.86-7.84 (m, 1H), 7.36-7.34 (m, 1H), 4.85-4.80 (m, 1H), 1.41 (s, 9H), 1.35-1.33 (d, 3H), 0.86 (s, 9H), −0.04 (s, 3H), −0.05 (s, 3H).

Example 109 Step 2

The racemate (36 g) was separated into its enantiomers (18 g, and 17.62 g) using the following preparative chiral HPLC: Column: IC (300×50 mm, 10 micron. Mobile phase: 20% IPA in NH$_3$H$_2$O. Flow rate: 200 mL/min The two enantiomers were arbitrarily assigned absolute stereochemistry.

to afford (R)-tert-butyl (6-(1-((tert-butyldimethylsilyl)oxy)ethyl)pyridin-3-yl)carbamate and (S)-tert-butyl (6-(1-((tert-butyldimethylsilyl)oxy)ethyl)pyridin-3-yl)carbamate.

Example 109 Steps 3 and 4

Cis/trans-racemic-benzyl-5-((tert-butoxycarbonyl)amino)-2-((R)-1-((tert-butyldimethylsilyl)oxy)ethyl)piperidine-1-carboxylate To a solution of (R)-tert-butyl (6-(1-((tert-butyldimethylsilyl)oxy)ethyl)pyridin-3-yl)carbamate (Example 109 Step 2, 18 g, 51 mmol) in EtOH (260 mL) and AcOH (130 mL) was added 10% PtO$_2$ and the reaction was hydrogenated under 55 psi at 65° C. for 18 hours. The reaction was filtered through Celite and concentrated in vacuo. The residue was dissolved in THF (300 mL) and treated with saturated aqueous NaHCO$_3$ solution (300 mL). CbzCl (13.3 g, 93 mmol) was added at 0° C. and the reaction stirred at this temperature for 1.5 hours. The reaction was extracted with EtOAc (3×300 mL), the organic layers were combined, dried over sodium sulfate and concentrated in vacuo to afford the title compound that was separated into its cis-racemic and trans-racemic isomers using silica gel column chromatography eluting with 0-10% MeOH in DCM:

Cis-racemic-benzyl-5-((tert-butoxycarbonyl)amino)-2-((R)-1-((tert-butyldimethylsilyl)oxy)ethyl)piperidine-1-carboxylate (7.9 g). $^1$H NMR (400 MHz, DMSO-$d_6$): δ ppm 7.35-7.21 (m, 5H), 6.85-6.84 (m, 1H), 5.17-4.96 (m, 2H), 4.49-4.48 (m, 2H), 4.06-3.89 (m, 3H), 3.26-3.24 (m, 0.5H), 1.67-1.47 (m, 2.5H), 1.36-1.34 (m, 9H), 1.18-1.08 (m, 4H), 0.84 (s, 9H), 0.04-0.01 (m, 6H).

Trans-racemic-benzyl-5-((tert-butoxycarbonyl)amino)-2-((R)-1-((tert-butyldimethylsilyl)oxy)ethyl)piperidine-1-carboxylate (6 g). $^1$H NMR (400 MHz, DMSO-$d_6$): δ ppm 7.34-7.30 (m, 5H), 6.81-6.79 (m, 1H), 5.16-4.97 (m, 2H), 4.06-3.99 (m, 3H), 3.80-3.74 (m, 1H), 3.25-3.15 (m, 0.5), 2.41-2.32 (m, 0.5H), 1.81-1.52 (m, 3H), 1.37-1.33 (m, 10H), 1.00-0.83 (m, 3H), 0.83 (s, 9H), 0.06-0.02 (m, 6H).

Example 112 Steps 3 and 4

Cis/trans-racemic-benzyl-5-((tert-butoxycarbonyl)amino)-2-((S)-1-((tert-butyldimethylsilyl)oxy)ethyl)piperidine-1-carboxylate The title compounds were prepared according to the method described for Example 109 Steps 3 and 4 using (R)-tert-butyl (6-(1-((tert-butyldimethylsilyl)oxy)ethyl)pyridin-3-yl)carbamate (Example 109 Step 2). The title compound that was separated into its cis-racemic and trans-racemic isomers using silica gel column chromatography eluting with 0-10% MeOH in DCM: Cis-racemic-benzyl-5-((tert-butoxycarbonyl)amino)-2-((S)-1-((tert-butyldimethylsilyl)oxy)ethyl)piperidine-1-carboxylate. $^1$H NMR (400 MHz, DMSO-$d_6$): δ ppm 7.35-7.21 (m, 5H), 6.85-6.84 (m, 1H), 5.17-4.96 (m, 2H), 4.49-4.48 (m, 2H), 4.06-3.89 (m, 3H), 3.26-3.24 (m, 0.5H), 1.67-1.47 (m, 2.5H), 1.36-1.34 (m, 9H), 1.18-1.08 (m, 4H), 0.84 (s, 9H), 0.04-0.01 (m, 6H).

Trans-racemic-benzyl-5-((tert-butoxycarbonyl)amino)-2-((S)-1-((tert-butyldimethylsilyl)oxy)ethyl)piperidine-1-carboxylate. $^1$H NMR (400 MHz, DMSO-$d_6$): δ ppm 7.34-7.30 (m, 5H), 6.81-6.79 (m, 1H), 5.14-4.97 (m, 2H), 4.06-3.99 (m, 3H), 3.80-3.74 (m, 1H), 3.25-3.15 (m, 0.5), 2.41-2.32 (m, 0.5H), 1.81-1.52 (m, 3H), 1.37-1.33 (m, 10H), 1.00-0.83 (m, 3H), 0.83 (s, 9H), 0.06-0.02 (m, 6H).

Example 109 Step 5

Trans-racemic-benzyl 2-((R)-1-((tert-butyldimethylsilyl)oxy)ethyl)-5-((2-chloro-7H-pyrrolo[2,3-d]pyrimidin-4-yl)amino)piperidine-1-carboxylate To a solution of trans-racemic-benzyl 5-((tert-butoxycarbonyl)amino)-2-((R)-1-((tert-butyldimethylsilyl)oxy)ethyl)piperidine-1-carboxylate (Example 109 Step 3 and 4, 7.0 g, 14.2 mmol) in DCM (400 mL) was added zinc bromide (18.1 g, 81 mmol) at 0° C. and the reaction was stirred at room temperature for 4 hours. The reaction was poured into ice and saturated aqueous NaHCO$_3$ solution (160 mL) and extracted into DCM (4×500 mL). The organic layers were combined, dried over sodium sulphate and concentrated in vacuo. The residue was purified using silica gel column chromatography using 0-15% MeOH with ammonia in DCM. The residue (2.5 g, 6.3 mmol) was dissolved in nBuOH (60 mL) and treated with DIPEA (4.13 g, 32 mmol). 2,4-dichloro-7H-pyrrolo[2,3-d]pyrimidine (1.26 g, 6.7 mmol) was added and the reaction heated to 130° C. for 24 hours. The reaction was cooled, concentrated in vacuo and partitioned between EtOAc (150 mL) and water (100 mL). The organic layer was washed with brine, dried over sodium sulphate and concentrated in vacuo. The residue was purified using silica gel column chromatography eluting with 10-20% EtOAc in petroleum ether to afford the title compound as a white solid (2.2 g, 64% over 2 steps). $^1$H NMR (400 MHz, CDCl$_3$): δ ppm 10.33 (br s, 1H), 7.39-7.02 (m, 7H), 5.23-5.01 (m, 2.5H), 4.59-4.00 (m, 4.5H), 3.50-3.39 (m, 1H), 2.75-2.60 (m, 0.5H), 2.30-1.90 (m, 1.5H), 1.75-1.60 (m, 1.5H), 1.28-1.14 (m, 3.5H), 0.90 (s, 9H), 0.09-0.04 (m, 6H).

Example 112 Step 5

Cis-racemic-benzyl ((2-((S)-1-((tert-butyldimethylsilyl)oxy)ethyl-5-((2-chloro-7H-pyrrolo[2,3-d]pyrimidin-4-yl)amino)piperidine-1-carboxylate The title compound was prepared according to the method described for Example 109 Step 5 using Cis/trans-racemic-benzyl-5-((tert-butoxycarbonyl)amino)-2-((S)-1-((tert-butyldimethylsilyl)oxy)ethyl)piperidine-1-carboxylate (Example 112 Steps 3 and 4). $^1$H NMR (400 MHz, DMSO-$d_6$): δ ppm 11.75 (br s, 1H), 7.74-7.73 (m, 1H), 7.38-7.25 (m, 4H), 7.12-7.10 (m, 1H), 6.67-6.55 (m, 1H), 5.10-4.98 (m, 2H), 4.30-4.00 (m, 5H), 2.77-2.68 (m, 1H), 1.75-1.50 (m, 2H), 1.20-1.16 (m, 4H), 0.82 (s, 9H), 0.07-0.01 (m, 6H).

Example 109 Step 6

Trans-racemic-1-[2-[(1R)-1-hydroxyethyl]-5-(7H-pyrrolo[2,3-d]pyrimidin-4-yl)amino)piperidin-1-yl]prop-2-en-1-one To a solution of trans-racemic-benzyl 2-((R)-1-((tert-butyldimethylsilyl)oxy)ethyl)-5-((2-chloro-7H-pyrrolo[2,3-d]pyrimidin-4-yl)amino)piperidine-1-carboxylate (Example 109 Step 5, 2.9 g, 5.34 mmol) in MeOH (100 mL) was added 10% Pd/C (600 mg) and the reaction was hydrogenated under 45 psi hydrogen at 40° C. for 4 days. The reaction was filtered and concentrated in vacuo to afford a white solid (1.9 g, 95%). The intermediate (1 g, 2.66 mol) was dissolved in THF (25 mL) and water (25 mL) and treated with DIPEA (1.38 g) dropwise. To the reaction was added acryloyl chloride with stirring at 0° C. for 3 hours. The reaction was extracted into EtOAc (2×20 mL), the organic layers combined, dried over sodium sulphate and concentrated in vacuo. The residue was purified using silica gel column chromatography eluting with 1-10% MeOH in DCM to afford a white solid (600 mg, 53%). This intermediate (380 mg, 0.884 mmol) was dissolved in THF (15 mL) and treated with TBAF (463 mg, 1.77 mmol) and stirred at 45° C. for 18 hours. The reaction was concentrated in vacuo and purified using silica gel column chromatography eluting with 1-10% MeOH in DCM (280 mg, 50% over three steps).

$^1$H NMR (400 MHz, DMSO-$d_6$): δ ppm 11.52-11.48 (br m, 1H), 8.13-8.09 (m, 1H), 7.31-7.23 (m, 1H), 7.09-7.06 (m, 1H), 6.86-6.54 (m, 2H), 6.25-6.09 (m, 1H), 5.83-5.69 (m, 1H), 4.32-4.04 (m, 4H), 2.86-2.80 (m, 1H), 2.34-1.55 (m, 4H), 1.00-0.99 (m, 3H). MS m/z 316 [M+H]$^+$ The cis-racemic material was separated into its enantiomers using preparative chiral column chromatography according to the conditions described below; Column: YMC-Actus Triart C18 150×30 mm, 5 micron. Mobile phase: 2-22% MeCN in water modified with 0.225% formic acid.

QC Analytical LCMS Method:

Column: Chiralcel OJ-H (250×4.6 mm, 5 micron); Mobile phase: 5-40% MeOH with 0.05% DEA in CO$_2$; Flow rate: 2.35 mL/min The two enantiomers were arbitrarily assigned absolute stereochemistry First Eluting Isomer: Example 110

1-[(2S,5R)-2-[(1R)-1-Hydroxyethyl]-5-(7H-pyrrolo[2,3-d]pyrimidin-4-ylamino)piperidin-1-yl]prop-2-en-1-one.
Rt=4.64 minutes MS m/z 316 [M+H]⁺

Second Eluting Isomer: Example 111

1-[(2R,5S)-2-[(1R)-1-Hydroxyethyl]-5-(7H-pyrrolo[2,3-d]pyrimidin-4-ylamino)piperidin-1-yl]prop-2-en-1-one.
Rt=5.19 minutes MS m/z 316 [M+H]⁺

Example 112 Step 6

Cis-racemic-1-[2-[(1S)-1-hydroxyethyl]-5-(7H-pyrrolo[2,3-d]pyrimidin-4-yl)amino)piperidin-1-yl]prop-2-en-1-one The title compound was prepared according to the method described for Example 109 Step 6 using cis-racemic-benzyl 2-((S)-1-((tert-butyldimethylsilyl)oxy)ethyl)-5-((2-chloro-7H-pyrrolo[2,3-d]pyrimidin-4-yl)amino)piperidine-1-carboxylate (Example 112 Step 5). The residue was purified using silica gel column chromatography eluting with 20-100% EtOAc in petroleum ether followed by preparative HPLC as described below:
Column: Phenomenex Gemini C18 250×21.2 mm, 8 micron
Mobile phase: 0-20% MeCN in water modified with ammonia to pH=10.
¹H NMR (400 MHz, DMSO-d₆): δ ppm 11.52 (br s, 1H), 8.15-8.09 (m, 1H), 7.28-7.26 (m, 1H), 7.09-7.08 (m, 1H), 6.84-6.80 (m, 1H), 6.54 (br s, 1H), 6.07-6.02 (m, 1H), 5.61-5.58 (m, 1H), 4.64-4.60 (m, 2H), 4.12-4.04 (m, 2H), 3.75-3.70 (m, 1H), 3.20-3.10 (m, 1H), 2.66-2.60 (m, 1H), 1.85-1.81 (m, 2H), 1.65-1.63 (m, 1H), 1.16-1.13 (m, 3H). MS m/z 316 [M+H]⁺

Example 113 was prepared according to the Scheme below:

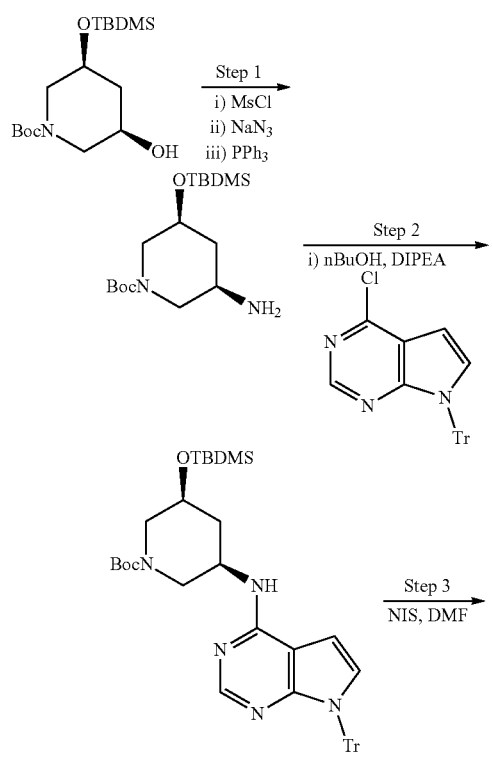

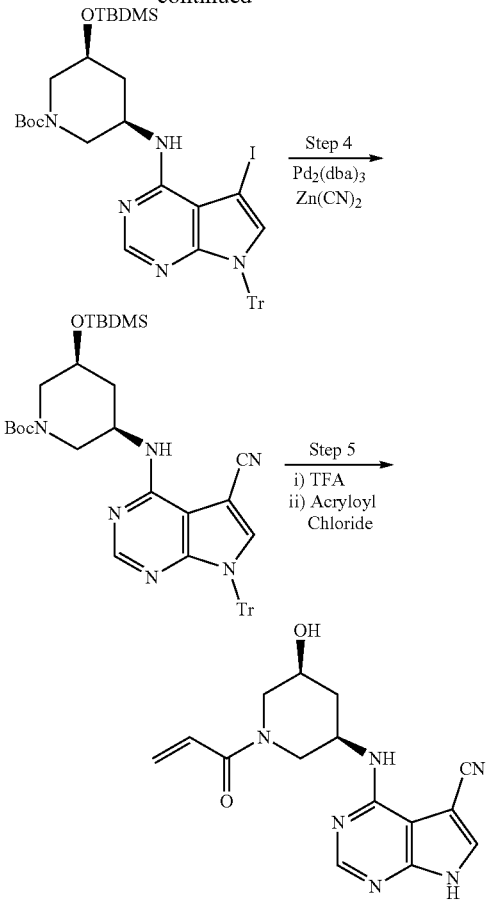

Example 113 Step 1 tert-Butyl (3R, 5S)-3-amino-5-((tert-butyldimethylsilyl)oxy)piperidine-1-carboxylate To a solution of (3S,5R)-tert-butyl 3-((tert-butyldimethylsilyl)oxy)-5-hydroxypiperidine-1-carboxylate (WO2011029046, 3.5 g, 10.55 mmol) in DCM (25 mL) was added TEA (4 4 mL, 31.6 mmol) followed by mesyl chloride (1.06 mL, 13.72 mmol) at 0° C. The reaction was stirred at room temperature for 4 hours before quenching with water and extracting into DCM (2×75 mL). The organic layers were combined, dried over sodium sulphate and concentrated in vacuo. The residue was dissolved in DMF (35 mL) and treated with sodium azide (2.05 g, 31.63 mmol). The reaction was heated to 100° C. for 16 hours before cooling and concentrating in vacuo. The residue was dissolved in EtOAc (200 mL) and washed with water (3×50 mL), dried over sodium sulphate and concentrated in vacuo. The residue was purified using silica gel column chromatography eluting with 0-20% EtOAc in heptanes to afford the azide intermediate (1.9 g, 51%). The azide intermediate was dissolved in THF (100 mL) and treated with water (0.67 mL) followed by triphenylphosphine (2.01 g, 7.9 mmol). The reaction was heated to reflux for 16 hours, cooled and concentrated in vacuo. The residue was purified using silica gel column chromatography eluting with 0-5% MeOH in DCM to afford the title compound as a light yellow oil (1.52 g, 86%). MS m/z 331 [M+H]⁺

Example 113 Step 2 tert-butyl (3S, 5R)-3-((tert-butyldimethylsilyl)oxy)-5-((7-trityl-7H-pyrrolo[2,3-d]pyrimidin-4-yl)amino)piperidine-1-carboxylate To a solution of tert-butyl (3R,5S)-3-amino-5-((tert-butyldimethylsilyl)oxy)piperidine-1-carboxylate (Example 113 Step 1, 9 g, 27.23 mmol) in n-BuOH (140 mL) was added 4-chloro-7-trityl-7H-pyrrolo[2,3-d]pyrimidine (16.17 g, 41 mmol) followed by DIPEA (10.54 g, 82 mmol). The reaction was heated to 120° C. for 72 hours. The reaction was cooled and concentrated in vacuo. The residue was partitioned between EtOAc (200 mL) and brine (200 mL), the organic layer was collected, washed with further brine (200 mL), dried over sodium sulphate and concentrated in vacuo. The residue was purified using silica gel column chromatography eluting with 10-30% EtOAc in petroleum ether to afford the title compound as a yellow solid (18 g, 95%) that was taken on directly to the next step.

Example 113 Step 3 tert-Butyl (3S, 5R)-3-((tert-butyldimethylsilyl)oxy)-5-((5-iodo-7-trityl-7H-pyrrolo[2,3-d]pyrimidin-4-yl)amino)piperidine-1-carboxylate To a solution of tert-butyl (3S,5R)-3-((tert-butyldimethylsilyl)oxy)-5-((7-trityl-7H-pyrrolo[2,3-d]pyrimidin-4-yl)amino)piperidine-1-carboxylate (Example 113 Step 2, 1.6 g 2.3 mmol) in DMF (30 mL) was added NIS (1.05 g, 4.6 mmol) and the reaction was stirred at room temperature for 2 hours. The reaction was filtered and the filtrate washed with water (20 mL) and concentrated in vacuo. The residue was purified using silica gel column chromatography eluting with 20-80% EtOAc in petroleum ether to afford the title compound as a yellow solid (1.2 g, 64%).
MS m/z 816 [M+H]$^+$

Example 113 Step 4 tert-butyl (3S,5R)-3-((tert-butyldimethylsilyl)oxy)-5-((5-cyano-7H-pyrrolo[2,3-d]pyrimidin-4-yl)amino)piperidine-1-carboxylate To a solution of tert-butyl (3S,5R)-3-((tert-butyldimethylsilyl)oxy)-5-((5-iodo-7-trityl-7H-pyrrolo[2,3-d]pyrimidin-4-yl)amino)piperidine-1-carboxylate (Example 113 Step 3, 500 mg, 0.6 mmol) in anhydrous DMF (10 mL) was added zinc cyanide (80 mg, 0.72 mmol) followed by dppf (66 mg, 0.12 mmol). The reaction was degassed under argon and purged with nitrogen. To the reaction was added Pd$_2$(dba)$_3$ (55 mg, 0.06 mmol) and the reaction heated to 130° C. for 18 hours. The reaction was cooled, concentrated in vacuo and purified using silica gel column chromatography eluting with 20-80% EtOAc in petroleum ether to afford the title compound as a brown solid (130 mg, 45%). $^1$H NMR (400 MHz, DMSO-d$_6$): δ ppm 12.76 (br s, 1H), 8.29 (s, 1H), 8.17 (s, 1H), 6.31-6.26 (m, 1H), 4.30-4.25 (m, 1H), 4.00-3.60 (m, 4H), 3.10-2.90 (m, 1H), 2.15-2.08 (m, 1H), 1.77-1.70 (m, 1H), 1.41-1.20 (m, 9H), 0.88 (s, 9H), 0.107-0.04 (m, 6H).

Example 113 Step 5

4-{[(3R,5S)-1-Acryloyl-5-hydroxypiperidin-3-yl]amino}-7H-pyrrolo[2,3-d]pyrimidine-5-carbonitrile To a solution of tert-butyl (3S,5R)-3-((tert-butyldimethylsilyl)oxy)-5-((5-cyano-7-trityl-7H-pyrrolo[2,3-d]pyrimidin-4-yl)amino)piperidine-1-carboxylate (Example 113 Step 4, 130 mg, 0.28 mmol) in DCM (5 mL) was added TFA (1 mL) and the reaction was stirred at room temperature for 4 hours. The reaction was concentrated in vacuo and dissolved in THF (5 mL) and water (5 mL). To the solution was added DIPEA (108 mg, 0.84 mmol) followed by acryloyl chloride (51 mg, 0.56 mmol) at 0° C. The reaction was stirred at 0° C. for 2 hours, then additional water was added (5 mL). The reaction was purified using preparative HPLC as described below to afford the title compound as a yellow solid (15 mg, 18%). Column: Phenomenex Gemini C18 250×21.2 mm, 24 micron. Mobile phase: 5-25% MeCN in water modified with ammonia to pH=10. $^1$H NMR (400 MHz, DMSO-d$_6$): δ ppm 12.59 (br s, 1H), 8.30-8.27 (m, 1H), 8.14-8.10 (m, 1H), 7.23-7.11 (m, 1H), 6.82-6.78 (m, 0.5H), 6.46-6.42 (m, 0.5H), 6.01-5.90 (m, 1H), 5.65-5.40 (m, 2H), 4.47-4.23 (m, 1.5H), 3.88-3.72 (m, 3H), 3.68-3.50 (m, 0.5H), 3.10-2.90 (br m, 1H), 2.12-2.04 (m, 1H), 1.85-1.76 (m, 1H). MS m/z 335 [M+Na]$^+$ Example 114 was prepared as described in the Scheme below:

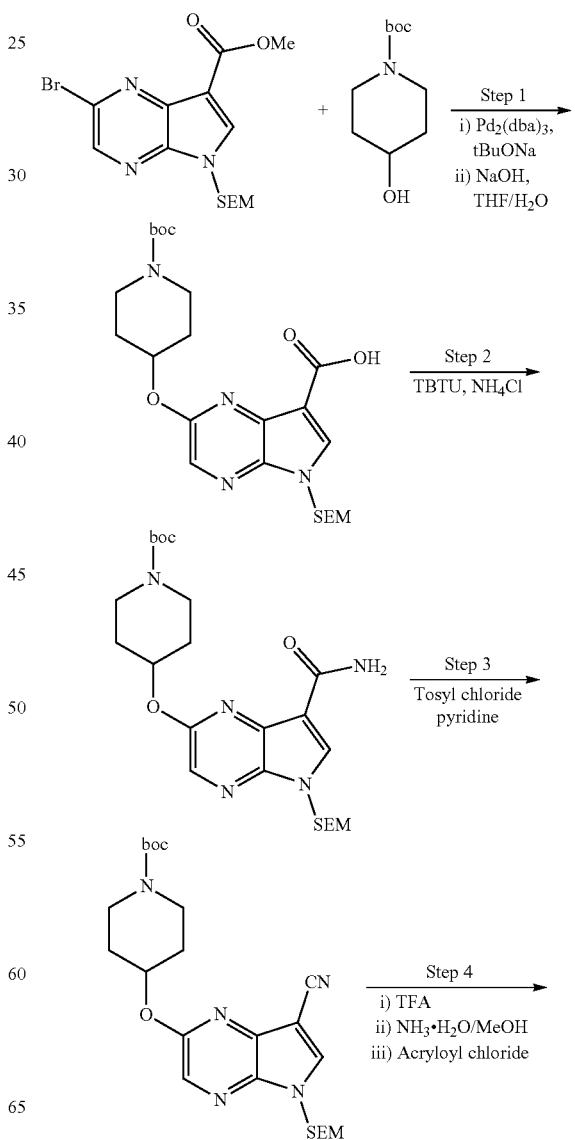

-continued

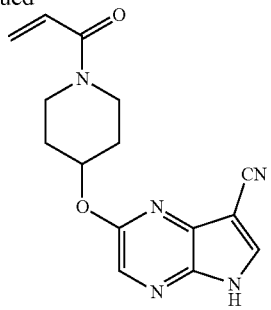

Example 114 Step 1

2-{[1-(tert-Butoxycarbonyl)piperidin-4-yl]oxy}-5-{[2-(trimethylsilyl)ethoxy]methyl}-5H-pyrrolo[2,3-b]pyrazine-7-carboxylic acid The title compound was prepared according to the method described for Example 83 Step 4 to afford methyl 2-{[1-(tert-butoxycarbonyl)piperidin-4-yl]oxy}-5-{[2-(trimethylsilyl)ethoxy]methyl}-5H-pyrrolo[2,3-b]pyrazine-7-carboxylate using methyl 2-bromo-5-((2-(trimethyl-silyl)ethoxy)methyl)-5H-pyrrolo[2,3-b]pyrazine-7-carboxylate (Example 83 Step 3) and tert-butyl 4-hydroxypiperidine-1-carboxylate followed by the method described for Example 83 Step 5. $^1$H NMR (400 MHz, DMSO-d$_6$): δ ppm 12.26 (br s, 1H), 8.48 (s, 1H), 8.00 (s, 1H), 5.62 (s, 2H), 5.30-5.27 (m, 1H), 3.66-3.63 (m, 2H), 3.54-3.50 (t, 2H), 3.34-3.26 (m, 2H), 2.02-1.98 (m, 2H), 1.66-1.60 (m, 2H), 1.41 (s, 9H), 0.82-0.78 (t, 2H), −0.11 (s, 9H). MS m/z 515 [M+Na]$^+$

Example 114 Step 2 tert-Butyl 4-[(7-carbamoyl-5-{[2-(trimethylsilyl)ethoxy]methyl}-5H-pyrrolo[2,3-b]pyrazin-2-yl)oxy]piperidine-1-carboxylate To a solution of 2-{[1-(tert-butoxycarbonyl)piperidin-4-yl]oxy}-5-{[2-(trimethylsilyl)ethoxy]methyl}-5H-pyrrolo[2,3-b]pyrazine-7-carboxylic acid (Example 114 Step 1, 1 g, 2 mmol) and TBTU (785 mg, 2.4 mmol) in DMF (10 mL) was added DIPEA (1 g, 8 mmol) followed by ammonium chloride (573 mg, 10 mmol) and the reaction was stirred at room temperature for 3 hours. The reaction was partitioned between EtOAc (20 mL) and water (20 mL), the organic layer collected, washed with brine (50 mL), dried over sodium sulphate and concentrated in vacuo. The residue was purified using silica gel column chromatography eluting with 5-15% MeOH in DCM to afford the title compound (832 mg, 83%) that was taken directly on to the next step.

Example 114 Step 3 tert-Butyl 4-[(7-cyano-5-{[2-(trimethylsilyl)ethoxy]methyl}-5H-pyrrolo[2,3-b]pyrazin-2-yl)oxy]piperidine-1-carboxylate A mixture of tert-butyl 4-[(7-carbamoyl-5-{[2-(trimethylsilyl)ethoxy]methyl})-5H-pyrrolo[2,3-b]pyrazin-2-yl)oxy]piperidine-1-carboxylate (Example 114 Step 2, 300 mg, 0.61 mmol) and tosyl chloride (350 mg, 1.83 mmol) in pyridine (5 mL) was stirred at room temperature for 4 hours. The reaction was partitioned between EtOAc (20 mL) and water (20 mL). The organic layer was collected, concentrated in vacuo and purified using silica gel column chromatography eluting with 20-80% EtOAc in petroleum ether to afford the title compound as a white solid (645 mg, 81%). MS m/z 496 [M+Na]$^+$

Example 114 Step 4

2-[(1-Acryloylpiperidin-4-yl)oxy]-5H-pyrrolo[2,3-b]pyrazine-7-carbonitrile

The title compound was prepared according to the method described for Example 1 Steps 5-7 using tert-butyl 4-[(7-cyano-5-{[2-(trimethylsilyl)ethoxy]methyl}-5H-pyrrolo[2,3-b]pyrazin-2-yl)oxy]piperidine-1-carboxylate (Example 114 Step 3). The residue was purified using silica gel column chromatography eluting with 2-15% MeOH in DCM followed by preparative HPLC as described below: Column: Phenomenex Gemini C18 250×21.2 mm, 24 micron Mobile phase: 17-37% MeCN in water modified with 0.225% formic acid. $^1$H NMR (400 MHz, DMSO-d$_6$): δ ppm 8.55 (s, 1H), 8.07 (s, 1H), 6.88-6.82 (m, 1H), 6.15-6.10 (m, 1H), 5.71-5.68 (m, 1H), 5.36-5.34 (m, 1H), 4.00-3.80 (m, 3H), 3.60-3.40 (m, 3H), 2.10-2.00 (m, 2H), 1.75-1.65 (m, 2H). MS m/z 320 [M+Na]$^+$ Examples 115-116 were prepared as described in the Scheme below:

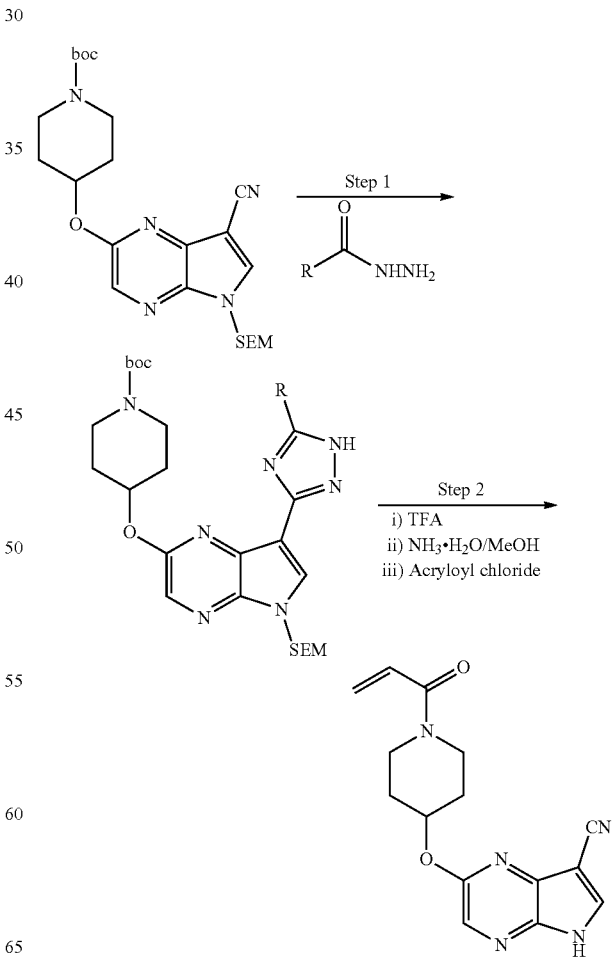

Example 115 Step 1 tert-Butyl 4-{[7-(5-methyl-1H-1,2,4-triazol-3-yl)-5-{[2-(trimethylsilyl)ethoxy]methyl}-5H-pyrrolo[2,3-b]pyrazin-2-yl]oxy}piperidine-1-carboxylate To a solution of tert-butyl 4-[(7-cyano-5-{[2-(trimethylsilyl)ethoxy]methyl}-5H-pyrrolo[2,3-b]pyrazin-2-yl)oxy]piperidine-1-carboxylate (Example 114 Step 3, 500 mg, 1.06 mmol) in nBuOH (15 mL) was added acetohydrazide (258 mg, 3.48 mmol) and potassium carbonate (292 mg, 2.11 mmol). The reaction was heated to 130° C. for 48 hours. The reaction was cooled, concentrated in vacuo and purified using silica gel column chromatography eluting with 50-100% EtOAc in petroleum ether to afford the title compound as a yellow solid (270 mg, 48%) that was taken directly on to the next step.

Example 115 Step 2

1-(4-{[7-(5-Methyl-1H-1,2,4-triazol-3-yl)-5H-pyrrolo[2,3-b]pyrazin-2-yl]oxy}piperidin-1-yl)prop-2-en-1-one The title compound was prepared according to the method described for Example 1 Steps 5-7 using tert-butyl 4-{[7-(5-methyl-1H-1,2,4-triazol-3-yl)-5-{[2-(trimethylsilyl)ethoxy]methyl}-5H-pyrrolo[2,3-b]pyrazin-2-yl]oxy}piperidine-1-carboxylate (Example 115 Step 1). The residue was purified using silica gel column chromatography eluting with 0-10% MeOH in DCM followed by preparative HPLC as described below: Column: Phenomenex Gemini C18 250×21.2 mm, 24 micron. Mobile phase: 17-37% MeCN in water modified with ammonia to pH=10.

$^1$H NMR (400 MHz, DMSO-$d_6$): δ ppm 13.24 (br m, 1H), 12.46 (br m, 1H), 8.30-7.90 (m, 2H), 6.90-6.80 (m, 1H), 6.15-6.05 (m, 1H), 5.74-5.39 (m, 3H), 4.00-3.80 (m, 1H), 3.56-3.45 (m, 2H), 2.40 (s, 3H), 2.10-2.00 (m, 2H), 1.80-1.60 (m, 2H).

Example 116 Steps 1 and 2

1-[4-({7-[5-(Propan-2-yl)-1H-1,2,4-triazol-3-yl]-5H-pyrrolo[2,3-b]pyrazin-2-yl}oxy)piperidin-1-yl]prop-2-en-1-one The title compound was prepared according to the method described for Example 115 Step 1 and Step 2 using isobutyrohydrazide. The residue was purified using silica gel column chromatography eluting with 0-10% MeOH in DCM followed by preparative HPLC as described below: Column: Phenomenex Gemini C18 250×21.2 mm, 24 micron. Mobile phase: 21-41% MeCN in water modified with ammonia to pH=10. $^1$H NMR (400 MHz, DMSO-$d_6$): δ ppm 13.43-13.16 (br m, 1H), 12.45-12.34 (br m, 1H), 8.22 (br s, 1H), 7.96 (s, 1H), 6.90-6.83 (m, 1H), 6.14-6.10 (m, 1H), 5.78-5.67 (m, 2H), 3.97-3.89 (m, 2H), 3.55-3.41 (m, 2H), 3.05-3.00 (m, 1H), 2.10-2.00 (m, 2H), 1.80-1.60 (br m, 2H), 1.32-1.30 (d, 6H). MS m/z 382 [M+H]$^+$ Examples 117-119 were prepared as described in the Scheme below:

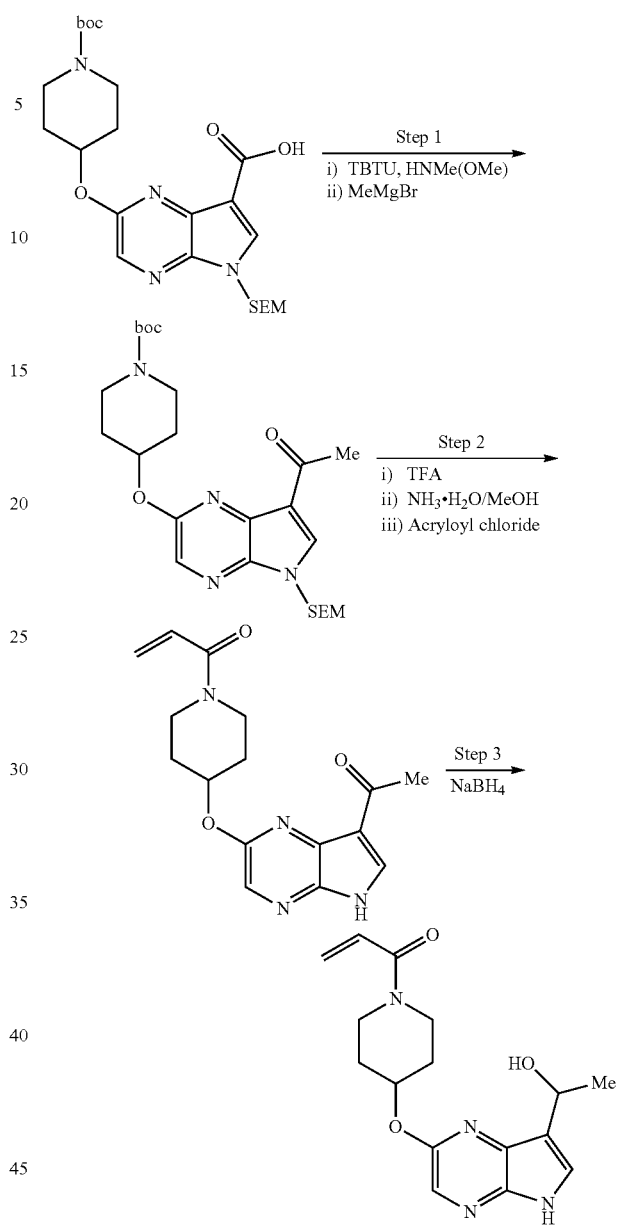

Example 117 Step 1 tert-Butyl 4-[(7-acetyl-5-{[2-(trimethylsilyl)ethoxy]methyl}-5H-pyrrolo[2,3-b]pyrazin-2-yl)oxy]piperidine-1-carboxylate To a solution of 2-{[1-(tert-butoxycarbonyl)piperidin-4-yl]oxy}-5-{[2-(trimethylsilyl)ethoxy]methyl}-5H-pyrrolo[2,3-b]pyrazine-7-carboxylic acid (Example 114 Step 1, 520 mg, 1.06 mmol), and TBTU (407 mg, 1.27 mmol) in DMF (30 mL) was added DIPEA (409 mg, 3.17 mmol) followed by N,O-dimethylhydroxylamine (206 mg, 3.17 mmol) at 0° C. The reaction was stirred at room temperature for 2 hours, quenched by the addition of water and extracted into EtOAc. The organic layer was collected, washed with brine, dried over sodium sulphate and concentrated in vacuo. The residue was purified using silica gel column chromatography eluting with 1-30% EtOAc in petroleum ether. The residue (600 mg, 1.12 mmol) was dissolved in THF (20 mL) and treated with methyl magnesium bromide (3M solution in THF, 0.75 mL, 2.24 mmol) at 0° C. under nitrogen. The reaction was stirred for 2 hours before quenching with water and extracting into EtOAc. The organic layer was collected, washed with brine, dried over sodium sulphate and concentrated in vacuo. The residue was purified using silica gel column chromatography eluting with 1-20% EtOAc in petroleum ether to afford the title compound as a colourless oil (350 mg, 64%). MS m/z 513 [M+Na]$^+$ Example 117 Step 2

1-{4-[(7-Acetyl-5H-pyrrolo[2,3-b]pyrazin-2-yl)oxy] piperidin-1-yl}prop-2-en-1-one The title compound was prepared according to the method described for Example 1 Steps 5-7 using tert-butyl 4-[(7-acetyl-5-{[2-(trimethylsilyl)ethoxy]methyl}-5H-pyrrolo[2,3-b]pyrazin-2-yl)oxy]piperidine-1-carboxylate (Example 117 Step 1). The residue was purified using silica gel column chromatography eluting with 5% MeOH in DCM. MS m/z 315 [M+H]$^+$ Example 117 Step 3

Racemic-1-(4-{[7-(1-hydroxyethyl-5H-pyrrolo[2,3-b]pyrazin-2-yl]oxy}piperidin-1-yl)prop-2-en-1-one To a solution of 1-{4-[(7-acetyl-5H-pyrrolo[2,3-b]pyrazin-2-yl)oxy]piperidin-1-yl}prop-2-en-1-one (Example 117 Step 2, 220 mg, 0.7 mmol) in MeOH (30 mL) was added sodium borohydride (106 mg, 2.8 mmol) at 0° C. and the reaction was stirred for 2 hours. The reaction was concentrated in vacuo and purified using silica gel column chromatography eluting with 5-10% MeOH in DCM followed by preparative HPLC as described below to afford the title compound as a white solid (100 mg, 45%).

Column: Phenomenex Gemini C18 250×21.2 mm, 10 micron

Mobile phase: 17-37% MeCN in water modified with ammonia to pH=10. $^1$H NMR (400 MHz, DMSO-d$_6$): δ ppm 11.65 (brs, 1H), 7.84 (s, 1H), 7.55 (s, 1H), 6.89-6.82 (m, 1H), 6.14-6.10 (m, 1H), 5.70-5.67 (m, 1H), 5.26-5.24 (m, 1H), 5.04-5.02 (m, 1H), 4.95-4.94 (m, 1H), 4.00-3.80 (m, 2H), 3.52-3.41 (m, 2H), 2.05-1.95 (m, 2H), 1.69-1.65 (m, 2H), 1.54-1.52 (d, 3H). MS m/z 339 [M+Na]$^+$ The racemate was separated into its enantiomers using the following chiral chromatography:

Column: Chiral Pak AD 250×30 mm, 5 micron; Mobile phase A: 35% MeOH with 0.1% NH$_3$.H$_2$O in supercritical CO$_2$.; Flow rate: 50 mL/min. LCMS QC: Column: Chiralpak AD-H 250×4.6 mm, 5 micron.

Mobile phase: 5-40% MeOH with 0.05% DEA in supercritical CO$_2$

Flow rate: 2.35 mL/min

The enantiomers were assigned arbitrarily:

First Eluting Isomer: Example 118

1-[4-({7-[(1S)-1-hydroxyethyl]-5H-pyrrolo[2,3-b]pyrazin-2-yl}oxy)piperidin-1-yl]prop-2-en-1-one.
Rt=8.35 minutes MS m/z 339 [M+H]$^+$ Second Eluting Isomer: Example 119

1-[4-({7-[(1R)-1-hydroxyethyl]-5H-pyrrolo[2,3-b]pyrazin-2-yl}oxy) piperidin-1-yl]prop-2-en-1-one.
Rt=8.68 minutes MS m/z 339 [M+H]$^+$ Examples 120470 were prepared as described in the Scheme:

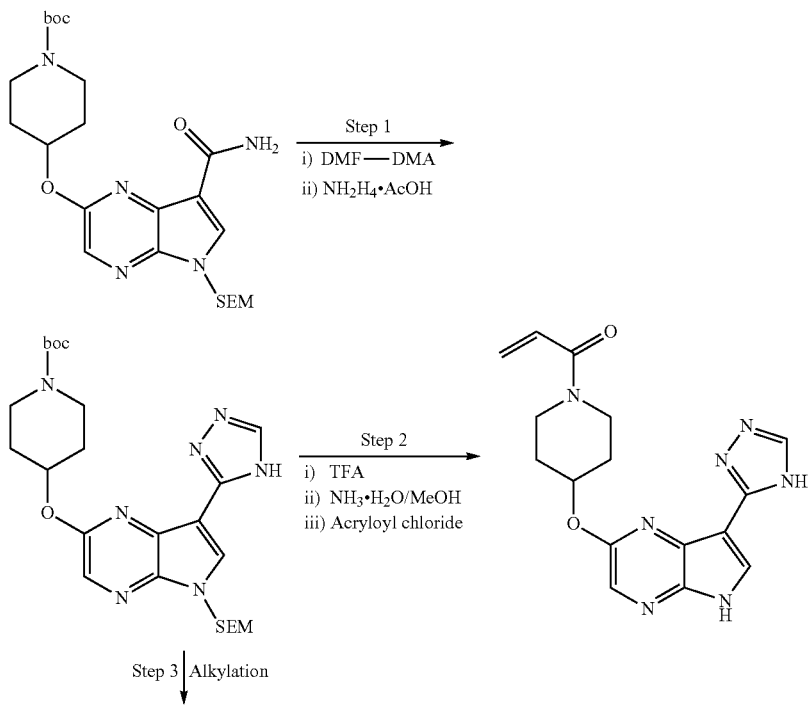

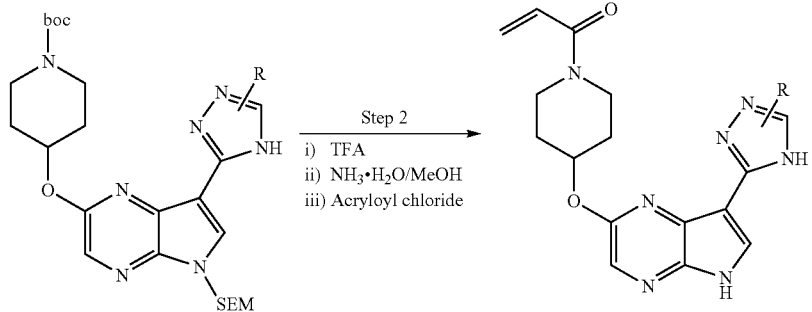

Example 120 Step 1 tert-Butyl 4-{[7-(4H-1,2,4-triazol-3-yl)-5-{[2-(trimethylsilyl)ethoxy]methyl}-5H-pyrrolo[2,3-b]pyrazin-2-yl]oxy}piperidine-1-carboxylate A solution of tert-butyl 4-[(7-carbamoyl-5-{[2-(trimethylsilyl)ethoxy]methyl}-5H-pyrrolo[2,3-b]pyrazin-2-yl)oxy]piperidine-1-carboxylate (Example 114 Step 2, 800 mg, 1.63 mmol) in DMF-DMA (10 mL) was heated to 80° C. for 1 hour. The reaction was cooled and concentrated in vacuo. The residue was dissolved in AcOH (20 mL) and treated with hydrazine acetate (1.35 g, 14.65 mmol) the solution was heated to 95° C. for 40 minutes before cooling, concentrating in vacuo and neutralising to pH=6-7 with saturated aqueous NaHCO₃ solution. The mixture was extracted into EtOAc (2×30 mL), the organic layers combined, washed with brine, dried over sodium sulphate and concentrated in vacuo. The residue was purified using silica gel column chromatography eluting with 0-12% MeOH in DCM to afford the title compound as an oil (500 mg, 68%).
MS m/z 538 [M+Na]⁺

Example 120 Step 2

1-(4-{[7-(4H-1,2,4-Triazol-3-yl)-5H-pyrrolo[2,3-b]pyrazin-2-yl]oxy}piperidin-1-yl)prop-2-en-1-one The title compound was prepared according to the method described for Example 1 Steps 5-7 using tert-butyl 4-{[7-(4H-1,2,4-triazol-3-yl)-5-{[2-(trimethylsilyl)ethoxy]methyl}-5H-pyrrolo[2,3-b]pyrazin-2-yl]oxy}piperidine-1-carboxylate (Example 120 Step 1). The residue was purified using preparative HPLC. Column: Phenomenex Gemini C18 25×21.2 mm*8 uM. Mobile Phase: 10%-30% MeCN in water with 0.05% ammonia. ¹H NMR (400 MHz, DMSO-d₆): δ ppm 8.22 (s, 1H), 8.12 (s, 1H), 7.96 (s, 1H), 6.88-6.81 (m, 1H), 6.14-6.09 (m, 1H), 5.69-5.66 (m, 2H), 4.00-3.86 (m, 2H), 3.60-3.40 (m, 4H), 2.10-1.95 (m, 2H), 1.75-1.55 (m, 2H). MS m/z 362 [M+Na]+

Example 121 Step 3 tert-Butyl 4-{[7-(1-ethyl-1H-1,2,4-triazol-5-yl)-5-{[2-(trimethylsilyl)ethoxy]methyl}-5H-pyrrolo[2,3-b]pyrazin-2-yl]oxy}piperidine-1-carboxylate To a solution of tert-butyl 4-{[7-(4H-1,2,4-triazol-3-yl)-5-{[2-(trimethylsilyl)ethoxy]methyl}-5H-pyrrolo[2,3-b]pyrazin-2-yl]oxy}piperidine-1-carboxylate (Example 120 Step 1, 500 mg, 0.97 mmol) in anhydrous DMF (15 mL) was added sodium hydride (77 mg, 1.94 mmol) at 0° C. Ethyl iodide (227 mg, 1.45 mmol) was added and the reaction stirred at room temperature for 18 hours. The reaction was poured into ice-water (30 mL) and extracted into EtOAc (2×30 mL). The combined organic layers were washed with brine (30 mL), dried over sodium sulphate and concentrated in vacuo. The residue was purified using silica gel column chromatography eluting with 0-5% MeOH in DCM to afford the title compound as an oil (230 mg, 44%).

Example 121 Step 2

1-(4-((7-(1-ethyl-1H-1,2,4-triazol-5-yl)-5H-pyrrolo[2,3-b]pyrazin-2-yl)oxy)piperidin-1-yl)prop-2-en-1-one The title compound was prepared according to the method described for Example 1 Steps 5-7 using tert-butyl 4-{[7-(1-ethyl-1H-1,2,4-triazol-5-yl)-5-{[2-(trimethylsilyl)ethoxy]methyl}-5H-pyrrolo[2,3-b]pyrazin-2-yl]oxy}piperidine-1-carboxylate (Example 120 Step 3). The residue was purified using silica gel column chromatography eluting with 2-10% MeOH in DCM followed by preparative HPLC as described below: Column: Phenomenex Gemini C18 250×21.2 mm, 8 micron. Mobile phase: 15-35% MeOH in water modified with 0.05% ammonia. ¹H NMR (400 MHz, DMSO-dₑ): δ ppm 8.87 (br s, 1H), 8.26 (s, 1H), 8.02 (s, 1H), 8.00 (s, 1H), 6.88-6.84 (m, 1H), 6.14-6.09 (m, 1H), 5.70-5.67 (m, 1H), 5.30-5.26 (m, 1H), 4.55-4.50 (m, 2H), 4.00-3.88 (m, 2H), 3.50-3.40 (m, 2H), 2.10-1.95 (m, 2H), 1.75-1.60 (m, 2H), 1.43-1.39 (t, 3H).
MS m/z 390 [M+Na]⁺
HMBC NMR confirms no coupling from ethyl CH₂ to the outer carbon of the triazole.

Example 122 Step 3 (ii)

tert-Butyl 4-{[7-(1-methyl-1H-1,2,4-triazol-5-yl)-5-yl)-{2-(trimethylsilyl)ethoxy]methyl}-5H-pyrrolo[2,3-b]pyrazin-2-yl}oxy)piperidine-1-carboxylate The title compound was prepared according to the method described for Example 121 Step 3 using methyl iodide. NOe and HMBC confirm the 1-isomer was isolated.

Example 122 Step 2

1-(4-{[7-(1-Methyl-1H-1,2,4-triazol-5-yl)-5H-pyrrolo[2,3-b]pyrazin-2-yl}oxy)piperidin-1-yl]prop-2-en-1-one The title compound was prepared according to the method described for Example 1 Step 5-7 using tert-butyl 4-{[7-(1- methyl-1H-1,2,4-triazol-5-yl)-5-{[2-(trimethylsilyl)ethoxy]methyl}-5H-pyrrolo[2,3-b]pyrazin-2-yl]oxy}piperidine-1-carboxylate (Example 122 Step 3). The residue was purified using silica gel column chromatography eluting with 2-10% MeOH in DCM followed by preparative HPLC as described below: Column: Phenomenex Gemini C18 250×21.2 mm, 8 micron. Mobile phase: 14-34% MeOH in water modified with 0.05% ammonia. $^1$H NMR (400 MHz, DMSO-d$_6$): δ ppm 12.65 (br s, 1H), 8.19 (s, 1H), 8.02 (s, 1H), 7.98 (s, 1H), 6.88-6.81 (m, 1H), 6.14-6.09 (m, 1H), 5.70-5.67 (m, 1H), 5.31-5.28 (m, 1H), 4.10 (s, 3H), 3.92-3.85 (m, 2H), 3.54-3.42 (m, 2H), 2.05-2.00 (m, 2H), 1.70-1.60 (m, 2H). MS m/z 376 [M+Na]$^+$ Example 123 Step 3 tert-Butyl 4-[(7-[1-(propan-2-yl)-1H-1,2,4-triazol-5-yl]-5-{[2-(trimethylsilyl)ethoxy]methyl}-5H-pyrrolo[2,3-b]pyrazin-2-yl)oxy]piperidine-1-carboxylate and tert-butyl 4-[(7-[1-(propan-2-yl)-1H-1,2,4-triazol-3-yl]-5-{[2-(trimethylsilyl)ethoxy]methyl}-5H-pyrrolo[2,3-b]pyrazin-2-yl)oxy]piperidine-1-carboxylate The title compounds were prepared according to the method described for Example 121 Step 3 using isopropyl iodide. The two isomers were separated using silica gel column chromatography eluting with 0-10% MeOH in DCM and structure elucidation was performed using NOe. tert-butyl-4-[(7-[1-(propan-2-yl)-1H-1,2,4-triazol-5-yl]-5-{[2-(trimethylsilyl)ethoxy]methyl}-5H-pyrrolo[2,3-b]pyrazin-2-yl)oxy]piperidine-1-carboxylate. $^1$H NMR (400 MHz, DMSO-d$_6$): δ ppm 8.36 (s, 1H), 8.08 (s, 1H), 8.04 (s, 1H), 5.67 (s, 2H), 5.23-5.14 (m, 2H), 3.70-3.67 (m, 2H), 3.58-3.55 (t, 2H), 3.17-3.15 (m, 2H), 2.00-1.97 (m, 2H), 1.65-1.40 (m, 2H), 1.44-1.40 (m, 14H), 0.83-0.80 (t, 2H), −0.11 (s, 9H).

tert-butyl-4-[(7-[1-(propan-2-yl)-1H-1,2,4-triazol-3-yl]-5-{[2-(trimethylsilyl)ethoxy]methyl}-5H-pyrrolo[2,3-b]pyrazin-2-yl)oxy]piperidine-1-carboxylate $^1$H NMR (400 MHz, DMSO-d$_6$): δ ppm 8.55 (s, 1H), 8.30 (s, 1H), 8.04 (s, 1H), 5.67 (s, 1H), 5.23-5.19 (m, 1H), 4.67-4.60 (m, 1H), 3.78-3.74 (m, 2H), 3.54-3.50 (m, 2H), 3.25-3.10 (m, 2H), 2.15-2.10 (m, 2H), 1.75-1.60 (m, 2H), 1.51 (d, 6H), 1.41 (s, 9H), 0.84-0.80 (t, 2H), −0.11 (s, 9H).

Example 123 Step 2

1-[4-({7-[1-(Propan-2-yl)-1H-1,2,4-triazol-5-yl]-5H-pyrrolo[2,3-b]pyrazin-2-yl}oxy)piperidin-1-yl]prop-2-en-1-one The title compound was prepared according to the method described for Example 1 Step 6-7 using tert-butyl 4-[(7-[1-(propan-2-yl)-1H-1,2,4-triazol-5-yl]-5-{[2-(trimethylsilyl)ethoxy]methyl}-5H-pyrrolo[2,3-b]pyrazin-2-yl)oxy]piperidine-1-carboxylate (Example 123 Step 3). The residue was purified by preparative HPLC as described below: Column: Phenomenex Gemini C18 250×21.2 mm, 8 micron. Mobile phase: 27-47% MeOH in water modified with 0.05% ammonia NOe and HMBC confirm the title isomer was isolated. $^1$H NMR (400 MHz, DMSO-d$_6$): δ ppm 12.61 (br s, 1H), 8.15 (s, 1H), 8.01 (s, 1H), 8.00 (s, 1H), 6.88-6.80 (m, 1H), 6.13-6.08 (m, 1H), 5.69-5.65 (m, 1H), 5.29-5.18 (m, 2H), 3.95-3.90 (m, 2H), 3.50-3.43 (m, 2H), 2.00-1.90 (m, 2H), 1.70-1.60 (m, 2H), 1.44-1.43 (m, 6H). MS m/z 382 [M+H]$^+$ Example 124 Step 2

1-[4-({7-[1-(Propan-2-yl)-1H-1,2,4-triazol-3-yl]-5H-pyrrolo[2,3-b]pyrazin-2-yl}oxy)piperidin-1-yl]prop-2-en-1-one The title compound was prepared according to the method described for Example 1 Steps 5-7 using tert-butyl 4-[(7-[1-(propan-2-yl)-1H-1,2,4-triazol-3-yl]-5-{[2-(trimethylsilyl)ethoxy]methyl}-5H-pyrrolo[2,3-b]pyrazin-2-yl)oxy]piperidine-1-carboxylate (Example 123 Step 3). The residue was purified by preparative HPLC as described below:

Column: Phenomenex Gemini C18 250×21.2 mm, 8 micron

Mobile phase: 19-39% MeOH in water modified with 0.05% ammonia $^1$H NMR (400 MHz, DMSO-d$_6$): δ ppm 8.53 (s, 1H), 8.09 (s, 1H), 7.93 (s, 1H), 6.90-6.83 (m, 1H), 6.14-6.10 (m, 1H), 5.70-5.67 (m, 1H), 5.29-5.25 (m, 1H), 4.65-4.60 (m, 1H), 4.05-3.92 (m, 2H), 3.49-3.43 (m, 2H), 2.19-2.17 (m, 2H), 1.70-1.65 (m, 2H), 1.52-1.50 (d, 6H). MS m/z 382 [M+H]$^+$ Example 125 Step 3 tert-Butyl 4-{[7-(1-ethyl-1H-1,2,4-triazol-3-yl)-5-{[2-(trimethylsilyl)ethoxy]methyl}-5H-pyrrolo[2,3-b]pyrazin-2-yl]oxy}piperidine-1-carboxylate To a solution of tert-butyl 4-{[7-(4H-1,2,4-triazol-3-yl)-5-{[2-(trimethylsilyl)ethoxy]methyl}-5H-pyrrolo[2,3-b]pyrazin-2-yl]oxy}piperidine-1-carboxylate (Example 120 Step 1, 300 mg, 0.582 mmol) in anhydrous THF (10 mL) was added LiHMDS (1M in THF, 2.33 mL, 2.33 mmol). The reaction was stirred at room temperature for 30 minutes before the addition of ethyl iodide (272 mg, 1.75 mmol) and stirring at room temperature for 18 hours. Additional LiHMDS (1.16 mL, 1.16 mmol) was added followed by ethyl iodide (136 mg, 0.873 mmol) and the reaction was stirred at room temperature for 18 hours. Further equivalents of LiHMDS (1.16 mL, 1.16 mmol) followed by ethyl iodide (136 mg, 0.873 mmol) were added and the reaction was stirred at room temperature for 18 hours.

The reaction was poured onto ice-water (20 mL) and extracted into EtOAc (2×20 mL). The organic layers were combined, washed with brine (20 mL), dried over sodium sulphate and concentrated in vacuo. The residue was purified using silica gel column chromatography eluting with 20-100% EtOAc in petroleum ether to afford the title compound (60 mg, 22%).

Example 125 Step 2

1-(4-{[7-(1-Ethyl-1H-1,2,4-triazol-3-yl)-5H-pyrrolo[2,3-b]pyrazin-2-yl]oxy}piperidin-1-yl)prop-2-en-1-one The title compound was prepared according to the method described for Example 1 Step 5-7 using tert-butyl 4-{[7-(1-ethyl-1H-1,2,4-triazol-3-yl)-5-{[2-(trimethylsilyl)ethoxy]methyl}-5H-pyrrolo[2,3-b]pyrazin-2-yl]oxy}piperidine-1-carboxylate (Example 125 Step 3 The residue was purified by preparative HPLC as described below: Column: Phenomenex Gemini C18 250×21.2 mm, 8 micron. Mobile phase: 12-42% MeOH in water modified with 0.05% ammonia HMBC confirms the title isomer was isolated. (CH$_2$ of ethyl signals with C in triazole).

<sup>1</sup>H NMR (400 MHz, DMSO-d$_6$): δ ppm 12.28 (br s, 1H), 8.50 (s, 1H), 8.23 (s, 1H), 7.93 (s, 1H), 6.89-6.82 (m, 1H), 6.14-6.09 (m, 1H), 5.70-5.67 (m, 1H), 5.31-5.28 (m, 1H), 4.26-4.21 (m, 2H), 4.00-3.80 (m, 2H), 3.50-3.46 (m, 2H), 2.10-2.00 (m, 2H), 1.80-1.60 (m, 2H), 1.31-1.29 (t, 3H). MS m/z 390 [M+Na]$^+$ Example 121 Step 3 tert-Butyl 4-{[7-(1-methyl-1H-1,2,4-triazol-3-yl)-5-{[2-(trimethylsilyl)ethoxy]methyl}-5H-pyrrolo[2,3-b]pyrazin-2-yl]oxy}piperidine-1-carboxylate The title compound was prepared according to the method described for Example 125 Step 3 using methyl iodide and taken on directly to the next step.

Example 126 Step 2

1-(4-{[7-(1-Methyl-1H-1,2,4-triazol-3-yl)-5H-pyrrolo[2,3-b]pyrazin-2-yl]oxy}piperidin-1-yl)prop-2-en-1-one The title compound was prepared according to the method described for Example 1 Steps 5-7 using tert-butyl 4-{[7-(1-methyl-1H-1,2,4-triazol-3-yl)-5-{[2-(trimethylsilyl)ethoxy]methyl}-5H-pyrrolo[2,3-b]pyrazin-2-yl]oxy}piperidine-1-carboxylate (Example 126 Step 3). The residue was purified by preparative HPLC as described below: Column: Phenomenex Gemini C18 250×21.2 mm, 8 micron. Mobile phase: 10-40% MeOH in water modified with 0.05% ammonia HMBC and NOe confirms the title isomer was isolated. (CH$_3$ of methyl signals with C in triazole).

<sup>1</sup>H NMR (400 MHz, DMSO-d$_6$): δ ppm 8.45 (s, 1H), 8.10 (s, 1H), 7.93 (s, 1H), 6.89-6.82 (m, 1H), 6.14-6.10 (m, 1H), 5.70-5.67 (m, 1H), 5.34-5.32 (m, 1H), 3.91-3.80 (m, 5H), 3.60-3.50 (br m, 2H), 2.20-2.00 (m, 2H), 1.75-1.60 (m, 2H). MS m/z 376 [M+Na]$^+$ Example 127 was prepared as described in the following Scheme:

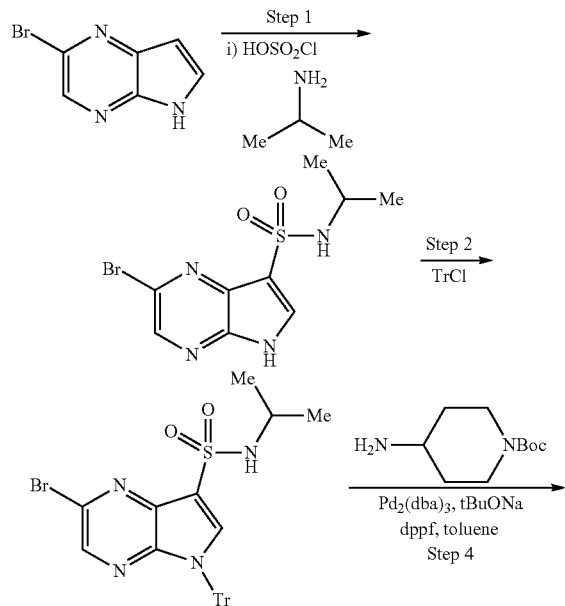

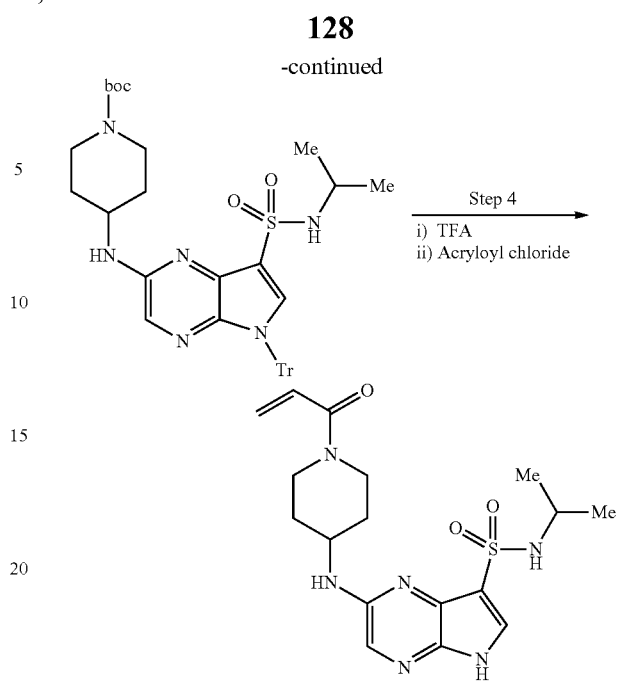

Example 127 Step 1

2-Bromo-N-isopropyl-5H-pyrrolo[2,3-b]pyrazine-7-sulfonamide 2-bromo-5H-pyrrolo[2,3-b]pyrazine (5 g, 25 mmol) was added to chlorosulfonic acid (20 mL) at 0° C. The reaction was heated to 100-120° C. for 2.5 hours before cooling and pouring into ice-water (80 mL). The solution was extracted into EtOAc (2×100 mL), the organic layers combined, washed with brine, dried over sodium sulphate and concentrated in vacuo. The residue was added to a solution of isopropylamine (881 mg, 15 mmol) and triethylamine (2.66 g, 26 mmol) in DCM (60 mL) at 0° C. The reaction was stirred at 0° C. for 3 hours, diluted with water (50 mL) and extracted into EtOAc (2×80 mL). The organic layers were combined, washed with brine, dried over sodium sulphate and concentrated in vacuo. The solid was triturated with TBME to afford the title compound (2 g, 49% over 2 steps) as a brown solid that was used directly in the next step.

Example 127 Step 2

2-Bromo-N-isopropyl-5-trityl-5H-pyrrolo[2,3-b]pyrazine-7-sulfonamide

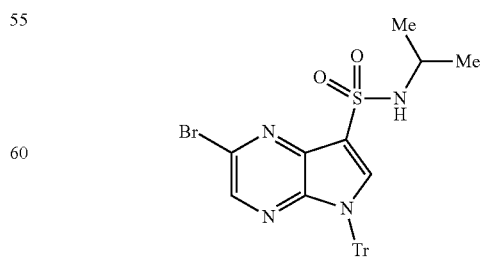

To a solution of 2-bromo-N-isopropyl-5H-pyrrolo[2,3-b]pyrazine-7-sulfonamide (Example 127 Step 1, 1.7 g, 5.33 mmol) and cesium carbonate (5.21 g, 16 mmol) in anhydrous DMF (45 mL) was added trityl chloride (1.51 g, 5.43 mmol) at room temperature and the reaction was stirred at 40° C. for 18 hours. The reaction was diluted with water (30 mL) and extracted into EtOAc (2×30 mL). The organic layers were combined, washed with brine, dried over sodium sulphate and concentrated in vacuo. The residue was purified using silica gel column chromatography eluting with 0-30% EtOAc in petroleum ether to afford the title compound as an off-yellow solid (2.8 g, 94%) that was taken on directly to the next step.

Example 127 Step 3 tert-Butyl 4-((7N-isopropylsulfamoyl-5-trityl-5H-pyrrolo[2,3-b]pyrazin-2-yl)amino)piperidine-1-carboxylate A suspension of 2-bromo-N-isopropyl-5-trityl-5H-pyrrolo[2,3-b]pyrazine-7-sulfonamide (Example 127 Step 2, 500 mg, 0.89 mmol), tert-butyl 4-aminopiperidine-1-carboxylate (357 mg, 1.78 mmol) and cesium carbonate (580 mg, 1.78 mmol) in toluene (20 mL) was purged with nitrogen 4 times. Dppf (99 mg, 0.178 mmol) and Pd$_2$(dba)$_3$ (163 mg, 0.178 mmol) was added and the reaction was heated at 110° C. for 18 hours. The reaction was concentrated in vacuo and purified using silica gel column chromatography eluting with 0-100% EtOAc in petroleum ether to afford the title compound as a brown solid (500 mg, 83%). $^1$H NMR (400 MHz, DMSO-d$_6$): δ ppm 7.40-7.30 (m, 11H), 7.14-6.90 (m, 8H), 3.90-3.81 (m, 4H), 3.00-2.80 (br m, 2H), 1.89-1.86 (m, 2H), 1.39 (s, 9H), 1.31-1.23 (m, 2H), 0.98-0.97 (d, 6H).

Example 127 Step 4

2-[(1-Acryloylpiperidin-4-yl)amino]-N-(propan-2-yl)-5H-pyrrolo[2,3-b]pyrazine-7-sulfonamide tert-butyl 4-((7-(N-isopropylsulfamoyl)-5-trityl-5H-pyrrolo[2,3-b]pyrazin-2-yl)amino)piperidine-1-carboxylate (Example 127 Step 3, 400 mg, 0.587 mmol) was dissolved in DCM (32 mL) and treated with TFA (10 mL) at 0° C. The reaction was stirred at room temperature for 18 hours and concentrated in vacuo. The residue was dissolved in THF (20 mL) and water (20 mL) and treated with DIPEA (229 mg, 1.77 mmol) followed by acryloyl chloride (91 mg, 1 mmol) at 0° C. The reaction was stirred at 0° C. for 2 hours and then extracted into EtOAc three times. The organic layers were combined, washed with brine, dried over sodium sulphate and concentrated in vacuo. The residue was purified using silica gel column chromatography eluting with 0-10% MeOH in DCM followed by preparative HPLC to afford the title compound as a yellow solid (110 mg, 47%). Column: Phenomenex Gemini C18*21.2 mm*8 μm; Mobile Phase: 24%-44% MeCN/H2O (0.05% ammonia). $^1$H NMR (400 MHz, DMSO-d$_6$): δ ppm 12.20 (br s, 1H), 7.80 (s, 1H), 7.70 (s, 1H), 6.96-6.82 (m, 3H), 6.12-8.08 (m, 1H), 5.68-5.65 (m, 1H), 4.30-4.27 (m, 1H), 4.10-4.01 (m, 2H), 3.81-3.76 (m, 1H), 3.25-3.20 (m, 1H), 2.96-2.90 (m, 1H), 2.00-1.90 (m, 2H), 1.40-1.30 (m, 2H), 1.01-1.00 (d, 6H). MS m/z 415 [M+Na]$^+$ Example 128 was prepared as described in the following Scheme:

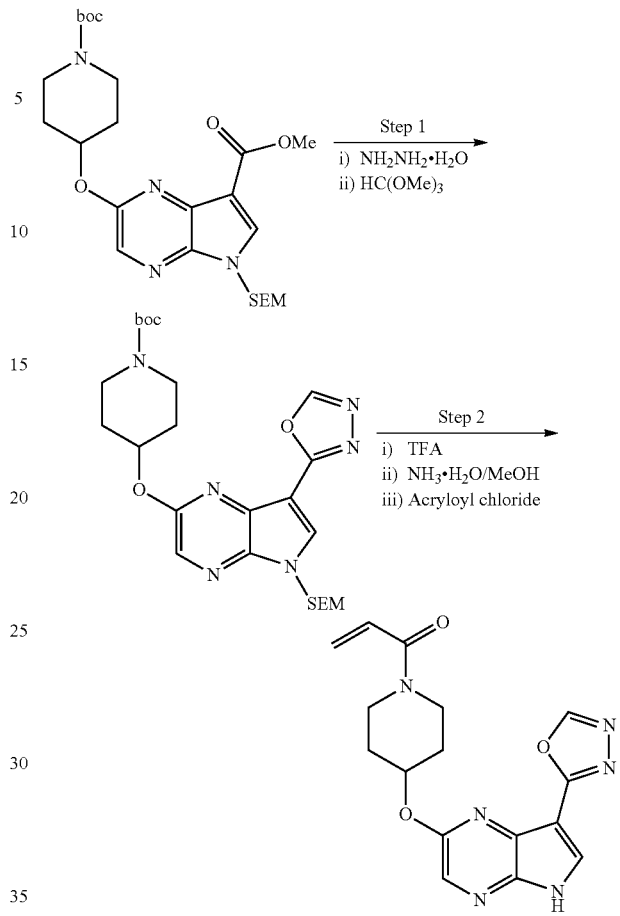

Example 128 Step 1

2-(2-(piperidin-4-yloxy)-5-((2-(trimethylsilyl)ethoxy)methyl-5H-pyrrolo[2,3-b]pyrazin-7-yl)-1,3,4-oxadiazole

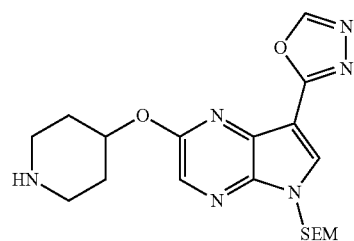 [SMILES: C[Si](C)(C)CCOCn1cc(-c2nnco2)c2nc(OC3CCNCC3)cnc21]

To a solution of methyl 2-{[1-(tert-butoxycarbonyl)piperidin-4-yl]oxy}-5-{[2-(trimethylsilyl)ethoxy]methyl}-5H-pyrrolo[2,3-b]pyrazine-7-carboxylate (Example 108 Step 1 intermediate, 500 mg, 0.66 mol) in EtOH (6 mL) was added hydrazine hydrate (414 mg, 6.61 mmol) and the reaction was heated to 110° C. under microwave irradiation for 1 hour. The reaction was cooled, concentrated in vacuo and dissolved in CH(OMe)$_3$ (8 mL). To the solution was added p-toluenesulfonic acid (22.6 mg, 0.119 mmol) and the reaction was heated to 140° C. under microwave irradiation for 1 hour. The reaction was cooled, concentrated in vacuo and purified using silica gel column chromatography eluting with 12-50% EtOAc in petroleum ether to afford the title compound as a yellow oil (90% over 2 steps).

MS m/z 417 [M+H]+

Example 128 Step 2

1-(4-{[7-(1,3,4-Oxadiazol-2-yl)-5H-pyrrolo[2,3-b]pyrazin-2-yl]oxy}piperidin-1-yl)propan-2-en-1-one The title compound was prepared according to the method described for Example 127 Step 4 using 2-(2-(piperidin-5-((2-(trimethylsilyl)ethoxy)methyl)-5H-pyrrolo[2,3-b]pyrazin-7-yl)-1,3,4-oxadiazole (Example 128 Step 1). The residue was purified using silica gel column chromatography eluting with 0-8% MeOH in DCM followed by preparative HPLC as described below: Column: Phenomenex Gemini C18 250×21.2 mm, 8 micron. Mobile phase: 16-36% MeCN in water modified with 0.05% ammonia. $^1$H NMR (400 MHz, DMSO-$d_6$): δ ppm 12.86 (br s, 1H), 9.26 (s, 1H), 8.50 (s, 1H), 8.05 (s, 1H), 6.90-6.80 (m, 1H), 6.14-6.10 (m, 1H), 5.70-5.67 (m, 1H), 5.40-5.30 (m, 1H), 4.00-3.80 (br m, 2H), 3.55-3.45 (m, 2H), 2.10-2.00 (m, 2H), 1.80-1.60 (m, 2H). MS m/z 363 [M+Na]+

Examples 129-131 were prepared as described in the following Scheme:

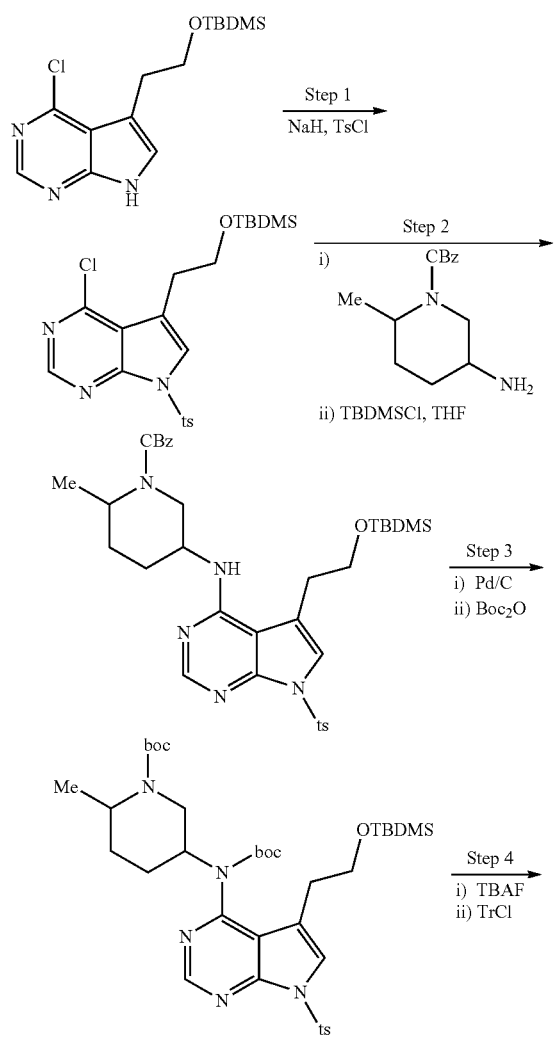

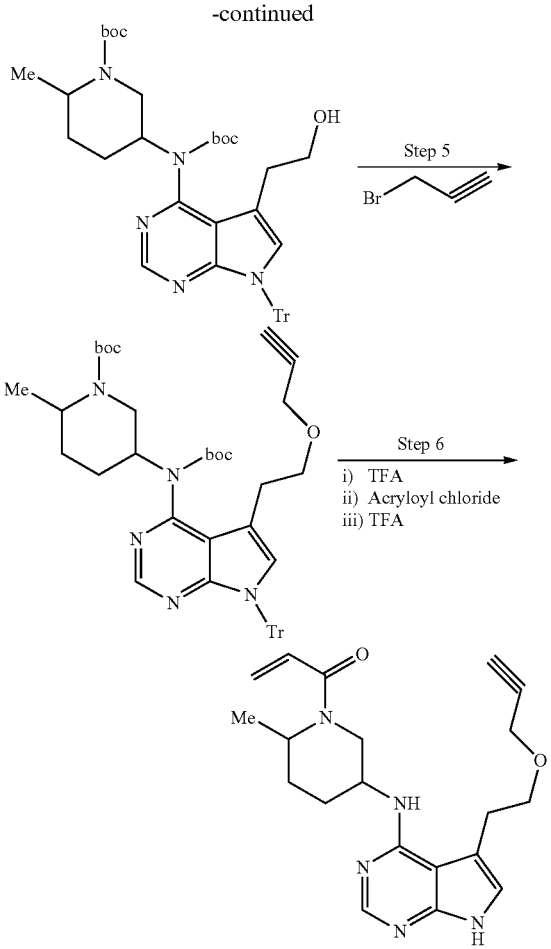

Example 129 Step 1

5-(2-((tert-Butyldimethylsilyl)oxy)ethyl-4-chloro-7-tosyl-7H-pyrrolo[2,3-d]pyrimidine To a solution of 5-(2-([tert-butyl(dimethyl)silyl]oxy)ethyl)-4-chloro-7H-pyrrolo[2,3-d]pyrimidine (WO 2005021568, 6 g, 19.24 mmol) in DMF (50 mL) at 0° C. was added sodium hydride (769 mg, 19.2 mmol) and the reaction was stirred at 0° C. for 10 minutes. Tosyl chloride (3.67 g, 19.2 mmol) was added and the reaction stirred at room temperature for 3 hours. The reaction was quenched by the addition of ice-water (100 mL) and extracted into EtOAc (2×100 mL). The combined organic layers were washed with brine (200 mL), dried over sodium sulphate and concentrated in vacuo. The residue was purified using silica gel column chromatography eluting with 5-35% EtOAc in petroleum ether to afford the title compound as a colourless oil (7.3 g, 81%). MS m/z 466 [M+H]+

Example 129 Step 2

Benzyl (2S,5R)-5-((5-(2-((tert-butyldimethylsilyl)oxy)ethyl)-7-tosyl-7H-pyrrolo[2,3-d]pyrimidin-4-yl)amino)-2-methylpiperidine-1-carboxylate To a solution of 5-(2-((tert-butyldimethylsilyl)oxy)ethyl)-4-chloro-7-tosyl-7H-pyrrolo[2,3-d]pyrimidine (Example 129 Step 1, 2.25 g, 4.83 mmol) in nBuOH (30 mL) was added benzyl (2S,5R)-5-amino-2-methylpiperidine-1-carboxylate (1 g, 4.02 mmol) followed by DIPEA (1 g, 16.1 mmol). The reaction was heated at 135° C. for 96 hours. The reaction was cooled and partitioned between EtOAc (30 mL) and water (20 mL). The aqueous layer was extracted with EtOAc (30 mL) and the organic layers were combined, washed with water and brine (30 mL), dried over sodium sulphate and concentrated in vacuo. The residue was purified using silica gel column chromatography eluting with 30-100% EtOAc in petroleum ether to afford benzyl 5-((5-(2-hydroxyethyl)-7-tosyl-7H-pyrrolo[2,3-d]pyrimidin-4-yl)amino)-2-methylpiperidine-1-carboxylate. The intermediate (900 mg, 1.6 mmol) was re-protected by dissolving in THF (10 mL) and treating with imidazole (217 mg, 3.19 mmol) followed by TBDMSCl (479 mg, 3.19 mmol) and the reaction was stirred at room temperature for 24 hours. The reaction was concentrated in vacuo and partitioned between EtOAc (20 mL) and water (10 mL). The organic layer was washed with 0.5M HCl (aq), brine (100 mL) and concentrated in vacuo. The residue was purified using silica gel column chromatography eluting with 0-50% EtOAc in petroleum ether to afford the title compound as a colourless oil (900 mg, 60% over 2 steps) that was taken on directly to the next step.

Example 129 Step 3 tert-butyl (2S,5R)-5-((5-(2-((tert-butyldimethylsilyl)oxy)ethyl)-7-tosyl-7H-pyrrolo[2,3-d]pyrimidin-4-yl)amino)-2-methylpiperidine-1-carboxylate The title compound was prepared according to the method described for Example 91 Step 2 using tert-butyl (2S,5R)-5-((5-(2-((tert-butyldimethylsilyl)oxy)ethyl)-7-tosyl-7H-pyrrolo[2,3-d]pyrimidin-4-yl)amino)-2-methylpiperidine-1-carboxylate (Example 129 Step 2).
MS m/z 644 [M-Boc+H]$^+$ Example 129 Step 4 tert-Butyl (2S,5R)-5-((tert-butoxycarbonyl)(5-(2-hydroxyethyl)-7-trityl-7H-pyrrolo[2,3-d]pyrimidin-4-yl)amino)-2-methylpiperidine-1-carboxylate To a solution of tert-butyl (2S,5R)-5-((5-(2-((tert-butyldimethylsilyl)oxy)ethyl)-7-tosyl-7H-pyrrolo[2,3-d]pyrimidin-4-yl)amino)-2-methylpiperidine-1-carboxylate (Example 129 Step 3, 450 mg, 0.6 mmol) in THF (10 mL) was added TBAF (316 mg, 1.21 mmol) dropwise at 35° C. The reaction was stirred at this temperature for 12 hours before being washed with brine (2×30 mL) and concentrating in vacuo. The residue was purified using silica gel column chromatography eluting with 30-70% EtOAc in petroleum ether. The residue was dissolved in DMF (5 mL) and treated with cesium carbonate (452 mg, 1.39 mmol) followed by trityl chloride (155 mg, 0.55 mmol). The reaction was stirred at room temperature for 12 hours and filtered. The filtrate was partitioned between water (20 mL) and EtOAc (20 mL). The aqueous layer was washed with EtOAc (2×30 mL), the organic layers were combined, washed with brine (50 mL), dried over sodium sulphate and concentrated in vacuo. The residue was purified using silica gel column chromatography eluting with 0-20% MeOH in DCM to afford the title compound as a yellow solid (350 mg, 80% over 2 steps). MS m/z 717 [M+H]$^+$ Example 129 Step 5 tert-Butyl (2S,5R)-5-((tert-butoxycarbonyl)(5-(2-(prop-2-yn-1-yloxy)ethyl)-7-trityl-7H-pyrrolo[2,3-d]pyrimidin-4-yl)amino)-2-methylpiperidine-1-carboxylate To a solution of tert-butyl (2S,5R)-5-((tert-butoxycarbonyl)(5-(2-hydroxyethyl)-7-trityl-7H-pyrrolo[2,3-d]pyrimidin-4-yl)amino)-2-methylpiperidine-1-carboxylate (Example 473 Step 4, 300 mg, 0.418 mmol) in anhydrous THF (10 mL) was added sodium hydride (60% dispersion in oil, 50 mg, 1.25 mmol) at 0° C. The reaction was stirred at this temperature for 30 minutes before the addition of propargyl bromide (99 mg, 0.84 mmol). The reaction was stirred at room temperature for 12 hours. The reaction was quenched with water (2 mL), concentrated in vacuo and purified using silica gel column chromatography eluting with 0-80% EtOAc in petroleum ether to afford the title compound as a yellow solid (160 mg, 51%). MS m/z 756 [M+H]$^+$ Example 129 Step 6

1-((2S,5R)-2-Methyl-5-((5-(2-(prop-2-yn-1-yloxy)ethyl)-7H-pyrrolo[2,3-d]pyrimidin-4-yl)amino)piperidin-1-yl)prop-2-en-1-one The title compound was prepared according to the method described for Example 100 Step 5 using tert-butyl (2S,5R)-5-((tert-butoxycarbonyl)(5-(2-(prop-2-yn-1-yloxy)ethyl)-7-trityl-7H-pyrrolo[2,3-d]pyrimidin-4-yl)amino)-2-methylpiperidine-1-carboxylate (Example 129 Step 5). The residue was purified using silica gel column chromatography eluting with 0-10% MeOH in DCM.

Example 131

1-[(2S,5R)-2-Methyl-5-({5-[2-(prop-2-yn-1-yloxy)ethyl]-7H-pyrrolo[2,3-d]pyrimidin-4-yl}amino)piperidin-1-yl]prop-2-en-1-one. $^1$H NMR (400 MHz, DMSO-d$_6$) δ ppm 1.22 (br. s., 3H) 1.56-1.98 (m, 4H) 2.68 (br. s., 1H) 3.05 (br. s., 2H) 3.41-3.51 (m, 1H) 3.70 (t, J=6.27 Hz, 2H) 4.07 (br. s., 1H) 4.22-4.24 (m, 2H) 4.34-4.90 (m, 2H) 5.68 (d, J=8.53 Hz, 1H) 6.10 (dd, J=16.81, 2.26 Hz, 1H) 6.27 (br. s., 1H) 6.80 (br. s., 1H) 6.94 (s, 1H) 8.09 (br. s., 1H) 11.37 (br. s., 1H). Rt=3.12 minutes (HPLC) MS m/z 390 [M+Na]$^+$; Rt=4.28 (Chiral-SFC)

Example 132 was prepared as described in the following Scheme:

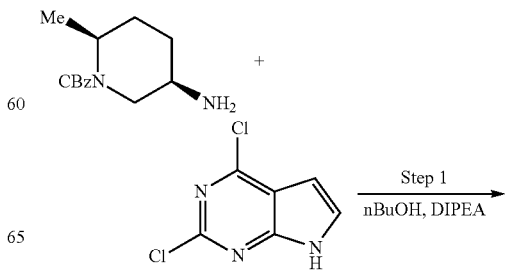

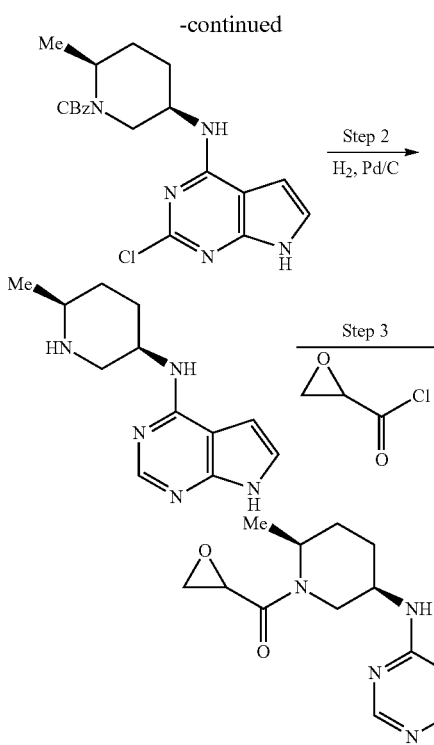

Example 132 Step 1

Benzyl (2S,5R)-5-((2-chloro-7H-pyrrolo[2,3-d]pyrimidin-4-yl)amino)-2-methylpiperidine-1-carboxylate The title compound was prepared according to the method described for Example 94 Step 1 using benzyl (2S,5R)-5-amino-2-methylpiperidine-1-carboxylate (WO2010016005). The residue was triturated with TBME and taken on directly to the next step.

Example 132 Step 2

N-((3R,6S)-6-Methylpiperidin-3-yl)-7H-pyrrolo[2,3-d]pyrimidin-4-amine (Example 5, Step 7

To a solution of benzyl (2S,5R)-5-((2-chloro-7H-pyrrolo[2,3-d]pyrimidin-4-yl)amino)-2-methylpiperidine-1-carboxylate (Example 132 Step 1, 39 g, 0.097 mol) in MeOH (1 L) and THF (300 mL) was added Pd/C (8 g) and the reaction was hydrogenated under 50 psi at 35° C. for 5 days. The reaction was filtered through Celite® and re-hydrogenated with further Pd/C (8 g) under 50 psi at 35° C. for 5 days. The reaction was filtered through Celite® and concentrated in vacuo to afford the title compound as a white solid (31 g, 90%). $^1$H NMR (400 MHz, D$_2$O): δ ppm 7.93 (s, 1H), 7.05-7.04 (m, 1H), 6.45-6.40 (m, 1H), 4.21-4.19 (m, 1H), 3.55-3.51 (m, 1H), 3.29-3.14 (m, 2H), 1.93-1.73 (m, 4H), 1.24-1.23 (d, 3H).

Example 132 Step 3

Racemic-[(2S,5R)-2-methyl-5-(7H-pyrrolo[2,3-d]pyrimidin-4-ylamino)piperidin-1-yl](oxiran-2-yl)methanone To a solution of racemic oxirane-2-carboxylic acid (114 mg, 0.89 mmol) in DCM (5 mL) was added a solution of oxalyl chloride (0.45 mL, 0.90 mmol) in DCM (2 mL) followed by DMF (1 drop). The reaction was stirred at room temperature for 30 minutes before the addition of a solution of N-((3R,6S)-6-methylpiperidin-3-yl)-7H-pyrrolo[2,3-d]pyrimidin-4-amine (see Example 132; Step 2, 200 mg, 0.86 mmol) and DIPEA (0.6 mL, 3.46 mmol) in DCM (2 mL). The reaction was stirred at room temperature for 1 hour before pouring into saturated aqueous NaHCO$_3$ solution and DCM. The organic layer was collected, dried over sodium sulphate and concentrated in vacuo. The residue was purified using silica gel column chromatography eluting with 5-30% MeOH in DCM to afford the title compound (60 mg, 23%). $^1$H NMR (400 MHz, DMSO-d$_6$) δ ppm 1.13-1.37 (m, 3H) 1.59-1.95 (m, 3H) 2.57-3.06 (m, 3H) 3.74-3.97 (m, 1H) 3.99-4.30 (m, 2H) 4.47 (br. s., 1H) 4.72 (br. s., 1H) 6.56 (d, J=6.63 Hz, 1H) 7.10 (d, J=2.73 Hz, 1H) 7.20-7.39 (m, 1H) 7.98-8.18 (m, 1H) 11.52 (br. s., 1H). MS m/z 302 [M+H]$^+$ Example 133 was prepared as described in the following Scheme:

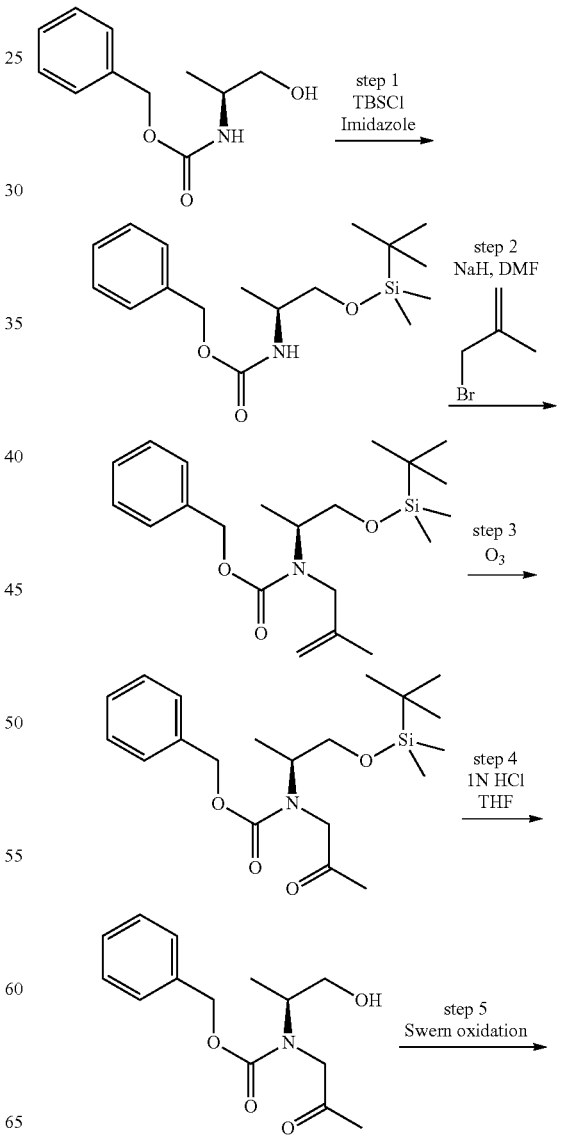

-continued

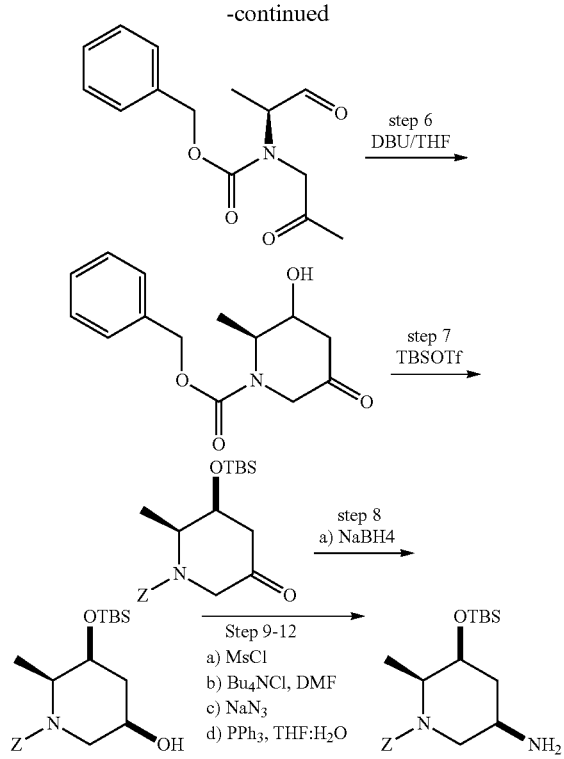

Example 133 Step 1

Benzyl (S)-(1-((tert-butyldimethylsilyl)oxy)propan-2-yl)carbamate

To a round bottom flask containing (benzyl (S)-(1-hydroxypropan-2-yl)carbamate (5 g, 23.9 mmol) dissolved in 50 mL of DCM was added imidazole (1.79 g, 26.3 mmol) and TBDMS-Cl (3.7 g, 23.9 mmol). The reaction was stirred at room temperature overnight. LCMS indicated the reaction was complete. The reaction was diluted with water (100 mL) and the mixture separated. The organic layer was collected and concentrated to give the desired product as a clear oil (8.2 g, 100%). $^1$H NMR (CDCl$_3$): δ 7.33-7.30 (5H, m), 5.06 (2H, s), 3.80-3.71 (1H, m), 3.59-3.47 (2H, m), 1.12 (2H, d), 0.85 (9H, s), 0.00 (s, 6H). Rt=1.14 minutes MS m/z 324.3 [M+H]$^+$

Example 133 Step 2

Benzyl (S)-(1-((tert-butyldimethylsilyl)oxy)propan-2-yl)(2-methylallyl)carbamate To a round bottom flask containing (Example 133, Step 1, 7.7 g, 23.8 mmol) in DMF (100 mL) at 0° C. was added NaH (60% in mineral oil, 1.9 g, 47.6 mmol) in portions. After 30 min, 3-bromo-2-methyl-propene (6.6 g, 47.6 mmol) was added. After stirring for 1.5 h, NH$_4$Cl (10%, 100 mL) was added and the aqueous mixture was extracted with EtOAc (3×). The combined organic extracts were washed with brine, dried (Na$_2$SO$_4$) and solvent removed to give crude product (9 g). The crude material was purified by chromatography (silica gel (combiflash, 80 g gold column, 0 to 10% EA in Hept) to give 6.1 g (68%) of desired product. $^1$H NMR (CDCl$_3$), d 7.33-7.30 (5H, m), 5.15-5.05 (2H, m) 4.79 (2H, s), 4.0-3.43 (5H, m), 1.74-1.62 (3H, m), 1.21-1.09 (2H, m), 0.85 (9H, s), 0.00 (s, 6H). LCMS=378.4 [M+H]$^+$ (1.28 minutes)

Example 133 Step 3

Benzyl (S)-(1-((tert-butyldimethylsilyl)oxy)propan-2-yl)(2-oxopropyl)carbamate

To a round bottom flask containing (Example 133, Step 2, 6.1 g, 16.2 mmol) in DCM/MeOH (50 mL: 50 mL) at −78° C. was bubbled O$_3$. After 5.5 hr, the solution became a light blue color and then Me$_2$S (3.6 mL, 48.5 mmol) was added and the mixture allowed to warm to room temperature overnight. The solvent was removed in vacuo to give the crude product (7 g, 110%) which was taken directly to the next step. LC/MS: Rt=1.14 min; MS m/z 380.4 [M+H]+

Example 133 Step 4

Benzyl (S)-(1-hydroxypropan-2-yl)(2-oxopropyl)carbamate

To a solution of (Example 133, Step 3, 9.95 g, 26.21 mmol) in THF (400 mL) was added HCl (1N, 105 mL, 105 mmol, 4 eq). The reaction was stirred for 3 hrs and then concentrated in vacuo. The aqueous mixture was extracted with DCM (3×). The organic extracts were collected and washed with NaHCO$_3$ (aq), dried (Na$_2$SO$_4$) and filtered. The filtrate was concentrated to give 4.3 g of crude alcohol, which was purified by combiflash (40 g gold column, 10 to 50% EA in Hept) to give 3.6 g (51%) of desired product as an oil. LC/MS: Rt=0.71 minutes. MS m/z 288.34 [M+Na]$^+$ GCMS: Rt=3.91 MS m/z 265 [M+1]

Example 133 Step 5

Benzyl (S)-(1-oxopropan-2-yl)(2-oxopropyl)carbamate

To a solution of DMSO (5.02 ml, 70 mmol) in anhydrous DCM (100 mL) was added dropwise (at −78° C.) oxalyl chloride (2.61 ml, 30.1 mmol) under an atmosphere of nitrogen. The resulting mixture was stirred for 15 minutes. A solution of (Example 133, Step 4, 6.95 g, 26.22 mmol) in DCM (10 ml) was then added dropwise over a period of 30 minutes. After 2 h, triethylamine (18 mL, 130 mmol) was added slowly. The reaction was stirred at −78° C. for 30 minutes, then the acetone-dry ice bath was removed. The reaction mixture was cooled with an ice bath for 30 min. The ice bath was removed and the reaction was stirred for 60 min. The reaction was then quenched with water. The aqueous mixture was extracted (DCM, 3×) and the organic extracts collected, dried (Na$_2$SO$_4$) and the solvent removed in vacuo. The residue was dissolved in ethyl acetate and the solution was washed with 10% NH$_4$Cl×2, 50% brine×3, brine and dried over Na$_2$SO$_4$. The solution was concentrated to give 6.9 g desired product as a yellow oil, which was taken on to next step without purification. GCMS: m/z=263 [M] (4.39 min).

Example 133 Step 6

Benzyl (2S,3S)-3-hydroxy-2-methyl-5-oxopiperidine-1-carboxylate

To a solution of (Example 133, Step 5, 6900 mg, 26.21 mmol) in THF (250 mL) at 0° C. was added DBU. After 48 hr the reaction mixture was treated with 10% NH$_4$Cl (100 mL). The organic layer was separated. The aqueous layer was extracted with ethyl acetate. The combined organic layers were washed with 10% NH$_4$Cl, water, dried (Na$_2$SO$_4$) and the solvent removed to give 6 g of crude product. The crude product was purified by combiflash (80 g gold column, 10 to 50 to 100% EA in hept) to give 1.8 g (25%) of desired product. 1H NMR (CDCl$_3$), 7.43-7.27 (5H, m), 5.18 (2H, s)_4.58-4.31 (3H, m), 4.30-4.13 (2H, m), 3.9 (1H, d), 2.73-2.58 (2H, m), 1.33 (3H, d), GCMS, m/z=263.1[M+1] (5.010 min)

Example 133 Step 7

Benzyl (2S,3S)-3-((tert-butyldimethylsilyl)oxy)-2-methyl-5-oxopiperidine-1-carboxylate To a flask containing (Example 133, Step 6, 870 mg, 3.30 mmol) and DCM (30 mL) at 0° C. was added 2,6-lutidine (673 mg, 6.15) followed by TBDMSOTf (1.22 g, 4.61 mmol). After 3.5 hr, the TLC indicated the reaction was complete. The reaction was treated with Na$_2$CO$_3$(aq) and the mixture separated. The ice bath was removed after 15 min. The mixture was stirred an additional 30 min. before the organic layer was separated and concentrated in vacuo. The residue was purified by combiflash (40 g gold column, 5 to 20% EA in Hept) to give 800 mg desired product. 1H NMR (CDCl$_3$) δ 7.35-7.22 (5H, m), 5.18-5.00 (2H, m) 4.56-4.31 (1H, m), 4.30-4.13 (2H, m), 3.65-3.46 (1H, m), 2.54-2.45 (2H, m), 1.19 (3H, s), 0.81 (9H, s), 0.00 (6H, s). GCMS, m/z=320.2 [M-t-Bu] (5.58 min)

Example 133 Step 8

Benzyl (2S,3S,5R)-3-((tert-butyldimethylsilyl)oxy)-5-hydroxy-2-methylpiperidine-1-carboxylate To a stirred solution of (Example 133, Step 7, 430 mg, 1.14 mmol) in 20 mL of MeOH at 0° C., was added NaBH$_4$ ((129 mg, 3.42 mmol) in 3 portions over 10 min. After 30 min. the solvent was removed and the residue dissolved in ethyl acetate. The organic mixture was washed with Na$_2$CO$_3$ (aq), dried (Na$_2$SO$_4$) and the solvent removed to give the desired product (420 mg, 97%). $^1$H NMR (CDCl$_3$), 7.33-7.23 (5H, m), 5.07 (2H, q, 11.32 Hz), 4.29 (1H, br), 4.11-4.02 (1H, m), 3.70-3.63 (1H, m), 3.62-3.53 (1H, m), 2.58 (1H, dd), 1.97-1.91 (1 h, m), 1.51 (1H, q), 1.05 (3H, d), 0.82 (9H, s), 0.00 (6H, s).
GCMS, m/z=322.2 [M-t-Bu] (5.657 min)

Example 133. Step 9/10

Benzyl (2S,3S,5S)-3-((tert-butyldimethylsilyl)oxy)-5-chloro-2-methylpiperidine-1-carboxylate To a solution of (Example 133, Step 8, 430 mg, 1.23 mmol) in 20 mL of dichloromethane at 0° C. was added triethylamine (3 eq) and methanesulfonyl chloride (0.13 ml, 1.7 mmol, 1.5 eq). The reaction mixture was allowed to stir at room temperature for 2 hours. The reaction mixture was diluted with 30 mL of EtOAc, washed with sodium carbonate, brine and then dried over anhydrous MgSO$_4$. The organic extracts were filtered and concentrated in vacuo to give 550 mg of mesylate. The oil was dissolved in DMF (20 mL) and Bu$_4$NCl (3.5 g, 11.3 mmol, 10 eq) was added. The reaction was heated to 90° C. for 5 hr and then stirred overnight at room temperature. The reaction was then diluted with 15 mL of ethyl acetate, washed with brine, dried (Na$_2$SO$_4$), and the solvent removed to give an oil (406 mg, 90%). GCMS, m/z=397 [M] (5.59 min)

Example 133. Step 11

Benzyl (2S,3S,5R)-5-azido-3-((tert-butyldimethylsilyl)oxy)-2-methylpiperidine-1-carboxylate To a solution of (Example 133, Step 9/10, 400 mg, 1.0 mmol) in 20 mL of DMSO at room temperature was added NaN$_3$. The reaction mixture was then heated to 90° C. over the weekend. The reaction was then allowed to cool to room temperature and diluted with 15 mL of ethyl acetate. The solution was washed with brine, dried (Na$_2$SO$_4$) and the solvent removed to give the crude product, which was purified by combiflash (12 g gold column 0 to 10% ethyl acetate in heptane) to give 170 mg of desired product (42% yield). $^1$H NMR (CDCl), 7.35-7.24 (5H, m), 5.17-5.01 (2H, m), 4.39 (0.5H, t,) 4.28 (0.5H, t), 4.18 (0.5H, dd), 4.03 (0.5H, dd), 2.26 (1H, q), 1.99-1.89 (1H, m) 1.56 (1H, q), 1.05 (3H, d), 0.83 (9H, s), 0.00 (6H, d,). LCMS, m/z=377.5 [M-N$_2$] (1.27 min)

Example 133. Step 12

Benzyl (2S,3S,5R)-5-amino-3-((tert-butyldimethylsilyloxy)-2-methylpiperidine-1-carboxylate To a flask containing (example 477, step 11, 170 mg, 0.42 mmol) was added THF:H$_2$O (10:1, 5 mL) and PPh$_3$ (124 mg, 0.462 mmol). The reaction was heated to 50° C. overnight and then allowed to cool to room temperature. The solvent was removed in vacuo to give a white solid, which was taken directly to the next step. MS m/z=379.5 [M+1] (0.76 min).

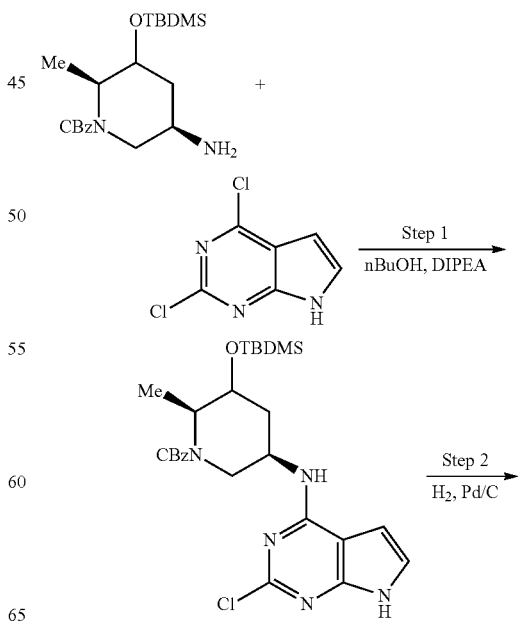

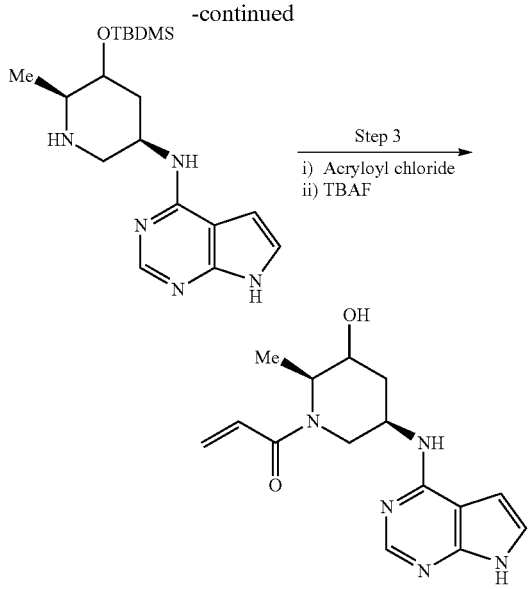

Example 133 Step 13

(2S,3S,5R)-Benzyl 3-(tert-butyldimethylsilyloxy)-5-(2-chloro-7H-pyrrolo[2,3-d]pyrimidin-4-ylamino)-2-methylpiperidine-1-carboxylate The title compound was prepared according to the method described for Example 94 Step 1 using benzyl (2S,3S,5R)-5-amino-3-((tert-butyldimethylsilyl)oxy)-2-methylpiperidine-1-carboxylate. The residue was purified using silica gel column chromatography eluting with 5-50% EtOAc in heptanes. MS m/z 530 [M+H]$^+$

Example 133 Step 14

N-((3R,5S,6S)-5-(tert-Butyldimethylsilyloxy)methylpiperidin-3-yl)-7H-pyrrolo[2,3-d]pyrimidin-4-amine The title compound was prepared according to the method described for Example 132 Step 2 using benzyl (2S,5R)-3-((tert-butyldimethylsilyl)oxy)-5-((2-chloro-7H-pyrrolo[2,3-d]pyrimidin-4-yl)amino)-2-methylpiperidine-1-carboxylate (Example 133 Step 1).
MS m/z 362 [M+H]$^+$

Example 133 Step 15

1-((2S,3S,5R)-5-(7H-pyrrolo[2,3-d]pyrimidin-4-yl)amino)-3-hydroxy-2-methylpiperidin-1-yl)prop-2-en-1-one To a solution of N-((3R,6S)-5-((tert-butyldimethylsilyl)oxy)-8-methylpiperidin-3-yl)-7H-pyrrolo[2,3-d]pyrimidin-4-amine (81 mg, 0.22 mmol) in THF (5 mL) and saturated aqueous NaHCO$_3$ solution (5 mL) at 0° C. was added acryloyl chloride (0.022 mL, 0.27 mmol) and the reaction was stirred at 0° C. for 1 hour. Further acryloyl chloride was added (0.011 mL, 0.14 mmol) with further stirring. The reaction was quenched by the addition of water (20 mL) and extracted into EtOAc (3×10 mL). The combined organic layers were washed with brine, dried over sodium sulphate and concentrated in vacuo. The residue was purified using silica gel column chromatography eluting with 0-10% MeOH in DCM. The residue was dissolved in THF and treated with a 1M solution of TBAF in THF (0.18 mL, 0.18 mmol) at 0° C. and the reaction was stirred at room temperature for 3 hours. Further TBAF was added (0.2 mL) and the reaction continued for 1.5 hours. The reaction was quenched by the addition of water (10 mL) and extracted into EtOAc (3×10 mL). The organic layers were collected, dried over sodium sulphate. The residue was purified by RP-HPLC: Column: Waters Sunfire C18 (19×100, 5 μm); CH$_3$CN:H$_2$O (0.05% TFA), 95:5 to 70:30 in 8.5 min then 100% CH$_3$CN to 9 min, hold @100% AcCN for 1 min, flow=25 mL/min to give (1-[(2S,3S,5R)-3-hydroxy-2-methyl-5-(7H-pyrrolo[2,3-d]pyrimidin-4-ylamino)piperidin-1-yl]prop-2-en-1-one, 27.6 mg). LC/MS: Rt=1.10, MS m/z 302 [M+H]$^+$; Column:Waters-Atlantis C18 (4.6×50 mm, 5 μm), 95:5 to 5:95 H$_2$O/CH$_3$CN (5 min), Flow: 2.0 mL/min Examples 134-169 were prepared according to Library Protocol 1 below:

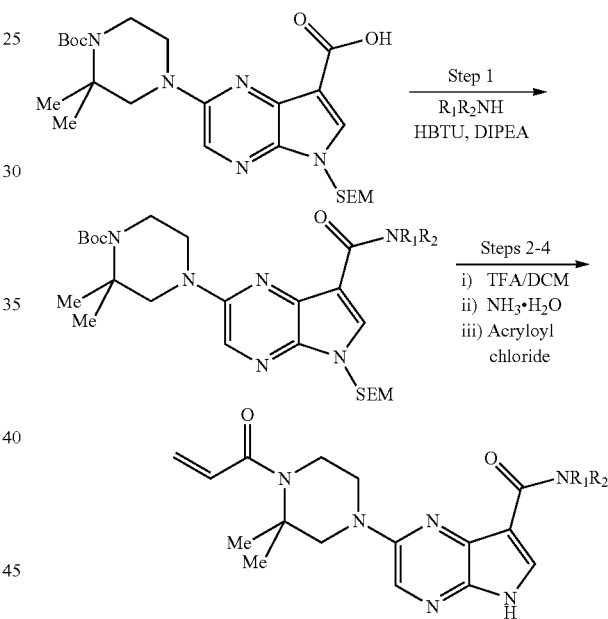

Library Protocol 1

Step 1

To a 0.25M solution of 2-(4-(tert-butoxycarbonyl)-3,3-dimethylpiperazin-1-yl)-5-((2-(trimethylsilyl)ethoxy)methyl)-5H-pyrrolo[2,3-b]pyrazine-7-carboxylic acid (Example 83 Step 5, 400 μL, 100 μmol) in DMF were added amines of formula R$_1$R$_2$NH (120 μmol) followed by DIPEA (39 mg, 300 μmol) and a 0.3M solution of HBTU in DMF (400 μL, 120 μmol). The reactions were shaken at 60° C. for 16 hours before cooling and concentrating in vacuo. The residues were washed with water (1 mL) and extracted into EtOAc (3×1 mL). The combined organic layers were concentrated in vacuo to afford the Step 1 intermediates.

Steps 2-4

To the Step 1 intermediates was added a solution of TFA in DCM (1.2 mL, v:v 1:5) and the reactions were shaken at 30° C. for 4 hours before concentrating in vacuo. The residues were treated with ammonium hydroxide in MeOH (1.6 mL, v:v 1:3) and shaken at 30° C. for 2 hours before concentrating in vacuo. The residues were treated with a saturated solution of NaHCO₃ in water (1 mL). To the solutions was added EtOAc (1 mL) followed by acryloyl chloride (18 mg, 200 μmol) and the reactions were shaken at 30° C. for 2 hours. The reactions were concentrated in vacuo and purified using preparative HPLC as described below to afford the following Examples:

Preparative HPLC:

Column: Phenomenex Gemini C18 250×21.2 mm, 8 micron; Mobile phase: Acetonitrile:ammonium hydroxide (pH=10); Gradient time: 8 minutes; Hold time: 1 minute at 100% organic; Flow rate: 35 mL/min.

QC Method 1:

Column: Xbridge C18 2.1×50 mm; 5 micron; Mobile phase A: 0.0375% TFA in water; Mobile phase B: 0.01875% TFA in MeCN. Gradient: initial—1% B; 0.6 minutes—5% B; 4 minutes—100% B; 4.3 minutes—1% B; 4.7 minutes—1% B. Flow rate: 0.8 mL/min QC Method 2:

Column: Xbridge C18 2.1×50 mm; 5 micron. Mobile phase A: 0.05% NH₄OH in water; Mobile phase B: 100% MeCN. Gradient: initial—5% B; 0.5 minutes—5% B; 3.4 minutes—100% B; 4.2 minutes—100% B; 4.21 minutes—5% B; 4.7 minutes—5% B.

Flow rate: 0.8 mL/min

| Ex. No. | Name | Structure | Data/% Organic Eluant |
|---|---|---|---|
| 134 | 2-(4-acryloyl-3,3-dimethylpiperazin-1-yl)-N-[(2S)-1-(benzyloxy)propan-2-yl]-5H-pyrrolo[2,3-b]pyrazine-7-carboxamide | 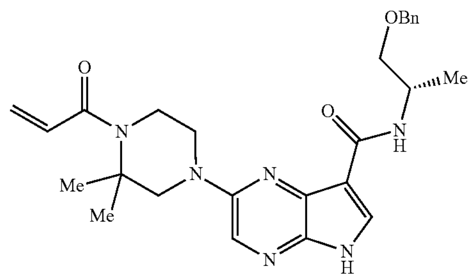 | MS m/z 477 [M + H]⁺<br>Rt = 2.87 minutes<br>QC Method 1<br>Prep HPLC gradient 35-75% organic. |
| 135 | 2-(4-acryloyl-3,3-dimethylpiperazin-1-yl)-N-[(2S)-1-methoxybutan-2-yl]-5H-pyrrolo[2,3-b]pyrazine-7-carboxamide | 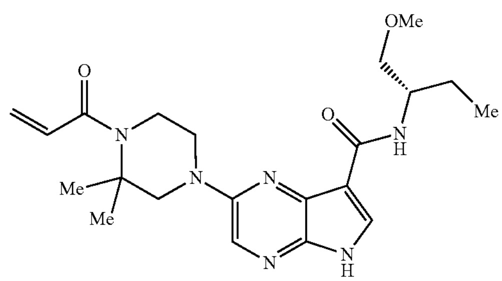 [SMILES: C=CC(=O)N1CCN(c2cnc3[nH]cc(C(=O)N[C@@H](CC)COC)c3n2)CC1(C)C] | MS m/z 415 [M + H]⁺<br>Rt = 2.61 minutes<br>QC Method 1<br>Prep HPLC gradient 25-65% organic. |
| 136 | Racemic-2-(4-acryloyl-3,3-dimethylpiperazin-1-yl)-N-[1-(3-fluorophenyl)-2-hydroxyethyl]-5H-pyrrolo[2,3-b]pyrazine-7-carboxamide | 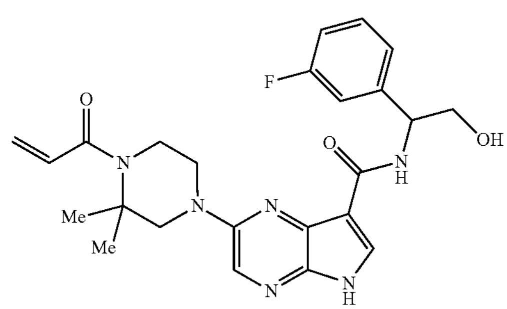 [SMILES: C=CC(=O)N1CCN(c2cnc3[nH]cc(C(=O)NC(CO)c4cccc(F)c4)c3n2)CC1(C)C] | MS m/z 467 [M + H]⁺<br>Rt = 2.60 minutes<br>QC Method 1<br>Prep HPLC gradient 25-65% organic. |
| 137 | 2-(4-acryloyl-3,3-dimethylpiperazin-1-yl)-N-[(2S)-3-ethyl-1-hydroxypentan-2-yl]-5H-pyrrolo[2,3-b]pyrazine-7-carboxamide | 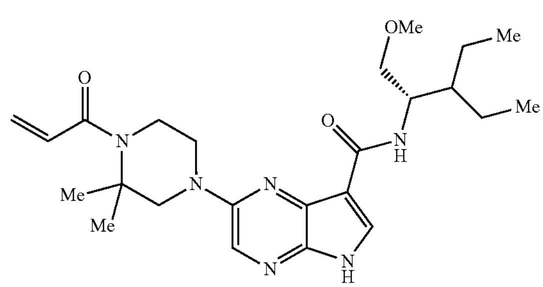 | MS m/z 443 [M + H]⁺<br>Rt = 2.68 minutes<br>QC Method 1<br>Prep HPLC gradient 30-70% organic. |

| Ex. No. | Name | Structure | Data/% Organic Eluant |
|---|---|---|---|
| 138 | 2-(4-acryloyl-3,3-dimethylpiperazin-1-yl)-N-[(1R)-2-methoxy-1-phenylethyl]-5H-pyrrolo[2,3-b]pyrazine-7-carboxamide | 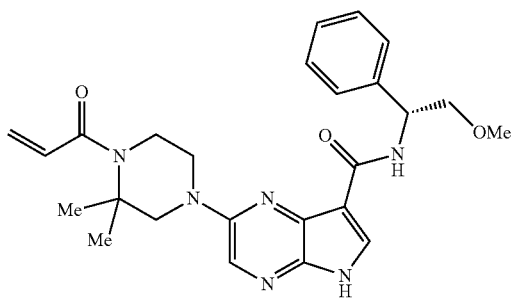 [SMILES: C=CC(=O)N1CCN(c2cnc3[nH]cc(C(=O)N[C@@H](COC)c4ccccc4)c3n2)CC1(C)C] | MS m/z 463 [M + H]+<br>Rt = 2.77 minutes<br>QC Method 1<br>Prep HPLC gradient 30-70% organic. |
| 139 | 2-(4-acryloyl-3,3-dimethylpiperazin-1-yl)-N-[(3S,4R)-4-cyclopropyltetrahydrofuran-3-yl]-5H-pyrrolo[2,3-b]pyrazine-7-carboxamide | 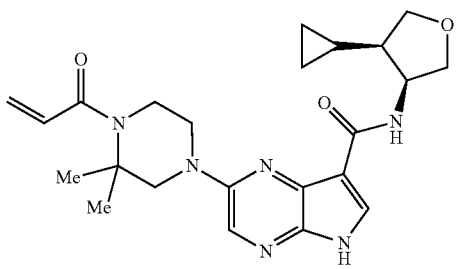 [SMILES: C=CC(=O)N1CCN(c2cnc3[nH]cc(C(=O)N[C@@H]4COC[C@@H]4C4CC4)c3n2)CC1(C)C] | MS m/z 439 [M + H]+<br>Rt = 2.57 minutes<br>QC Method 1<br>Prep HPLC gradient 25-65% organic. |
| 140 | Racemic-2-(4-acryloyl-3,3-dimethylpiperazin-1-yl)-N-(1,3-dimethoxypropan-2-yl)-5H-pyrrolo[2,3-b]pyrazine-7-carboxamide | 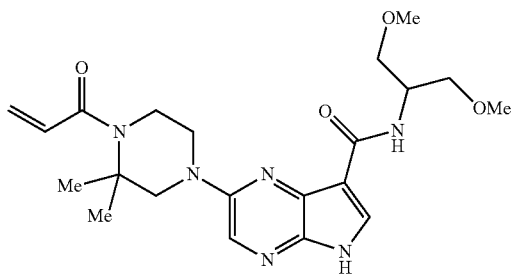 [SMILES: C=CC(=O)N1CCN(c2cnc3[nH]cc(C(=O)NC(COC)COC)c3n2)CC1(C)C] | MS m/z 431 [M + H]+<br>Rt = 2.29 minutes<br>QC Method 2<br>Prep HPLC gradient 20-60% organic. |
| 141 | Racemic-2-(4-acryloyl-3,3-dimethylpiperazin-1-yl)-N-(1-methoxybutan-2-yl)-5H-pyrrolo[2,3-b]pyrazine-7-carboxamide | 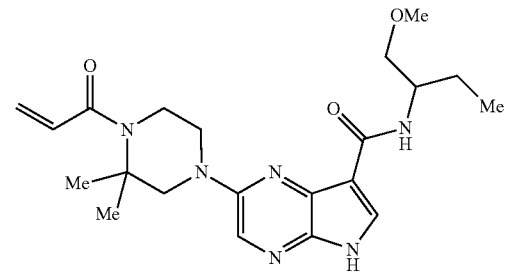 [SMILES: C=CC(=O)N1CCN(c2cnc3[nH]cc(C(=O)NC(CC)COC)c3n2)CC1(C)C] | MS m/z 415 [M + H]+<br>Rt = 2.61 minutes<br>QC Method 1<br>Prep HPLC gradient 25-65% organic. |
| 142 | 2-(4-acryloyl-3,3-dimethylpiperazin-1-yl)-N-[(3S,4R)-4-(2-methylpropyl)tetrahydrofuran-3-yl]-5H-pyrrolo[2,3-b]pyrazine-7-carboxamide | 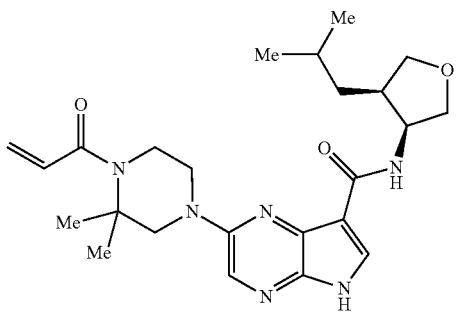 [SMILES: C=CC(=O)N1CCN(c2cnc3[nH]cc(C(=O)N[C@@H]4COC[C@@H]4CC(C)C)c3n2)CC1(C)C] | MS m/z 455 [M + H]+<br>Rt = 2.78 minutes<br>QC Method 1<br>Prep HPLC gradient 30-70% organic. |

-continued

| Ex. No. | Name | Structure | Data/% Organic Eluant |
|---|---|---|---|
| 143 | 2-(4-acryloyl-3,3-dimethylpiperazin-1-yl)-N-[4-(4-fluorophenyl)tetrahydrofuran-3-yl]-5H-pyrrolo[2,3-b]pyrazine-7-carboxamide | 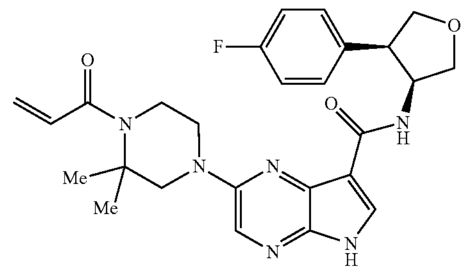 [SMILES: C=CC(=O)N1CCN(c2cnc3[nH]cc(C(=O)N[C@@H]4COC[C@@H]4c4ccc(F)cc4)c3n2)CC1(C)C] | MS m/z 493 [M + H]+ Rt = 2.68 minutes QC Method 1 Prep HPLC gradient 30-70% organic. |
| 144 | Racemic-2-(4-acryloyl-3,3-dimethylpiperazin-1-yl)-N-(3,4-dihydro-1H-isochromen-4-yl)-5H-pyrrolo[2,3-b]pyrazine-7-carboxamide | 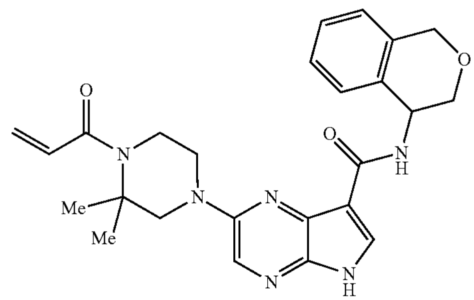 [SMILES: C=CC(=O)N1CCN(c2cnc3[nH]cc(C(=O)NC4COCc5ccccc54)c3n2)CC1(C)C] | MS m/z 461 [M + H]+ Rt = 2.69 minutes QC Method 1 Prep HPLC gradient 30-70% organic. |
| 145 | 2-(4-acryloyl-3,3-dimethylpiperazin-1-yl)-N-[(2S,3S)-1-hydroxy-3-methylpentan-2-yl]-5H-pyrrolo[2,3-b]pyrazine-7-carboxamide | 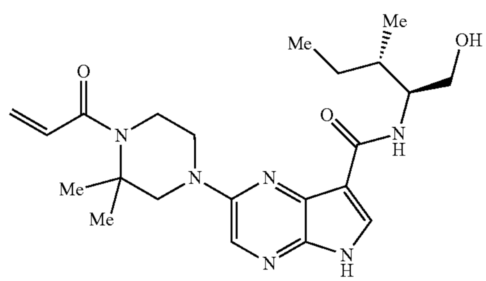 [SMILES: C=CC(=O)N1CCN(c2cnc3[nH]cc(C(=O)N[C@H](CO)[C@@H](C)CC)c3n2)CC1(C)C] | MS m/z 429 [M + H]+ Rt = 2.58 minutes QC Method 1 Prep HPLC gradient 25-65% organic. |
| 146 | 2-(4-acryloyl-3,3-dimethylpiperazin-1-yl)-N-[(1R)-1-(4-fluorophenyl)-2-hydroxyethyl]-5H-pyrrolo[2,3-b]pyrazine-7-carboxamide | 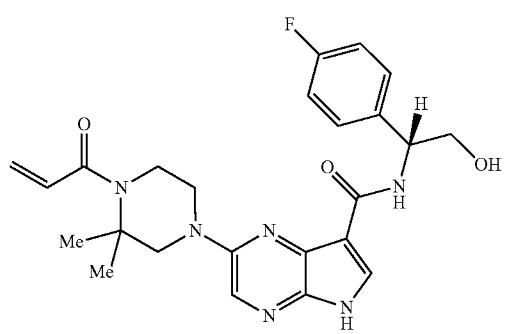 [SMILES: C=CC(=O)N1CCN(c2cnc3[nH]cc(C(=O)N[C@@H](CO)c4ccc(F)cc4)c3n2)CC1(C)C] | MS m/z 467 [M + H]+ Rt = 2.56 minutes QC Method 1 Prep HPLC gradient 25-65% organic. |
| 147 | 2-(4-acryloyl-3,3-dimethylpiperazin-1-yl)-N-[(2S)-1-phenoxypropan-2-yl]-5H-pyrrolo[2,3-b]pyrazine-7-carboxamide | 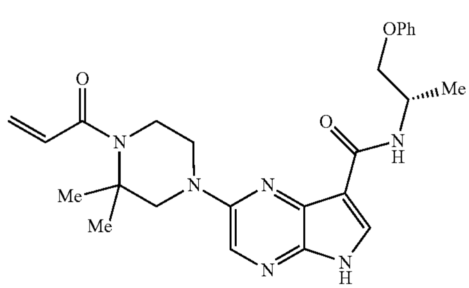 | MS m/z 463 [M + H]+ Rt = 2.88 minutes QC Method 1 Prep HPLC gradient 35-75% organic. |

| Ex. No. | Name | Structure | Data/% Organic Eluant |
|---|---|---|---|
| 148 | Racemic-2-(4-acryloyl-3,3-dimethylpiperazin-1-yl)-N-(1-methoxypropan-2-yl)-5H-pyrrolo[2,3-b]pyrazine-7-carboxamide | 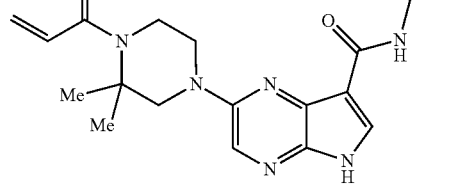 | MS m/z 401 [M + H]+<br>Rt = 2.52 minutes<br>QC Method 1<br>Prep HPLC gradient 25-65% organic. |
| 149 | Racemic-2-(4-acryloyl-3,3-dimethylpiperazin-1-yl)-N-(tetrahydro-2H-pyran-3-yl)-5H-pyrrolo[2,3-b]pyrazine-7-carboxamide | 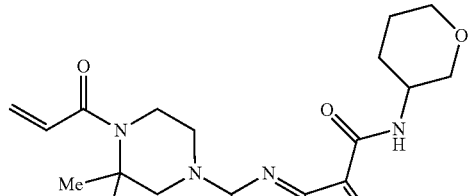 | MS m/z 413 [M + H]+<br>Rt = 2.28 minutes<br>QC Method 2<br>Prep HPLC gradient 20-60% organic. |
| 150 | 2-(4-acryloyl-3,3-dimethylpiperazin-1-yl)-N-[(3S)-tetrahydrofuran-3-yl]-5H-pyrrolo[2,3-b]pyrazine-7-carboxamide | 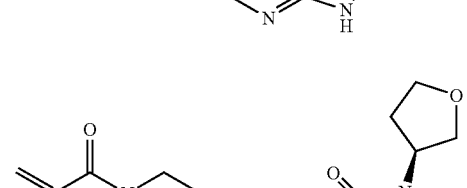 | MS m/z 399 [M + H]+<br>Rt = 2.18 minutes<br>QC Method 2<br>Prep HPLC gradient 20-60% organic. |
| 151 | 2-(4-acryloyl-3,3-dimethylpiperazin-1-yl)-N-(1-methoxy-2-methylpropan-2-yl)-5H-pyrrolo[2,3-b]pyrazine-7-carboxamide | 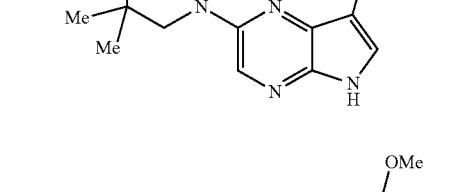 | MS m/z 415 [M + H]+<br>Rt = 2.65 minutes<br>QC Method 1<br>Prep HPLC gradient 25-65% organic. |
| 152 | 2-(4-acryloyl-3,3-dimethylpiperazin-1-yl)-N-[(2R)-1-cyanopropan-2-yl]-5H-pyrrolo[2,3-b]pyrazine-7-carboxamide | 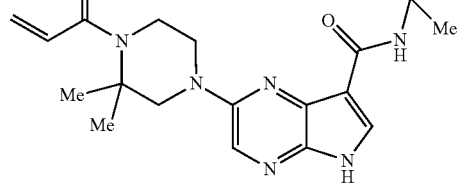 | MS m/z 396 [M + H]+<br>Rt = 2.25 minutes<br>QC Method 2<br>Prep HPLC gradient 20-60% organic. |

-continued

| Ex. No. | Name | Structure | Data/% Organic Eluant |
|---|---|---|---|
| 153 | 2-(4-acryloyl-3,3-dimethylpiperazin-1-yl)-N-[(3R)-3,4-dihydro-2H-chromen-3-yl]-5H-pyrrolo[2,3-b]pyrazine-7-carboxamide | 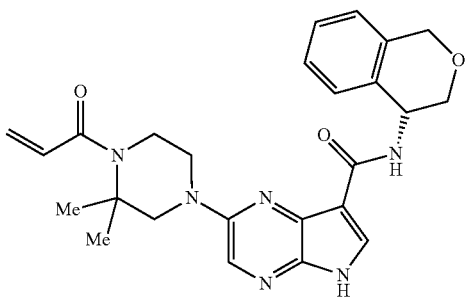 | MS m/z 461 [M + H]+<br>Rt = 2.78 minutes<br>QC Method 1<br>Prep HPLC gradient 30-70% organic. |
| 154 | Racemic-2-(4-acryloyl-3,3-dimethylpiperazin-1-yl)-N-[1-(2-fluorophenyl)-2-hydroxyethyl]-5H-pyrrolo[2,3-b]pyrazine-7-carboxamide | 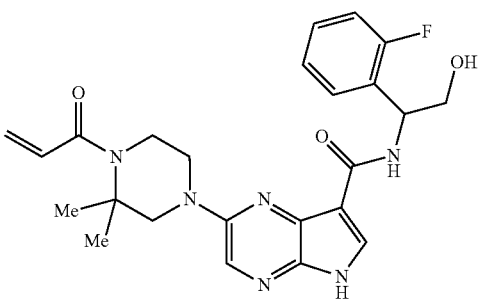 [SMILES: C=CC(=O)N1CCN(c2cnc3[nH]cc(C(=O)NC(CO)c4ccccc4F)c3n2)CC1(C)C] | MS m/z 467 [M + H]+<br>Rt = 2.58 minutes<br>QC Method 1<br>Prep HPLC gradient 25-65% organic. |
| 155 | Racemic-2-(4-acryloyl-3,3-dimethylpiperazin-1-yl)-N-(1-hydroxyhexan-2-yl)-5H-pyrrolo[2,3-b]pyrazine-7-carboxamide | 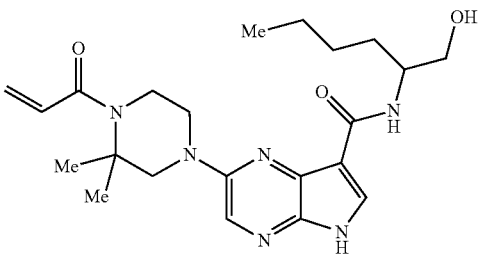 [SMILES: C=CC(=O)N1CCN(c2cnc3[nH]cc(C(=O)NC(CO)CCCC)c3n2)CC1(C)C] | MS m/z 429 [M + H]+<br>Rt = 2.61 minutes<br>QC Method 1<br>Prep HPLC gradient 26-66% organic. |
| 156 | 2-(4-acryloyl-3,3-dimethylpiperazin-1-yl)-N-[(1R,2S)-1-hydroxy-1-phenylpropan-2-yl]-5H-pyrrolo[2,3-b]pyrazine-7-carboxamide | 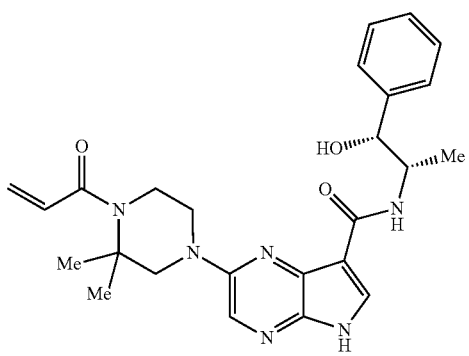 [SMILES: C=CC(=O)N1CCN(c2cnc3[nH]cc(C(=O)N[C@@H](C)[C@H](O)c4ccccc4)c3n2)CC1(C)C] | MS m/z 463 [M + H]+<br>Rt = 2.66 minutes<br>QC Method 1<br>Prep HPLC gradient 25-65% organic. |
| 157 | 2-(4-acryloyl-3,3-dimethylpiperazin-1-yl)-N-[(2R)-1-(3-cyanophenyl)-3-hydroxypropan-2-yl]-5H-pyrrolo[2,3-b]pyrazine-7-carboxamide | 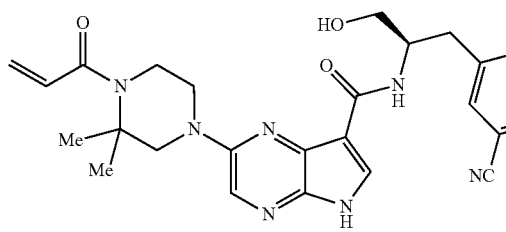 | MS m/z 488 [M + H]+<br>Rt = 2.53 minutes<br>QC Method 1<br>Prep HPLC gradient 25-65% organic. |

| Ex. No. | Name | Structure | Data/% Organic Eluant |
|---|---|---|---|
| 158 | Methyl N-{[2-(4-acryloyl-3,3-dimethylpiperazin-1-yl)-5H-pyrrolo[2,3-b]pyrazin-7-yl]carbonyl}-L-alaninate | 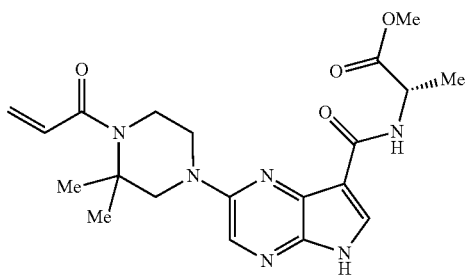 [SMILES: C=CC(=O)N1CCN(c2cnc3[nH]cc(C(=O)N[C@@H](C)C(=O)OC)c3n2)CC1(C)C] | MS m/z 415 [M + H]+<br>Rt = 2.32 minutes<br>QC Method 2<br>Prep HPLC gradient 25-65% organic. |
| 159 | 2-(4-acryloyl-3,3-dimethylpiperazin-1-yl)-N-[(3S,4R)-4-(4-fluoro-1H-pyrazol-1-yl)tetrahydrofuran-3-yl]-5H-pyrrolo[2,3-b]pyrazine-7-carboxamide | 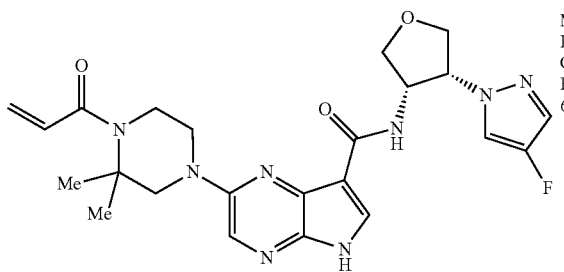 | MS m/z 483 [M + H]+<br>Rt = 2.48 minutes<br>QC Method 1<br>Prep HPLC gradient 20-60% organic. |
| 160 | 3-({[2-(4-acryloyl-3,3-dimethylpiperazin-1-yl)-5H-pyrrolo[2,3-b]pyrazin-7-yl]carbonyl}amino)-2,5-anhydro-1,3,4-trideoxy-D-erythro-pentitol | 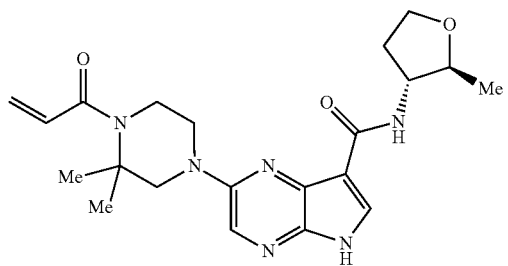 [SMILES: C=CC(=O)N1CCN(c2cnc3[nH]cc(C(=O)N[C@@H]4CCO[C@H]4C)c3n2)CC1(C)C] | MS m/z 413 [M + H]+<br>Rt = 2.45 minutes<br>QC Method 1<br>Prep HPLC gradient 20-60% organic. |
| 161 | 2-(4-acryloyl-3,3-dimethylpiperazin-1-yl)-N-[(2S)-1-hydroxypentan-2-yl]5H-pyrrolo[2,3-b]pyrazine-7-carboxamide | 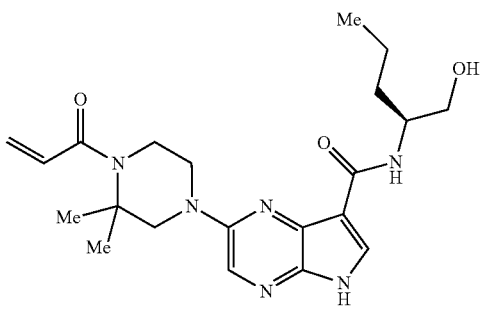 [SMILES: C=CC(=O)N1CCN(c2cnc3[nH]cc(C(=O)N[C@H](CO)CCC)c3n2)CC1(C)C] | MS m/z 415 [M + H]+<br>Rt = 2.50 minutes<br>QC Method 1<br>Prep HPLC gradient 20-60% organic. |
| 162 | 2-(4-acryloyl-3,3-dimethylpiperazin-1-yl)-N-[(1S)-2-hydroxy-2-methyl-1-phenylpropyl]-5H-pyrrolo[2,3-b]pyrazine-7-carboxamide | 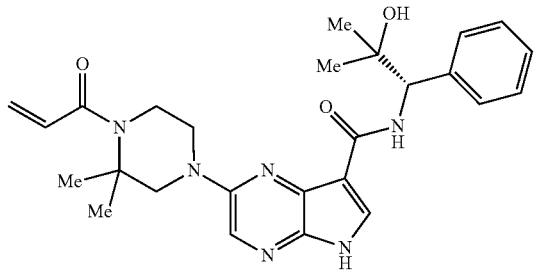 [SMILES: C=CC(=O)N1CCN(c2cnc3[nH]cc(C(=O)N[C@@H](c4ccccc4)C(C)(C)O)c3n2)CC1(C)C] | MS m/z 477 [M + H]+<br>Rt = 2.68 minutes<br>QC Method 1<br>Prep HPLC gradient 30-70% organic. |

| Ex. No. | Name | Structure | Data/% Organic Eluant |
|---|---|---|---|
| 163 | 2-(4-acryloyl-3,3-dimethylpiperazin-1-yl)-N-[3-(hydroxymethyl)pentan-3-yl]5H-pyrrolo[2,3-b]pyrazine-7-carboxamide | 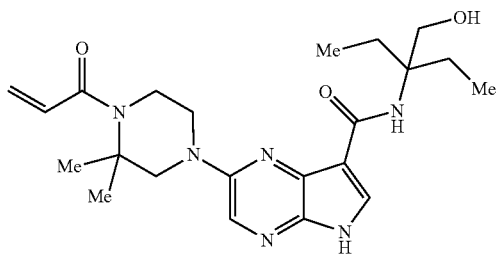 [SMILES: C=CC(=O)N1CCN(c2cnc3[nH]cc(C(=O)NC(CC)(CC)CO)c3n2)CC1(C)C] | MS m/z 429 [M + H]+<br>Rt = 2.62 minutes<br>QC Method 1<br>Prep HPLC gradient 26-66% organic. |
| 164 | Racemic-2-(4-acryloyl-3,3-dimethylpiperazin-1-yl)-N-(tetrahydrofuran-3-yl)-5H-pyrrolo[2,3-b]pyrazine-7-carboxamide | 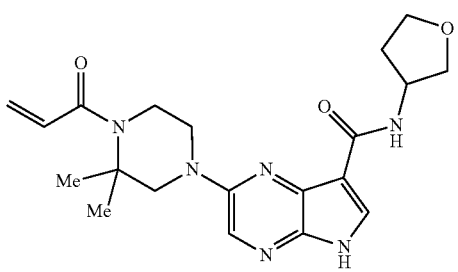 [SMILES: C=CC(=O)N1CCN(c2cnc3[nH]cc(C(=O)NC4CCOC4)c3n2)CC1(C)C] | MS m/z 399 [M + H]+<br>Rt = 2.21 minutes<br>QC Method 2<br>Prep HPLC gradient 20-60% organic. |
| 165 | Racemic-2-(4-acryloyl-3,3-dimethylpiperazin-1-yl)-N-[1-(4-fluorophenyl)-2-hydroxyethyl]-5H-pyrrolo[2,3-b]pyrazine-7-carboxamide | 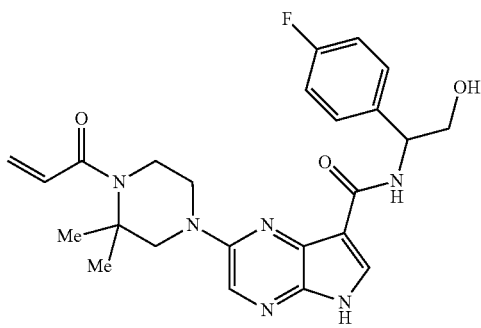 [SMILES: C=CC(=O)N1CCN(c2cnc3[nH]cc(C(=O)NC(CO)c4ccc(F)cc4)c3n2)CC1(C)C] | MS m/z 467 [M + H]+<br>Rt = 2.60 minutes<br>QC Method 1<br>Prep HPLC gradient 25-65% organic. |
| 166 | 3-({[2-(4-acryloyl-3,3-dimethylpiperazin-1-yl)-5H-pyrrolo[2,3-b]pyrazin-7-yl]carbonyl}amino)-2,5-anhydro-1,3,4-trideoxy-L-threo-pentitol | 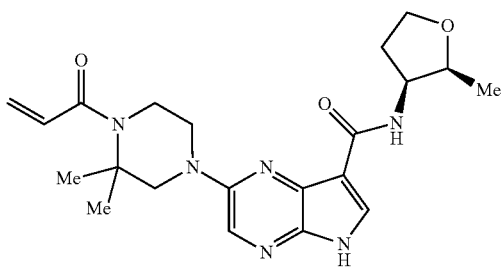 [SMILES: C=CC(=O)N1CCN(c2cnc3[nH]cc(C(=O)N[C@H]4CCO[C@H]4C)c3n2)CC1(C)C] | MS m/z 413 [M + H]+<br>Rt = 2.43 minutes<br>QC Method 1<br>Prep HPLC gradient 20-60% organic. |
| 167 | 2-(4-acryloyl-3,3-dimethylpiperazin-1-yl)-N-[(2R)-1-phenoxypropan-2-yl]-5H-pyrrolo[2,3-b]pyrazine-7-carboxamide | 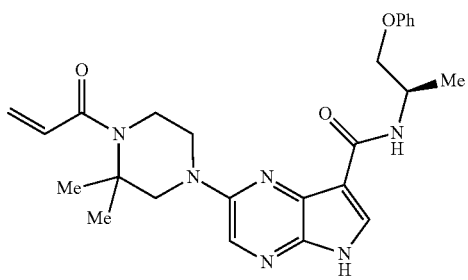 | MS m/z 463 [M + H]+<br>Rt = 2.87 minutes<br>QC Method 1<br>Prep HPLC gradient 35-75% organic. |

| Ex. No. | Name | Structure | Data/% Organic Eluant |
|---|---|---|---|
| 168 | 2-(4-acryloyl-3,3-dimethylpiperazin-1-yl)-N-[(3S)-3,4-dihydro-2H-chromen-3-yl]-5H-pyrrolo[2,3-b]pyrazine-7-carboxamide | 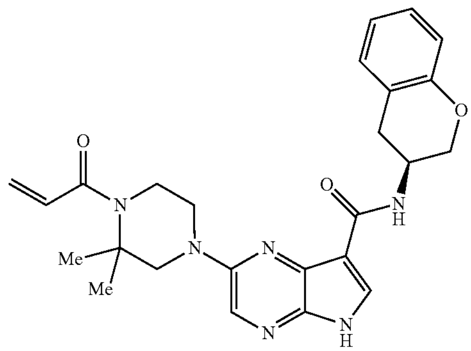 [SMILES: C=CC(=O)N1CCN(c2cnc3[nH]cc(C(=O)N[C@@H]4COc5ccccc5C4)c3n2)CC1(C)C] | MS m/z 461 [M + H]+<br>Rt = 2.76 minutes<br>QC Method 1<br>Prep HPLC gradient 30-70% organic. |
| 169 | 2-(4-acryloyl-3,3-dimethylpiperazin-1-yl)-N-[(2R)-1-(benzyloxy)propan-2-yl]-5H-pyrrolo[2,3-b]pyrazine-7-carboxamide | 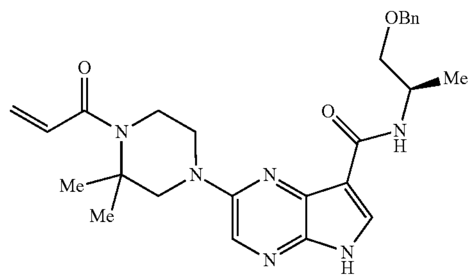 [SMILES: C=CC(=O)N1CCN(c2cnc3[nH]cc(C(=O)N[C@H](C)COCc4ccccc4)c3n2)CC1(C)C] | MS m/z 477 [M + H]+<br>Rt = 2.87 minutes<br>QC Method 1<br>Prep HPLC gradient 35-75% organic. |

Examples 170-196 were prepared according to Library Protocol 2 below:

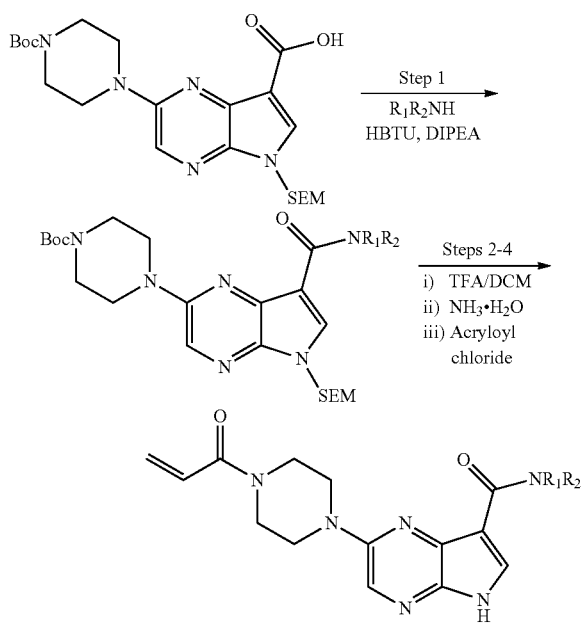

Library Protocol 2

Step 1

To a 0.25M solution of 2-((1-(tert-butoxycarbonyl)piperidin-4-yl)amino)-5-((2-(trimethylsilyl)ethoxy)methyl)-5H-pyrrolo[2,3-b]pyrazine-7-carboxylic acid in DMF (Prepared in the same way as for Example 83 Steps 4 and 5 using tert-butyl-4-aminopiperidine-1-carboxylate, 400 µL, 100 µmol) were added amines of formula $R_1R_2NH$ (120 µmol) followed by DIPEA (70 µL, 400 µmol) and a 0.2M solution of HBTU in DMF (600 µL, 120 µmol). The reactions were shaken at 60° C. for 16 hours before cooling and concentrating in vacuo to afford the Step 1 intermediates.

Steps 2-4

To the Step 1 intermediates was added a solution of TFA in DCM (1 mL, v:v 1:3) and the reactions were shaken at 30° C. for 4 hours before concentrating in vacuo. The residues were treated with ammonium hydroxide in MeOH (1 mL, v:v 1:1) and shaken at 30° C. for 16 hours before concentrating in vacuo. The residues were treated with a saturated solution of $NaHCO_3$ in water (1 mL). To the solutions was added EtOAc (1 mL) followed by acryloyl chloride (18 mg, 200 µmol) and the reactions were shaken at 30° C. for 2 hours. The reactions were concentrated in vacuo and purified using preparative HPLC as described below to afford the following Examples:

Preparative HPLC:

Column: Phenomenex Gemini C18 250×21.2 mm, 8 micron. Mobile phase: Acetonitrile:ammonium hydroxide (pH=10). Gradient time: 8 minutes; Hold time: 1 minute at 100% organic; Flow rate: 35 mL/min.

QC Method:

Column: Xbridge C18 2.1×50 mm; 5 micron. Mobile phase A: 0.0375% TFA in water; Mobile phase B: 0.01875% TFA in MeCN. Gradient: initial—1% B; 0.6 minutes—5% B; 4 minutes—100% B; 4.3 minutes—1% B; 4.7 minutes—1% B. Flow rate: 0.8 mL/min

| Ex. No. | Name | Structure | Data/% Organic Eluant |
|---|---|---|---|
| 170 | 2-[(1-acryloylpiperidin-4-yl)amino]-N-propyl-5H-pyrrolo[2,3-b]pyrazine-7-carboxamide | 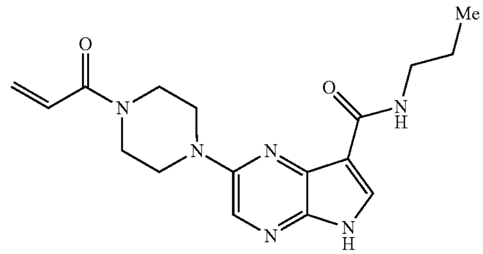 | MS m/z 357 [M + H]+<br>Rt = 2.44 minutes<br>Prep HPLC gradient<br>15-55% organic. |
| 171 | 2-[(1-acryloylpiperidin-4-yl)amino]-N-{[4-methyl-6-(trifluoromethyl)pyrimidin-2-yl]methyl}-5H-pyrrolo[2,3-b]pyrazine-7-carboxamide | 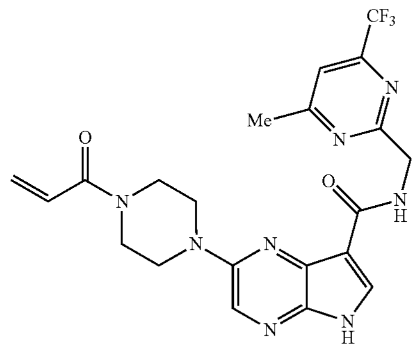 | MS m/z 489 [M + H]+<br>Rt = 2.60 minutes<br>Prep HPLC gradient<br>21-51% organic. |
| 172 | 2-[(1-acryloylpiperidin-4-yl)amino]-N-(cyclopropylmethyl)-5H-pyrrolo[2,3-b]pyrazine-7-carboxamide | 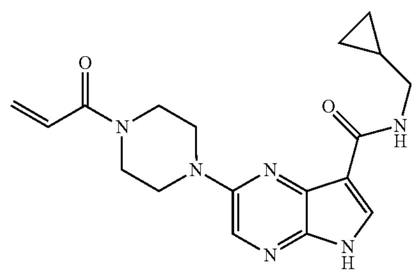 | MS m/z 369 [M + H]+<br>Rt = 2.48 minutes<br>Prep HPLC gradient<br>16-56% organic. |
| 173 | 2-[(1-acryloylpiperidin-4-yl)amino]-N-[(3-cyclobutyl-1-methyl-1H-pyrazol-5-yl)methyl]-5H-pyrrolo[2,3-b]pyrazine-7-carboxamide | 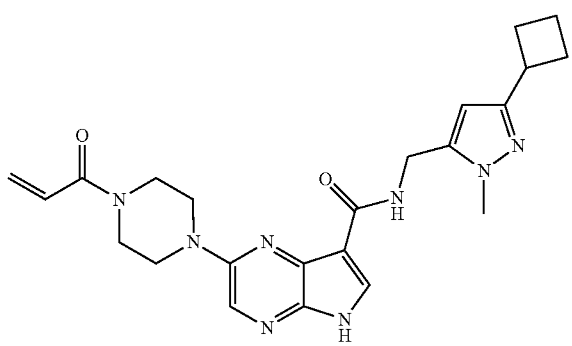 | MS m/z 463 [M + H]+<br>Rt = 2.57 minutes<br>Prep HPLC gradient<br>19-59% organic. |
| 174 | 2-[(1-acryloylpiperidin-4-yl)amino]-N-(4-fluoro-3-methoxybenzyl)-5H-pyrrolo[2,3-b]pyrazine-7-carboxamide | 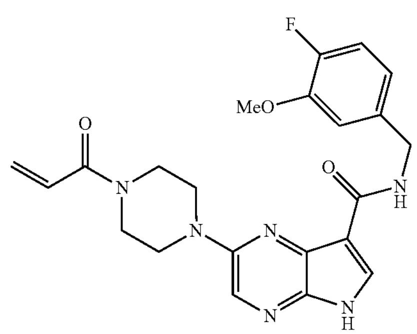 | MS m/z 453 [M + H]+<br>Rt = 2.64 minutes<br>Prep HPLC gradient<br>19-59% organic. |

-continued

| Ex. No. | Name | Structure | Data/% Organic Eluant |
|---|---|---|---|
| 175 | 2-[(1-acryloylpiperidin-4-yl)amino]-N-{[3-(propan-2-yl)-1,2-oxazol-5-yl]methyl}-5H-pyrrolo[2,3-b]pyrazine-7-carboxamide | 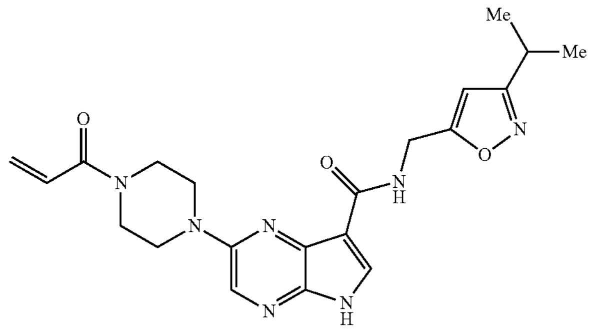 | MS m/z 438 [M + H]+<br>Rt = 2.62 minutes<br>Prep HPLC gradient 26-66% organic. |
| 176 | 2-[(1-acryloylpiperidin-4-yl)amino]-N-(3-fluorobenzyl)-5H-pyrrolo[2,3-b]pyrazine-7-carboxamide | 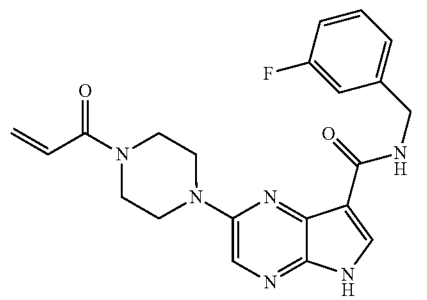 | MS m/z 423 [M + H]+<br>Rt = 2.66 minutes<br>Prep HPLC gradient 21-61% organic. |
| 177 | 2-[(1-acryloylpiperidin-4-yl)amino]-N-[(5-fluoro-1,3-benzoxazol-2-yl)methyl]-5H-pyrrolo[2,3-b]pyrazine-7-carboxamide | 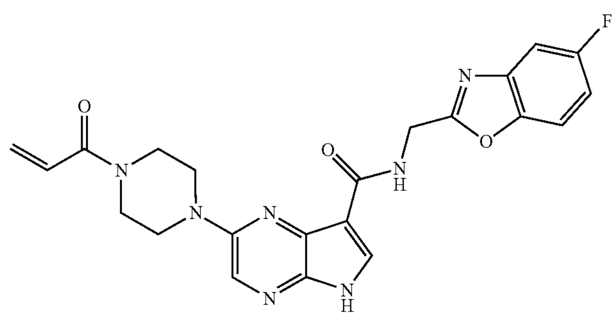 | MS m/z 464 [M + H]+<br>Rt = 2.65 minutes<br>Prep HPLC gradient 20-60% organic. |
| 178 | 2-[(1-acryloylpiperidin-4-yl)amino]-N-(2-cyclopropylethyl)-5H-pyrrolo[2,3-b]pyrazine-7-carboxamide | 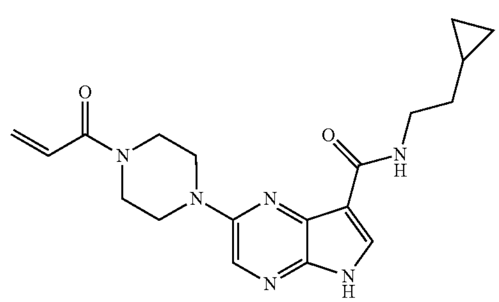 | MS m/z 383 [M + H]+<br>Rt = 2.59 minutes<br>Prep HPLC gradient 19-59% organic. |
| 179 | 2-[(1-acryloylpiperidin-4-yl)amino]-N-(2,2,3,3,3-pentafluoropropyl)-5H-pyrrolo[2,3-b]pyrazine-7-carboxamide | 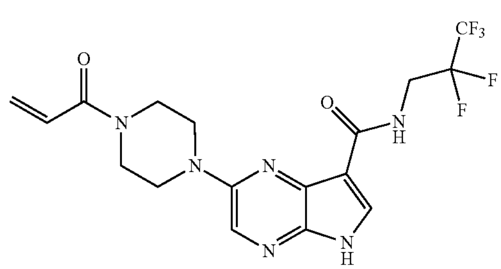 | MS m/z 447 [M + H]+<br>Rt = 2.66 minutes<br>Prep HPLC gradient 21-61% organic. |

-continued

| Ex. No. | Name | Structure | Data/% Organic Eluant |
|---|---|---|---|
| 180 | 2-[(1-acryloylpiperidin-4-yl)amino]-N-{[4-methyl-2-(trifluoromethyl)-1,3-thiazol-5-yl]methyl}-5H-pyrrolo[2,3-b]pyrazine-7-carboxamide | 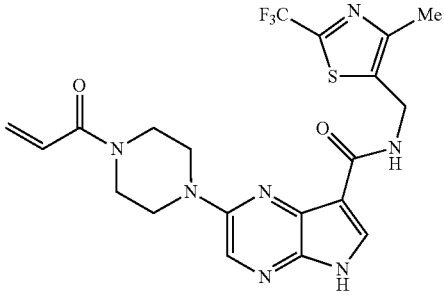 | MS m/z 494 [M + H]+ Rt = 2.76 minutes Prep HPLC gradient 24-64% organic. |
| 181 | 2-[(1-acryloylpiperidin-4-yl)amino]-N-[4-(difluoromethoxy)benzyl]-5H-pyrrolo[2,3-b]pyrazine-7-carboxamide | 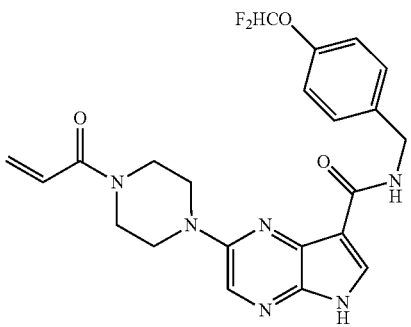 | MS m/z 471 [M + H]+ Rt = 2.75 minutes Prep HPLC gradient 23-63% organic. |
| 182 | 2-[(1-acryloylpiperidin-4-yl)amino]-N-[2-(6,7-difluoro-1,3-benzoxazol-2-yl)ethyl]-5H-pyrrolo[2,3-b]pyrazine-7-carboxamide | 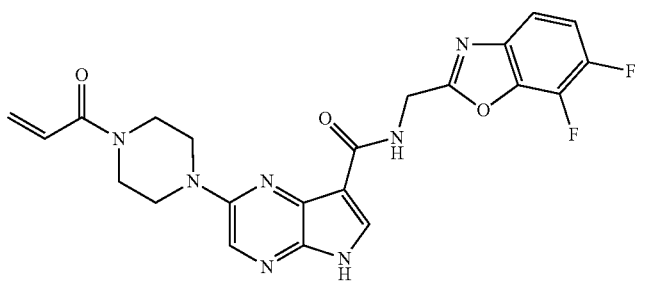 | MS m/z 496 [M + H]+ Rt = 2.73 minutes Prep HPLC gradient 23-63% organic. |
| 183 | 2-[(1-acryloylpiperidin-4-yl)amino]-N-[4-(1H-pyrazol-1-yl)benzyl]-5H-pyrrolo[2,3-b]pyrazine-7-carboxamide | 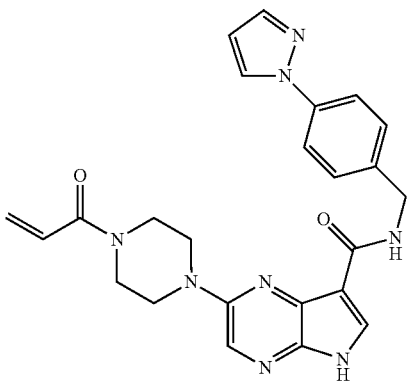 | MS m/z 471 [M + H]+ Rt = 2.59 minutes Prep HPLC gradient 19-59% organic. |

| Ex. No. | Name | Structure | Data/% Organic Eluant |
|---|---|---|---|
| 184 | 2-[(1-acryloylpiperidin-4-yl)amino]-N-[(5-ethyl-6-methylpyridin-2-yl)methyl]-5H-pyrrolo[2,3-b]pyrazine-7-carboxamide | 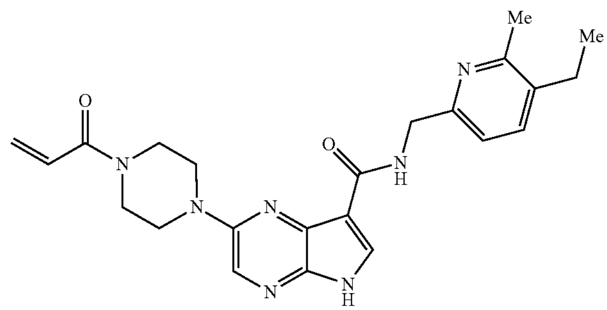 | MS m/z 448 [M + H]+<br>Rt = 2.23 minutes<br>Prep HPLC gradient 19-59% organic. |
| 185 | 2-[(1-acryloylpiperidin-4-yl)amino]-N-{[4-(trifluoromethyl)-1,3-thiazol-5-yl]methyl}-5H-pyrrolo[2,3-b]pyrazine-7-carboxamide | 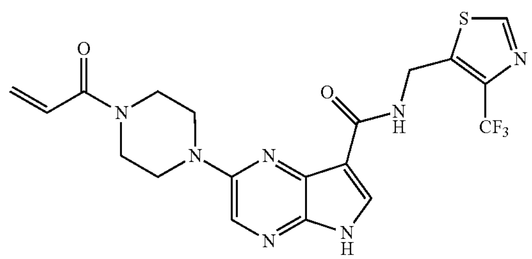 | MS m/z 480 [M + H]+<br>Rt = 2.59 minutes<br>Prep HPLC gradient 19-59% organic. |
| 186 | 2-[(1-acryloylpiperidin-4-yl)amino]-N-[(5-chloropyridin-2-yl)methyl]-5H-pyrrolo[2,3-b]pyrazine-7-carboxamide | 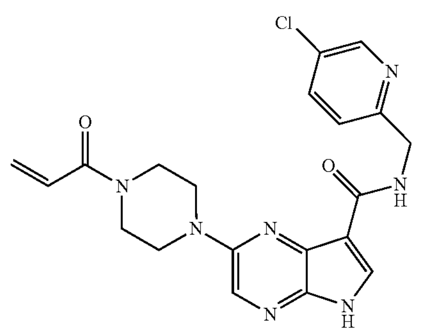 | MS m/z 440 [M + H]+<br>Rt = 2.53 minutes<br>Prep HPLC gradient 18-58% organic. |
| 187 | 2-[(1-acryloylpiperidin-4-yl)amino]-N-benzyl-5H-pyrrolo[2,3-b]pyrazine-7-carboxamide | 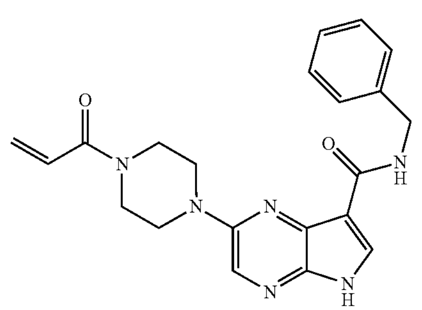 | MS m/z 405 [M + H]+<br>Rt = 2.62 minutes<br>Prep HPLC gradient 20-60% organic. |
| 188 | 2-[(1-acryloylpiperidin-4-yl)amino]-N-(4-fluorobenzyl)-5H-pyrrolo[2,3-b]pyrazine-7-carboxamide | 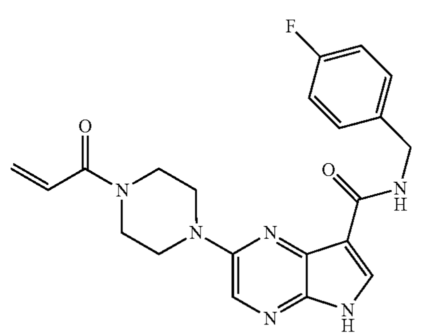 | MS m/z 423 [M + H]+<br>Rt = 2.66 minutes<br>Prep HPLC gradient 21-61% organic. |

| Ex. No. | Name | Structure | Data/% Organic Eluant |
|---|---|---|---|
| 189 | 2-[(1-acryloylpiperidin-4-yl)amino]-N-(3-cyano-4-fluorobenzyl)-5H-pyrrolo[2,3-b]pyrazine-7-carboxamide | 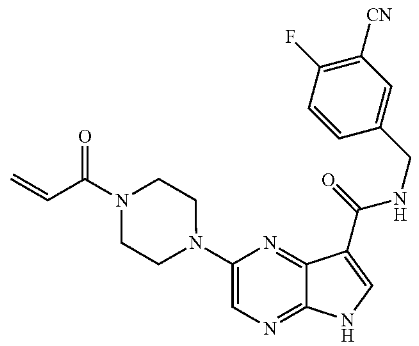 | MS m/z 448 [M + H]+<br>Rt = 2.63 minutes<br>Prep HPLC gradient 20-60% organic. |
| 190 | 2-[(1-acryloylpiperidin-4-yl)amino]-N-(3-fluoro-4-methoxybenzyl)-5H-pyrrolo[2,3-b]pyrazine-7-carboxamide | 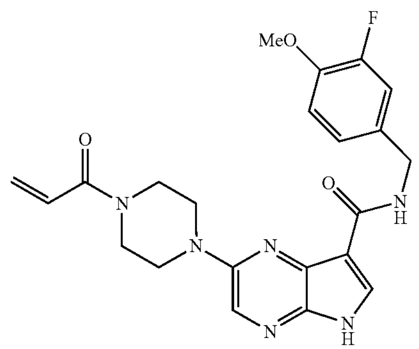 | MS m/z 453 [M + H]+<br>Rt = 2.63 minutes<br>Prep HPLC gradient 20-60% organic. |
| 191 | 2-[(1-acryloylpiperidin-4-yl)amino]-N-(4-methoxybenzyl)-5H-pyrrolo[2,3-b]pyrazine-7-carboxamide | 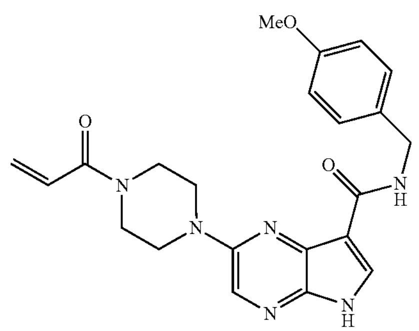 | MS m/z 435 [M + H]+<br>Rt = 2.60 minutes<br>Prep HPLC gradient 20-60% organic. |
| 192 | 2-[(1-acryloylpiperidin-4-yl)amino]-N-{[1-(3-fluorophenyl)-1H-pyrazol-4-yl]methyl}-5H-pyrrolo[2,3-b]pyrazine-7-carboxamide | 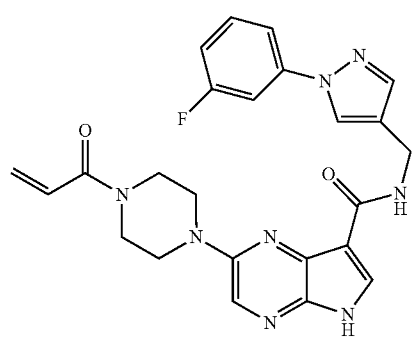 | MS m/z 489 [M + H]+<br>Rt = 2.70 minutes<br>Prep HPLC gradient 22-62% organic. |

| Ex. No. | Name | Structure | Data/% Organic Eluant |
|---|---|---|---|
| 193 | 2-[(1-acryloylpiperidin-4-yl)amino]-N-(cyclobutylmethyl)-5H-pyrrolo[2,3-b]pyrazine-7-carboxamide | 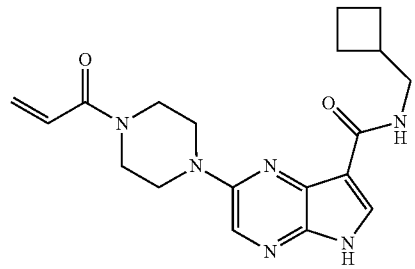 | MS m/z 383 [M + H]+ Rt = 2.61 minutes Prep HPLC gradient 20-60% organic. |
| 194 | 2-[(1-acryloylpiperidin-4-yl)amino]-N-[(6-fluoro-1,3-benzoxazol-2-yl)methyl]-5H-pyrrolo[2,3-b]pyrazine-7-carboxamide | 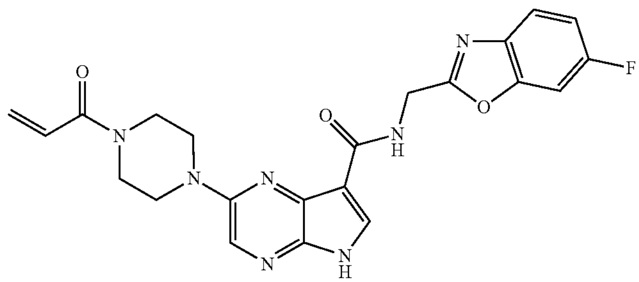 | MS m/z 464 [M + H]+ Rt = 2.65 minutes Prep HPLC gradient 21-61% organic. |
| 195 | 2-[(1-acryloylpiperidin-4-yl)amino]-N-{[2-methyl-4-(trifluoromethyl)-1,3-thiazol-5-yl]methyl}-5H-pyrrolo[2,3-b]pyrazine-7-carboxamide | 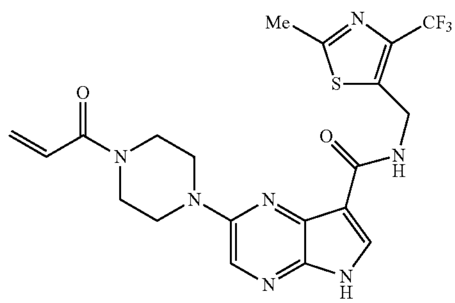 | MS m/z 494 [M + H]+ Rt = 2.65 minutes Prep HPLC gradient 20-60% organic. |
| 196 | 2-[(1-acryloylpiperidin-4-yl)amino]-N-(2-fluorobenzyl)-5H-pyrrolo[2,3-b]pyrazine-7-carboxamide | 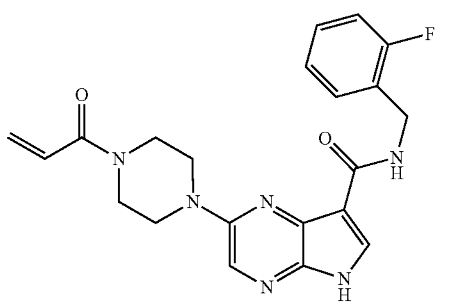 | MS m/z 423 [M + H]+ Rt = 2.65 minutes Prep HPLC gradient 21-61% organic. |

Examples 197-230 were prepared according to Library Protocol 3 below:

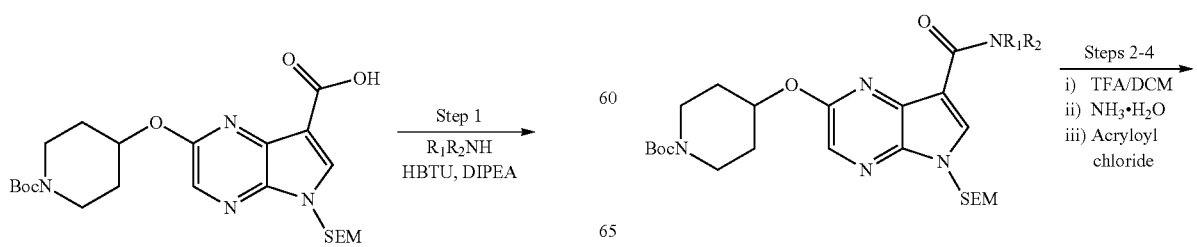

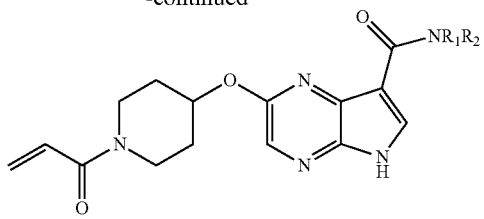

Library Protocol 3
Step 1

To a 0.1 M solution of 2{[1-(tert-butoxycarbonyl)piperidin-4-yl]oxy}-5-{[2-(trimethylsilyl)ethoxy]methyl}-5H-pyrrolo[2,3-b]pyrazine-7-carboxylic acid in DMF (Preparation 114 Step 1, 1.2 mL, 125 μmol) were added amines of formula $R_1R_2NH$ (187 μmol) followed by DIPEA (500 μmol) and HBTU (212 μmol). The reactions were shaken at 30° C. for 16 hours before cooling and concentrating in vacuo. To the residues was added saturated aqueous $NaHCO_3$ (1 mL) and the solutions were extracted into EtOAc (3×1 mL). The organic layers were collected, dried over sodium sulphate and concentrated in vacuo to afford the Step 1 intermediates.

Steps 2-4

To the Step 1 intermediates was added a solution of TFA in DCM (1.2 mL, v:v 1:4) and the reactions were shaken at 30° C. for 4 hours before concentrating in vacuo. The residues were treated with ammonium hydroxide in MeOH (1.2 mL, v:v 1:3) and shaken at 30° C. for 16 hours before concentrating in vacuo. The residues were treated with a saturated solution of $NaHCO_3$ in water (800 μL). To the solutions was added EtOAc (800 μL) followed by acryloyl chloride (250 μmol) and the reactions were shaken at 30° C. for 2 hours. The reactions were concentrated in vacuo and purified using preparative HPLC as described below to afford the following Examples:

Preparative HPLC:

Column: Phenomenex Gemini C18 250×21.2 mm, 8 micron. Mobile phase: Acetonitrile:ammonium hydroxide (pH=10). Gradient time: 8 minutes; Hold time: 1 minute at 100% organic; Flow rate: 35 mL/min.

QC Method 1:

Column: Xbridge C18 2.1×50 mm; 5 micron. Mobile phase A: 0.0375% TFA in water; Mobile phase B: 0.01875% TFA in MeCN. Gradient: initial—1% B; 0.6 minutes—5% B; 4 minutes—100% B; 4.3 minutes—1% B; 4.7 minutes—1% B. Flow rate: 0.8 mL/min QC Method 2:

Column: Xbridge C18 2.1×50 mm; 5 micron. Mobile phase A: 0.05% $NH_4OH$ in water; Mobile phase B: 100% MeCN. Gradient: initial—5% B; 0.5 minutes—5% B; 3.4 minutes—100% B; 4.2 minutes—100% B; 4.21 minutes—5% B; 4.7 minutes—5% B. Flow rate: 0.8 mL/min QC Method 1 was used unless otherwise specified:

| Ex. No. | Name | Structure | Data/% Organic Eluant/QC Method |
|---|---|---|---|
| 197 | 2-[(1-acryloylpiperidin-4-yl)oxy]-N-[(3,3-difluorocyclobutyl)methyl]-5H-pyrrolo[2,3-b]pyrazine-7-carboxamide | 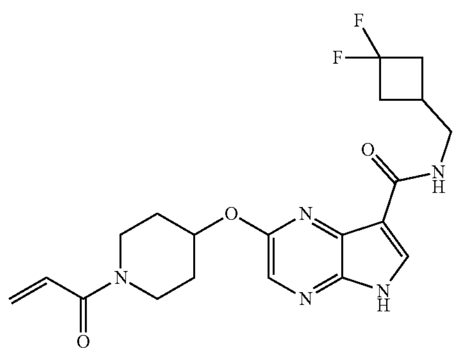 [SMILES: C=CC(=O)N1CCC(Oc2cnc3[nH]cc(C(=O)NCC4CC(F)(F)C4)c3n2)CC1] | MS m/z 420 [M + H]$^+$ Rt = 2.75 minutes Prep HPLC gradient 21-61% organic. |
| 198 | 2-[(1-acryloylpiperidin-4-yl)oxy]-N-(3,3,3-trifluoropropyl)-5H-pyrrolo[2,3-b]pyrazine-7-carboxamide | 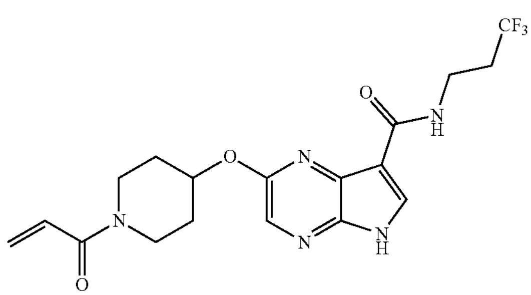 [SMILES: C=CC(=O)N1CCC(Oc2cnc3[nH]cc(C(=O)NCCC(F)(F)F)c3n2)CC1] | MS m/z 412 [M + H]$^+$ Rt = 2.71 minutes Prep HPLC gradient 21-61% organic. |

-continued

| Ex. No. | Name | Structure | Data/% Organic Eluant/QC Method |
|---|---|---|---|
| 199 | 2-[(1-acryloylpiperidin-4-yl)oxy]-N-[(1R,3S)-3-fluorocyclopentyl]-5H-pyrrolo[2,3-b]pyrazine-7-carboxamide | 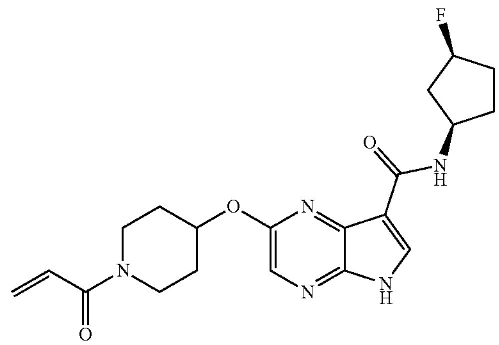 [SMILES: C=CC(=O)N1CCC(Oc2cnc3[nH]cc(C(=O)N[C@@H]4CC[C@H](F)C4)c3n2)CC1] | MS m/z 402 [M + H]+<br>Rt = 2.64 minutes<br>Prep HPLC gradient<br>18-58% organic. |
| 200 | 2-[(1-acryloylpiperidin-4-yl)oxy]-N-(bicyclo[1.1.1]pent-1-yl)-5H-pyrrolo[2,3-b]pyrazine-7-carboxamide | 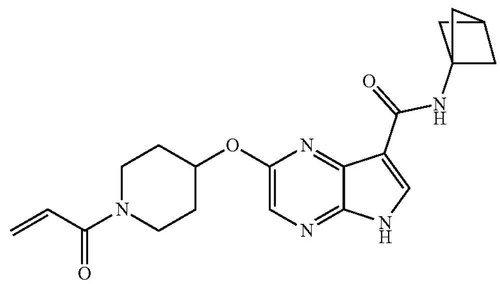 [SMILES: C=CC(=O)N1CCC(Oc2cnc3[nH]cc(C(=O)NC45CC(C4)C5)c3n2)CC1] | MS m/z 382 [M + H]+<br>Rt = 2.79 minutes<br>Prep HPLC gradient<br>32-72% organic. |
| 201 | Racemic-2-[(1-acryloylpiperidin-4-yl)oxy]-N-[(1-hydroxy-3-methylcyclopentyl)methyl]-5H-pyrrolo[2,3-b]pyrazine-7-carboxamide | 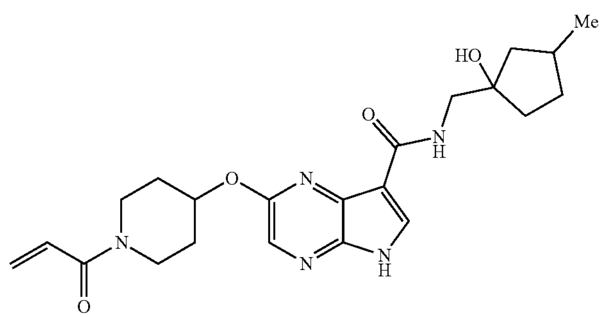 [SMILES: C=CC(=O)N1CCC(Oc2cnc3[nH]cc(C(=O)NCC4(O)CCC(C)C4)c3n2)CC1] | MS m/z 428 [M + H]+<br>Rt = 2.71 minutes<br>Prep HPLC gradient<br>20-60% organic. |
| 202 | 2-[(1-acryloylpiperidin-4-yl)oxy]-N-[(2R,3R)-1,1,1-trifluoro-2-hydroxy-4-methylpentan-3-yl]-5H-pyrrolo[2,3-b]pyrazine-7-carboxamide | 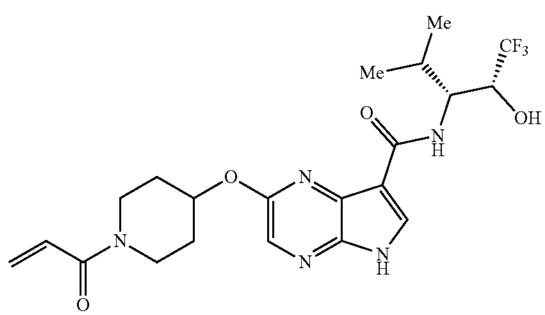 | MS m/z 402 [M + H]+<br>Rt = 2.64 minutes<br>Prep HPLC gradient<br>18-58% organic. |
| 203 | 2-[(1-acryloylpiperidin-4-yl)oxy]-N-[(1-hydroxycyclobutyl)methyl]-5H-pyrrolo[2,3-b]pyrazine-7-carboxamide | 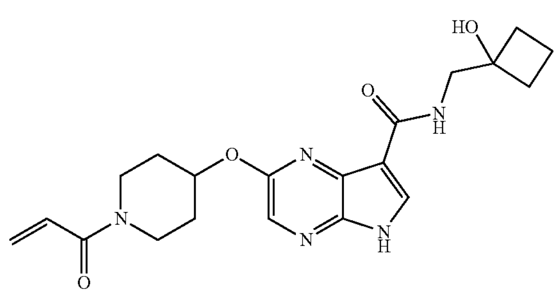 [SMILES: C=CC(=O)N1CCC(Oc2cnc3[nH]cc(C(=O)NCC4(O)CCC4)c3n2)CC1] | MS m/z 400 [M + H]+<br>Rt = 2.24 minutes<br>Prep HPLC gradient<br>23-63% organic.<br>Method 2. |

| Ex. No. | Name | Structure | Data/% Organic Eluant/QC Method |
|---|---|---|---|
| 204 | Racemic-2-[(1-acryloylpiperidin-4-yl)oxy]-N-cyclopentyl-5H-pyrrolo[2,3-b]pyrazine-7-carboxamide | 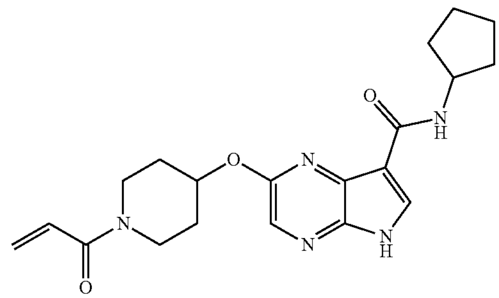 [SMILES: C=CC(=O)N1CCC(Oc2cnc3[nH]cc(C(=O)NC4CCCC4)c3n2)CC1] | MS m/z 384 [M + H]+ Rt = 2.74 minutes Prep HPLC gradient 31-71% organic. |
| 205 | 2-[(1-acryloylpiperidin-4-yl)oxy]-N-[(2S)-butan-2-yl]-5H-pyrrolo[2,3-b]pyrazine-7-carboxamide | 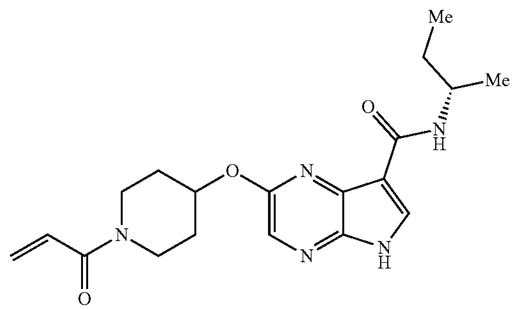 [SMILES: C=CC(=O)N1CCC(Oc2cnc3[nH]cc(C(=O)N[C@@H](C)CC)c3n2)CC1] | MS m/z 372 [M + H]+ Rt = 2.71 minutes Prep HPLC gradient 30-70% organic. |
| 206 | Racemic-2-[(1-acryloylpiperidin-4-yl)oxy]-N-[(1-hydroxycyclopentyl)methyl]-5H-pyrrolo[2,3-b]pyrazine-7-carboxamide | 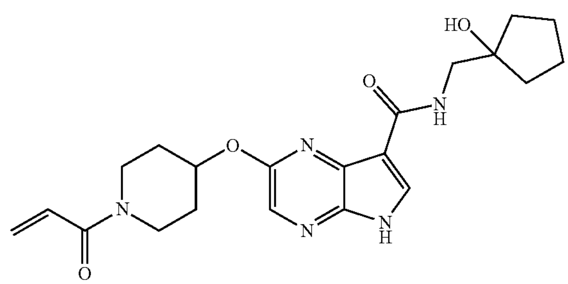 [SMILES: C=CC(=O)N1CCC(Oc2cnc3[nH]cc(C(=O)NCC4(O)CCCC4)c3n2)CC1] | MS m/z 414 [M + H]+ Rt = 2.59 minutes Prep HPLC gradient 14-44% organic. |
| 207 | 2-[(1-acryloylpiperidin-4-yl)oxy]-N-[(4,4-difluoro-1-hydroxycyclohexyl)methyl]-5H-pyrrolo[2,3-b]pyrazine-7-carboxamide | 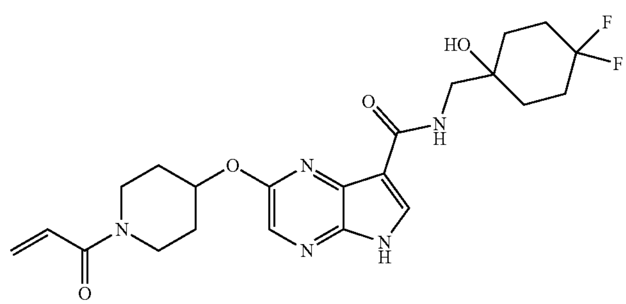 [SMILES: C=CC(=O)N1CCC(Oc2cnc3[nH]cc(C(=O)NCC4(O)CCC(F)(F)CC4)c3n2)CC1] | MS m/z 464 [M + H]+ Rt = 2.70 minutes Prep HPLC gradient 30-70% organic. |
| 208 | 2-[(1-acryloylpiperidin-4-yl)oxy]-N-{[(2R)-2-fluoro-1-hydroxycyclohexyl]methyl}-5H-pyrrolo[2,3-b]pyrazine-7-carboxamide | 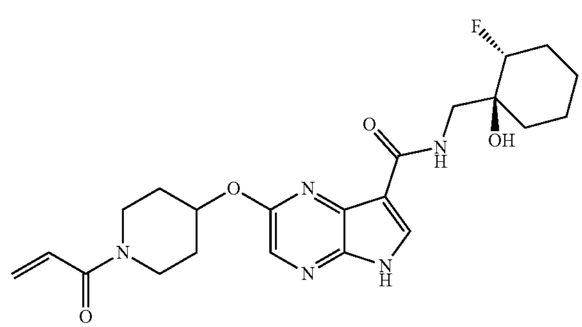 [SMILES: C=CC(=O)N1CCC(Oc2cnc3[nH]cc(C(=O)NC[C@@]4(O)CCCC[C@H]4F)c3n2)CC1] | MS m/z 446 [M + H]+ Rt = 2.64 minutes Prep HPLC gradient 28-68% organic. |

| Ex. No. | Name | Structure | Data/% Organic Eluant/QC Method |
|---|---|---|---|
| 209 | 2-[(1-acryloylpiperidin-4-yl)oxy]-N-(2-methylbutan-2-yl)-5H-pyrrolo[2,3-b]pyrazine-7-carboxamide | 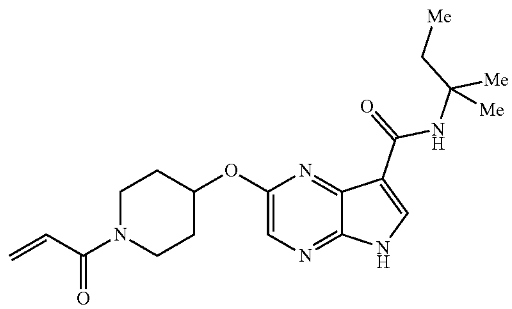 [SMILES: C=CC(=O)N1CCC(Oc2cnc3[nH]cc(C(=O)NC(C)(C)CC)c3n2)CC1] | MS m/z 386 [M + H]+<br>Rt = 2.85 minutes<br>Prep HPLC gradient<br>34-74% organic. |
| 210 | 2-[(1-acryloylpiperidin-4-yl)oxy]-N-[(1S,3S)-3-fluorocyclopentyl]-5H-pyrrolo[2,3-b]pyrazine-7-carboxamide | 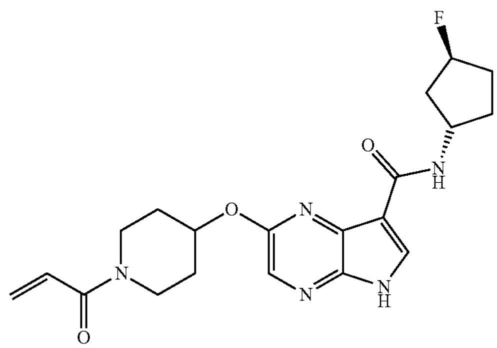 | MS m/z 402 [M + H]+<br>Rt = 2.66 minutes<br>Prep HPLC gradient<br>29-69% organic. |
| 211 | 2-[(1-acryloylpiperidin-4-yl)oxy]-N-(2-methoxyethyl)-5H-pyrrolo[2,3-b]pyrazine-7-carboxamide | 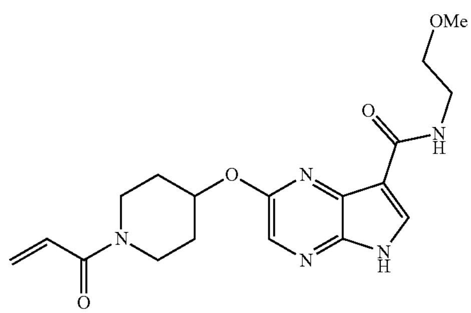 [SMILES: C=CC(=O)N1CCC(Oc2cnc3[nH]cc(C(=O)NCCOC)c3n2)CC1] | MS m/z 374 [M + H]+<br>Rt = 2.71 minutes<br>Prep HPLC gradient<br>21-61% organic.<br>Method 2. |
| 212 | 2-[(1-acryloylpiperidin-4-yl)oxy]-N-(3,3-difluorocyclobutyl)-5H-pyrrolo[2,3-b]pyrazine-7-carboxamide | 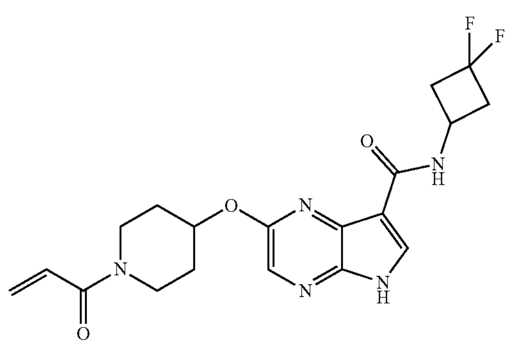 [SMILES: C=CC(=O)N1CCC(Oc2cnc3[nH]cc(C(=O)NC4CC(F)(F)C4)c3n2)CC1] | MS m/z 406 [M + H]+<br>Rt = 2.43 minutes<br>Prep HPLC gradient<br>29-69% organic.<br>Method 2. |

| Ex. No. | Name | Structure | Data/% Organic Eluant/QC Method |
|---|---|---|---|
| 213 | Racemic-2-[(1-acryloylpiperidin-4-yl)oxy]-N-[1-(1-hydroxycyclobutyl)propyl]-5H-pyrrolo[2,3-b]pyrazine-7-carboxamide | 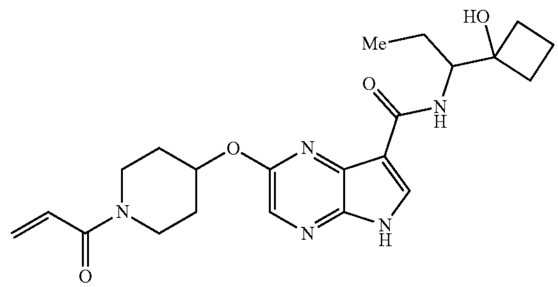 [SMILES: C=CC(=O)N1CCC(Oc2cnc3[nH]cc(C(=O)NC(CC)C4(O)CCC4)c3n2)CC1] | MS m/z 428 [M + H]+<br>Rt = 2.61 minutes<br>Prep HPLC gradient 28-68% organic. |
| 214 | 2-[(1-acryloylpiperidin-4-yl)oxy]-N-[(2R)-1-methoxypropan-2-yl]-5H-pyrrolo[2,3-b]pyrazine-7-carboxamide | 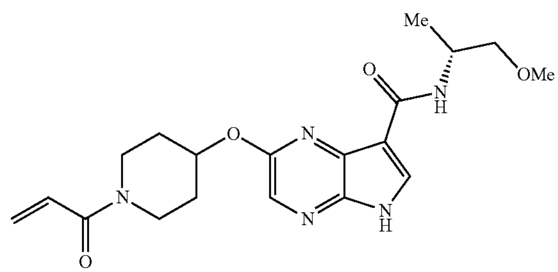 [SMILES: C=CC(=O)N1CCC(Oc2cnc3[nH]cc(C(=O)N[C@H](C)COC)c3n2)CC1] | MS m/z 388 [M + H]+<br>Rt = 2.32 minutes<br>Prep HPLC gradient 26-66% organic.<br>Method 2. |
| 215 | 2-[(1-acryloylpiperidin-4-yl)oxy]-N-(2,2-difluoropropyl)-5H-pyrrolo[2,3-b]pyrazine-7-carboxamide | 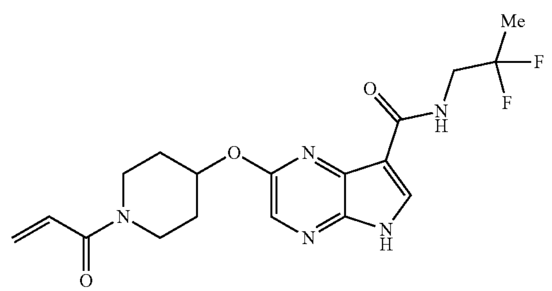 [SMILES: C=CC(=O)N1CCC(Oc2cnc3[nH]cc(C(=O)NCC(C)(F)F)c3n2)CC1] | MS m/z 394 [M + H]+<br>Rt = 2.65 minutes<br>Prep HPLC gradient 28-68% organic. |
| 216 | 2-[(1-acryloylpiperidin-4-yl)oxy]-N-[(1R,2R)-2-(trifluoromethyl)cyclopropyl]-5H-pyrrolo[2,3-b]pyrazine-7-carboxamide | 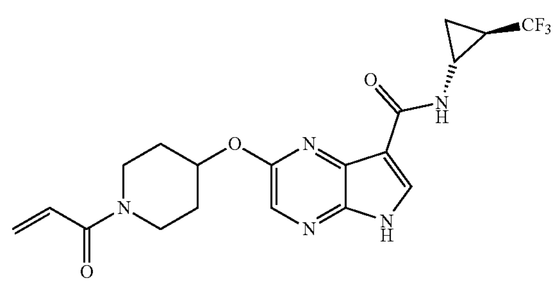 | MS m/z 424 [M + H]+<br>Rt = 2.80 minutes<br>Prep HPLC gradient 32-72% organic. |
| 217 | 2-[(1-acryloylpiperidin-4-yl)Oxy]-N-[(2S,3S)-1,1,1-trifluoro-2-hydroxy-4-methylpentan-3-yl]-5H-pyrrolo[2,3-b]pyrazine-7-carboxamide | 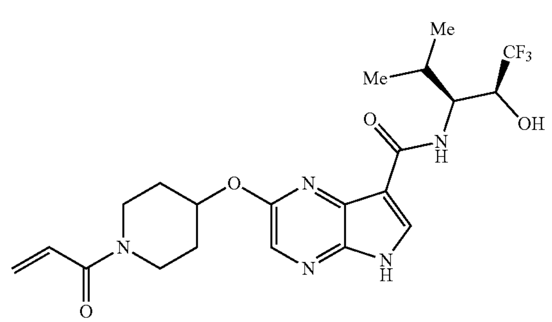 [SMILES: C=CC(=O)N1CCC(Oc2cnc3[nH]cc(C(=O)N[C@@H](C(C)C)[C@H](O)C(F)(F)F)c3n2)CC1] | MS m/z 470 [M + H]+<br>Rt = 2.76 minutes<br>Prep HPLC gradient 29-69% organic. |

| Ex. No. | Name | Structure | Data/% Organic Eluant/QC Method |
|---|---|---|---|
| 218 | 2-[(1-acryloylpiperidin-4-yl)oxy]-N-(3-cyanopropyl)-5H-pyrrolo[2,3-b]pyrazine-7-carboxamide | 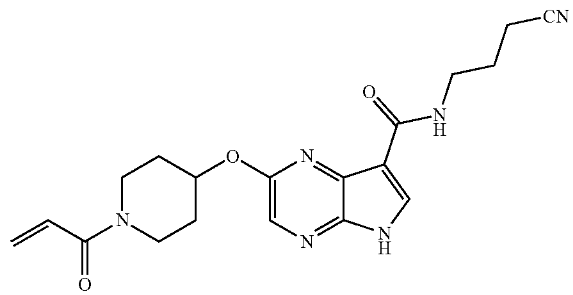 [SMILES: C=CC(=O)N1CCC(Oc2cnc3[nH]cc(C(=O)NCCCC#N)c3n2)CC1] | MS m/z 383 [M + H]+<br>Rt = 2.23 minutes<br>Prep HPLC gradient<br>23-63% organic.<br>Method 2. |
| 219 | 2-[(1-acryloylpiperidin-4-yl)oxy]-N-(2,2-difluorocyclopentyl)-5H-pyrrolo[2,3-b]pyrazine-7-carboxamide | 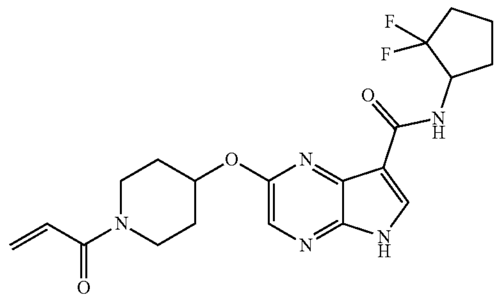 [SMILES: C=CC(=O)N1CCC(Oc2cnc3[nH]cc(C(=O)NC4CCCC4(F)F)c3n2)CC1] | MS m/z 420 [M + H]+<br>Rt = 2.75 minutes<br>Prep HPLC gradient<br>31-71% organic. |
| 220 | Racemic-2-[(1-acryloylpiperidin-4-yl)oxy]-N-(1-cyclopropylethyl)-5H-pyrrolo[2,3-b]pyrazine-7-carboxamide | 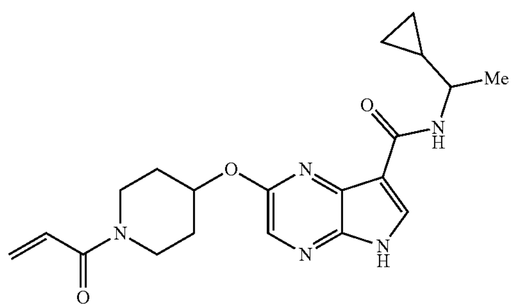 [SMILES: C=CC(=O)N1CCC(Oc2cnc3[nH]cc(C(=O)NC(C)C4CC4)c3n2)CC1] | MS m/z 384 [M + H]+<br>Rt = 2.74 minutes<br>Prep HPLC gradient<br>31-71% organic. |
| 221 | 2-[(1-acryloylpiperidin-4-yl)oxy]-N-(2,2-dimethylpropyl)-5H-pyrrolo[2,3-b]pyrazine-7-carboxamide | 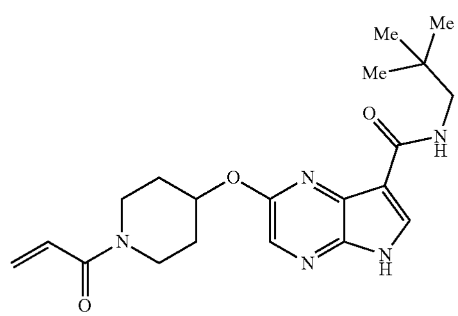 [SMILES: C=CC(=O)N1CCC(Oc2cnc3[nH]cc(C(=O)NCC(C)(C)C)c3n2)CC1] | MS m/z 386 [M + H]+<br>Rt = 2.82 minutes<br>Prep HPLC gradient<br>33-73% organic. |
| 222 | 2-[(1-acryloylpiperidin-4-yl)oxy]-N-(2-methylpropyl)-5H-pyrrolo[2,3-b]pyrazine-7-carboxamide | 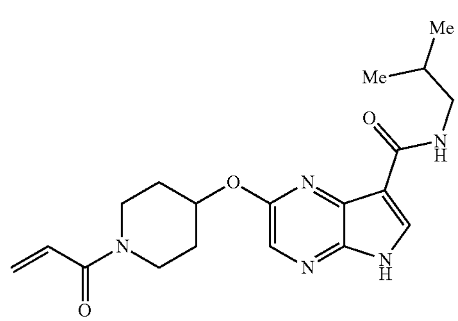 [SMILES: C=CC(=O)N1CCC(Oc2cnc3[nH]cc(C(=O)NCC(C)C)c3n2)CC1] | MS m/z 372 [M + H]+<br>Rt = 2.71 minutes<br>Prep HPLC gradient<br>30-70% organic. |

| Ex. No. | Name | Structure | Data/% Organic Eluant/QC Method |
|---|---|---|---|
| 223 | Racemic-2-[(1-acryloylpiperidin-4-yl)oxy]-N-[(3,3-difluoro-1-hydroxycyclohexyl)methyl]-5H-pyrrolo[2,3-b]pyrazine-7-carboxamide | 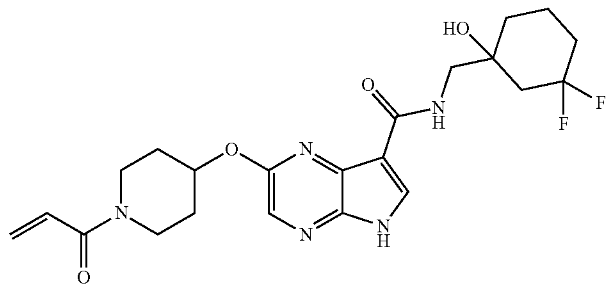 [SMILES: C=CC(=O)N1CCC(Oc2cnc3[nH]cc(C(=O)NCC4(O)CCCC(F)(F)C4)c3n2)CC1] | MS m/z 464 [M + H]+ Rt = 2.65 minutes Prep HPLC gradient 29-69% organic. |
| 224 | Racemic-2-[(1-acryloylpiperidin-4-yl)oxy]-N-{[(2S)-2-fluoro-1-hydroxycyclohexyl]methyl}-5H-pyrrolo[2,3-b]pyrazine-7-carboxamide | 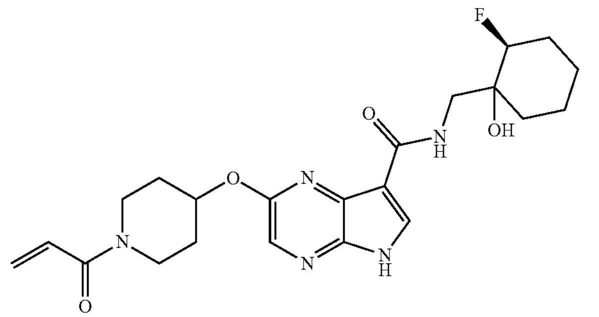 [SMILES: C=CC(=O)N1CCC(Oc2cnc3[nH]cc(C(=O)NCC4(O)CCCC[C@@H]4F)c3n2)CC1] | MS m/z 446 [M + H]+ Rt = 2.71 minutes Prep HPLC gradient 30-70% organic. |
| 225 | 2-[(1-acryloylpiperidin-4-yl)oxy]-N-[(1S,3R)-3-fluorocyclopentyl]-5H-pyrrolo[2,3-b]pyrazine-7-carboxamide | 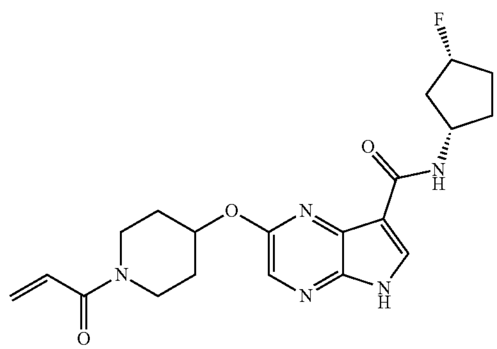 [SMILES: C=CC(=O)N1CCC(Oc2cnc3[nH]cc(C(=O)N[C@H]4CC[C@@H](F)C4)c3n2)CC1] | MS m/z 402 [M + H]+ Rt = 2.63 minutes Prep HPLC gradient 28-68% organic. |
| 226 | Racemic-2-[(1-acryloylpiperidin-4-yl)oxy]-N-{[(3R)-1-hydroxy-3-methylcyclopentyl]methyl}-5H-pyrrolo[2,3-b]pyrazine-7-carboxamide | 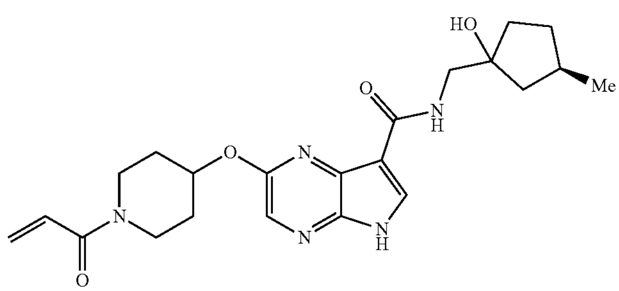 [SMILES: C=CC(=O)N1CCC(Oc2cnc3[nH]cc(C(=O)NCC4(O)CC[C@@H](C)C4)c3n2)CC1] | MS m/z 428 [M + H]+ Rt = 2.71 minutes Prep HPLC gradient 20-60% organic. |
| 227 | 2-[(1-acryloylpiperidin-4-yl)oxy]-N-[(2R)-butan-2-yl]-5H-pyrrolo[2,3-b]pyrazine-7-carboxamide | 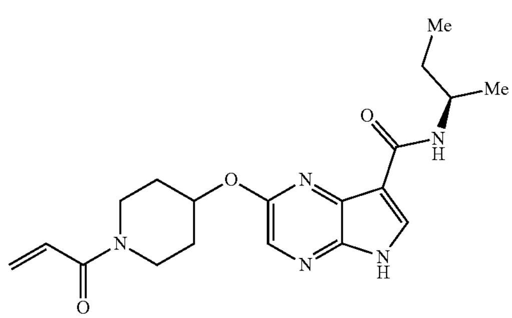 [SMILES: C=CC(=O)N1CCC(Oc2cnc3[nH]cc(C(=O)N[C@H](C)CC)c3n2)CC1] | MS m/z 372 [M + H]+ Rt = 2.71 minutes Prep HPLC gradient 30-70% organic. |

| Ex. No. | Name | Structure | Data/% Organic Eluant/QC Method |
|---|---|---|---|
| 228 | 2-[(1-acryloylpiperidin-4-yl)oxy]-N-[(2S)-1-methoxypropan-2-yl]-5H-pyrrolo[2,3-b]pyrazine-7-carboxamide | 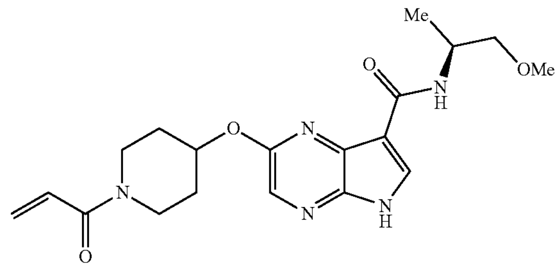 [SMILES: C=CC(=O)N1CCC(Oc2cnc3[nH]cc(C(=O)N[C@@H](C)COC)c3n2)CC1] | MS m/z 388 [M + H]$^+$<br>Rt = 2.33 minutes<br>Prep HPLC gradient 26-66% organic.<br>Method 2. |
| 229 | 2-[(1-acryloylpiperidin-4-yl)oxy]-N-[(1R,2R)-2-fluorocyclopentyl]-5H-pyrrolo[2,3-b]pyrazine-7-carboxamide | 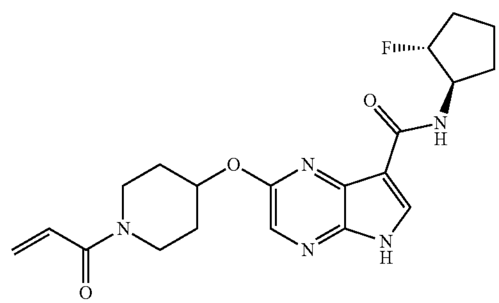 [SMILES: C=CC(=O)N1CCC(Oc2cnc3[nH]cc(C(=O)N[C@@H]4CCC[C@H]4F)c3n2)CC1] | MS m/z 402 [M + H]$^+$<br>Rt = 2.75 minutes<br>Prep HPLC gradient 30-70% organic. |
| 230 | 2-[(1-acryloylpiperidin-4-yl)oxy]-N-[(1R,2S)-2-fluorocyclopentyl]-5H-pyrrolo[2,3-b]pyrazine-7-carboxamide | 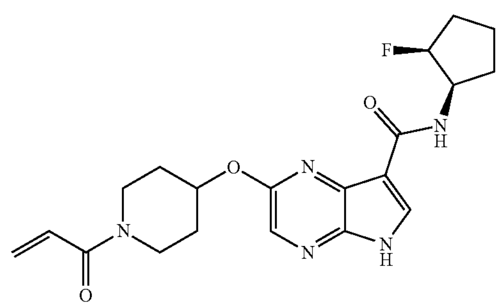 [SMILES: C=CC(=O)N1CCC(Oc2cnc3[nH]cc(C(=O)N[C@@H]4CCC[C@@H]4F)c3n2)CC1] | MS m/z 402 [M + H]$^+$<br>Rt = 2.72 minutes<br>Prep HPLC gradient 31-71% organic. |

Examples 231-264 were prepared according to Library Protocol 4 below:

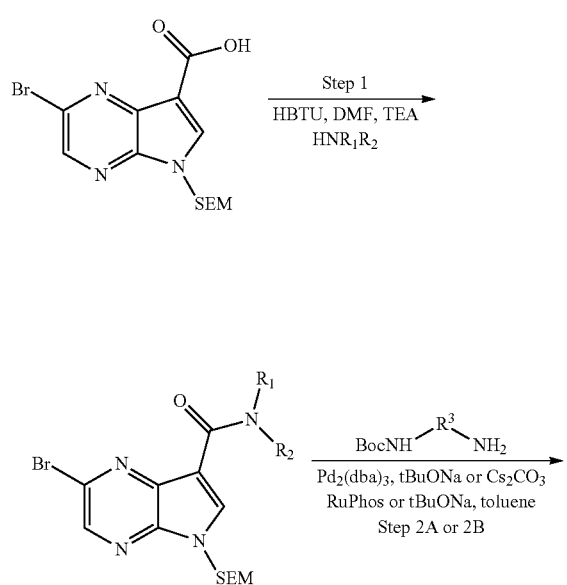

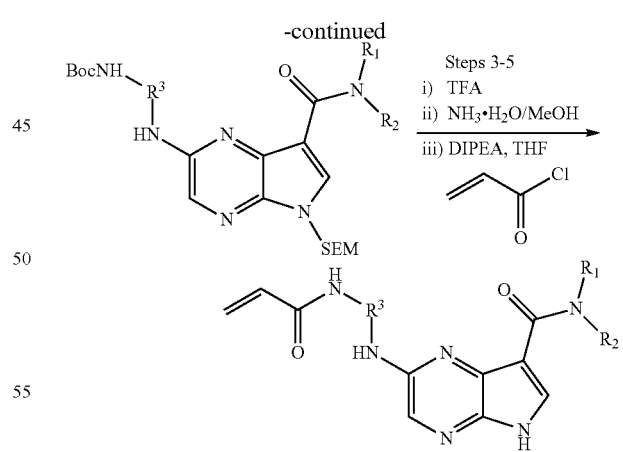

Library Protocol 4

Step 1

To a 0.2M solution of 2-bromo-{[2-(trimethylsilyl)ethoxy]methyl}-5H-pyrrolo[2,3-b]pyrazine-7-carboxylic acid in DMF (Example 1 Step 2, 1 mL, 200 μmol) was added the appropriate amine (300 μmol) followed by DIPEA (77.4 mg, 600 μmol) and a 0.22M solution of HBTU in DMF (1 mL, 220 μmol). The reactions were shaken at 60° C. for 16 hours before cooling and concentrating in vacuo. The residues were purified using preparative TLC to afford the Step 1 amide intermediate.

Either step 2A or Step 2B was employed for the Buchwald step:

Step 2A

To the Step 1 amide intermediate (100 μmol) was added cesium carbonate (65 mg, 200 μmol), a 0.25M solution of the appropriate Boc-protected amine in toluene (800 μL, 200 μmol), Pd$_2$dba$_3$ (4.6 mg, 5 μmol) and Ruphos (2.8 mg, 6 μmol) under nitrogen. The reactions were capped and shaken at 100° C. for 16 hours before cooling and concentrating in vacuo. The residue was washed with water (1 mL) and extracted into EtOAc (3×1 mL). The organic layers were collected and concentrated in vacuo to afford the Step 2 intermediate.

Step 2B

To the amide intermediate (100 μmol) was added sodium tert-butoxide (19.2 mg, 200 μmol), a 0.25M solution of the appropriate Boo-protected amine in toluene (800 μL, 200 μmol), Pd$_2$dba$_3$ (4.6 mg, 5 μmol) and Ruphos (2.8 mg, 6 μmol) under nitrogen. The reactions were capped and shaken at 65° C. for 40 hours before cooling and concentrating in vacuo. The residue was washed with water (1 mL) and extracted into EtOAc (3×1 mL). The organic layers were collected and concentrated in vacuo to afford the step 2 intermediate.

Steps 3-5

To the Step 2 intermediates was added a solution of TFA in DCM (1 mL, v:v 1:6) and the reactions were shaken at 30° C. for 16 hours before concentrating in vacuo. The residues were treated with ammonium hydroxide in MeOH (1.5 mL, v:v 1:4) and shaken at 30° C. for 2 hours before concentrating in vacuo. The residues were treated with a saturated solution of NaHCO$_3$ in water (1 mL). To the solutions was added EtOAc (1 mL) followed by acryloyl chloride (200 μmol) and the reactions were shaken at 30° C. for 2 hours. The reactions were concentrated in vacuo and purified using preparative HPLC as described below to afford the following Examples:

Preparative HPLC:

Column: Phenomenex Gemini C18 250×21.2 mm, 8 micron. Mobile phase: Acetonitrile:ammonium hydroxide (pH=10). Gradient time: 8 minutes; Hold time: 1 minute at 100% organic; Flow rate: 35 mL/min.

QC Method 1:

Column: Xbridge C18 2.1×50 mm; 5 micron. Mobile phase A: 0.0375% TFA in water; Mobile phase B: 0.01875% TFA in MeCN. Gradient: initial—1% B; 0.6 minutes—5% B; 4 minutes—100% B; 4.3 minutes—1% B; 4.7 minutes—1% B. Flow rate: 0.8 mL/min QC Method 2:

Column: Xbridge C18 2.1×50 mm; 5 micron. Mobile phase A: 0.05% NH$_4$OH in water; Mobile phase B: 100% MeCN. Gradient: initial—5% B; 0.5 minutes—5% B; 3.4 minutes—100% B; 4.2 minutes—100% B; 4.21 minutes—5% B; 4.7 minutes—5% B. Flow rate: 0.8 mL/min QC Method 1 was used unless otherwise specified:

| Ex. No. | Name | Structure | Data/% Organic Eluant/QC Method |
|---|---|---|---|
| 231 | 2-{[(3S)-1-acryloylpyrrolidin-3-yl]amino}-N-(2,2,2-trifluoroethyl)-5H-pyrrolo[2,3-b]pyrazine-7-carboxamide | 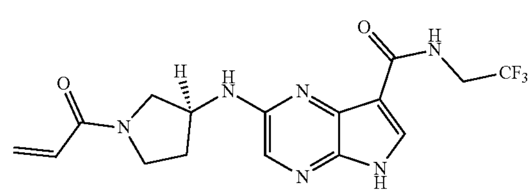 [SMILES: C=CC(=O)N1CC[C@H](Nc2cnc3[nH]cc(C(=O)NCC(F)(F)F)c3n2)C1] | MS m/z 383 [M + H]$^+$ Rt = 2.55 minutes Prep HPLC gradient 18-58% organic. |
| 232 | 2-{[(3R,4S)-1-acryloyl-4-cyano-4-methylpyrrolidin-3-yl]amino}-N-(2-methoxyethyl)-5H-pyrrolo[2,3-b]pyrazine-7-carboxamide | 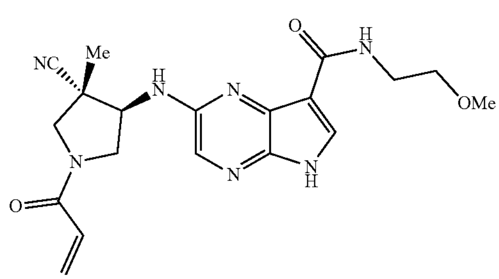 [SMILES: C=CC(=O)N1C[C@H](Nc2cnc3[nH]cc(C(=O)NCCOC)c3n2)[C@@](C)(C#N)C1] | MS m/z 398 [M + H]$^+$ Rt = 2.33 minutes Prep HPLC gradient 5-45% organic. |
| 233 | 2-{[(3R,5S)-1-acryloyl-5-(ethoxymethyl)pyrrolidin-3-yl]amino}-N-(2-methoxyethyl)-5H-pyrrolo[2,3-b]pyrazine-7-carboxamide | 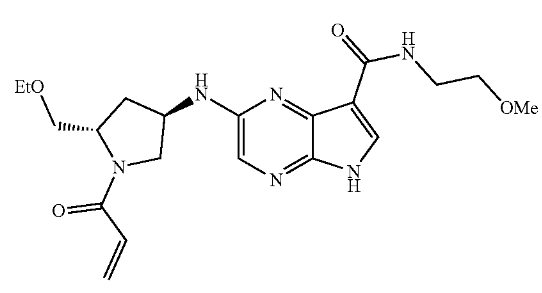 [SMILES: C=CC(=O)N1C[C@H](Nc2cnc3[nH]cc(C(=O)NCCOC)c3n2)C[C@H]1COCC] | MS m/z 417 [M + H]$^+$ Rt = 2.54 minutes Prep HPLC gradient 18-58% organic. |

| Ex. No. | Name | Structure | Data/% Organic Eluant/QC Method |
|---|---|---|---|
| 234 | 2-{[(3R)-1-acryloylpyrrolidin-3-yl]amino}-N-ethyl-5H-pyrrolo[2,3-b]pyrazine-7-carboxamide | 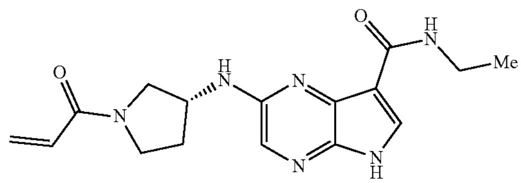 [SMILES: C=CC(=O)N1CC[C@@H](Nc2cnc3[nH]cc(C(=O)NCC)c3n2)C1] | MS m/z 329 [M + H]+<br>Rt = 2.33 minutes<br>Prep HPLC gradient<br>5-45% organic. |
| 235 | 2-{[(3S)-1-acryloylpyrrolidin-3-yl]amino}-N-(3,3,3-trifluoropropyl)-5H-pyrrolo[2,3-b]pyrazine-7-carboxamide | 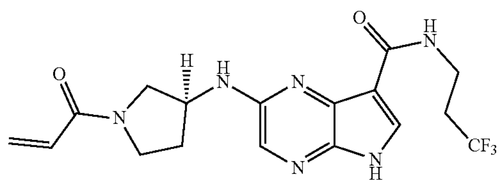 [SMILES: C=CC(=O)N1CC[C@H](Nc2cnc3[nH]cc(C(=O)NCCC(F)(F)F)c3n2)C1] | MS m/z 397 [M + H]+<br>Rt = 2.55 minutes<br>Prep HPLC gradient<br>18-58% organic. |
| 236 | 2-[(5-acryloyl-5-azaspiro[2.4]hept-7-yl)amino]-N-(2-methylpropyl)-5H-pyrrolo[2,3-b]pyrazine-7-carboxamide | 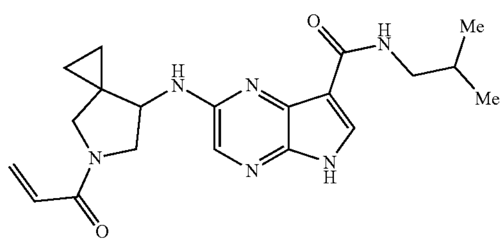 [SMILES: C=CC(=O)N1CC(Nc2cnc3[nH]cc(C(=O)NCC(C)C)c3n2)C2(CC2)C1] | MS m/z 383 [M + H]+<br>Rt = 2.72 minutes<br>Prep HPLC gradient<br>16-56% organic. |
| 237 | 2-{[(3S)-1-acryloylpyrrolidin-3-yl]amino}-N-(4,4,4-trifluorobutyl)-5H-pyrrolo[2,3-b]pyrazine-7-carboxamide | 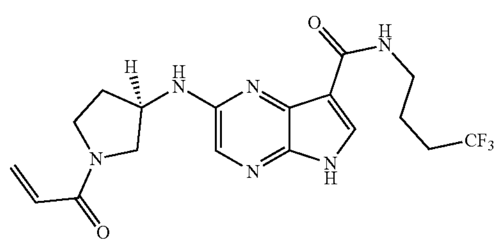 [SMILES: C=CC(=O)N1CC[C@@H](Nc2cnc3[nH]cc(C(=O)NCCCC(F)(F)F)c3n2)C1] | MS m/z 411 [M + H]+<br>Rt = 2.64 minutes<br>Prep HPLC gradient<br>21-61% organic. |
| 238 | 2-{[(3S,4S)-1-acryloyl-4-cyclopropylpyrrolidin-3-yl]amino}-N-ethyl-5H-pyrrolo[2,3-b]pyrazine-7-carboxamide | 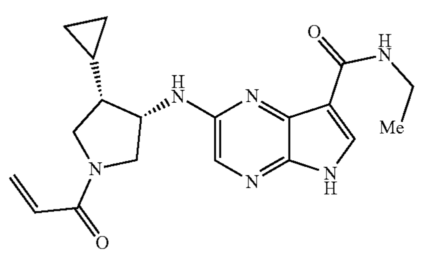 [SMILES: C=CC(=O)N1C[C@H](C2CC2)[C@H](Nc2cnc3[nH]cc(C(=O)NCC)c3n2)C1] | MS m/z 369 [M + H]+<br>Rt = 2.58 minutes<br>Prep HPLC gradient<br>12-52% organic. |
| 239 | 2-{[(3R,5S)-1-acryloyl-5-(methoxymethyl)pyrrolidin-3-yl]amino}-N-ethyl-5H-pyrrolo[2,3-b]pyrazine-7-carboxamide | 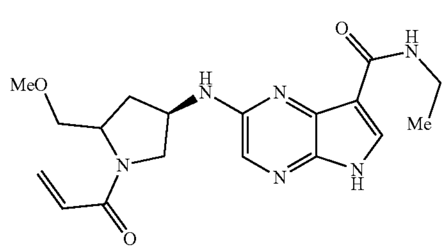 [SMILES: C=CC(=O)N1C[C@H](Nc2cnc3[nH]cc(C(=O)NCC)c3n2)CC1COC] | MS m/z 373 [M + H]+<br>Rt = 2.44 minutes<br>Prep HPLC gradient<br>8-48% organic. |

-continued

| Ex. No. | Name | Structure | Data/% Organic Eluant/QC Method |
|---|---|---|---|
| 240 | 2-{[(3R,4S)-1-acryloyl-4-cyano-4-methylpyrrolidin-3-yl]amino}-N-ethyl-5H-pyrrolo[2,3-b]pyrazine-7-carboxamide | 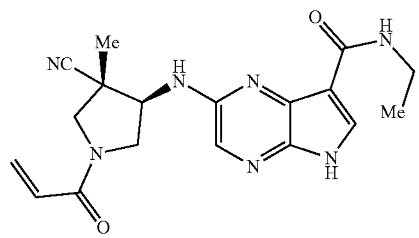 [SMILES: C=CC(=O)N1C[C@H](Nc2cnc3[nH]cc(C(=O)NCC)c3n2)[C@@](C)(C#N)C1] | MS m/z 368 [M + H]+ Rt = 2.37 minutes Prep HPLC gradient 6-46% organic. |
| 241 | 2-{[(3S,4S)-1-acryloyl-4-ethylpyrrolidin-3-yl]amino}-N-ethyl-5H-pyrrolo[2,3-b]pyrazine-7-carboxamide | 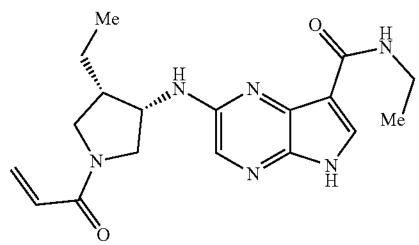 [SMILES: C=CC(=O)N1C[C@H](CC)[C@H](Nc2cnc3[nH]cc(C(=O)NCC)c3n2)C1] | MS m/z 357 [M + H]+ Rt = 2.58 minutes Prep HPLC gradient 12-52% organic. |
| 242 | 2-[(5-acryloyl-5-azaspiro[2.4]hept-7-yl)amino]-N-(2,2,2-trifluoroethyl)-5H-pyrrolo[2,3-b]pyrazine-7-carboxamide | 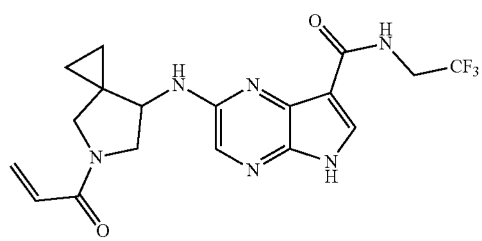 [SMILES: C=CC(=O)N1CC(Nc2cnc3[nH]cc(C(=O)NCC(F)(F)F)c3n2)C2(CC2)C1] | MS m/z 409 [M + H]+ Rt = 2.71 minutes Prep HPLC gradient 15-55% organic. |
| 243 | 2-{[(3S)-1-acryloylpyrrolidin-3-yl]amino}-N-ethyl-5H-pyrrolo[2,3-b]pyrazine-7-carboxamide | 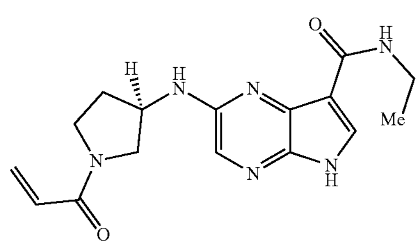 [SMILES: C=CC(=O)N1CC[C@@H](Nc2cnc3[nH]cc(C(=O)NCC)c3n2)C1] | MS m/z 329 [M + H]+ Rt = 2.34 minutes Prep HPLC gradient 4-44% organic. |
| 244 | 2-[(5-acryloyl-5-azaspiro[2.4]hept-7-yl)amino]-N-ethyl-5H-pyrrolo[2,3-b]pyrazine-7-carboxamide | 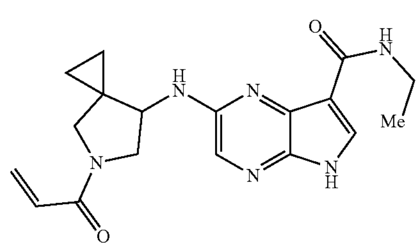 [SMILES: C=CC(=O)N1CC(Nc2cnc3[nH]cc(C(=O)NCC)c3n2)C2(CC2)C1] | MS m/z 355 [M + H]+ Rt = 2.49 minutes Prep HPLC gradient 9-49% organic. |
| 245 | 2-{[(3R,4R)-1-acryloyl-4-cyano-4-methylpyrrolidin-3-yl]amino}-N-(2-methoxyethyl)-5H-pyrrolo[2,3-b]pyrazine-7-carboxamide | 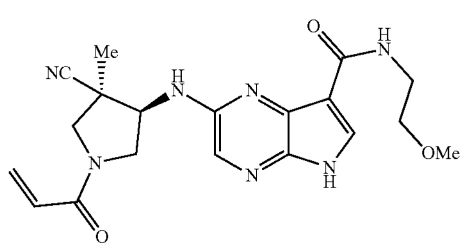 [SMILES: C=CC(=O)N1C[C@H](Nc2cnc3[nH]cc(C(=O)NCCOC)c3n2)[C@](C)(C#N)C1] | MS m/z 398 [M + H]+ Rt = 2.36 minutes Prep HPLC gradient 5-45% organic. |

-continued

| Ex. No. | Name | Structure | Data/% Organic Eluant/QC Method |
|---|---|---|---|
| 246 | 2-{[(3R,5R)-1-acryloyl-5-(methoxymethyl)pyrrolidin-3-yl]amino}-N-(2-methoxyethyl)-5H-pyrrolo[2,3-b]pyrazine-7-carboxamide | 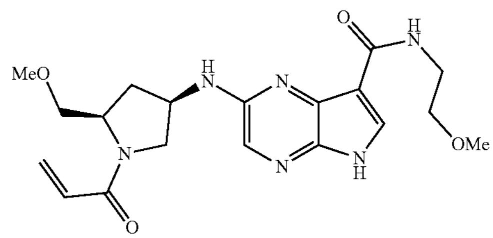 [SMILES: C=CC(=O)N1C[C@H](Nc2cnc3[nH]cc(C(=O)NCCOC)c3n2)C[C@@H]1COC] | MS m/z 403 [M + H]+ Rt = 2.16 minutes Prep HPLC gradient 6-46% organic. Method 2. |
| 247 | 2-{[(3S,4S)-1-acryloyl-4-cyclopropylpyrrolidin-3-yl]amino}-N-(2-methoxyethyl)-5H-pyrrolo[2,3-b]pyrazine-7-carboxamide | 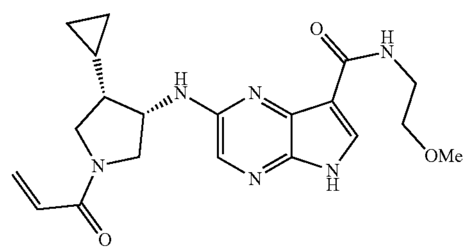 [SMILES: C=CC(=O)N1C[C@H](C2CC2)[C@H](Nc2cnc3[nH]cc(C(=O)NCCOC)c3n2)C1] | MS m/z 399 [M + H]+ Rt = 2.54 minutes Prep HPLC gradient 11-51% organic. |
| 248 | 2-[(1-acryloyl-4-methylpyrrolidin-3-yl)amino]-N-ethyl-5H-pyrrolo[2,3-b]pyrazine-7-carboxamide | 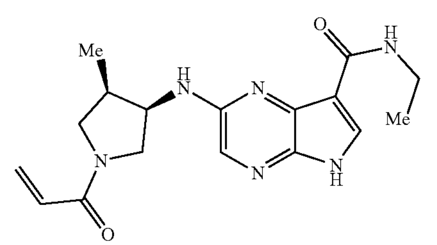 [SMILES: C=CC(=O)N1C[C@@H](C)[C@@H](Nc2cnc3[nH]cc(C(=O)NCC)c3n2)C1] | MS m/z 343 [M + H]+ Rt = 2.45 minutes Prep HPLC gradient 8-48% organic. |
| 249 | 2-[(5-acryloyl-5-azaspiro[2.4]hept-7-yl)amino]-N-(4,4,4-trifluorobutyl)-5H-pyrrolo[2,3-b]pyrazine-7-carboxamide | 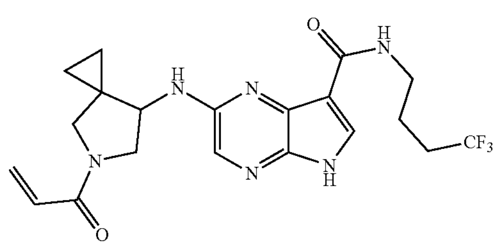 [SMILES: C=CC(=O)N1CC(Nc2cnc3[nH]cc(C(=O)NCCCC(F)(F)F)c3n2)C2(CC2)C1] | MS m/z 437 [M + H]+ Rt = 2.79 minutes Prep HPLC gradient 8-48% organic. |
| 250 | 2-{[(3R,5S)-1-acryloyl-5-(ethoxymethyl)pyrrolidin-3-yl]amino}-N-ethyl-5H-pyrrolo[2,3-b]pyrazine-7-carboxamide | 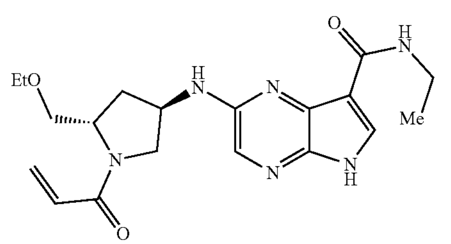 [SMILES: C=CC(=O)N1C[C@H](Nc2cnc3[nH]cc(C(=O)NCC)c3n2)C[C@H]1COCC] | MS m/z 387 [M + H]+ Rt = 2.59 minutes Prep HPLC gradient 19-59% organic. |
| 251 | 2-{[(3R,4R)-1-acryloyl-4-cyano-4-methylpyrrolidin-3-yl]amino}-N-ethyl-5H-pyrrolo[2,3-b]pyrazine-7-carboxamide | 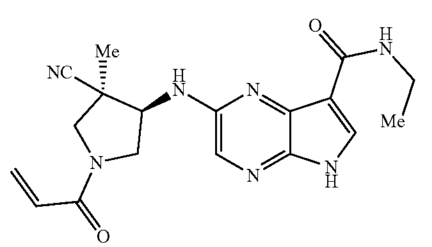 [SMILES: C=CC(=O)N1C[C@H](Nc2cnc3[nH]cc(C(=O)NCC)c3n2)[C@](C)(C#N)C1] | MS m/z 368 [M + H]+ Rt = 2.38 minutes Prep HPLC gradient 6-46% organic. |

| Ex. No. | Name | Structure | Data/% Organic Eluant/QC Method |
|---|---|---|---|
| 252 | 2-[(5-acryloyl-5-azaspiro[2.4]hept-7-yl)amino]-N-(3,3,3-trifluoropropyl)-5H-pyrrolo[2,3-b]pyrazine-7-carboxamide | 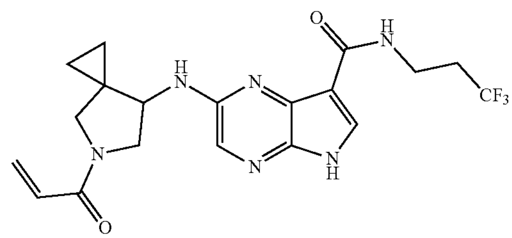 [SMILES: C=CC(=O)N1CC(Nc2cnc3[nH]cc(C(=O)NCCC(F)(F)F)c3n2)C2(CC2)C1] | MS m/z 423 [M + H]⁺<br>Rt = 2.70 minutes<br>Prep HPLC gradient<br>15-55% organic. |
| 253 | 2-[(1-acryloyl-4-methylpyrrolidin-3-yl)amino]-N-(2-methoxyethyl)-5H-pyrrolo[2,3-b]pyrazine-7-carboxamide | 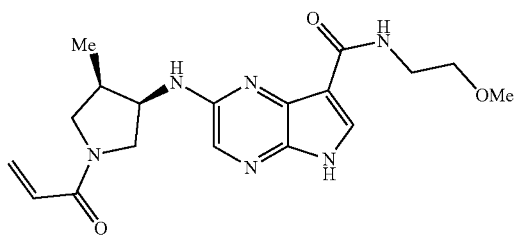 [SMILES: C=CC(=O)N1C[C@@H](C)[C@@H](Nc2cnc3[nH]cc(C(=O)NCCOC)c3n2)C1] | MS m/z 373 [M + H]⁺<br>Rt = 2.41 minutes<br>Prep HPLC gradient<br>7-47% organic. |
| 254 | 2-{[(3R)-1-acryloylpyrrolidin-3-yl]amino}-N-(2,2,2-trifluoroethyl)-5H-pyrrolo[2,3-b]pyrazine-7-carboxamide | 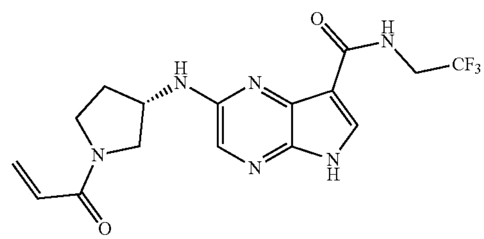 [SMILES: C=CC(=O)N1CC[C@H](Nc2cnc3[nH]cc(C(=O)NCC(F)(F)F)c3n2)C1] | MS m/z 383 [M + H]⁺<br>Rt = 2.54 minutes<br>Prep HPLC gradient<br>11-51% organic. |
| 255 | 2-{[(3R)-1-acryloylpyrrolidin-3-yl]amino}-N-(3,3,3-trifluoropropyl)-5H-pyrrolo[2,3-b]pyrazine-7-carboxamide | 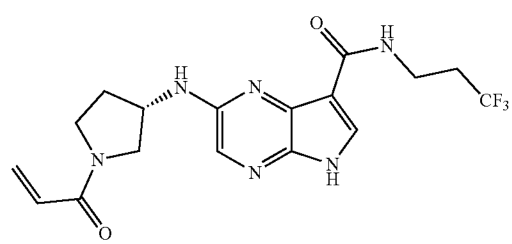 [SMILES: C=CC(=O)N1CC[C@H](Nc2cnc3[nH]cc(C(=O)NCCC(F)(F)F)c3n2)C1] | MS m/z 397 [M + H]⁺<br>Rt = 2.54 minutes<br>Prep HPLC gradient<br>10-50% organic. |
| 256 | 2-{[(3S)-1-acryloylpyrrolidin-3-yl]amino}-N-(2-methylpropyl)-5H-pyrrolo[2,3-b]pyrazine-7-carboxamide | 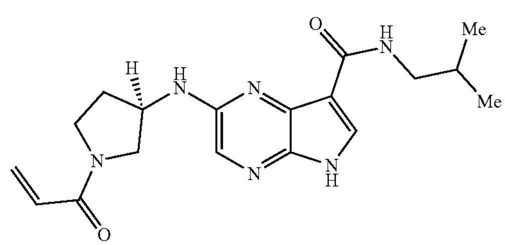 [SMILES: C=CC(=O)N1CC[C@@H](Nc2cnc3[nH]cc(C(=O)NCC(C)C)c3n2)C1] | MS m/z 357 [M + H]⁺<br>Rt = 2.55 minutes<br>Prep HPLC gradient<br>11-51% organic. |
| 257 | 2-{[(3R,4R)-1-acryloyl-4-ethylpyrrolidin-3-yl]amino}-N-(2-methoxyethyl)-5H-pyrrolo[2,3-b]pyrazine-7-carboxamide | 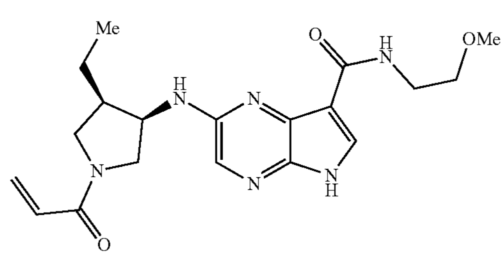 [SMILES: C=CC(=O)N1C[C@@H](CC)[C@@H](Nc2cnc3[nH]cc(C(=O)NCCOC)c3n2)C1] | MS m/z 387 [M + H]⁺<br>Rt = 2.54 minutes<br>Prep HPLC gradient<br>11-51% organic. |

-continued

| Ex. No. | Name | Structure | Data/% Organic Eluant/QC Method |
|---|---|---|---|
| 258 | 2-{[(3R,5S)-1-acryloyl-5-(methoxymethyl)pyrrolidin-3-yl]amino}-N-(2-methoxyethyl)-5H-pyrrolo[2,3-b]pyrazine-7-carboxamide | 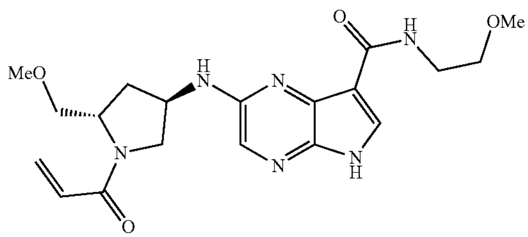 [SMILES: C=CC(=O)N1C[C@H](Nc2cnc3[nH]cc(C(=O)NCCOC)c3n2)C[C@H]1COC] | MS m/z 403 [M + H]+<br>Rt = 2.19 minutes<br>Prep HPLC gradient<br>7-47% organic.<br>Method 2. |
| 259 | 2-{[(3R,4R)-1-acryloyl-4-cyclopropylpyrrolidin-3-yl]amino}-N-(2-methoxyethyl)-5H-pyrrolo[2,3-b]pyrazine-7-carboxamide | 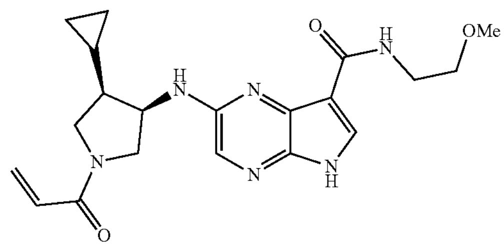 [SMILES: C=CC(=O)N1C[C@H](Nc2cnc3[nH]cc(C(=O)NCCOC)c3n2)[C@H](C2CC2)C1] | MS m/z 399 [M + H]+<br>Rt = 2.55 minutes<br>Prep HPLC gradient<br>11-51% organic. |
| 260 | 2-[(1-acryloyl-4-methylpyrrolidin-3-yl)amino]-N-ethyl-5H-pyrrolo[2,3-b]pyrazine-7-carboxamide | 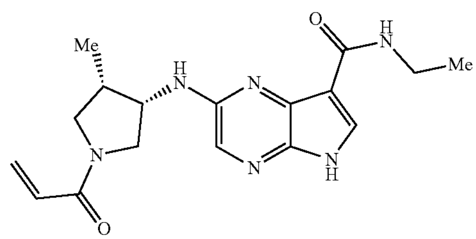 [SMILES: C=CC(=O)N1C[C@H](C)[C@H](Nc2cnc3[nH]cc(C(=O)NCC)c3n2)C1] | MS m/z 343 [M + H]+<br>Rt = 2.55 minutes<br>Prep HPLC gradient<br>11-51% organic. |
| 261 | 2-{[(3R,4R)-1-acryloyl-4-cyclopropylpyrrolidin-3-yl]amino}-N-ethyl-5H-pyrrolo[2,3-b]pyrazine-7-carboxamide | 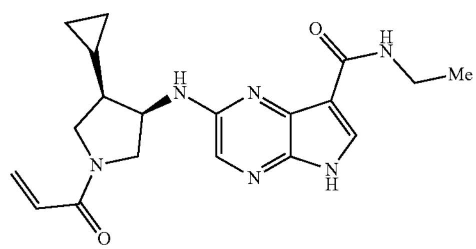 [SMILES: C=CC(=O)N1C[C@H](Nc2cnc3[nH]cc(C(=O)NCC)c3n2)[C@H](C2CC2)C1] | MS m/z 369 [M + H]+<br>Rt = 2.56 minutes<br>Prep HPLC gradient<br>12-52% organic. |
| 262 | 2-{[(3R,5R)-1-acryloyl-5-(methoxymethyl)pyrrolidin-3-yl]amino}-N-ethyl-5H-pyrrolo[2,3-b]pyrazine-7-carboxamide | 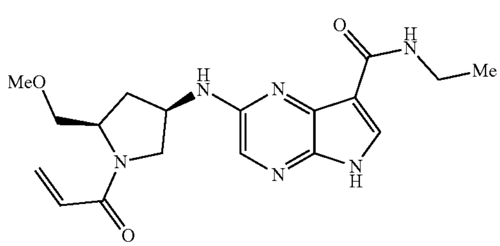 [SMILES: C=CC(=O)N1C[C@H](Nc2cnc3[nH]cc(C(=O)NCC)c3n2)C[C@@H]1COC] | MS m/z 373 [M + H]+<br>Rt = 2.42 minutes<br>Prep HPLC gradient<br>7-47% organic. |
| 263 | 2-{[(3R,4R)-1-acryloyl-4-ethylpyrrolidin-3-yl]amino}-N-ethyl-5H-pyrrolo[2,3-b]pyrazine-7-carboxamide | 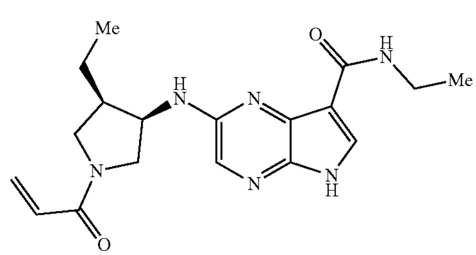 [SMILES: C=CC(=O)N1C[C@@H](CC)[C@@H](Nc2cnc3[nH]cc(C(=O)NCC)c3n2)C1] | MS m/z 357 [M + H]+<br>Rt = 2.58 minutes<br>Prep HPLC gradient<br>12-52% organic. |

| Ex. No. | Name | Structure | Data/% Organic Eluant/QC Method |
|---|---|---|---|
| 264 | 2-{[(3S,4S)-1-acryloyl-4-methylpyrrolidin-3-yl]amino}-N-(2-methoxyethyl)-5H-pyrrolo[2,3-b]pyrazine-7-carboxamide | 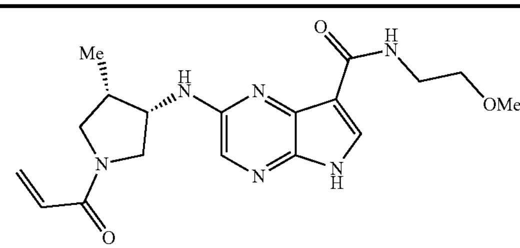 | MS m/z 373 [M + H]+<br>Rt = 2.41 minutes<br>Prep HPLC gradient 7-47% organic. |

Examples 265-337 were prepared according to Library Protocol 5 below:

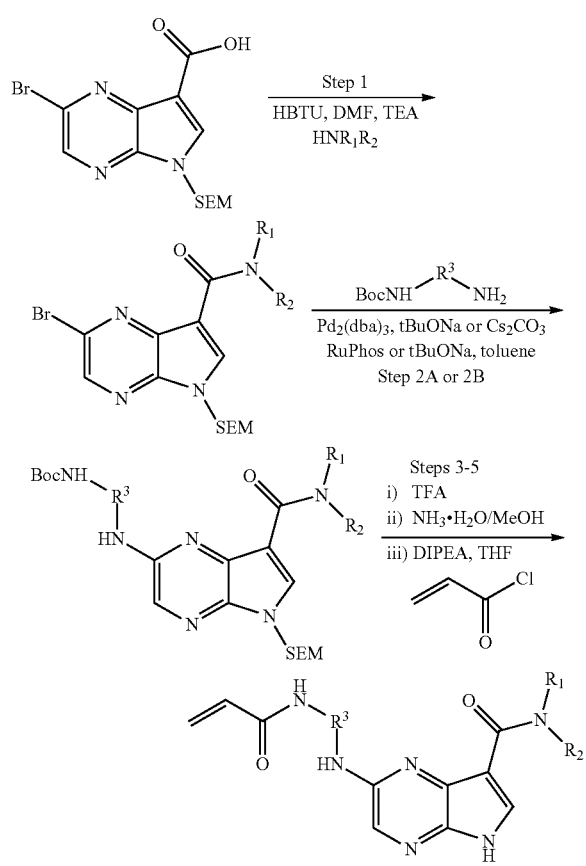

Library Protocol 5

Step 1

To a 0.4M solution of 2-bromo-{[2-(trimethylsilyl)ethoxy]methyl}-5H-pyrrolo[2,3-b]pyrazine-7-carboxylic acid in DMF (Example 1 Step 2, 250 μL, 100 μmol) was added the appropriate amine (120 μmol) followed by DIPEA (51 μL, 300 μmol) and a 0.48M solution of HBTU in DMF (250 μL, 120 μmol). The reactions were shaken at 60° C. for 16 hours before cooling and concentrating in vacuo. The residues were purified using preparative TLC to afford the Step 1 amide intermediate.

Either step 2A or Step 2B was employed for the Buchwald step:

Step 2A

To a 0.2M solution of the Step 1 amide intermediate in toluene (500 μL, 75 μmol) was added cesium carbonate (65 mg, 200 μmol), the appropriate Boc-protected amine (150 μmol), $Pd_2dba_3$ (4.6 mg, 5 μmol) and Ruphos (2.8 mg, 6 μmol) under nitrogen. The reactions were capped and shaken at 120° C. for 16 hours before cooling and concentrating in vacuo. The residue was washed with water (1 mL) and extracted into EtOAc (3×1 mL). The organic layers were collected and concentrated in vacuo to afford the Step 2 intermediate.

Step 2B

To a 0.2M solution of the amide intermediate in toluene (500 μL, 75 μmol) was added sodium tert-butoxide (19.2 mg, 200 μmol), the appropriate Boc-protected amine (150 μmol), $Pd_2dba_3$ (4.6 mg, 5 μmol) and Ruphos (2.8 mg, 6 μmol) under nitrogen. The reactions were capped and shaken at 65° C. for 48 hours before cooling and concentrating in vacuo. The residue was washed with water (1 mL) and extracted into EtOAc (3×1 mL). The organic layers were collected and concentrated in vacuo to afford the step 2 intermediate.

Steps 3-5

To the Step 2 intermediates was added a solution of TFA in DCM (1 mL, v:v 1:5) and the reactions were shaken at 30° C. for 4 hours before concentrating in vacuo. The residues were treated with ammonium hydroxide in MeOH (1.5 mL, v:v 1:3) and shaken at 30° C. for 2 hours before concentrating in vacuo. The residues were treated with a saturated solution of $NaHCO_3$ in water (1 mL). To the solutions was added EtOAc (1 mL) followed by acryloyl chloride (200 μmol) and the reactions were shaken at 30° C. for 2 hours. The reactions were concentrated in vacuo and purified using preparative HPLC as described below to afford the following Examples:

Preparative HPLC Method 1:

Column: Phenomenex Gemini C18 250×21.2 mm, 8 micron

Mobile phase: Acetonitrile:ammonium hydroxide (pH=10) or Acetonitrile:formic acid (0.225%).

Gradient time: 8 minutes; Hold time: 1 minute at 100% organic; Flow rate: 35 mL/min.

Preparative HPLC Method 2:

Column: DIKMA Diamonsil(2) C18 200×20 mm, 5 micron.

Mobile phase: Acetonitrile:formic acid (0.225%)

Gradient time: 8 minutes; Hold time: 1 minute at 100% organic; Flow rate: 35 mL/min.

QC Method 1:

Column: Xbridge C18 2.1×50 mm; 5 micron

Mobile phase A: 0.0375% TFA in water; Mobile phase B: 0.01875% TFA in MeCN.

Gradient: initial—1% B; 0.6 minutes—5% B; 4 minutes—100% B; 4.3 minutes—1% B; 4.7 minutes—1% B. Flow rate: 0.8 mL/min QC Method 2:
Column: Xbridge C18 2.1×50 mm; 5 micron. Mobile phase A: 0.05% NH₄OH in water; Mobile phase B: 100% MeCN. Gradient: initial—5% B; 0.5 minutes—5% B; 3.4 minutes—100% B; 4.2 minutes—100% B; 4.21 minutes—5% B; 4.7 minutes—5% B. Flow rate: 0.8 mL/min QC Method 1 was used unless otherwise specified:

| Ex. No. | Name | Structure | Data/% Organic Eluant/QC Method |
|---|---|---|---|
| 265 | 2-(4-acryloyl-3,3-dimethylpiperazin-1-yl)-N-(2-methoxyethyl)-5H-pyrrolo[2,3-b]pyrazine-7-carboxamide | 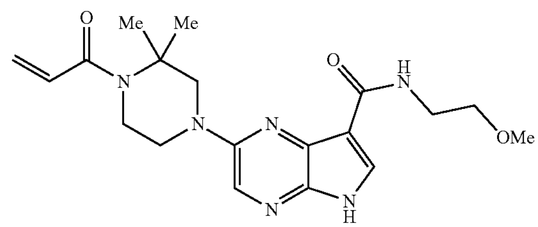 [SMILES: C=CC(=O)N1CCN(c2cnc3[nH]cc(C(=O)NCCOC)c3n2)CC1(C)C] | MS m/z 387 [M + H]⁺<br>Rt = 2.58 minutes<br>Prep HPLC gradient 18-58% organic. |
| 266 | 2-(4-acryloylpiperazin-1-yl)-N-(cyclopentylmethyl)-5H-pyrrolo[2,3-b]pyrazine-7-carboxamide | 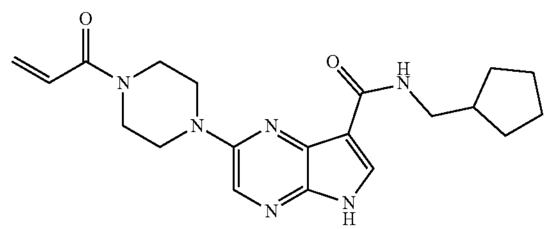 [SMILES: C=CC(=O)N1CCN(c2cnc3[nH]cc(C(=O)NCC4CCCC4)c3n2)CC1] | MS m/z 383 [M + H]⁺<br>Rt = 2.85 minutes<br>Prep HPLC gradient 28-59% organic. |
| 267 | Racemic-2-[(1-acryloyl-2-methylpiperidin-4-yl)amino]-N-(2,2-dimethylpropyl)-5H-pyrrolo[2,3-b]pyrazine-7-carboxamide | 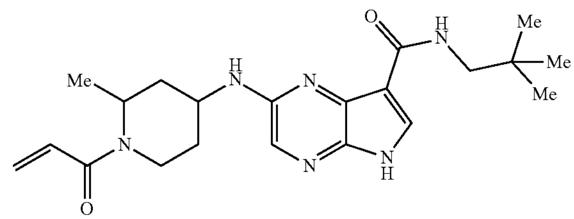 [SMILES: C=CC(=O)N1CCC(Nc2cnc3[nH]cc(C(=O)NCC(C)(C)C)c3n2)CC1C] | MS m/z 399 [M + H]⁺<br>Rt = 2.82 minutes<br>Prep HPLC gradient 29-69% organic. |
| 268 | 2-{[(3S,4R)-1-acryloyl-3-methoxypiperidin-4-yl]amino}-N-[(4,4-difluoro-1-hydroxycyclohexyl)methyl]-5H-pyrrolo[2,3-b]pyrazine-7-carboxamide | 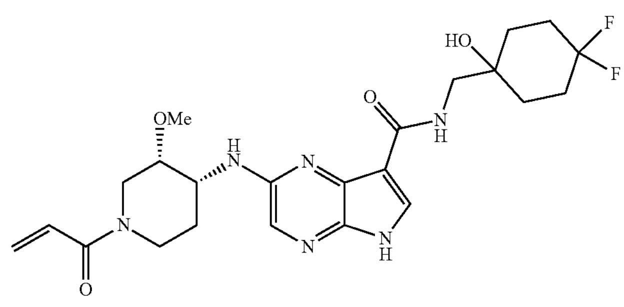 [SMILES: C=CC(=O)N1CC[C@@H](Nc2cnc3[nH]cc(C(=O)NCC4(O)CCC(F)(F)CC4)c3n2)[C@@H](OC)C1] | MS m/z 493 [M + H]⁺<br>Rt = 2.42 minutes<br>Prep HPLC gradient 13-53% organic.<br>Method 2. |
| 269 | Racemic-2-{[(3S,4R)-1-acryloyl-3-methoxypiperidin-4-yl]amino}-N-(4,4,4-trifluoro-2-methylbutyl)-5H-pyrrolo[2,3-b]pyrazine-7-carboxamide | 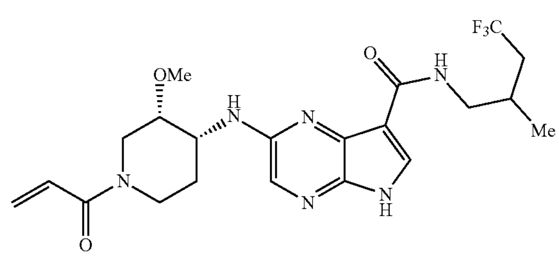 [SMILES: C=CC(=O)N1CC[C@@H](Nc2cnc3[nH]cc(C(=O)NCC(C)CC(F)(F)F)c3n2)[C@@H](OC)C1] | MS m/z 469 [M + H]⁺<br>Rt = 2.82 minutes<br>Prep HPLC gradient 18-58% organic. |

-continued

| Ex. No. | Name | Structure | Data/% Organic Eluant/QC Method |
|---|---|---|---|
| 270 | Racemic-2-[(1-acryloyl-4-methylpiperidin-4-yl)amino]-N-(4,4,4-trifluoro-2-methylbutyl)-5H-pyrrolo[2,3-b]pyrazine-7-carboxamide | 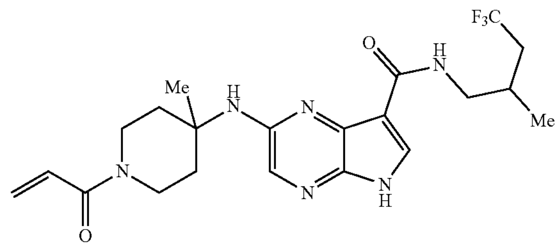 [SMILES: C=CC(=O)N1CCC(C)(Nc2cnc3[nH]cc(C(=O)NCC(C)CC(F)(F)F)c3n2)CC1] | MS m/z 453 [M + H]$^+$<br>Rt = 2.95 minutes<br>Prep HPLC gradient<br>34-74% organic. |
| 271 | 2-{[(3R,4S)-1-acryloyl-3-methoxypiperidin-4-yl]amino}-N-[(1R,2R)-2-(trifluoromethyl)cyclopropyl]-5H-pyrrolo[2,3-b]pyrazine-7-carboxamide | 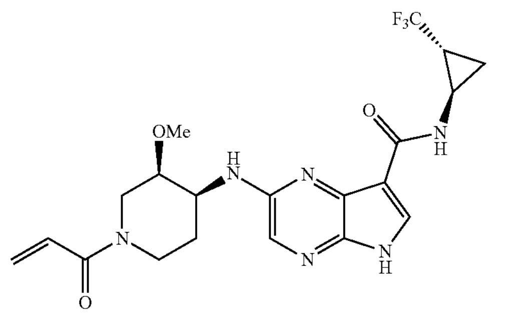 [SMILES: C=CC(=O)N1CC[C@H](Nc2cnc3[nH]cc(C(=O)N[C@@H]4C[C@H]4C(F)(F)F)c3n2)[C@H](OC)C1] | MS m/z 453 [M + H]$^+$<br>Rt = 2.50 minutes<br>Prep HPLC gradient<br>16-56% organic.<br>Method 2. |
| 272 | 2-(4-acryloyl-3,3-dimethylpiperazin-1-yl)-N-(4,4,4-trifluorobutyl)-5H-pyrrolo[2,3-b]pyrazine-7-carboxamide | 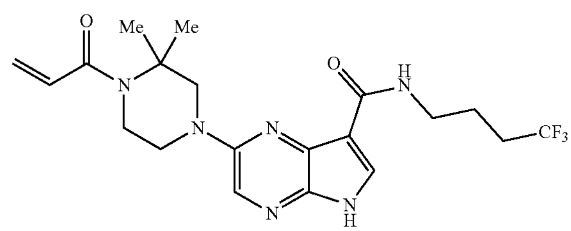 [SMILES: C=CC(=O)N1CCN(c2cnc3[nH]cc(C(=O)NCCCC(F)(F)F)c3n2)CC1(C)C] | MS m/z 439 [M + H]$^+$<br>Rt = 2.64 minutes<br>Prep HPLC gradient<br>32-72% organic.<br>Method 2. |
| 273 | 2-[(3S)-4-acryloyl-3-(2-methylpropyl)piperazin-1-yl]-N-(3,3-difluorocyclobutyl)-5H-pyrrolo[2,3-b]pyrazine-7-carboxamide | 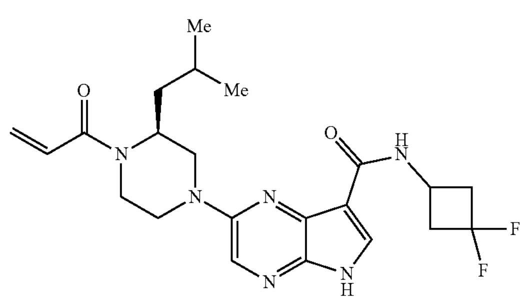 [SMILES: C=CC(=O)N1CCN(c2cnc3[nH]cc(C(=O)NC4CC(F)(F)C4)c3n2)C[C@@H]1CC(C)C] | MS m/z 447 [M + H]$^+$<br>Rt = 3.07 minutes<br>Prep HPLC gradient<br>36-76% organic. |
| 274 | 2-[(3S)-4-acryloyl-3-(2-methylpropyl)piperazin-1-yl]-N-[(3,3-difluorocyclobutyl)methyl]-5H-pyrrolo[2,3-b]pyrazine-7-carboxamide | 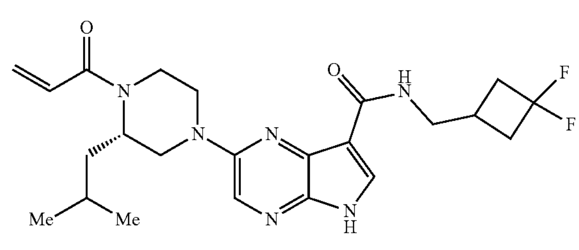 [SMILES: C=CC(=O)N1CCN(c2cnc3[nH]cc(C(=O)NCC4CC(F)(F)C4)c3n2)C[C@@H]1CC(C)C] | MS m/z 461 [M + H]$^+$<br>Rt = 3.12 minutes<br>Prep HPLC gradient<br>39-79% organic. |
| 275 | 2-(4-acryloyl-3,3-dimethylpiperazin-1-yl)-N-(2,2-difluoropropyl)-5H-pyrrolo[2,3-b]pyrazine-7-carboxamide | 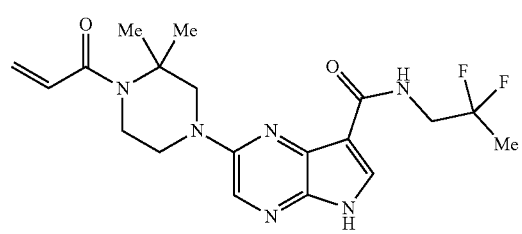 [SMILES: C=CC(=O)N1CCN(c2cnc3[nH]cc(C(=O)NCC(C)(F)F)c3n2)CC1(C)C] | MS m/z 407 [M + H]$^+$<br>Rt = 2.78 minutes<br>Prep HPLC gradient<br>17-57% organic. |

| Ex. No. | Name | Structure | Data/% Organic Eluant/QC Method |
|---|---|---|---|
| 276 | 2-(4-acryloylpiperazin-1-yl)-N-[(3,3-difluorocyclobutyl)methyl]-5H-pyrrolo[2,3-b]pyrazine-7-carboxamide | 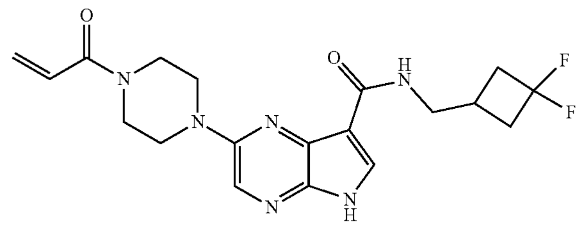 [SMILES: C=CC(=O)N1CCN(c2cnc3[nH]cc(C(=O)NCC4CC(F)(F)C4)c3n2)CC1] | MS m/z 405 [M + H]+ Rt = 2.71 minutes Prep HPLC gradient 27-67% organic. |
| 277 | 2-{[(3R,4S)-1-acryloyl-3-methoxypiperidin-4-yl]amino}-N-(3,3-difluorocyclobutyl)-5H-pyrrolo[2,3-b]pyrazine-7-carboxamide | 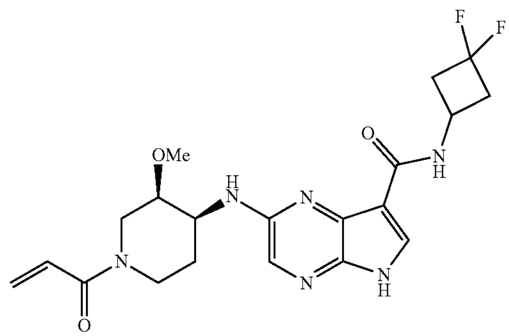 [SMILES: C=CC(=O)N1CC[C@H](Nc2cnc3[nH]cc(C(=O)NC4CC(F)(F)C4)c3n2)[C@H](OC)C1] | MS m/z 435 [M + H]+ Rt = 2.41 minutes Prep HPLC gradient 25-65% organic. Method 2. |
| 278 | 2-{[(3S,4R)-1-acryloyl-3-methoxypiperidin-4-yl]amino}-N-(3,3,3-trifluoropropyl)-5H-pyrrolo[2,3-b]pyrazine-7-carboxamide | 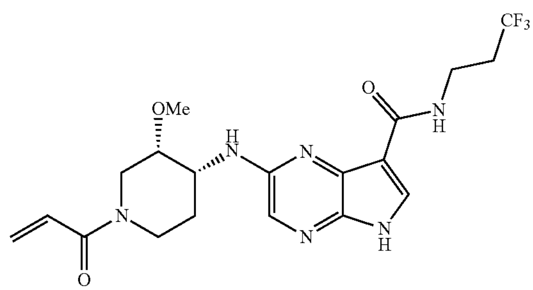 [SMILES: C=CC(=O)N1CC[C@@H](Nc2cnc3[nH]cc(C(=O)NCCC(F)(F)F)c3n2)[C@@H](OC)C1] | MS m/z 441 [M + H]+ Rt = 2.58 minutes Prep HPLC gradient 25-65% organic. |
| 279 | Racemic-2-(4-acryloylpiperazin-1-yl)-N-(4,4,4-trifluoro-2-methylbutyl)-5H-pyrrolo[2,3-b]pyrazine-7-carboxamide | 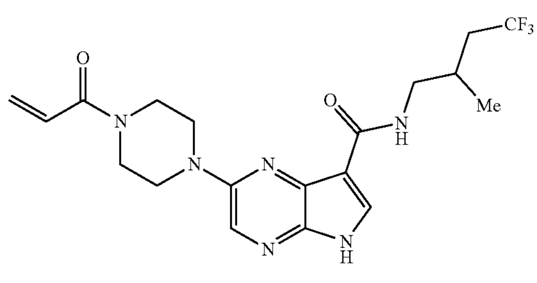 [SMILES: C=CC(=O)N1CCN(c2cnc3[nH]cc(C(=O)NCC(C)CC(F)(F)F)c3n2)CC1] | MS m/z 425 [M + H]+ Rt = 2.85 minutes Prep HPLC gradient 25-55% organic. |
| 280 | 2-[(1-acryloyl-2-methylpiperidin-4-yl)amino]-N-[(2R)-4,4,4-trifluoro-2-methylbutyl]-5H-pyrrolo[2,3-b]pyrazine-7-carboxamide | 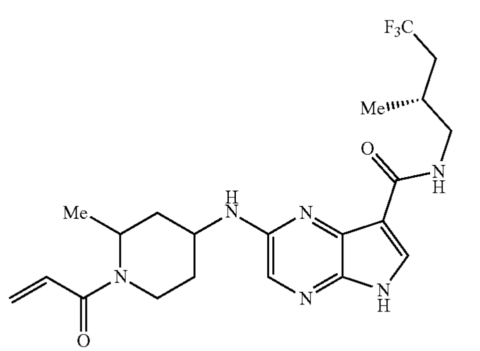 [SMILES: C=CC(=O)N1CCC(Nc2cnc3[nH]cc(C(=O)NC[C@H](C)CC(F)(F)F)c3n2)CC1C] | MS m/z 453 [M + H]+ Rt = 2.89 minutes Prep HPLC gradient 20-60% organic. |

| Ex. No. | Name | Structure | Data/% Organic Eluant/QC Method |
|---|---|---|---|
| 281 | 2-[(1-acryloyl-4-methylpiperidin-4-yl)amino]-N-ethyl-5H-pyrrolo[2,3-b]pyrazine-7-carboxamide | 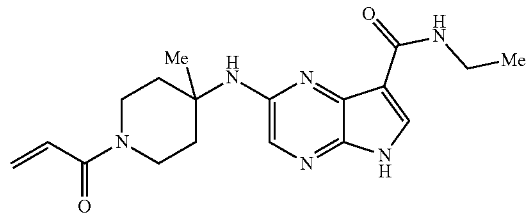 [SMILES: C=CC(=O)N1CCC(C)(Nc2cnc3[nH]cc(C(=O)NCC)c3n2)CC1] | MS m/z 357 [M + H]+ Rt = 2.35 minutes Prep HPLC gradient 10-50% organic. Method 2. |
| 282 | Racemic-2-[(1-acryloyl-2-methylpiperidin-4-yl)amino]-N-(4,4,4-trifluorobutyl)-5H-pyrrolo[2,3-b]pyrazine-7-carboxamide | 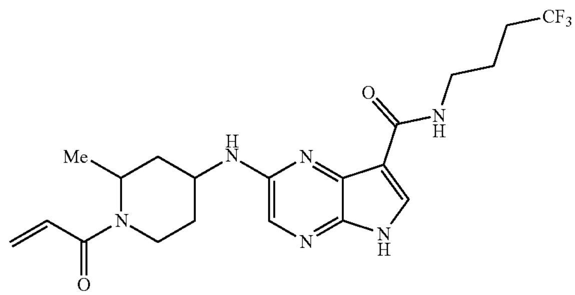 [SMILES: C=CC(=O)N1CCC(Nc2cnc3[nH]cc(C(=O)NCCCC(F)(F)F)c3n2)CC1C] | MS m/z 439 [M + H]+ Rt = 2.81 minutes Prep HPLC gradient 28-68% organic. |
| 283 | 2-(4-acryloylpiperazin-1-yl)-N-(3,3-difluorocyclobutyl)-5H-pyrrolo[2,3-b]pyrazine-7-carboxamide | 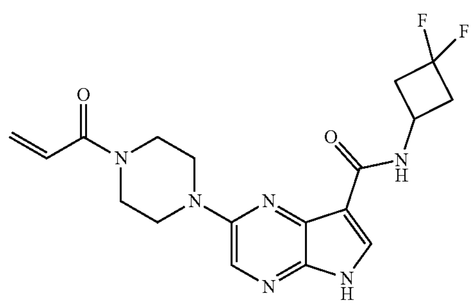 [SMILES: C=CC(=O)N1CCN(c2cnc3[nH]cc(C(=O)NC4CC(F)(F)C4)c3n2)CC1] | MS m/z 391 [M + H]+ Rt = 2.65 minutes Prep HPLC gradient 24-64% organic. |
| 284 | 2-{[(3R,4S)-1-acryloyl-3-methoxypiperidin-4-yl]amino}-N-(cyclopentylmethyl)-5H-pyrrolo[2,3-b]pyrazine-7-carboxamide | 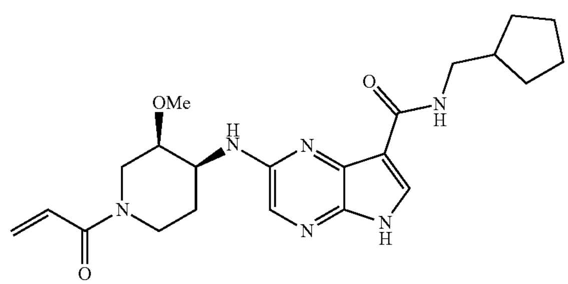 [SMILES: C=CC(=O)N1CC[C@H](Nc2cnc3[nH]cc(C(=O)NCC4CCCC4)c3n2)[C@H](OC)C1] | MS m/z 427 [M + H]+ Rt = 2.54 minutes Prep HPLC gradient 30-70% organic. Method 2. |
| 285 | 2-(4-acryloyl-3,3-dimethylpiperazin-1-yl)-N-(2,2-dimethylpropyl)-5H-pyrrolo[2,3-b]pyrazine-7-carboxamide | 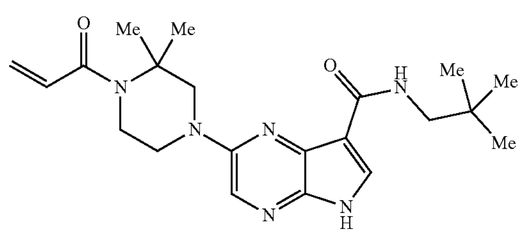 [SMILES: C=CC(=O)N1CCN(c2cnc3[nH]cc(C(=O)NCC(C)(C)C)c3n2)CC1(C)C] | MS m/z 399 [M + H]+ Rt = 2.96 minutes Prep HPLC gradient 22-62% organic. |
| 286 | 2-(4-acryloyl-3,3-dimethylpiperazin-1-yl)-N-(2,2,2-trifluoroethyl)-5H-pyrrolo[2,3-b]pyrazine-7-carboxamide | 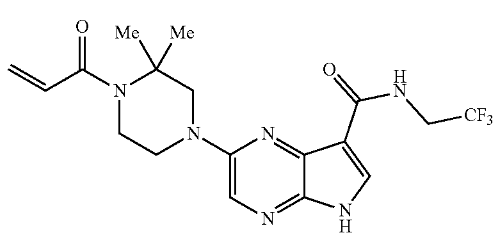 [SMILES: C=CC(=O)N1CCN(c2cnc3[nH]cc(C(=O)NCC(F)(F)F)c3n2)CC1(C)C] | MS m/z 411 [M + H]+ Rt = 2.58 minutes Prep HPLC gradient 19-59% organic. Method 2. |

| Ex. No. | Name | Structure | Data/% Organic Eluant/QC Method |
|---|---|---|---|
| 287 | 2-(4-acryloylpiperazin-1-yl)-N-[(1R,2R)-2-(trifluoromethyl)cyclopropyl]-5H-pyrrolo[2,3-b]pyrazine-7-carboxamide | 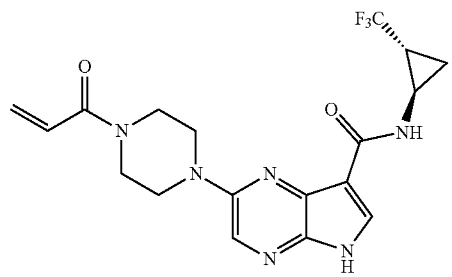 [SMILES: C=CC(=O)N1CCN(c2cnc3[nH]cc(C(=O)N[C@@H]4C[C@H]4C(F)(F)F)c3n2)CC1] | MS m/z 409 [M + H]+ Rt = 2.52 minutes Prep HPLC gradient 17-57% organic. Method 2. |
| 288 | 2-[(3S)-4-acryloyl-3-(2-methylpropyl)piperazin-1-yl]-N-(2-methylpropyl)-5H-pyrrolo[2,3-b]pyrazine-7-carboxamide | 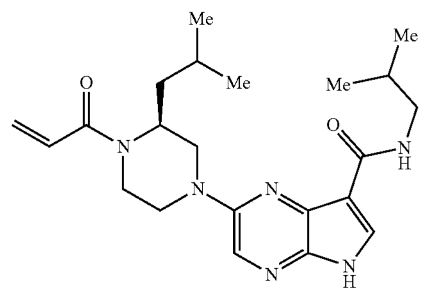 [SMILES: C=CC(=O)N1CCN(c2cnc3[nH]cc(C(=O)NCC(C)C)c3n2)C[C@@H]1CC(C)C] | MS m/z 413 [M + H]+ Rt = 3.10 minutes Prep HPLC gradient 39-79% organic. |
| 289 | 2-(4-acryloyl-3,3-dimethylpiperazin-1-yl)-N-cyclobutyl-5H-pyrrolo[2,3-b]pyrazine-7-carboxamide | 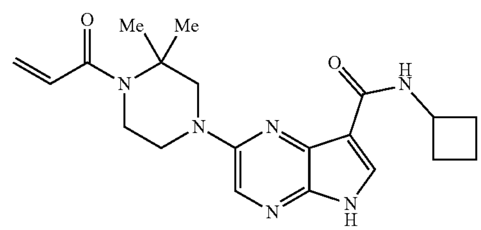 [SMILES: C=CC(=O)N1CCN(c2cnc3[nH]cc(C(=O)NC4CCC4)c3n2)CC1(C)C] | MS m/z 383 [M + H]+ Rt = 2.81 minutes Prep HPLC gradient 29-69% organic. |
| 290 | 2-(4-acryloyl-3,3-dimethylpiperazin-1-yl)-N-[(1R,2R)-2-(trifluoromethyl)cyclopropyl]-5H-pyrrolo[2,3-b]pyrazine-7-carboxamide | 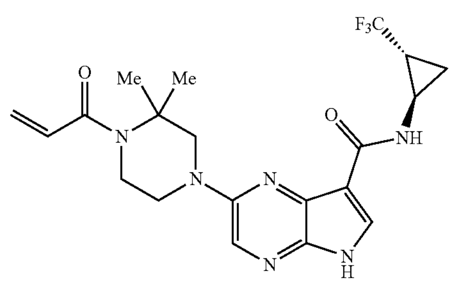 [SMILES: C=CC(=O)N1CCN(c2cnc3[nH]cc(C(=O)N[C@@H]4C[C@H]4C(F)(F)F)c3n2)CC1(C)C] | MS m/z 437 [M + H]+ Rt = 2.95 minutes Prep HPLC gradient 34-74% organic. |
| 291 | 2-(4-acryloyl-3,3-dimethylpiperazin-1-yl)-N-[(4,4-difluoro-1-hydroxycyclohexyl)methyl]-5H-pyrrolo[2,3-b]pyrazine-7-carboxamide | 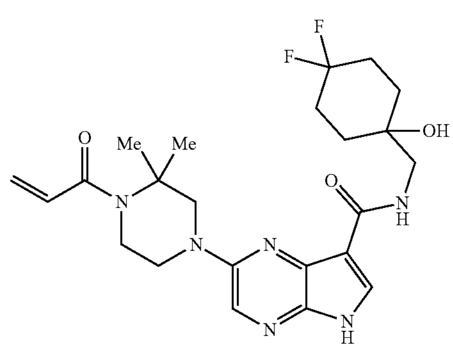 [SMILES: C=CC(=O)N1CCN(c2cnc3[nH]cc(C(=O)NCC4(O)CCC(F)(F)CC4)c3n2)CC1(C)C] | MS m/z 477 [M + H]+ Rt = 2.81 minutes Prep HPLC gradient 29-69% organic. |

-continued

| Ex. No. | Name | Structure | Data/% Organic Eluant/QC Method |
|---|---|---|---|
| 292 | Racemic-2-(4-acryloylpiperazin-1-yl)-N-cyclopentyl-5H-pyrrolo[2,3-b]pyrazine-7-carboxamide | 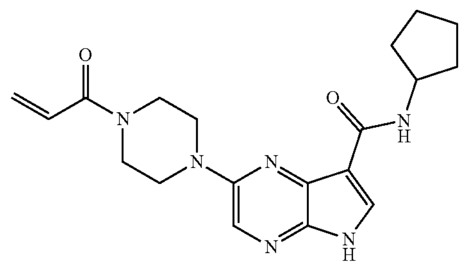 [SMILES: C=CC(=O)N1CCN(c2cnc3[nH]cc(C(=O)NC4CCCC4)c3n2)CC1] | MS m/z 369 [M + H]+<br>Rt = 2.70 minutes<br>Prep HPLC gradient<br>26-66% organic. |
| 293 | 2-{[(3R,4S)-1-acryloyl-3-methoxypiperidin-4-yl]amino}-N-(2,2,2-trifluoroethyl)-5H-pyrrolo[2,3-b]pyrazine-7-carboxamide | 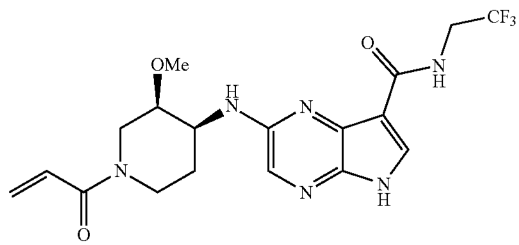 [SMILES: C=CC(=O)N1CC[C@H](Nc2cnc3[nH]cc(C(=O)NCC(F)(F)F)c3n2)[C@H](OC)C1] | MS m/z 427 [M + H]+<br>Rt = 2.64 minutes<br>Prep HPLC gradient<br>25-65% organic. |
| 294 | 2-[((3R,4S)-1-acryloyl-3-methoxypiperidin-4-yl)amino]-N-([2R]-4,4,4-trifluoro-2-methylbutyl)-5H-pyrrolo[2,3-b]pyrazine-7-carboxamide | 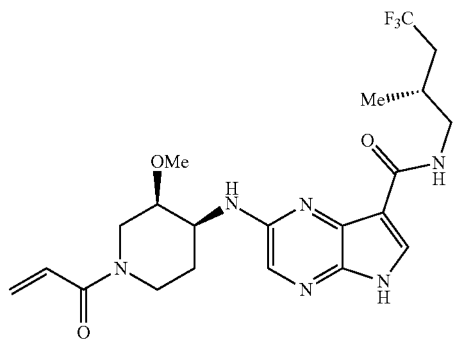 [SMILES: C=CC(=O)N1CC[C@H](Nc2cnc3[nH]cc(C(=O)NC[C@H](C)CC(F)(F)F)c3n2)[C@H](OC)C1] | MS m/z 469 [M + H]+<br>Rt = 2.83 minutes<br>Prep HPLC gradient<br>18-58% organic. |
| 295 | 2-(4-acryloylpiperazin-1-yl)-N-[(2S)-1-methoxypropan-2-yl]-5H-pyrrolo[2,3-b]pyrazine-7-carboxamide(worng structure) | 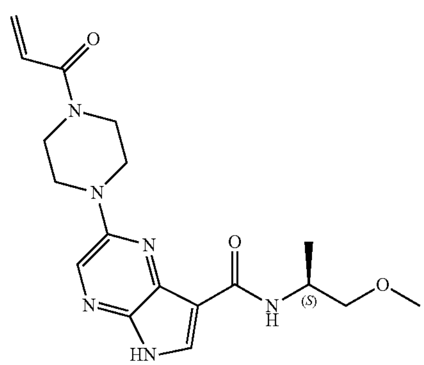 | MS m/z 373 [M + H]+<br>Rt = 2.29 minutes<br>Prep HPLC gradient<br>21-61% organic.<br>Method 2. |
| 296 | 2-[(1-acryloyl-4-methylpiperidin-4-yl)amino]-N-(2,2-difluoropropyl)-5H-pyrrolo[2,3-b]pyrazine-7-carboxamide | 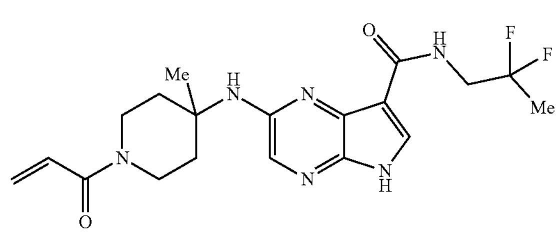 [SMILES: C=CC(=O)N1CCC(C)(Nc2cnc3[nH]cc(C(=O)NCC(C)(F)F)c3n2)CC1] | MS m/z 407 [M + H]+<br>Rt = 2.48 minutes<br>Prep HPLC gradient<br>27-67% organic.<br>Method 2. |

-continued

| Ex. No. | Name | Structure | Data/% Organic Eluant/QC Method |
|---|---|---|---|
| 297 | 2-(4-acryloylpiperazin-1-yl)-N-cyclobutyl-5H-pyrrolo[2,3-b]pyrazine-7-carboxamide | 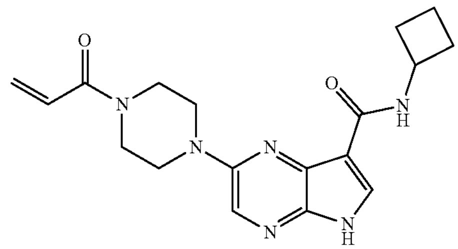 [SMILES: C=CC(=O)N1CCN(c2cnc3[nH]cc(C(=O)NC4CCC4)c3n2)CC1] | MS m/z 355 [M + H]+ Rt = 2.39 minutes Prep HPLC gradient 24-64% organic. Method 2. |
| 298 | 2-(4-acryloyl-3,3-dimethylpiperazin-1-yl)-N-[(2S)-1-methoxypropan-2-yl]-5H-pyrrolo[2,3-b]pyrazine-7-carboxamide | 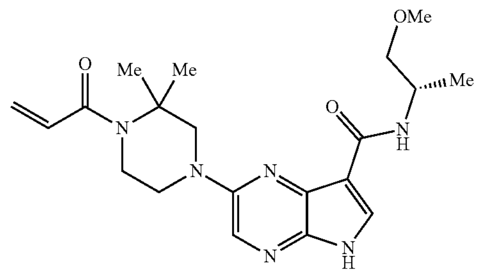 [SMILES: C=CC(=O)N1CCN(c2cnc3[nH]cc(C(=O)N[C@@H](C)COC)c3n2)CC1(C)C] | MS m/z 401 [M + H]+ Rt = 2.70 minutes Prep HPLC gradient 25-65% organic. |
| 299 | Racemic-2-{[(3S,4R)-1-acryloyl-3-methoxypiperidin-4-yl]amino}-N-cyclopentyl-5H-pyrrolo[2,3-b]pyrazine-7-carboxamide | 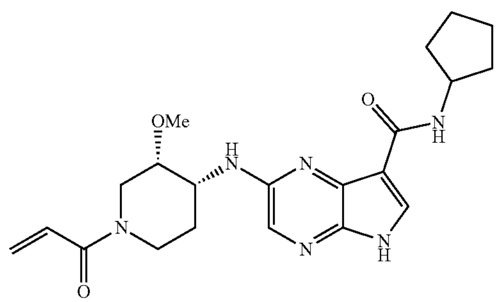 [SMILES: C=CC(=O)N1CC[C@@H](Nc2cnc3[nH]cc(C(=O)NC4CCCC4)c3n2)[C@@H](OC)C1] | MS m/z 413 [M + H]+ Rt = 2.67 minutes Prep HPLC gradient 25-65% organic. |
| 300 | 2-{[(3S,4R)-1-acryloyl-3-methoxypiperidin-4-yl]amino}-N-(2,2-dimethylpropyl)-5H-pyrrolo[2,3-b]pyrazine-7-carboxamide | 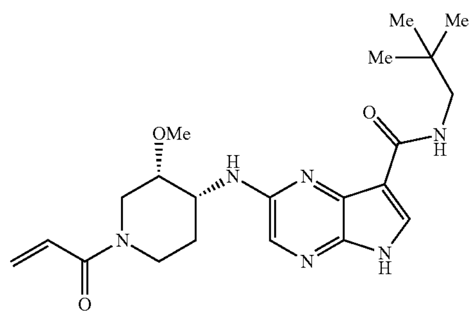 [SMILES: C=CC(=O)N1CC[C@@H](Nc2cnc3[nH]cc(C(=O)NCC(C)(C)C)c3n2)[C@@H](OC)C1] | MS m/z 415 [M + H]+ Rt = 2.75 minutes Prep HPLC gradient 28-68% organic. |
| 301 | 2-[(1-acryloyl-4-methylpiperidin-4-yl)amino]-N-(2-methylpropyl)-5H-pyrrolo[2,3-b]pyrazine-7-carboxamide | 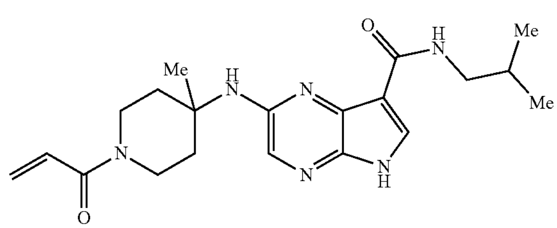 [SMILES: C=CC(=O)N1CCC(C)(Nc2cnc3[nH]cc(C(=O)NCC(C)C)c3n2)CC1] | MS m/z 385 [M + H]+ Rt = 2.67 minutes Prep HPLC gradient 23-53% organic. |

-continued

| Ex. No. | Name | Structure | Data/% Organic Eluant/QC Method |
|---|---|---|---|
| 302 | 2-[(3S)-4-acryloyl-3-(2-methylpropyl)piperazin-1-yl]-N-[(4,4-difluoro-1-hydroxycyclohexyl)methyl]-5H-pyrrolo[2,3-b]pyrazine-7-carboxamide | 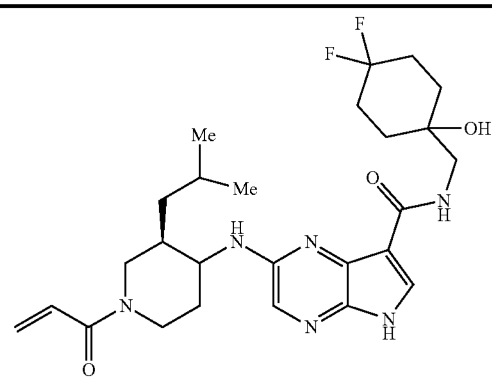 | MS m/z 505 [M + H]+ Rt = 3.04 minutes Prep HPLC gradient 36-76% organic. |
| 303 | 2-[(3S)-4-acryloyl-3-(2-methylpropyl)piperazin-1-yl]-N-[(1R,2R)-2-(trifluoromethyl)cyclopropyl]-5H-pyrrolo[2,3-b]pyrazine-7-carboxamide | 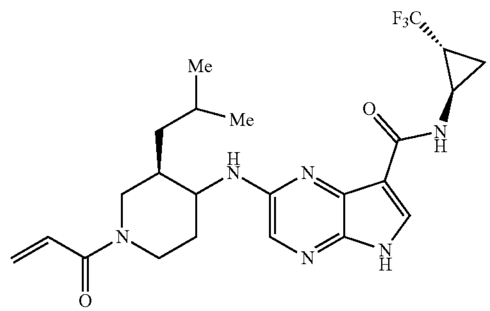 | MS m/z 465 [M + H]+ Rt = 2.78 minutes Prep HPLC gradient 37-67% organic. Method 2. |
| 304 | 2-(4-acryloylpiperazin-1-yl)-N-(2,2-dimethylpropyl)-5H-pyrrolo[2,3-b]pyrazine-7-carboxamide | 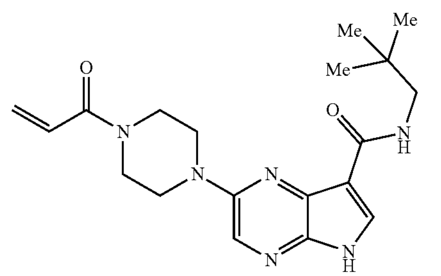 [SMILES: C=CC(=O)N1CCN(c2cnc3[nH]cc(C(=O)NCC(C)(C)C)c3n2)CC1] | MS m/z 371 [M + H]+ Rt = 2.78 minutes Prep HPLC gradient 28-68% organic. |
| 305 | 2-{[(3R,4S)-1-acryloyl-3-methoxypiperidin-4-yl]amino}-N-(3,3,3-trifluoropropyl)-5H-pyrrolo[2,3-b]pyrazine-7-carboxamide | 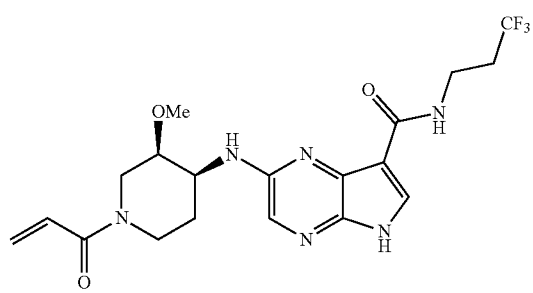 [SMILES: C=CC(=O)N1CC[C@H](Nc2cnc3[nH]cc(C(=O)NCCC(F)(F)F)c3n2)[C@H](OC)C1] | MS m/z 441 [M + H]+ Rt = 2.41 minutes Prep HPLC gradient 25-65% organic. Method 2. |
| 306 | 2-[(1-acryloyl-4-methylpiperidin-4-yl)amino]-N-[(3,3-difluorocyclobutyl)methyl]-5H-pyrrolo[2,3-b]pyrazine-7-carboxamide | 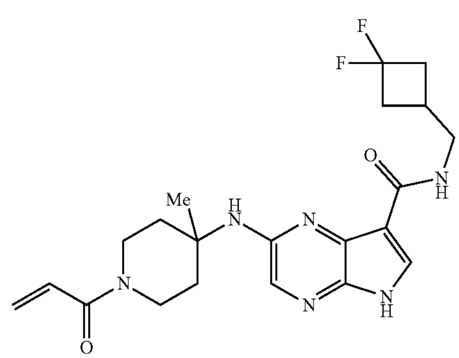 [SMILES: C=CC(=O)N1CCC(C)(Nc2cnc3[nH]cc(C(=O)NCC4CC(F)(F)C4)c3n2)CC1] | MS m/z 433 [M + H]+ Rt = 2.69 minutes Prep HPLC gradient 26-56% organic. |

-continued

| Ex. No. | Name | Structure | Data/% Organic Eluant/QC Method |
|---|---|---|---|
| 307 | 2-(4-acryloyl-3,3-dimethylpiperazin-1-yl)-N-ethyl-5H-pyrrolo[2,3-b]pyrazine-7-carboxamide | 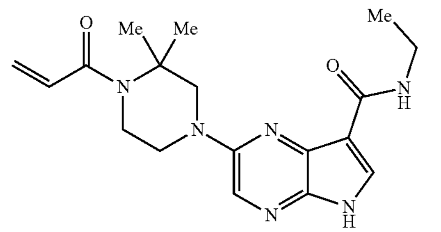 | MS m/z 433 [M + H]+<br>Rt = 2.64 minutes<br>Prep HPLC gradient<br>24-64% organic. |
| 308 | 2-{[(3S,4R)-1-acryloyl-3-methoxypiperidin-4-yl]amino}-N-(4,4,4-trifluorobutyl)-5H-pyrrolo[2,3-b]pyrazine-7-carboxamide | 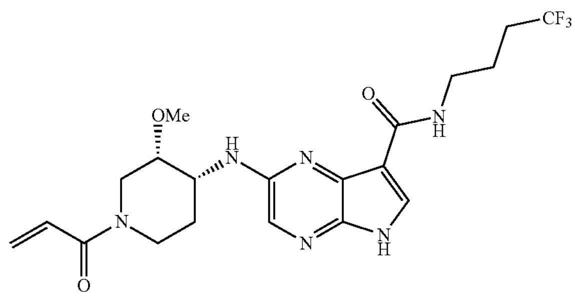 [SMILES: C=CC(=O)N1CC[C@@H](Nc2cnc3[nH]cc(C(=O)NCCCC(F)(F)F)c3n2)[C@@H](OC)C1] | MS m/z 455 [M + H]+<br>Rt = 2.64 minutes<br>Prep HPLC gradient<br>24-64% organic. |
| 309 | 2-{[(3S,4R)-1-acryloyl-3-methoxypiperidin-4-yl]amino}-N-[(3,3-difluorocyclobutyl)methyl]-5H-pyrrolo[2,3-b]pyrazine-7-carboxamide | 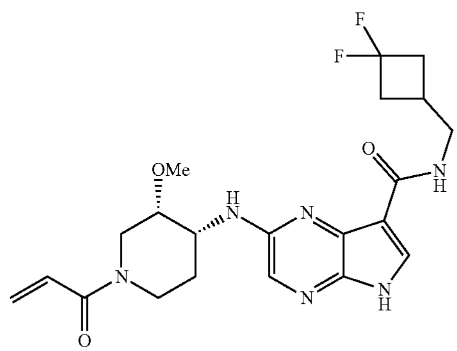 [SMILES: C=CC(=O)N1CC[C@@H](Nc2cnc3[nH]cc(C(=O)NCC4CC(F)(F)C4)c3n2)[C@@H](OC)C1] | MS m/z 449 [M + H]+<br>Rt = 2.64 minutes<br>Prep HPLC gradient<br>23-53% organic. |
| 310 | Racemic-2-[(1-acryloyl-2-methylpiperidin-4-yl)amino]-N-(4,4,4-trifluoro-2-methylbutyl)-5H-pyrrolo[2,3-b]pyrazine-7-carboxamide | 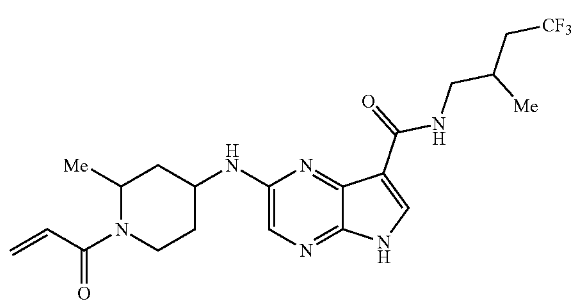 [SMILES: C=CC(=O)N1CCC(Nc2cnc3[nH]cc(C(=O)NCC(C)CC(F)(F)F)c3n2)CC1C] | MS m/z 453 [M + H]+<br>Rt = 2.81 minutes<br>Prep HPLC gradient<br>29-59% organic. |
| 311 | 2-[(3S)-4-acryloyl-3-(2-methylpropyl)piperazin-1-yl]-N-(2,2,2-trifluoroethyl)-5H-pyrrolo[2,3-b]pyrazine-7-carboxamide | 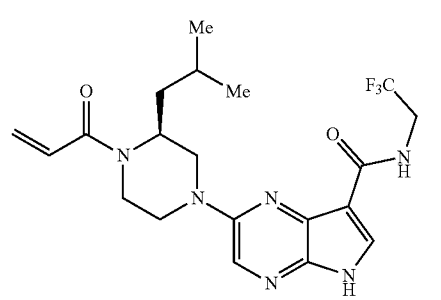 [SMILES: C=CC(=O)N1CCN(c2cnc3[nH]cc(C(=O)NCC(F)(F)F)c3n2)C[C@@H]1CC(C)C] | MS m/z 439 [M + H]+<br>Rt = 3.09 minutes<br>Prep HPLC gradient<br>26-66% organic. |

| Ex. No. | Name | Structure | Data/% Organic Eluant/QC Method |
| --- | --- | --- | --- |
| 312 | 2-{[(3S,4R)-1-acryloyl-3-methoxypiperidin-4-yl]amino}-N-[(2S)-1-methoxypropan-2-yl]-5H-pyrrolo[2,3-b]pyrazine-7-carboxamide | 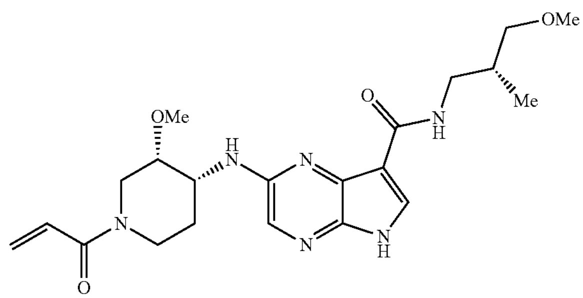 | MS m/z 417 [M + H]+ Rt = 2.16 minutes Prep HPLC gradient 13-53% organic. Method 2. |
| 313 | 2-{[(3S,4R)-1-acryloyl-3-methoxypiperidin-4-yl]amino}-N-(cyclopentylmethyl)-5H-pyrrolo[2,3-b]pyrazine-7-carboxamide | 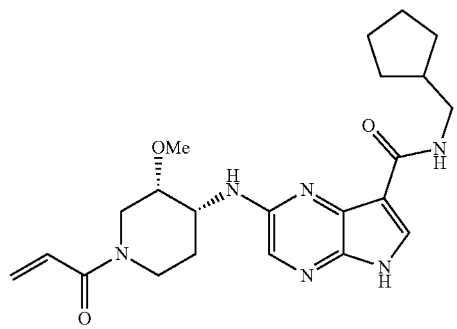 [SMILES: C=CC(=O)N1CC[C@@H](Nc2cnc3[nH]cc(C(=O)NCC4CCCC4)c3n2)[C@@H](OC)C1] | MS m/z 427 [M + H]+ Rt = 2.16 minutes Prep HPLC gradient 13-53% organic. |
| 314 | 2-[(3S)-4-acryloyl-3-(2-methylpropyl)piperazin-1-yl]-N-[(2R)-1-cyanobutan-2-yl]-5H-pyrrolo[2,3-b]pyrazine-7-carboxamide | 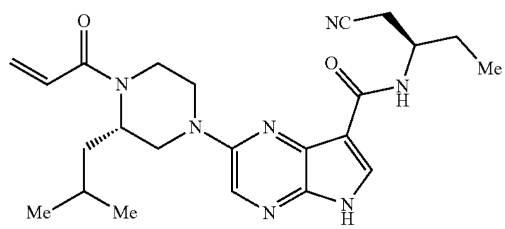 [SMILES: C=CC(=O)N1CCN(c2cnc3[nH]cc(C(=O)N[C@H](CC)CC#N)c3n2)C[C@@H]1CC(C)C] | MS m/z 438 [M + H]+ Rt = 2.88 minutes Prep HPLC gradient 28-58% organic. |
| 315 | 2-(4-acryloylpiperazin-1-yl)-N-[(2R)-1-cyanobutan-2-yl]-5H-pyrrolo[2,3-b]pyrazine-7-carboxamide | 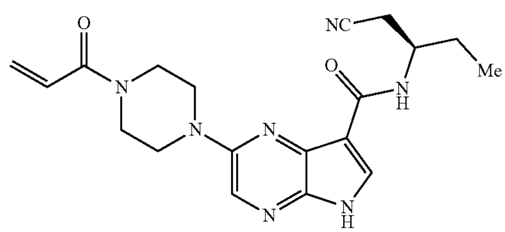 [SMILES: C=CC(=O)N1CCN(c2cnc3[nH]cc(C(=O)N[C@H](CC)CC#N)c3n2)CC1] | MS m/z 382 [M + H]+ Rt = 2.21 minutes Prep HPLC gradient 16-46% organic. Method 2. |
| 316 | 2-{[(3S,4R)-1-acryloyl-3-methoxypiperidin-4-yl]amino}-N-[(1R,2R)-2-(trifluoromethyl)cyclopropyl]-5H-pyrrolo[2,3-b]pyrazine-7-carboxamide | 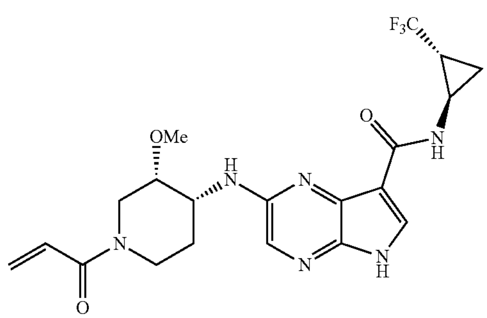 [SMILES: C=CC(=O)N1CC[C@@H](Nc2cnc3[nH]cc(C(=O)N[C@@H]4C[C@H]4C(F)(F)F)c3n2)[C@@H](OC)C1] | MS m/z 453 [M + H]+ Rt = 2.64 minutes Prep HPLC gradient 25-55% organic. |

| Ex. No. | Name | Structure | Data/% Organic Eluant/QC Method |
|---|---|---|---|
| 317 | 2-{[(3S,4R)-1-acryloyl-3-methoxypiperidin-4-yl]amino}-N-(2,2,2-trifluoroethyl)-5H-pyrrolo[2,3-b]pyrazine-7-carboxamide | 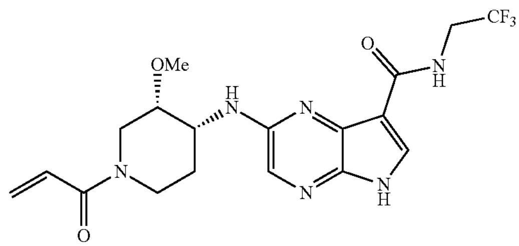 [SMILES: C=CC(=O)N1CC[C@@H](Nc2cnc3[nH]cc(C(=O)NCC(F)(F)F)c3n2)[C@@H](OC)C1] | MS m/z 427 [M + H]+ Rt = 2.64 minutes Prep HPLC gradient 26-66% organic. |
| 318 | 2-(4-acryloyl-3,3-dimethylpiperazin-1-yl)-N-[(2R)-1-cyanobutan-2-yl]-5H-pyrrolo[2,3-b]pyrazine-7-carboxamide | 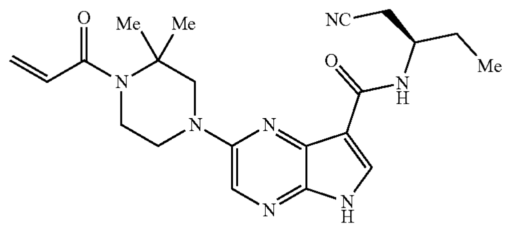 [SMILES: C=CC(=O)N1CCN(c2cnc3[nH]cc(C(=O)N[C@H](CC)CC#N)c3n2)CC1(C)C] | MS m/z 410 [M + H]+ Rt = 2.24 minutes Prep HPLC gradient 21-51% organic. |
| 319 | 2-{[(3R,4S)-1-acryloyl-3-methoxypiperidin-4-yl]amino}-N-(4,4,4-trifluorobutyl)-5H-pyrrolo[2,3-b]pyrazine-7-carboxamide | 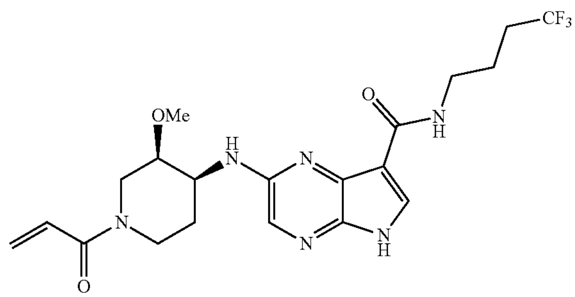 [SMILES: C=CC(=O)N1CC[C@H](Nc2cnc3[nH]cc(C(=O)NCCCC(F)(F)F)c3n2)[C@H](OC)C1] | MS m/z 455 [M + H]+ Rt = 2.64 minutes Prep HPLC gradient 21-51% organic. |
| 320 | Racemic-2-[(1-acryloyl-2-methylpiperidin-4-yl)amino]-N-cyclobutyl-5H-pyrrolo[2,3-b]pyrazine-7-carboxamide | 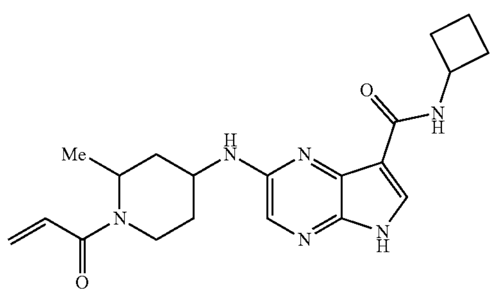 [SMILES: C=CC(=O)N1CCC(Nc2cnc3[nH]cc(C(=O)NC4CCC4)c3n2)CC1C] | MS m/z 383 [M + H]+ Rt = 2.42 minutes Prep HPLC gradient 26-66% organic. Method 2. |
| 321 | 2-{[(3S,4R)-1-acryloyl-3-methoxypiperidin-4-yl]amino}-N-(2,2-difluoropropyl)-5H-pyrrolo[2,3-b]pyrazine-7-carboxamide | 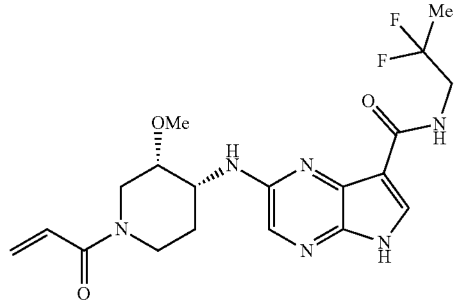 [SMILES: C=CC(=O)N1CC[C@@H](Nc2cnc3[nH]cc(C(=O)NCC(C)(F)F)c3n2)[C@@H](OC)C1] | MS m/z 423 [M + H]+ Rt = 2.47 minutes Prep HPLC gradient 20-50% organic. |

| Ex. No. | Name | Structure | Data/% Organic Eluant/QC Method |
|---|---|---|---|
| 322 | 2-{[(3R,4S)-1-acryloyl-3-methoxypiperidin-4-yl]amino}-N-[(3,3-difluorocyclobutyl)methyl]-5H-pyrrolo[2,3-b]pyrazine-7-carboxamide | 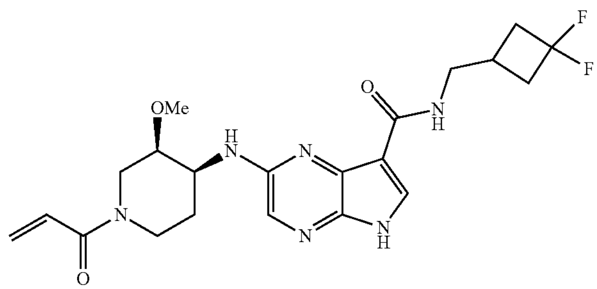 [SMILES: C=CC(=O)N1CC[C@H](Nc2cnc3[nH]cc(C(=O)NCC4CC(F)(F)C4)c3n2)[C@H](OC)C1] | MS m/z 449 [M + H]$^+$<br>Rt = 2.58 minutes<br>Prep HPLC gradient 23-53% organic. |
| 323 | 2-{[(3S,4R)-1-acryloyl-3-methoxypiperidin-4-yl]amino}-N-[(2R)-4,4,4-trifluoro-2-methylbutyl]-5H-pyrrolo[2,3-b]pyrazine-7-carboxamide | 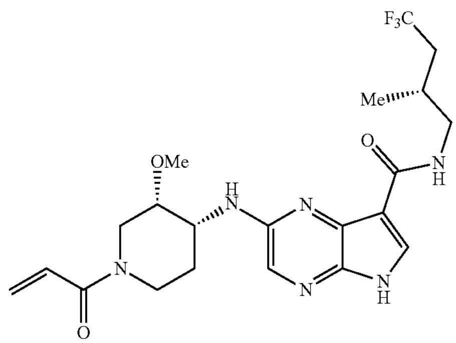 [SMILES: C=CC(=O)N1CC[C@@H](Nc2cnc3[nH]cc(C(=O)NC[C@H](C)CC(F)(F)F)c3n2)[C@@H](OC)C1] | MS m/z 469 [M + H]$^+$<br>Rt = 2.83 minutes<br>Prep HPLC gradient 30-70% organic. |
| 324 | 2-[(1-acryloyl-4-methylpiperidin-4-yl)amino]-N-cyclobutyl-5H-pyrrolo[2,3-b]pyrazine-7-carboxamide | 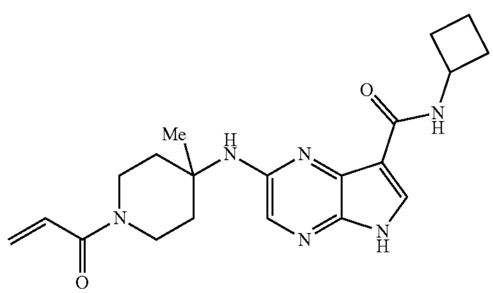 [SMILES: C=CC(=O)N1CCC(C)(Nc2cnc3[nH]cc(C(=O)NC4CCC4)c3n2)CC1] | MS m/z 383 [M + H]$^+$<br>Rt = 2.61 minutes<br>Prep HPLC gradient 21-51% organic. |
| 325 | 2-(4-acryloyl-3,3-dimethylpiperazin-1-yl)-N-(3,3-difluorocyclobutyl)-5H-pyrrolo[2,3-b]pyrazine-7-carboxamide | 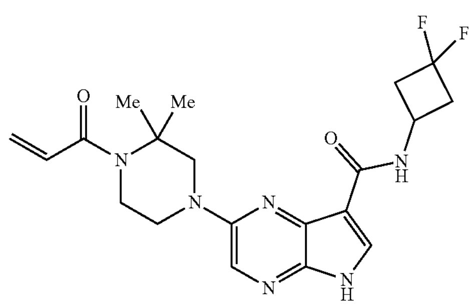 [SMILES: C=CC(=O)N1CCN(c2cnc3[nH]cc(C(=O)NC4CC(F)(F)C4)c3n2)CC1(C)C] | MS m/z 419 [M + H]$^+$<br>Rt = 2.55 minutes<br>Prep HPLC gradient 31-71% organic.<br>Method 2. |
| 326 | 2-{[(3R,4S)-1-acryloyl-3-methoxypiperidin-4-yl]amino}-N-ethyl-5H-pyrrolo[2,3-b]pyrazine-7-carboxamide | 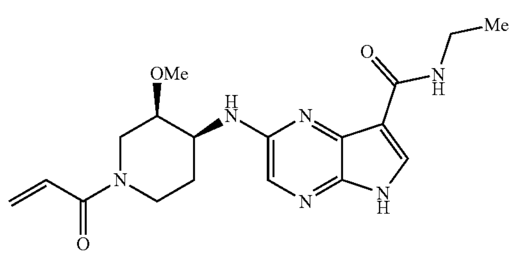 [SMILES: C=CC(=O)N1CC[C@H](Nc2cnc3[nH]cc(C(=O)NCC)c3n2)[C@H](OC)C1] | MS m/z 373 [M + H]$^+$<br>Rt = 2.42 minutes<br>Prep HPLC gradient 18-58% organic. |

-continued

| Ex. No. | Name | Structure | Data/% Organic Eluant/QC Method |
|---|---|---|---|
| 327 | 2-(4-acryloyl-3,3-dimethylpiperazin-1-yl)-N-[(2R)-1-methoxypropan-2-yl]-5H-pyrrolo[2,3-b]pyrazine-7-carboxamide | 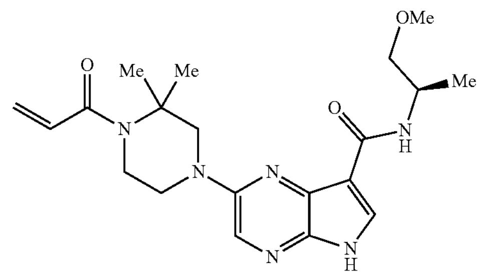 [SMILES: C=CC(=O)N1CCN(c2cnc3[nH]cc(C(=O)N[C@H](C)COC)c3n2)CC1(C)C] | MS m/z 401 [M + H]+ Rt = 2.59 minutes Prep HPLC gradient 23-53% organic. |
| 328 | Racemic-2-{[(3R,4S)-1-acryloyl-3-methoxypiperidin-4-yl]amino}-N-(4,4,4-trifluoro-2-methylbutyl)-5H-pyrrolo[2,3-b]pyrazine-7-carboxamide | 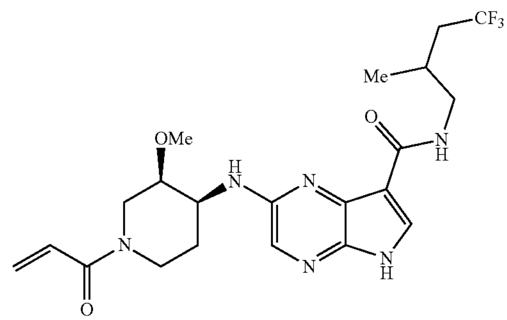 [SMILES: C=CC(=O)N1CC[C@H](Nc2cnc3[nH]cc(C(=O)NCC(C)CC(F)(F)F)c3n2)[C@H](OC)C1] | MS m/z 469 [M + H]+ Rt = 2.73 minutes Prep HPLC gradient 27-57% organic. |
| 329 | 2-[(3S)-4-acryloyl-3-(2-methylpropyl)piperazin-1-yl]-N-(3,3,3-trifluoropropyl)-5H-pyrrolo[2,3-b]pyrazine-7-carboxamide | 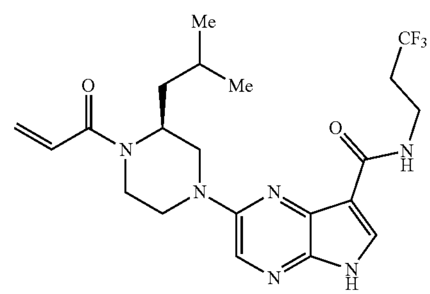 [SMILES: C=CC(=O)N1CCN(c2cnc3[nH]cc(C(=O)NCCC(F)(F)F)c3n2)C[C@@H]1CC(C)C] | MS m/z 453 [M + H]+ Rt = 3.09 minutes Prep HPLC gradient 37-77% organic. |
| 330 | 2-[(3S)-4-acryloyl-3-(2-methylpropyl)piperazin-1-yl]-N-(2,2-dimethylpropyl)-5H-pyrrolo[2,3-b]pyrazine-7-carboxamide | 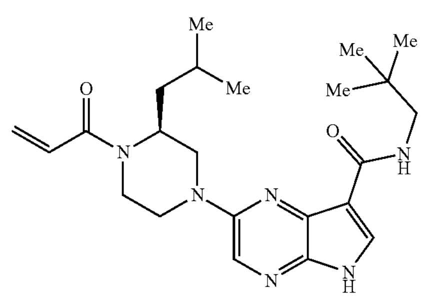 [SMILES: C=CC(=O)N1CCN(c2cnc3[nH]cc(C(=O)NCC(C)(C)C)c3n2)C[C@@H]1CC(C)C] | MS m/z 427 [M + H]+ Rt = 3.01 minutes Prep HPLC gradient 29-69% organic. |
| 331 | 2-{[(3S,4R)-1-acryloyl-3-methoxypiperidin-4-yl]amino}-N-[(2R)-1-methoxypropan-2-yl]-5H-pyrrolo[2,3-b]pyrazine-7-carboxamide | 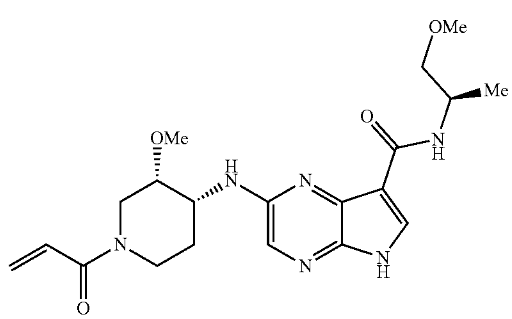 [SMILES: C=CC(=O)N1CC[C@@H](Nc2cnc3[nH]cc(C(=O)N[C@H](C)COC)c3n2)[C@@H](OC)C1] | MS m/z 417 [M + H]+ Rt = 2.37 minutes Prep HPLC gradient 17-47% organic. |

-continued

| Ex. No. | Name | Structure | Data/% Organic Eluant/QC Method |
|---|---|---|---|
| 332 | 2-(4-acryloylpiperazin-1-yl)-N-[(2R)-1-methoxypropan-2-yl]-5H-pyrrolo[2,3-b]pyrazine-7-carboxamide | 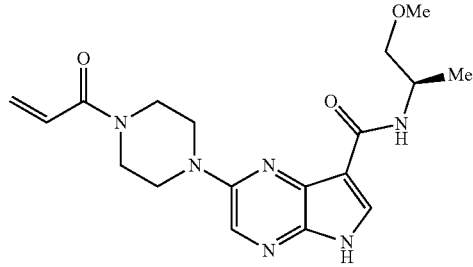 [SMILES: C=CC(=O)N1CCN(c2cnc3[nH]cc(C(=O)N[C@H](C)COC)c3n2)CC1] | MS m/z 373 [M + H]+<br>Rt = 2.17 minutes<br>Prep HPLC gradient<br>14-44% organic.<br>Method 2. |
| 333 | 2-[(1-acryloyl-4-methylpiperidin-4-yl)amino]-N-(4,4,4-trifluorobutyl)-5H-pyrrolo[2,3-b]pyrazine-7-carboxamide | 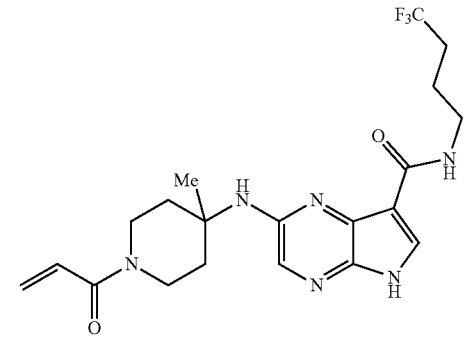 [SMILES: C=CC(=O)N1CCC(C)(Nc2cnc3[nH]cc(C(=O)NCCCC(F)(F)F)c3n2)CC1] | MS m/z 439 [M + H]+<br>Rt = 2.75 minutes<br>Prep HPLC gradient<br>24-54% organic. |
| 334 | 2-(4-acryloyl-3,3-dimethylpiperazin-1-yl)-N-cyclopentyl-5H-pyrrolo[2,3-b]pyrazine-7-carboxamide | 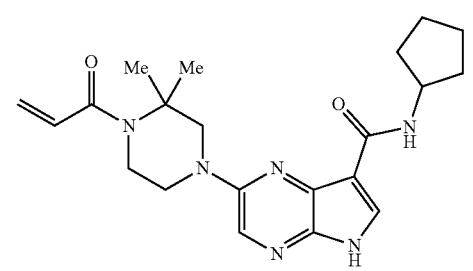 [SMILES: C=CC(=O)N1CCN(c2cnc3[nH]cc(C(=O)NC4CCCC4)c3n2)CC1(C)C] | MS m/z 397 [M + H]+<br>Rt = 2.88 minutes<br>Prep HPLC gradient<br>32-72% organic. |
| 335 | 2-[(1-acryloyl-4-methylpiperidin-4-yl)amino]-N-[(2R)-1-methoxypropan-2-yl]-5H-pyrrolo[2,3-b]pyrazine-7-carboxamide | 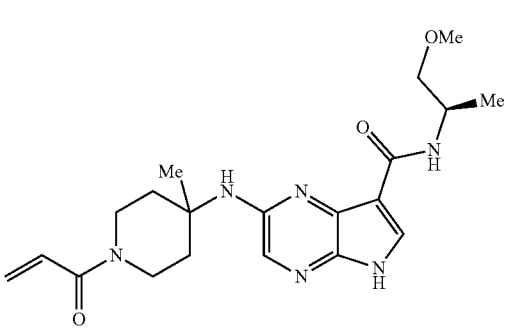 [SMILES: C=CC(=O)N1CCC(C)(Nc2cnc3[nH]cc(C(=O)N[C@H](C)COC)c3n2)CC1] | MS m/z 401 [M + H]+<br>Rt = 2.48 minutes<br>Prep HPLC gradient<br>17-47% organic. |
| 336 | 2-(4-acryloylpiperazin-1-yl)-N-[(2R)-4,4,4-trifluoro-2-methylbutyl]-5H-pyrrolo[2,3-b]pyrazine-7-carboxamide | 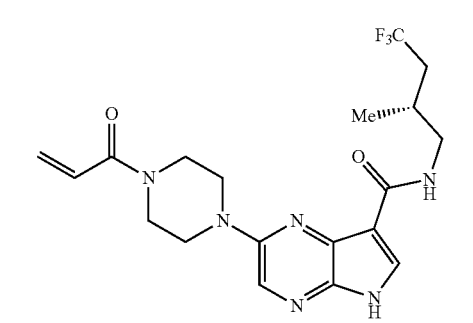 [SMILES: C=CC(=O)N1CCN(c2cnc3[nH]cc(C(=O)NC[C@H](C)CC(F)(F)F)c3n2)CC1] | MS m/z 425 [M + H]+<br>Rt = 2.86 minutes<br>Prep HPLC gradient<br>19-59% organic. |

| Ex. No. | Name | Structure | Data/% Organic Eluant/QC Method |
|---|---|---|---|
| 337 | Racemic-2-[(1-acryloyl-2-methylpiperidin-4-yl)amino]-N-[(1R,2R)-2-(trifluoromethyl)cyclopropyl]-5H-pyrrolo[2,3-b]pyrazine-7-carboxamide | 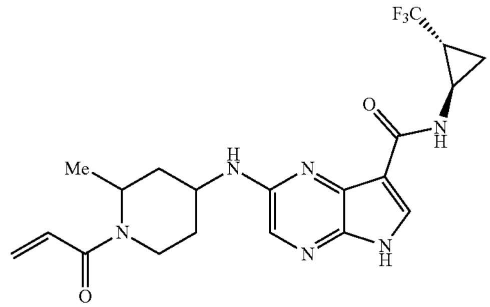 [SMILES: C=CC(=O)N1CCC(Nc2cnc3[nH]cc(C(=O)N[C@@H]4C[C@H]4C(F)(F)F)c3n2)CC1C] | MS m/z 437 [M + H]+ Rt = 2.83 minutes Prep HPLC gradient 18-58% organic. |

Examples 338-348 were prepared according to the synthesis and Library Protocol 6 below:

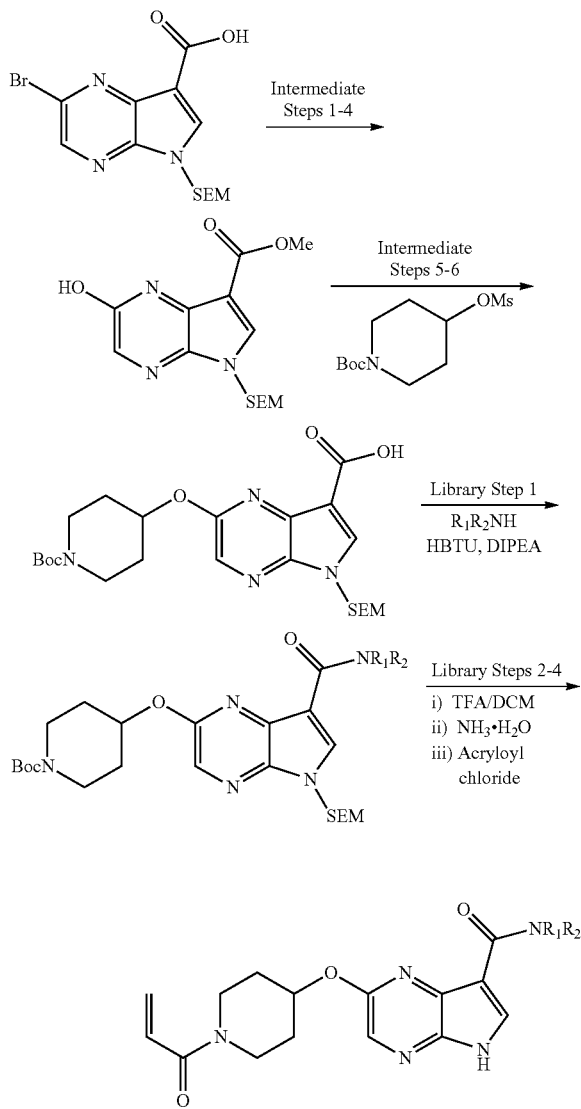

Intermediate Steps 1-4

Methyl 5-hydroxy-1-((2-(trimethylsilyl)ethoxy)methyl)-1H-pyrrolo[2,3-b]pyridine-3-carboxylate To a solution of 5-bromo-1H-pyrrolo[2,3-b]pyridine-3-carboxylic acid (22 g, 92 mmol) in MeOH (220 mL) was added thionyl chloride (33 mL) and the reaction was heated to 70° C. for 18 hours. The reaction was concentrated in vacuo and the residue treated with saturated aqueous NaHCO$_3$ solution (200 mL) to afford a precipitate. The solid was filtered and dried to afford the methyl ester intermediate. A solution of this intermediate (9.1 g, 35 mmol) in DMF (150 mL) was treated with sodium hydride (3.57 g, 89 mmol) and stirred at 0° C. for 30 minutes. SEMCl (11.9 g, 71 mmol) was added and the reaction stirred at room temperature for 2 hours. The reaction was quenched by the addition of ice-water (100 mL) and extracted into EtOAc (2×100 mL). The combined organic layers were washed with brine, dried over sodium sulphate and concentrated in vacuo. The residue was purified using silica gel column chromatography eluting with 0-30% EtOAc in petroleum ether to afford the SEM protected intermediate. To a solution of this intermediate (4.20 g, 10.9 mmol) in dioxane (100 mL) was added bispinacolatodiborane (3.32 g, 13.1 mmol) and potassium acetate (3.21 g, 32 mmol). The reaction was degassed with nitrogen before the addition of Pd(dppt)Cl$_2$ (798 mg, 1.09 mmol) and heating to 100° C. for 18 hours. The reaction was cooled, concentrated in vacuo and purified using silica gel column chromatography eluting with 0-30% EtOAc in petroleum ether. The residue was dissolved in THF (50 mL) and water (50 mL) and treated with NaBO$_3$.4H$_2$O (8.36 g, 54 mmol) at 10° C. The reaction was stirred at room temperature for 2 hrs and then partitioned between EtOAc and water. The organic layer was collected, washed with brine, dried over sodium sulphate and concentrated in vacuo to afford the title compound (4 g, 90% over 4 steps) that was taken on directly to the next step.

Intermediate Steps 5-6

5-((1-(tert-butoxycarbon)piperidin-4-yloxy)-1-((2-(trimethylsilyl)ethoxy)methyl)-1H-pyrrolo[2,3-b]pyridine-3-carboxylic acid To a solution of methyl 5-hydroxy-1-((2-(trimethylsilyl)ethoxy)methyl)-1H-pyrrolo[2,3-b]pyridine-3-carboxylate (Intermediate Steps 1-4, 4 g, 11 mmol) in DMF (50 mL) was added potassium carbonate (5.41 g, 25 mmol) and the reaction was heated to 110° C. for 5 minutes. tert-butyl 4-((methylsulfonyl)oxy)piperidine-1-carboxylate (2.5 g, 12.4 mmol) was added and the reaction was heated at 70° C. for 2 hours. Further tert-butyl 4-((methylsulfonyl)oxy)piperidine-1-carboxylate (2.5 g, 12.4 mmol) was added and the reaction heated to 110° C. for 18 hours. The reaction was cooled and partitioned between EtOAc (130 mL) and water (120 mL). The aqueous layer was extracted with EtOAc (50 mL) and the organic extracts were combined, dried over sodium sulphate and concentrated in vacuo. The residue was purified using silica gel column chromatography eluting with 0-20% EtOAc in petroleum ether. The residue was dissolved in MeOH (50 mL) and treated with a solution of sodium hydroxide (2.26 g, 56 mmol) in water (30 mL). The reaction was heated to 60° C. for 18 hours. The reaction was cooled, concentrated in vacuo, acidified to pH=4-5 with 1N HCl (aq) and extracted into EtOAc (2×100 mL). The combined organic layers were washed with brine, dried over sodium sulphate and concentrated in vacuo to afford the title compound as a white solid (4.2 g, 94 over 2 steps).

$^1$H NMR (400 MHz, DMSO-d$_6$): δ ppm 12.34 (br s, 1H), 8.32 (s, 1H), 8.15 (s, 1H), 7.90 (s, 1H), 5.63 (s, 2H), 4.62-4.59 (m, 1H), 3.68-3.65 (m, 2H), 3.56-3.53 (m, 2H), 3.30-3.20 (m, 2H), 1.98-1.90 (m, 2H), 1.61-1.55 (m, 2H), 0.84-0.81 (m, 2H), −0.09 (s, 9H). MS m/z 514 [M+Na]$^+$ Library Protocol 6

Step 1

To a 0.25M solution of 5-((1-(tert-butoxycarbonyl)piperidin-4-yl)oxy)-1-((2-(trimethylsilyl)ethoxy)methyl)-1H-pyrrolo[2,3-b]pyridine-3-carboxylic acid (Intermediate Steps 5-6, 400 μL, 100 μmol) in DMF were added amines of formula R$_1$R$_2$NH (150 μmol) followed by DIPEA (39 mg, 300 μmol) and a 0.27M solution of HBTU in DMF (400 μL, 110 μmol). The reactions were shaken at 60° C. for 16 hours before cooling and concentrating in vacuo. The residues were washed with water (1 mL) and extracted into EtOAc (3×1 mL). The combined organic layers were concentrated in vacuo to afford the Step 1 intermediates.

Steps 2-4

To the Step 1 intermediates was added a solution of TFA in DCM (1.2 mL, v:v 1:5) and the reactions were shaken at 30° C. for 4 hours before concentrating in vacuo. The residues were treated with ammonium hydroxide in MeOH (1.6 mL, v:v 1:3) and shaken at 30° C. for 6 hours before concentrating in vacuo. The residues were treated with a saturated solution of NaHCO$_3$ in water (1 mL). To the solutions was added EtOAc (1 mL) followed by acryloyl chloride (18 mg, 200 μmol) and the reactions were shaken at 30° C. for 2 hours. The reactions were concentrated in vacuo and purified using preparative HPLC as described below to afford the following Examples:

Preparative HPLC:

Column: Phenomenex Gemini C18 250×21.2 mm, 8 micron. Mobile phase: Acetonitrile:ammonium hydroxide (pH=10). Gradient time: 8 minutes; Hold time: 1 minute at 100% organic; Flow rate: 35 mL/min.

QC Method:

Column: Xbridge C18 2.1×50 mm; 5 micron. Mobile phase A: 0.0375% TFA in water; Mobile phase B: 0.01875% TFA in MeCN. Gradient: initial—1% B; 0.6 minutes—5% B; 4 minutes—100% B; 4.3 minutes—1% B; 4.7 minutes—1% B. Flow rate: 0.8 mL/min

| Ex. No. | Name | Structure | Data/% Organic Eluant |
|---|---|---|---|
| 338 | 5-[(1-acryloylpiperidin-4-yl)oxy]-N-(3,3,3-trifluoropropyl)-1H-pyrrolo[2,3-b]pyridine-3-carboxamide | 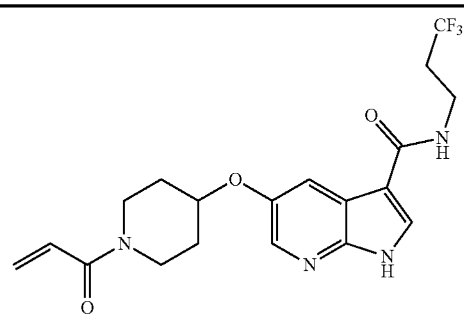 | MS m/z 411 [M + H]$^+$<br>Rt = 2.56 minutes<br>Prep HPLC gradient 22-62% organic. |
| 339 | 5-[(1-acryloylpiperidin-4-yl)oxy]-N-(3,3-difluorocyclohexyl)-1H-pyrrolo[2,3-b]pyridine-3-carboxamide | 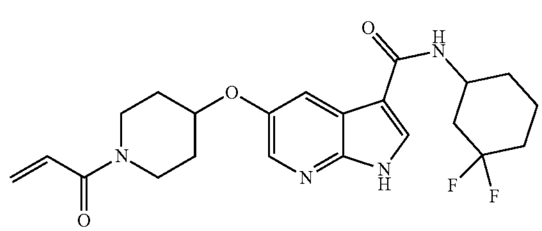 [SMILES: C=CC(=O)N1CCC(Oc2cnc3[nH]cc(C(=O)NC4CCCC(F)(F)C4)c3c2)CC1] | MS m/z 433 [M + H]$^+$<br>Rt = 2.65 minutes<br>Prep HPLC gradient 25-65% organic. |
| 340 | 5-[(1-acryloylpiperidin-4-yl)oxy]-N-(3-fluorobenzyl)-1H-pyrrolo[2,3-b]pyridine-3-carboxamide | 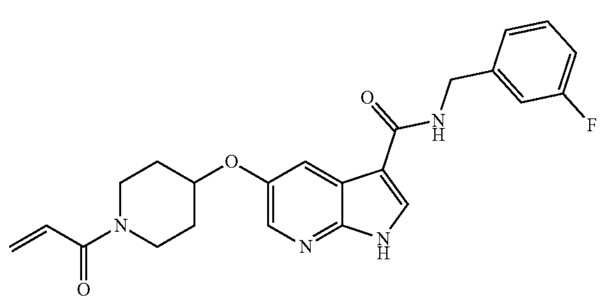 [SMILES: C=CC(=O)N1CCC(Oc2cnc3[nH]cc(C(=O)NCc4cccc(F)c4)c3c2)CC1] | MS m/z 423 [M + H]$^+$<br>Rt = 2.70 minutes<br>Prep HPLC gradient 26-66% organic. |

| Ex. No. | Name | Structure | Data/% Organic Eluant |
|---|---|---|---|
| 341 | 5-[(1-acryloylpiperidin-4-yl)oxy]-N-(3,3-difluorocyclohexyl)-1H-pyrrolo[2,3-b]pyridine-3-carboxamide | 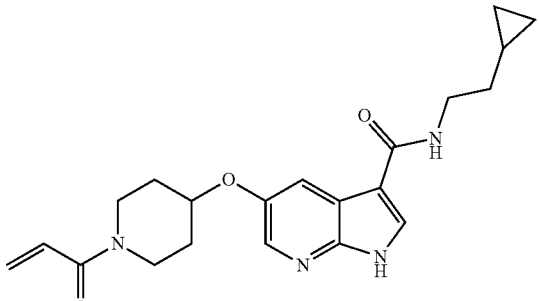 | MS m/z 423 [M + H]+<br>Rt = 2.70 minutes<br>Prep HPLC gradient<br>26-66% organic. |
| 342 | 5-[(1-acryloylpiperidin-4-yl)oxy]-N-benzyl-1H-pyrrolo[2,3-b]pyridine-3-carboxamide | 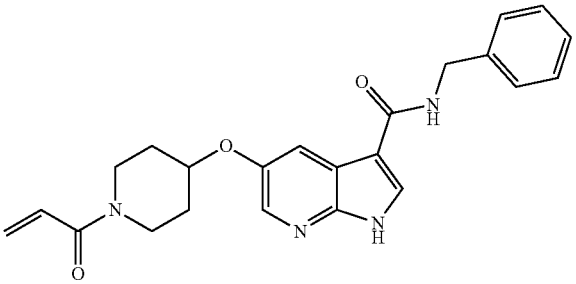 | MS m/z 383 [M + H]+<br>Rt = 2.59 minutes<br>Prep HPLC gradient<br>28-68% organic. |
| 343 | 5-[(1-acryloylpiperidin-4-yl)oxy]-N-(cyclopropylmethyl)-1H-pyrrolo[2,3-b]pyridine-3-carboxamide | 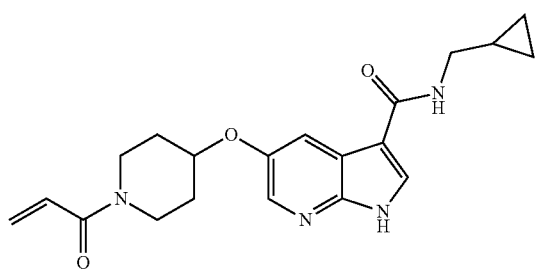 [SMILES: C=CC(=O)N1CCC(Oc2cnc3[nH]cc(C(=O)NCC4CC4)c3c2)CC1] | MS m/z 369 [M + H]+<br>Rt = 2.46 minutes<br>Prep HPLC gradient<br>19-59% organic. |
| 344 | 5-[(1-acryloylpiperidin-4-yl)oxy]-N-[(1S,3R)-3-fluorocyclopentyl]-1H-pyrrolo[2,3-b]pyridine-3-carboxamide | 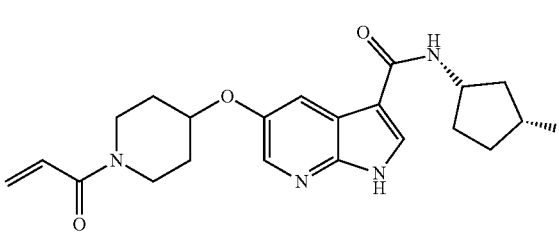 | MS m/z 401 [M + H]+<br>Rt = 2.47 minutes<br>Prep HPLC gradient<br>19-59% organic. |
| 345 | 5-[(1-acryloylpiperidin-4-yl)oxy]-N-(cyclobutylmethyl)-1H-pyrrolo[2,3-b]pyridine-3-carboxamide | 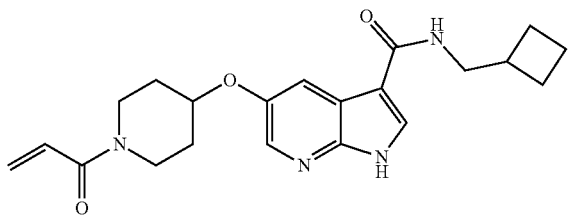 [SMILES: C=CC(=O)N1CCC(Oc2cnc3[nH]cc(C(=O)NCC4CCC4)c3c2)CC1] | MS m/z 383 [M + H]+<br>Rt = 2.62 minutes<br>Prep HPLC gradient<br>24-64% organic. |
| 346 | 5-[(1-acryloylpiperidin-4-yl)oxy]-N-(2-fluorobenzyl)-1H-pyrrolo[2,3-b]pyridine-3-carboxamide | 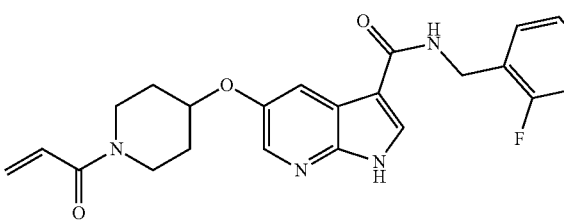 | MS m/z 423 [M + H]+<br>Rt = 2.69 minutes<br>Prep HPLC gradient<br>26-66% organic. |

| Ex. No. | Name | Structure | Data/% Organic Eluant |
|---|---|---|---|
| 347 | 5-[(1-acryloylpiperidin-4-yl)oxy]-N-propyl-1H-pyrrolo[2,3-b]pyridine-3-carboxamide | 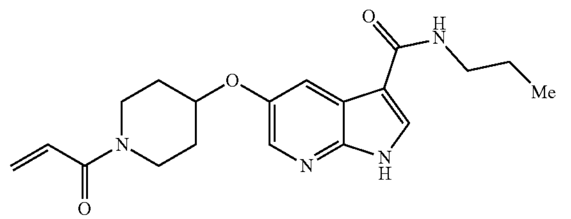 [SMILES: C=CC(=O)N1CCC(Oc2cnc3[nH]cc(C(=O)NCCC)c3c2)CC1] | MS m/z 357 [M + H]+<br>Rt = 2.41 minutes<br>Prep HPLC gradient<br>18-58% organic. |
| 348 | 5-[(1-acryloylpiperidin-4-yl)oxy]-N-butyl-1H-pyrrolo[2,3-b]pyridine-3-carboxamide | 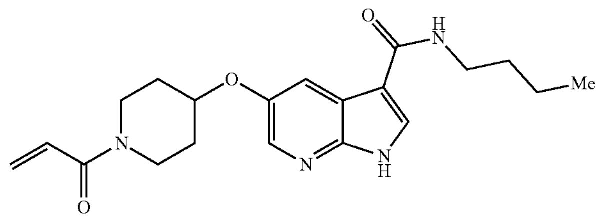 [SMILES: C=CC(=O)N1CCC(Oc2cnc3[nH]cc(C(=O)NCCCC)c3c2)CC1] | MS m/z 371 [M + H]+<br>Rt = 2.57 minutes<br>Prep HPLC gradient<br>23-63% organic. |

Example 349

2-(((2S,4S)-1-acryloyl-2-methylpiperidin-4-yl)amino)-N-ethyl-5H-pyrrolo[2,3-b]pyrazine-7-carboxamide (cis racemic)

The title compound was prepared according to the method described for Example__ using cis-racemic-benzyl 4-amino-2-methylpiperidine-1-carboxylate. The residue was purified using silica gel column chromatography eluting with 5% MeOH in DCM followed by preparative HPLC eluting with 18-38% MeCN in water modified with ammonia to pH=10. $^1$H NMR (400 MHz, CHCl$_3$-d) d ppm 9.69 (br. s., 1H) 8.15 (br. s., 1H) 8.04 (br. s., 1H) 7.60-7.75 (m, 1H) 6.59 (dd, J=16.56, 10.54 Hz, 1H) 6.33 (d, J=17.07 Hz, 1H) 5.72 (d, J=11.04 Hz, 1H) 4.73 (d, J=4.52 Hz, 1H) 4.54 (br. s., 1H) 4.15 (d, J=4.52 Hz, 2H) 3.44-3.65 (m, 2H) 3.32 (t, J=11.54 Hz, 1H) 2.06-2.26 (m, 2H) 1.93 (d, J=13.05 Hz, 2H) 1.26-1.40 (m, 6H) MS m/z [M+H]+=357.0

QC Analytical LC Method

Column: Xtimate C18 (5×30 mm, 3 μm). Mobile Phase: 1-100% MeCN/H$_2$O (0.05% TFA)

Rt=3.19 min. LC/MS=3.19 min (XTimate C18 5*30 mm, 3 um)

The cis-racemic material was separated into its enantiomers using preparative chiral chromatography according to conditions described below:

Prep Chiral LC Method:

Column: AS-H (21×250 mm, 5 um); CO$_2$/EtOH; 85:15 A/B hold for 15 min, T=40° C., flow: 75 mL/min Chiral LC QC Method:

Column: AS-H (4.6×100 mm, 5 um); CO$_2$/EtOH; 80:20 A/B hold for 15 min, T=40° C., flow: 1.5 mL/min The two enantiomers were arbitrarily assigned absolute stereochemistry First Eluting Isomer: Example 350

2-(((2S,4S)-1-Acryloyl-2-methylpiperidin-4-yl)amino)-N-ethyl-5-methyl-5H-pyrrolo[2,3-b]pyrazine-7-carboxamide. Rt=5.29 MS m/z 357 [M+H]+

Second Eluting Isomer: Example 351

2-(((2R,4R)-1-Acryloyl-2-methylpiperidin-4-yl)amino)-N-ethyl-5-methyl-5H-pyrrolo[2,3-b]pyrazine-7-carboxamide. Rt=7.43 MS m/z 379 [M+H]+

Example 352

5-((1-Acryloylpiperidin-4-yl)amino)-N-ethyl-1-methyl-1H-pyrrolo[2,3-b]pyridine-3-carboxamide Prepared according to scheme below

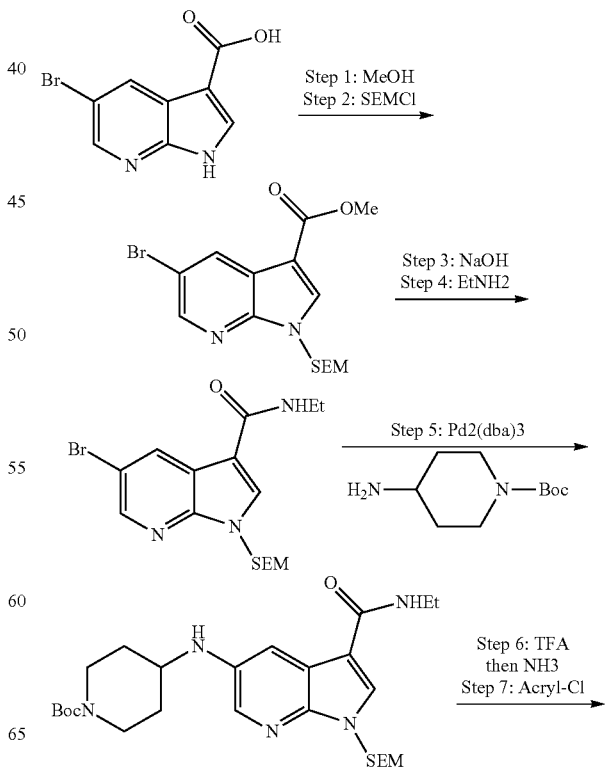

-continued

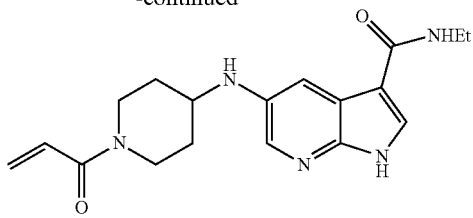

Example 352. Step 1

To a mixture of 5-bromo-1H-pyrrolo[2,3-b]pyridine-3-carboxylic acid (20 g, 82.99 mmol) in MeOH (200 mL) was added SOCl$_2$ (30 ml) dropwise at room temperature. After addition, the resulting mixture was heated to 70° C. and stirred overnight. TLC (EtOAc) showed the reaction was completed. The solvent was removed in vacuo and then aqueous NaHCO$_3$ (20 mL) was added at which time a precipitate formed. The solid was filtered and dried to give methyl 5-bromo-1H-pyrrolo[2,3-b]pyridine-3-carboxylate (15.3 g, 72.3%) as a brown solid.

Example 352 Step 2

To a solution of Example 352, step 1 (14.3 g, 56.1 mmol) in DMF (200 mL) at 0° C. was added NaH (5.61 g, 140.25 mmol) in portions. After addition, the mixture was stirred at 0° C. for 0.5 then SEM-Cl (18.7 g, 112.2 mmol) was added dropwise and the reaction stirred at room temperature for 4 h. TLC (Petroleum ether/EtOAc=2/1) showed most of the starting material was consumed and the reaction mixture was poured into ice-water and extracted with EtOAc (300 mL*2). The combined organic layers were washed with brine and dried over Na$_2$SO$_4$, filtered, and concentrated to give the crude product, which was purified by silica-gel column (eluting with EtOAc/Petroleum ether=5%-10%) to obtain methyl 5-bromo-1-((2-(trimethylsilyl)ethoxy)methyl)-1H-pyrrolo[2,3-b]pyridine-3-carboxylate (10.1 g, 46.8%) as a white solid. $^1$H NMR (400 MHz, DMSO-d$_6$) d ppm 8.33-8.61 (m, 3H) 5.68 (s, 2H) 3.87 (s, 3H) 3.56 (t, J=8.03 Hz, 2H) 0.82 (t, J=8.03 Hz, 2H) −0.10 (s, 9H).

Example 352 Step 3

To a solution of Example 352, Step 2 (5.0 g, 13.0 mmol) in THF (150 mL) was added a solution of NaOH (2.6 g, 65.0 mmol) in H$_2$O (50 mL) and the mixture refluxed overnight. TLC (EtOAc/Petroleum ether=1:2) showed the starting material was consumed completely. The solvent was removed and the residue was diluted with H$_2$O (30 ml), the solution was adjusted to pH=6 with conc'd HCl. The solution was extracted with EtOAc (200 ml×2) and the combined organic layers were washed with brine, dried over Na$_2$SO$_4$, filtered, and concentrated to give 5-bromo-1-((2-(trimethylsilyl)ethoxy)methyl)-1H-pyrrolo[2,3-b]pyridine-3-carboxylic acid (4.2 g, 87.1%) as a white solid. $^1$H NMR (400 MHz, DMSO-d$_6$) δ ppm 12.66 (br. s., 1H) 8.22-8.65 (m, 3H) 5.67 (s, 2H) 3.55 (t, J=8.03 Hz, 2H) 0.82 (t, J=8.03 Hz, 2H) −0.35-0.05 (m, 9H)

Example 352 Step 4

To a solution of Example 352, Step 3 (1.1 g, 2.96 mmol) in DMF (20 mL) was added Et$_3$N (598 mg, 5.92 mmol) and HATU (1.35 g, 3.55 mmol), followed by EtNH$_2$ (267 mg, 5.92 mmol). The mixture was stirred at room temperature overnight. TLC (EtOAc/Petroleum ether=1:2) showed the starting material was consumed completely. H$_2$O (30 mL) was added and the mixture was extracted with EtOAc (50 mL×2) and the combined organic layers were washed with H$_2$O (30 mL), brine (50 mL), dried over Na$_2$SO$_4$, filtered, and concentrated to give the crude material, which was purified by silica-gel column eluting with EtOAc/Petroleum ether=1/12~1/2 to provide 5-bromo-N-ethyl-1-((2-(trimethylsilyl)ethoxy)methyl)-1H-pyrrolo[2,3-b]pyridine-3-carboxamide (1.02 g, 86.6%) as a white solid. 1H NMR (400 MHz, DMSO-d$_6$) d ppm 8.63 (s, 1H) 8.44 (s, 1H) 8.35 (s, 1H), 8.22-8.19 (m, 1H), 5.65 (s, 2H), 3.54-3.51 (m, 2H) 3.31-3.28 (m, 2H) 1.16-1.12 (m, 3H) 0.86-0.82 (m, 2H) −0.09 (s, 9H)

Example 352 Step 5

To a stirred solution of Example 352 Step 4 (700 mg, 1.75 mmol) in toluene (20 mL) was added tert-butyl 4-aminopiperidine-1-carboxylate (700 mg, 3.5 mmol), and t-BuONa (504 mg, 5.25 mmol) at room temperature. The resulting mixture was degassed and purged with N$_2$ twice and then Pd$_2$(dba)$_3$ (320 mg, 0.35 mmol) and X-phos (167 mg, 0.35 mmol) were added. The resulting mixture was degassed and purged with N$_2$ again and stirred at 100° C. overnight under N$_2$ atmosphere. TLC (EtOAc/Petroleum ether=1:1) showed the starting material was consumed completely. The solvent was removed and the residue was diluted with H$_2$O (20 mL) and extracted with EtOAc (40 mL×2).

The combined organic layers were washed with brine, dried over Na$_2$SO$_4$, filtered, and concentrated in vacuo. The crude product was purified via Biotage SP1 (EtOAc/PE from 25% to 100% as eluent) to give tert-butyl 4-((3-(ethylcarbamoyl)-1-((2-(trimethylsilyl)ethoxy)methyl)-1H-pyrrolo[2,3-b]pyridin-5-yl)amino)piperidine-1-carboxylate (422 mg, 46.5%) as yellow oil. MS m/z 518 [M+H]+

Example 352 Step 6/7

To a solution of Example 352, Step 5 (422 mg, 0.82 mmol) in DCM (4 mL) at 0° C. was added TFA (5 mL). The mixture was warmed to room temperature and stirred for 3 hours, after which LCMS showed the reaction was completed. The mixture was evaporated to dryness to give crude product (655 mg, 100%) as a yellow oil which was used in the next step. To the crude product (655 mg, 1.40 mmol) in MeOH (4 mL) at 0° C. was added NH$_3$/H$_2$O (3 mL). The mixture was stirred at room temperature for 2 hrs, after which LC/MS indicated no starting material remained. The reaction was evaporated to give desired product (400 mg, 99.2%), which was taken directly to the next step.

MS m/z 288 [M+H]+

Example 352 Step 8

To a stirred solution of Example 352, Step 7 (400 mg, 1.39 mmol,) in THF/H$_2$O (3 mL/3 mL) was added DIPEA (360 mg, 2.78 mmol), followed by acryloyl chloride (252 mg, 2.78 mmol) dropwise at 0° C. carefully. After the addition, the resulting mixture was stirred at 0° C. for 2 hours. LCMS showed the start material had been consumed. The mixture was purified via Biotage SP1 (MeOH/DCM from 0~10%) to give 5-((1-acryloylpiperidin-4-yl)amino)-N-ethyl-1H-pyrrolo[2,3-b]pyridine-3-carboxamide (142 mg, 35.5%) as a yellow solid, this was further purified by HPLC give desired product.

Prep HPLC

Column: Kromasil Eternity XT C18 250*21.2*10 µm. Mobile phase: 5% MeCN/H$_2$O to 25% MeCN/H$_2$O, pH=10

QC Analytical HPLC

Column: Ultimate XB-C18, 3 µm, 3*50 mm. Mobile Phase 1% CH$_3$CN/H$_2$O to 100% CH$_3$CN/H$_2$O (0.1% TFA). Rt=2.63 min; MS m/z 342 [M+H]+. $^1$H NMR (400 MHz, DMSO-d$_6$) δ ppm 11.59 (br. s., 1H) 7.75-8.02 (m, 3H) 7.67 (br. s., 1H) 6.85 (dd, J=16.56, 10.54 Hz, 1H) 6.11 (d, J=16.06 Hz, 1H) 5.68 (d, J=10.04 Hz, 1H) 5.31 (d, J=8.03 Hz, 1H) 4.30 (d, J=12.55 Hz, 1H) 4.03 (d, J=13.05 Hz, 1H) 3.51 (br. s., 1H) 3.15-3.31 (m, 4H) 2.95 (t, J=11.54 Hz, 1H) 1.98 (br. s., 2H) 1.29 (br. s., 2H) 1.13 (t, J=7.03 Hz, 3H)

Example 353

2-(((2S,4S)-1-Acryloyl-2-methylpiperidin-4-yl) amino)-N—((S)-1-methoxypropan-2-yl)-5H-pyrrolo [2,3-b]pyrazine-7-carboxamide (cis-racemic)

The title compound was prepared analogous to the method described for Example 71, using cis-racemic benzyl (2S,4S)-4-amino-2-methylpiperidine-1-carboxylate and (S)-2-bromo-N-(1-methoxypropan-2-yl)-5-((2-(trimethylsilyl) ethoxy)methyl)-5H-pyrrolo[2,3-b]pyrazine-7-carboxamide.

The residue was purified using silica gel column chromatography eluting with 0 to 10% MeOH in DCM followed by preparative HPLC eluting with 24-44% MeCN in water modified with ammonia to pH=10 (Phenomenex Gemini C18 250*211.2 mm*8 um). LCMS analysis: Xtimate C18 5*30 mm, 3 um; 1 to 100% MeCN/H$_2$O in 0.1% TFA. Rt=3.27 min MS m/z 423 [M+Na]+. $^1$H NMR (400 MHz, DMSO-d$_6$) δ ppm 12.10 (br. s., 1H) 8.21-8.53 (m, 1H) 7.88 (s, 1H) 7.79 (s, 1H) 7.09 (dd, J=14.31, 5.77 Hz, 1H) 6.80 (dd, J=16.81, 10.29 Hz, 1H) 6.12 (dd, J=16.81, 2.26 Hz, 1H) 5.67 (dd, J=10.54, 2.51 Hz, 1H) 4.41 (br. s., 1H) 3.81-4.29 (m, 3H) 3.10-3.30 (m, 6H) 1.63-2.14 (m, 4H) 1.05-1.37 (m, 6H)

Example 354

2-(((2S,4S)-1-Acryloyl-2-methylpiperidin-4-yl) amino)-N—((R)-1-methoxypropan-2-yl)-5H-pyrrolo [2,3-b]pyrazine-7-carboxamide (cis-racemic)

The title compound was prepared analogous to the method described for Example 71 using cis-racemic benzyl (2S,4S)-4-amino-2-methylpiperidine-1-carboxylate and (R)-2-bromo-N-(1-methoxypropan-2-yl)-5-((2-(trimethylsilyl)ethoxy)methyl)-5H-pyrrolo[2,3-b]pyrazine-7-carboxamide The residue was purified using silica gel column chromatography eluting with 0 to 10% MeOH in DCM followed by preparative HPLC eluting with 24-44% MeCN in water modified with ammonia to pH=10 (Phenomenex Gemini C18 250*211.2 mm*8 µm)

LCMS analysis: Xtimate C18 5*30 mm, 3 um; 1 to 100% MeCN/H$_2$O in 0.1% TFA. Rt=3.25 min MS m/z 423 [M+Na]+. $^1$H NMR (400 MHz, DMSO-d$_6$) δ ppm 8.20-8.44 (m, 1H) 7.83-7.96 (m, 1H) 7.79 (s, 1H) 7.03 (dd, J=13.55, 5.52 Hz, 1H) 6.79 (dd, J=16.56, 10.54 Hz, 1H) 6.12 (dd, J=16.56, 2.51 Hz, 1H) 5.67 (dd, J=10.54, 2.51 Hz, 1H) 4.41 (br. s., 1H) 3.87-4.26 (m, 3H) 3.09-3.49 (m, 9H) 1.88-2.15 (m, 3H) 1.77 (br. s., 1H) 0.97-1.40 (m, 6H)

Example 355 and Example 356

2-(((3S,4R)-1-Acryloyl-3-methoxypiperidin-4-yl) amino)-N—((S)-1-methoxypropan-2-yl)-5H-pyrrolo [2,3-b]pyrazine-7-carboxamide and 2-(((3R,4S)-1-Acryloyl-3-methoxypiperidin-4-yl) amino)-N—((S)-1-methoxypropan-2-yl)-5H-pyrrolo [2,3-b]pyrazine-7-carboxamide The title compounds were prepared analogous to the method described for Example 71, using cis-racemic tert-butyl (3S,4R)-4-amino-3-methoxypiperidine-1-carboxylate and (S)-2-bromo-N-(1-methoxypropan-2-yl)-5-((2-(trimethylsilyl)ethoxy)methyl)-5H-pyrrolo[2,3-b]pyrazine-7-carboxamide.

The residue was purified using silica gel column chromatography eluting with 0 to 10% MeOH in DCM (800 mg, 94%) followed by preparative HPLC eluting with 22-42% MeCN in water modified with ammonia to pH=10 (Phenomenex Gemini C18 250*211.2 mm*8 um) to give racemic-cis material (350 mg, 41%).

The rac-cis material was separated by chiral SFC to give the enantiomeric pair, stereochemistry arbitrarily assigned:

Prep SFC Conditions

Column: OD (250 mm*30 mm, 10 µm); Mobile phase: 35% MeOH, NH$_3$H$_2$O; Flow: 80 mL/min Peak 1. Example 355

HPLC: Column: UtimateXB-C18, 3 µm, 3*50 mm; Mobile phase 1-100% CH$_3$CN/H$_2$O (0.1% TFA); Rt=3.71 min Chiral SFC QC: Column: Chiralcel OD-3, 150*4.6 mm; Mobile phase: MeOH/CO$_2$ (0.05% DEA) 5-40%; flow=2.5 mL/min, Rt=7.55 min.

$^1$H NMR (400 MHz, DMSO-d$_6$) d ppm 12.11 (br. s., 1H) 8.15-8.39 (m, 1H) 7.63-7.99 (m, 2H) 6.67-7.07 (m, 2H) 6.13 (d, J=16.56 Hz, 1H) 5.69 (dd, J=10.29, 2.26 Hz, 1H) 4.69 (d, J=12.55 Hz, 1H) 3.93-4.49 (m, 4H) 3.55-3.79 (m, 1H) 3.46 (d, J=4.52 Hz, 1H) 3.11-3.30 (m, 7H) 2.67-3.02 (m, 1H) 1.50-1.91 (m, 2H) 1.22 (d, J=6.53 Hz, 3H)

Peak 2. Example 356

HPLC: Column: UltimateXB-C18, 3 µm, 3*50 mm; Mobile phase 1-100% CH$_3$CN/H$_2$O (0.1% TFA); Rt=3.72 min Chiral SFC QC: Column: Chiralcel OD-3, 150*4.6 mm; Mobile phase: MeOH/CO$_2$ (0.05% DEA) 5-40%; flow=2.5 mL/min, Rt=8.62 min. $^1$H NMR (400 MHz, DMSO-d$_6$) δ ppm 12.11 (br. s., 1H) 8.15-8.39 (m, 1H) 7.63-7.99 (m, 2H) 6.67-7.07 (m, 2H) 6.13 (d, J=16.56 Hz, 1H) 5.69 (dd, J=10.29, 2.26 Hz, 1H) 4.69 (d, J=12.55 Hz, 1H) 3.93-4.49 (m, 4H) 3.55-3.79 (m, 1H) 3.46 (d, J=4.52 Hz, 1H) 3.11-3.30 (m, 7H) 2.67-3.02 (m, 1H) 1.50-1.91 (m, 2H) 1.22 (d, J=6.53 Hz, 3H)

Biological Evaluation

JAK Caliper Enzyme Assay at 4 µM or 1 mM ATP

Test article was solubilized in dimethyl sulfoxide (DMSO) to a stock concentration of 30 mM. An 11-point half log dilution series was created in DMSO with a top concentration of 600 µM. The test compound plate also contained positive control wells containing a known inhibitor to define 100% inhibition and negative control wells containing DMSO to define no inhibition. The compound plates were diluted 1 to 60 resulting in a top final assay compound concentration of 10 µM and a 2% DMSO concentration.

Test article and assay controls were added to a 384-well plate. Reaction mixtures contained 20 mM HEPES, pH 7.4, 10 mM magnesium chloride, 0.01% bovine serum albumin (BSA), 0.0005% Tween 20, 4 µM or 1 mM ATP and 1 µM peptide substrate. The JAK3 assays contained 1 µM of the JAKtide peptide (FITC-KGGEEEEYFELVKK). The assays were initiated by the addition 1 nM JAK3 enzyme and were incubated at room temperature 75 minutes for JAK3. Enzyme concentrations and incubation times were optimized for each new enzyme preps and were modified slightly over time to ensure 20%-30% phosphorylation. The assays were stopped with a final concentration of 10 mM EDTA, 0.1% Coating Reagent and 100 mM HEPES, pH=7.4. The assay plates were placed on a Caliper Life Science Lab Chip 3000 (LC3000) instrument, and each well was sampled using appropriate separation conditions to measure the unphosphorylated and phosphorylated peptide.

Stability of JAK3 Covalent Inhibitors in Rat and Human Whole Blood

Rat blood was collected from 3 male Sprague-Dawley rats (200-250 g, Charles River Laboratories) and pooled for each study. Human blood was collected from one male and one female healthy subjects at the Occupational Health & Wellness Center at Pfizer, Groton, Conn. and pooled for each study. Both rat and human blood was collected freshly into $K_2$-EDTA tubes and kept on ice. An aliquot of the blood was transferred to microtubes and pre-warmed for 10 min at 37° C. using a heat block. The test compound was then added (1 µM final concentration) and the incubation was continued for 180 min at 37° C. in duplicates. An aliquot of the incubation mixture was removed at designated time points during the course of the incubation, mixed with an aliquot of acetonitrile containing an internal standard, vortexed and centrifuged. The resulting supernatants were removed and subjected to LC-MS/MS analyses to determine parent compound concentrations. Peak area ratios of the parent compound vs the internal standard were used to determine the % of parent compound remaining vs incubation time.

HWB IL-15 Induced STAT5 Phosphorylation Assay

After serial dilution of the test compounds 1:2 in DMSO at desired concentration (500× of final), the compounds were further diluted in PBS (by adding 4 µL compound/DMSO in 96 µL PBS, [DMSO]=4%, 20× final). To 96-well polypropylene plates were added 90 µl HWB (heparin treated Human Whole Blood)/well, followed by 5 µl/well 4% DMSO in D-PBS or various concentrations of 20× inhibitor in 4% DMSO in D-PBS (w/o $Ca^{+2}$ or $Mg^{+2}$) to give 1× in 0.2% DMSO. After mixing and incubating for 45 minutes at 37° C., 5 µl D-PBS (unstimulated control) or 20× stocks of 5 µl human IL-15 (final concentration is 50 ng/ml) were added, and mixed three times. After incubating 15 minutes at 37° C., 1× Lyse/Fix Buffer (BD Phosflow 5× Lyse/Fix Buffer) was added to all wells at 1000 µl/well, then incubated for 20 minutes at 37° C. and spun 5 mins at 1200 rpm. After washing in 1000 µl FACS buffer 1× and spinning for 5 mins at 1200 rpm, 400 µl ice cold Perm Buffer III were added to each well. After mixing gently (1-2×) and incubating on ice for 30 minutes, spinning for 5 mins at 1200 rpm without interruption, and washing 1× in cold 1000 ml FACS buffer (D-PBS containing 0.1% BSA and 0.1% sodium azide) 250 µl/well of the desired AlexaFluor647-conjugated anti-phospho STAT5 antibody at 1:125 dilution in FACS buffer was added. Following incubating at 4° C.

over night, all the samples were transferred to 96-well polypropylene U-bottom plate, and checked by flow cytometry gated on total lymphocytes. $IC_{50}$ values obtained are listed in the Table.

PBMC IL-15 Induced P-STAT5

Test compounds were serially diluted in DMSO, with further dilution of the compounds in RPMI 1640 medium (Invitrogen #72400) supplemented with 10 mM HEPES, pH 7.4, 1 mM sodium pyruvate, and Penicillin/Streptomycin (by adding 5 µL compound/DMSO in 120 µL Dulbecco's Phosphate-Buffered Saline (D-PBS, 1×), [DMSO]=4%, and mixing the solution by repeated pipetting, 6×). IL-15 was diluted to the concentration at 820 ng/mL in RPMI 1640 medium.

Frozen human PBMC (200-250 million cells/vial) was thawed at 37° C. The cells were transferred to 10 mL warm medium in a 50-mL conical tube, and centrifuged at 1,200 RPM at room temperature for 5 min. The supernatant was aspirated. Cells were suspended in 3 mL warm human plasma and incubated at 37° C. in a tissue culture incubator for 1.5 to 2 h. After adding 47 ml D-PBS (37° C.) to PBMC/FBS suspension, centrifuging at 1,200 RPM at room temperature for 5 min, and aspirating the supernatant, the cells were resuspended in 20 mL warm RPMI medium. Ninety µL of cell suspension were pipetted per well in a 96-well, deep-well, V-bottom plate, and the plate was incubated at 37° C. for 30 min. Five µL of compound were transferred to each well (final 0.2% DMSO), vortex gently and incubate at 37° C. for 15 min; 5 µL 4% DMSO/PBS were added to the control wells. After adding 5 µL 820 ng/mL of human IL-15 (final 41 ng/mL) to each well (5 µL PBS to the control wells), vortexing gently and incubating at 37° C. for 15 min, followed by 0.3 mL 1% paraformaldehyde/PBS (37° C.) to each well, and incubating the plate at room temperature for 15 min, the plates were centrifuged at 1,200 RPM (Beckman GS-6R or Sorvall Legend) at room temperature for 5 min, and the supernatant was aspirated using a 8-channel or 12-channel manifold. After adding 0.8 mL staining buffer per well, the plates were centrifuged at 1,200 RPM (Beckman GS-6R or Sorvall Legend) at room temperature for 5 min, and again the supernatant was aspirated using a 8-channel or 12-channel manifold. The plate was vortexed, and 0.35 mL 90% methanol/10% $H_2O$ (−20° C.) was added per well, and the plate incubated on ice for 20 min. After again adding 0.8 mL staining buffer per well, the plates were centrifuged at 1,200 RPM (Beckman GS-6R or Sorvall Legend) at room temperature for 5 min, and again the supernatant was aspirated using a 8-channel or 12-channel manifold, and then 0.8 mL Staining buffer was added per well. After once again adding 0.8 mL staining buffer per well, the plates were centrifuged at 1,200 RPM (Beckman GS-6R or Sorvall Legend) at room temperature for 5 min, and again the supernatant was aspirated using a 8-channel or 12-channel manifold. Then the plate was vortexed, and 250 µL/well of Alexa Fluor® 647 conjugated anti-STAT5 antibody (1 to 125 dilution; 1 µL antibody per 250 µL staining buffer) was added, and the plate was incubated at 4° C. overnight in the dark. Samples of 250 µL/well were transferred to a 96-well U-bottom plate, and the FACS analysis was performed gating on total lymphocytes. Samples were analyzed using a BD Calibur™ or BD FACSCanto™ flow cytometer equipped with the BD High Throughput Sampler.

TABLE I

Enzyme Assay and Blood Stability Data.

| Ex | JAK3 4 μM ATP IC$_{50}$ (nM) | JAK3 1 mM ATP IC$_{50}$ (nM) | PBMC IL15_pSTAT5_IC$_{50}$ (nM) | HWB_IL15 pSTAT5 IC$_{50}$ (nM) | Human blood stability t$_{1/2}$ (min) |
|---|---|---|---|---|---|
| 5 | 0.408 | 46 | | | |
| 6 | 10.102 | 1,320 | | | |
| 7 | 1.485 | 106 | 403.119 | | 158 |
| 8 | 0.355 | 46 | 133.236 | | >360.000 |
| 9 | 8.862 | 1,211 | | | |
| 10 | 2.766 | 632 | | | |
| 11 | 1.613 | 308 | | | 207.759 |
| 12 | 5.281 | 766 | | | |
| 14 | 54.789 | 3,008 | | | |
| 15 | 31.369 | 3,285 | | | |
| 17 | 0.319 | 37 | 2561.816 | | 189.399 |
| 18 | 0.491 | 96 | 5985.753 | | >360.000 |
| 20 | 5.416 | 926 | | | |
| 21 | 4.694 | 633 | | | |
| 22 | 1.288 | 134 | | | |
| 23 | 3.582 | 651 | | | |
| 24 | 1.113 | 295 | | | |
| 25 | 1.332 | 92 | 1603.173 | | |
| 26 | 1.649 | 99 | 1926.549 | | |
| 27 | 0.468 | 19 | 382.483 | | >360.000 |
| 28 | 13.706 | 1,159 | | | |
| 29 | | 8307 | | | |
| 30 | 6.865 | 865 | | | |
| 31 | 0.211 | 47 | 3866.586 | | 294 |
| 32 | 0.848 | 138 | 9099.464 | | >360.000 |
| 33 | 0.23 | 34 | 2812.08 | | 208 |
| 34 | 0.501 | 105 | 580.327 | | >360.000 |
| 35 | 6.768 | 621 | | | |
| 36 | 0.875 | 54 | 175.991 | 1092.17 | >360.000 |
| 37 | 0.375 | 51 | 675.816 | 1942.711 | 305 |
| 38 | 0.328 | 30 | 204.524 | 1161.485 | 263 |
| 39 | 1.014 | 202 | 2376.484 | | >360.000 |
| 40 | 0.384 | 24 | 134.246 | 841.679 | 243 |
| 41 | 0.159 | 22 | 146.605 | 515.375 | 225 |
| 42 | 0.4 | 50 | 356.609 | 1059.915 | 281 |
| 43 | 0.258 | 50 | 411.297 | | 223.838 |
| 44 | 0.35 | 47 | 315.212 | 1233.751 | 256.048 |
| 45 | 0.39 | 57 | 459.995 | | 202.192 |
| 46 | 3.381 | 209 | 870.704 | | |
| 47 | 1.178 | 87 | 362.653 | 3577.789 | 108 |
| 48 | 49.105 | 3,061 | 6689.177 | | |
| 49 | 27.087 | 2,101 | | | 196.039 |
| 50 | 1.089 | 91 | 430.547 | | >360.000 |
| 51 | 2.932 | 212 | 998.72 | | 158.879 |
| 52 | 1.023 | 153 | 626.827 | | 167 |
| 53 | 31.168 | 4,003 | | | |
| 54 | 2.486 | 345 | 1639.582 | | |
| 55 | 2.213 | 192 | 2258.051 | | >360.000 |
| 56 | 0.927 | 70 | 1603.309 | | >360.000 |
| 57 | 4.446 | 241 | 3216.686 | | >360.000 |
| 58 | 2.77 | 282 | 4737.71 | | >360.000 |
| 59 | 6.265 | 1,196 | 4868.413 | | |
| 60 | 0.448 | 130 | 379.473 | | 178.134 |
| 61 | 3.394 | 564 | 2172.11 | | |
| 62 | 13.47 | 2,700 | | | |
| 63 | 2.439 | 379 | | | |
| 64 | 0.408 | 50 | 227.603 | 3128.272 | 265.131 |
| 65 | 1.024 | 53 | 585.305 | | >360.000 |
| 66 | 6.214 | 412 | | | >360.000 |
| 67 | 0.511 | 25 | 439.296 | | >360.000 |
| 68 | 2.172 | 247 | 4571.172 | | >360.000 |
| 69 | 0.782 | 137 | 2607.954 | | >360.000 |
| 70 | 9.097 | 1,391 | | | >360.000 |
| 71 | 1.129 | 54 | 260.396 | 931.362 | 309 |
| 72 | 1.134 | 80 | 415.042 | | 166 |
| 73 | 0.971 | 33 | 173.619 | 738.297 | >360.000 |
| 74 | 0.995 | 177 | 1180.961 | | >360.000 |
| 75 | 1.599 | 316 | 2276.87 | | >360.000 |
| 76 | 0.566 | 136 | 1147.608 | | >360.000 |
| 77 | 0.702 | 115 | 560.626 | 2450.401 | >320.333 |
| 78 | 1.832 | 314 | 935.276 | | >360.000 |
| 79 | 0.608 | 77 | 264.358 | 2711.879 | 329.878 |
| 80 | 1.32 | 160 | 828.951 | | 288.261 |

TABLE I-continued

Enzyme Assay and Blood Stability Data.

| Ex | JAK3 4 µM ATP IC$_{50}$ (nM) | JAK3 1 mM ATP IC$_{50}$ (nM) | PBMC IL15_pSTAT5_IC$_{50}$ (nM) | HWB_IL15 pSTAT5 IC$_{50}$ (nM) | Human blood stability t$_{1/2}$ (min) |
|---|---|---|---|---|---|
| 81 | | 76.9 | | | >360 |
| 83 | 10.656 | 1,107 | | | |
| 84 | 1.666 | 329 | 1223.734 | | |
| 85 | 2.906 | 467 | | | 83 |
| 86 | 0.515 | 94 | 259.72 | 2917.627 | 100 |
| 87 | 14.002 | 1,322 | 6485.529 | | >360.000 |
| 88 | 1.5 | 137 | 3453 | 5048 | >360.0 |
| 89 | 76.421 | 7,673 | | | |
| 90 | 1.038 | 152 | 3220.504 | | |
| 92 | 20.944 | 2,436 | | | |
| 93 | 710.72 | >3,160 | | | |
| 94 | 0.8 | 148 | 1078.3 | | |
| 95 | 0.466 | 65 | 478.942 | 804.421 | 188 |
| 96 | 432.968 | >10,000 | | | |
| 97 | 1.713 | 187 | 1063.965 | | |
| 98 | 1.264 | 152 | 932.175 | | 105.768 |
| 99 | 89.202 | 8,988 | | | |
| 100 | 76.266 | 2,661 | >10000.000 | | 211 |
| 101 | 0.219 | 28 | 226.783 | 703.427 | 114 |
| 102 | 1.899 | 142 | 236.784 | 1532.345 | 121 |
| 103 | 0.424 | 38 | 155.243 | 658.882 | 137 |
| 105 | 0.408 | 54 | 324.218 | 1069.197 | 138 |
| 106 | 0.125 | 25 | 191.916 | 287.035 | 112 |
| 107 | 11.807 | 1,243 | 8260.517 | | |
| 108 | 0.769 | 136 | 3260.465 | 3483.335 | 133.832 |
| 109 | 0.713 | 155 | 320.415 | | 132.105 |
| 110 | 867.417 | >10,000 | | | |
| 111 | 0.858 | 77 | 536.695 | | 172.108 |
| 112 | 1.028 | 181 | 1012.124 | | |
| 113 | 2.395 | 589 | 1942.788 | | >360.000 |
| 114 | 19.662 | 3,811 | | | |
| 115 | 8.315 | 929 | | | 226.018 |
| 116 | 14.665 | 2,549 | | | |
| 117 | 11.872 | 1,493 | | | |
| 118 | 16.084 | 1,892 | | | |
| 119 | 34.246 | 3,927 | 9310.19 | | |
| 120 | 4.479 | 725 | | | >360.000 |
| 121 | 6.961 | 921 | | | 160.212 |
| 122 | 8.968 | 1,465 | | | |
| 123 | 7.649 | 1,104 | 3043.142 | | 146.779 |
| 124 | 5.891 | 1,102 | 2430.305 | | 291.809 |
| 125 | 7.816 | 1,878 | | | |
| 126 | 14.918 | 3,527 | | | |
| 127 | 9.426 | 1,083 | | | |
| 128 | 6.667 | 787 | | | >360.000 |
| 129 | 0.534 | 24 | 86.171 | | 267.223 |
| 131 | 0.182 | 33 | | | |
| 132 | 1.672 | 255 | 523.984 | | |
| 133 | 1.111 | 76 | 302.319 | | 238 |
| 134 | 12.382 | 2,528 | | | |
| 135 | 1.489 | 168 | 759.164 | | |
| 136 | 5.82 | 632 | | | |
| 137 | 28.077 | 3,024 | | | |
| 138 | 46.72 | 4,839 | | | |
| 139 | 1.57 | 109 | 711.345 | | >360.000 |
| 140 | 2.71 | 384 | 1707.879 | | |
| 141 | 0.794 | 103 | 346.533 | | |
| 142 | 60.402 | 4,432 | | | |
| 143 | 22.609 | 1,920 | | | |
| 144 | 3.318 | 430 | | | |
| 145 | 18.372 | 1,933 | | | |
| 146 | 12.23 | 1,367 | | | |
| 147 | 41.719 | 3,712 | | | |

TABLE I-continued

Enzyme Assay and Blood Stability Data.

| Ex | JAK3 4 μM ATP IC$_{50}$ (nM) | JAK3 1 mM ATP IC$_{50}$ (nM) | PBMC IL15_pSTAT5_IC$_{50}$ (nM) | HWB_IL15 pSTAT5 IC$_{50}$ (nM) | Human blood stability t$_{1/2}$ (min) |
|---|---|---|---|---|---|
| 148 | 0.773 | 111 | 312.169 | | >360.000 |
| 149 | 0.565 | 134 | 163.308 | 4236.663 | |
| 150 | 8.087 | 1,115 | | | |
| 151 | 13.568 | 1,515 | | | |
| 152 | 1.973 | 256 | 509.756 | | |
| 153 | 5.207 | 538 | | | |
| 154 | 4.683 | 590 | | | |
| 155 | 4.916 | 721 | | | |
| 156 | 28.9 | 4,089 | | | |
| 157 | 20.627 | 2,898 | | | |
| 158 | 3.07 | 365 | 888.383 | | |
| 159 | 6.307 | 865 | | | |
| 160 | 4.33 | 463 | | | |
| 161 | 7.348 | 1,118 | | | |
| 162 | 6.192 | 581 | | | |
| 163 | 1.241 | 160 | 408.899 | | |
| 164 | 4.338 | 726 | | | |
| 165 | 10.683 | 957 | | | |
| 166 | 0.667 | 58 | 167.842 | 1205.374 | >360.000 |
| 167 | 4.605 | 599 | | | |
| 168 | 7.756 | 769 | | | |
| 169 | 7.309 | 845 | | | |
| 170 | 0.508 | 4 | | | 307.85 |
| 171 | 0.928 | 55 | 946.664 | | |
| 172 | 0.448 | 5 | 81.314 | 321.705 | 326 |
| 173 | 0.681 | 43 | 1415.742 | | |
| 174 | 0.368 | 13 | 161.927 | 1730.052 | |
| 175 | 0.426 | 8 | 77.33 | 1322.928 | |
| 176 | 0.437 | 3 | 23.956 | 318.21 | ok291 |
| 177 | 0.626 | 25 | 420.375 | | |
| 178 | 0.442 | 6 | 88.6 | 360.009 | ok334.132 |
| 179 | 0.596 | 18 | 94.819 | 849.931 | |
| 180 | 0.481 | 12 | 203.604 | 944.012 | |
| 181 | 0.379 | 5 | 159.433 | 1815.479 | |
| 182 | 2.444 | 165 | >10000.000 | | |
| 183 | 1.034 | 41 | 1587.648 | | |
| 184 | 1.394 | 68 | 1190.05 | | |
| 185 | 0.372 | 6 | 73.025 | 541.837 | |
| 186 | 0.485 | 15 | 212.715 | 870.057 | |
| 187 | 0.503 | 6 | 54.697 | 240.33 | >360.000ok |
| 188 | 0.515 | 6 | 88.047 | 913.058 | >360.000 |
| 189 | 0.689 | 6 | 202.772 | 1144.319 | >360.000 |
| 190 | 0.193 | 7 | 96.87 | 618.953 | |
| 191 | 0.484 | 9 | 136.883 | 777.795 | |
| 192 | 0.627 | 29 | 906.631 | | |
| 193 | 0.393 | 5 | 68.408 | 637.257 | |
| 194 | 0.993 | 22 | | | |
| 195 | 0.494 | 7 | 82.676 | 687.986 | |
| 196 | 0.479 | 5 | 54.667 | 362.206 | >360.000 |
| 197 | 0.788 | 147 | 706.383 | | |
| 198 | 0.361 | 53 | 249.879 | 1404.891 | |
| 199 | 0.414 | 47 | 250.141 | 2020.346 | |
| 200 | 0.411 | 46 | 148.58 | 1520.388 | >360.000 |
| 201 | 3.624 | 411 | | | |
| 202 | 5.311 | 697 | | | |
| 203 | 2.819 | 370 | 4462.504 | | |
| 204 | 0.272 | 49 | 130.142 | 1390.465 | >360.000 |
| 205 | 0.138 | 16 | 92.35 | 513.012 | 250.221 |
| 206 | 2.788 | 325 | 3100.582 | | |
| 207 | 4.071 | 538 | | | |
| 208 | 6.987 | 734 | | | |
| 209 | 0.609 | 64 | 206.051 | >10000.000 | 267 |
| 210 | 0.435 | 54 | 325.117 | | |
| 211 | 0.5 | 74 | 395.002 | 1744.169 | |
| 212 | 0.922 | 328 | 1340.35 | | |
| 213 | 3.071 | 343 | 1724.477 | | |
| 214 | 0.209 | 20 | 56.941 | 194.733 | ok287.47 |
| 215 | 0.782 | 97 | 618.746 | | |
| 216 | 3.269 | 463 | | | |
| 217 | 1.968 | 272 | 2093.153 | | |
| 218 | 0.627 | 105 | 1202.186 | | |
| 219 | 0.363 | 25 | 134.493 | 888.536 | 243 |
| 220 | 0.211 | 18 | 100.287 | 1074.161 | 222 |

TABLE I-continued

Enzyme Assay and Blood Stability Data.

| Ex | JAK3 4 µM ATP IC$_{50}$ (nM) | JAK3 1 mM ATP IC$_{50}$ (nM) | PBMC IL15_pSTAT5_IC$_{50}$ (nM) | HWB_IL15 pSTAT5 IC$_{50}$ (nM) | Human blood stability t$_{1/2}$ (min) |
|---|---|---|---|---|---|
| 221 | 4.4 | 713 | | | |
| 222 | 0.38 | 53 | 280.092 | 1017.369 | |
| 223 | 4.134 | 344 | 3334.709 | | |
| 224 | 3.542 | 526 | | | |
| 225 | 0.233 | 25 | 170.257 | 772.383 | 236 |
| 226 | 2.116 | 430 | | | |
| 227 | 0.279 | 22 | 145.723 | 681.633 | 270.193 |
| 228 | 0.229 | 18 | 93.296 | 378.222 | 253.848 |
| 229 | 0.582 | 60 | 220.861 | 2387.609 | 356 |
| 230 | 0.305 | 34 | 155.156 | 1705.739 | 351.124 |
| 231 | 0.322 | 85 | 353.117 | | 321 |
| 232 | 2.497 | 606 | | | |
| 233 | 6.789 | 1,095 | | | |
| 234 | 17.916 | 2,269 | | | |
| 235 | 0.304 | 37 | 207.51 | | 347 |
| 236 | 45.087 | 6,550 | | | |
| 237 | 0.25 | 56 | 780.068 | | 259 |
| 238 | 9.478 | 1,358 | | | |
| 239 | 3.78 | 757 | | | |
| 240 | 10.889 | 4,059 | | | |
| 241 | 3.795 | 857 | | | |
| 242 | 62.118 | >10,000 | | | |
| 243 | 0.586 | 141 | 1731.02 | | >360.000 |
| 244 | 82.347 | >10,000 | | | |
| 245 | 1.775 | 297 | >10000.000 | | |
| 246 | 7.792 | 1,113 | | | |
| 247 | 3.337 | 829 | | | |
| 248 | 48.658 | 5,334 | | | |
| 249 | 75.293 | >10,000 | | | |
| 250 | 4.312 | 798 | | | |
| 251 | 5.118 | 1,316 | | | |
| 252 | 110.446 | >10,000 | | | |
| 253 | 72.015 | 7,678 | | | |
| 254 | 17.204 | 2,544 | | | |
| 255 | 6.373 | 846 | | | |
| 256 | 0.124 | 23 | 531.251 | | 275 |
| 257 | 55.343 | 6,455 | | | |
| 258 | 6.226 | 1,048 | | | |
| 259 | 180.34 | >10,000 | | | |
| 260 | 2.137 | 676 | | | |
| 261 | 259.415 | >10,000 | | | |
| 262 | 11.594 | 2,181 | | | |
| 263 | 52.389 | 6,461 | | | |
| 264 | 2.412 | 479 | | | |
| 265 | 4.627 | 742 | 2063.272 | | |
| 266 | 0.2 | 22 | 64.232 | 528.022 | |
| 267 | 4.986 | 802 | | | |
| 268 | 1.434 | 330 | >10000.000 | | |
| 269 | 0.888 | 82 | 219.991 | 1385.249 | |
| 270 | 0.526 | 63 | 670.261 | | |
| 271 | 0.676 | 144 | 1144.556 | | |
| 272 | 3.825 | 651 | | | |
| 273 | 1.587 | 204 | 388.534 | | |
| 274 | 0.984 | 157 | 506.646 | | |
| 275 | 3.186 | 418 | 1032.718 | | |
| 276 | 0.479 | 111 | 622.954 | | |
| 277 | 0.59 | 155 | 2317.882 | | |
| 278 | 1.227 | 70 | 271.528 | 2464.465 | |
| 279 | 0.343 | 31 | 107.438 | 765.352 | |
| 280 | 2.494 | 501 | | | |
| 281 | 1.021 | 73 | 1221.893 | | |
| 282 | 2.454 | 359 | 3090.779 | | |
| 283 | 0.509 | 97 | 256.746 | 1197.298 | |
| 284 | 0.301 | 42 | 185.811 | 819.008 | >360.000 |
| 285 | 4.049 | 515 | 1793.745 | | |
| 286 | 12.435 | 1,023 | | | |
| 287 | 2.709 | 499 | | | |
| 288 | 0.376 | 57 | 150.849 | 2155.905 | >360.000 |
| 289 | 1.292 | 209 | 453.834 | | |
| 290 | 20.826 | 2,148 | | | |
| 291 | 15.468 | 1,491 | | | |
| 292 | 0.315 | 17 | 27.682 | 841.226 | |
| 293 | 0.68 | 51 | 217.689 | 817.839 | 204 |

TABLE I-continued

Enzyme Assay and Blood Stability Data.

| Ex | JAK3 4 µM ATP IC$_{50}$ (nM) | JAK3 1 mM ATP IC$_{50}$ (nM) | PBMC IL15_pSTAT5_IC$_{50}$ (nM) | HWB_IL15 pSTAT5 IC$_{50}$ (nM) | Human blood stability t$_{1/2}$ (min) |
|---|---|---|---|---|---|
| 294 | 1.16 | 62 | 575.453 | | |
| 295 | 0.179 | 29 | 71.014 | 199.062 | ok133.207 |
| 296 | 0.519 | 57 | 609.211 | | |
| 297 | 0.43 | 45 | 150.267 | 718.167 | |
| 298 | 0.485 | 69 | 210.494 | 1282.125 | >360.000 |
| 299 | 1.205 | 57 | 305.123 | 913.169 | |
| 300 | 0.69 | 92 | 699.748 | | |
| 301 | 0.431 | 44 | 386.705 | 3026.667 | |
| 302 | 2.89 | 385 | 1186.599 | | |
| 303 | 4.808 | 731 | | | |
| 304 | 0.194 | 29 | 96.793 | 524.121 | |
| 305 | 0.496 | 53 | 277.881 | 6384.984 | |
| 306 | 0.705 | 107 | 1571.655 | | |
| 307 | 9.821 | 1,076 | 2133.638 | | |
| 308 | 0.531 | 48 | 305.873 | 775.119 | |
| 309 | 0.898 | 59 | 526.112 | | |
| 310 | 2.08 | 170 | 1196.196 | | |
| 311 | 1.783 | 223 | 586.459 | | |
| 312 | 1.053 | 56 | 310.139 | 703.955 | |
| 313 | 0.736 | 46 | 242.669 | 986.468 | |
| 314 | 0.24 | 30 | 115.347 | 401.86 | 186.987 |
| 315 | 0.348 | 26 | 74.904 | 210.675 | ok |
| 316 | 0.643 | 129 | 294.486 | 1454.374 | |
| 317 | 0.979 | 77 | 314.798 | 834.96 | |
| 318 | 0.535 | 59 | 214.491 | 1758.629 | |
| 319 | 0.404 | 45 | 210.832 | 396.387 | 334 |
| 320 | 2.158 | 182 | 1253.422 | | |
| 321 | 0.448 | 46 | 310.342 | 999.032 | >360.000 |
| 322 | 0.269 | 47 | 427.563 | | |
| 323 | 0.392 | 69 | 430.342 | | |
| 324 | 0.418 | 21 | 202.933 | 1267.22 | 257.921 |
| 325 | 12.797 | 1,264 | | | |
| 326 | 0.455 | 50 | 329.899 | 780.409 | >360.000 |
| 327 | 0.546 | 56 | 260.694 | 1037.851 | >360.000 |
| 328 | 0.578 | 37 | 143.2 | 287.352 | 251.86 |
| 329 | 0.587 | 60 | 246.862 | 6286.522 | |
| 330 | 0.287 | 45 | 122.071 | 1971.669 | |
| 331 | 0.313 | 42 | 288.136 | 263.22 | ok331.235 |
| 332 | 0.262 | 22 | 87.738 | 220.984 | 144.963 |
| 333 | 0.307 | 44 | 773.506 | | |
| 334 | 0.703 | 93 | 73.642 | 3916.304 | |
| 335 | 0.262 | 57 | 848.914 | | |
| 336 | 0.24 | 26 | 107.382 | 372.581 | ok |
| 337 | 14.372 | 1,845 | | | |
| 338 | 31.42 | 2,776 | | | |
| 339 | 16.469 | 2,699 | | | |
| 340 | 29.951 | 3,469 | | | |
| 341 | 20.947 | 2,605 | | | |
| 342 | 26.446 | 2,634 | | | |
| 343 | 75.132 | 4,879 | | | |
| 344 | 26.678 | 2,537 | | | |
| 345 | 43.652 | 4,026 | | | |
| 346 | 40.914 | 4,439 | | | |
| 347 | 24.176 | 3,078 | | | |
| 348 | 10.239 | 1,188 | | | |
| 349 | 2.12 | 367 | 2929.437 | | |
| 350 | 32.115 | 4,368 | | | >360.000 |
| 351 | 2.877 | 838 | | | 331 |
| 352 | 52.311 | 4,497 | | | |
| 353 | 1.478 | 123 | 2203.352 | | >360.000 |
| 354 | 3.408 | 261 | 4518.962 | | |
| 355 | 0.327 | 30 | | | |
| 356 | 4.074 | 831 | | | |

What is claimed is:

1. The compound 2-{[(2S)-1-acryloylpyrrolidin-2-yl]methoxy}-N-[(2S)-1-methoxypropan-2-yl]-5H-pyrrolo[2,3-b]pyrazine-7-carboxamide; or, a pharmaceutically acceptable salt thereof.

2. The compound 2-[(1-acryloylpiperidin-4-yl)amino]-N-(3-fluorobenzyl)-5H-pyrrolo[2,3-b]pyrazine-7-carboxamide; or, a pharmaceutically acceptable salt thereof.

3. The compound 2-[(1-acryloylpiperidin-4-yl)amino]-N-(2-cyclopropylethyl)-5H-pyrrolo[2,3-b]pyrazine-7-carboxamide; or, a pharmaceutically acceptable salt thereof.

4. The compound 2-[(1-acryloylpiperidin-4-yl)amino]-N-benzyl-5H-pyrrolo[2,3-b]pyrazine-7-carboxamide; or, a pharmaceutically acceptable salt thereof.

5. The compound 2-[(1-acryloylpiperidin-4-yl)oxy]-N-[(2R)-1-methoxypropan-2-yl]-5H-pyrrolo[2,3-b]pyrazine-7-carboxamide; or a pharmaceutically acceptable salt thereof.

* * * * *